US007709188B2

(12) United States Patent
Kostrikis

(10) Patent No.: US 7,709,188 B2
(45) Date of Patent: *May 4, 2010

(54) MULTI-ALLELIC DETECTION OF SARS-ASSOCIATED CORONAVIRUS

(75) Inventor: Leondios G. Kostrikis, Kapsalos Limassol (CY)

(73) Assignee: Birch Biomedical Research LLC, New York, NY (US)

( * ) Notice: Subject to any disclaimer, the term of this patent is extended or adjusted under 35 U.S.C. 154(b) by 653 days.

This patent is subject to a terminal disclaimer.

(21) Appl. No.: 10/569,070

(22) PCT Filed: Aug. 13, 2004

(86) PCT No.: PCT/US2004/026380

§ 371 (c)(1), (2), (4) Date: Nov. 7, 2006

(87) PCT Pub. No.: WO2005/021798

PCT Pub. Date: Mar. 10, 2005

(65) Prior Publication Data

US 2007/0042351 A1 Feb. 22, 2007

Related U.S. Application Data

(60) Provisional application No. 60/496,995, filed on Aug. 22, 2003, provisional application No. 60/576,314, filed on Jun. 3, 2004.

(51) Int. Cl.

| | |
|---|---|
| ***C12Q 1/00*** | (2006.01) |
| ***C12Q 1/70*** | (2006.01) |
| ***C12Q 1/68*** | (2006.01) |

(52) U.S. Cl. .................................... 435/4; 435/5; 435/6

(58) Field of Classification Search ....................... None
See application file for complete search history.

(56) References Cited

U.S. PATENT DOCUMENTS

| | | | | |
|---|---|---|---|---|
| 7,220,852 | B1 * | 5/2007 | Rota et al. | 536/23.72 |
| 2004/0229211 | A1 * | 11/2004 | Yeung | 435/5 |
| 2006/0257852 | A1 * | 11/2006 | Rappuoli et al. | 435/5 |

FOREIGN PATENT DOCUMENTS

WO WO-2004/094675 A 11/2004

OTHER PUBLICATIONS

Buck et al. Design Strategies and Performance of Custom DNA Sequencing Primers. BioTechniques 1999, vol. 27, pp. 528-536.*

Thiel V., et al., "Mechanisms and Enzymes Involved in SARS Coronavirus Genome Expression", Journal of General Virology, Society for General Microbiology, Reading, GB, vol. 84, No. 9, Jun. 19, 2003, pp. 2305-2315.

Azri Adzhar et al.,"Universal Oligonucleotides for the Detection of Infectious Bronchitis Virus by the Polymerase Chain Reaction", Avian Pathology, vol. 25, No. 4, 1996, pp. 817-836.

C. T. Wittwer et al., "Real-Time Multiplex PCR Assays", Methods: A companion to methods in enzymology, Academic Press Inc., New York, NY, US, vol. 25, No. 4, Dec. 2001, pp. 430-442.

D. Zhou et al.,"One-Step Duplex RT-PCR Assay for Detection SARS Associated Coronavirus", Bingduxue Zazhi-Virologica Sinica, Kexue Chubanshe, Beijing, CN, vol. 18, No. 3, Jun. 2003, pp. 232-236.

P. A. Rota et al., "Characterization of a Novel Coronavirus Associated With Severe Acute Respiratory Syndrome", Science, American Association for the Advancement of Science, US, vol. 300, No. 5624, May 30, 2003, pp. 1394-1399.

Ho-Sheng Wu et al., "Early Detection of Antibodies Against Various Structural Proteins of the SARS-Associated Coronavirus in SARS Patients", Journal of Biomedical Science, vol. 11, No. 1, Feb. 2004, pp. 117-126.

Li-Rung Huang et al., "Evaluation of Antibody Responses Against SARS Coronaviral Nucleocapsid or Spike Proteins by Immunoblotting or ELISA", Journal of Medical Virology, vol. 73, No. 3, Jul. 2004, pp. 338-346.

S. L. Emery et al., Real-Time Reverse Transcription-Polymerase Chain Reaction Assay for SARS-Assocatied Coronavirus Emerging Infectious Diseases, EID, Atlanta, GA, US, vol. 10, No. 2, Feb. 2004, pp. 311-316.

J. Zhai et al., "Real-Time Polymerase Chain Reaction for Detecting SARS Coronavirus", Beijing, 2003, Emerging Infectious Diseases, EID, Atlantia, GA, US, vol. 10, No. 2, Feb. 2004, pp. 300-303.

* cited by examiner

*Primary Examiner*—Robert B Mondesi
*Assistant Examiner*—Louise Humphrey
(74) *Attorney, Agent, or Firm*—Smith, Gambrell & Russell, LLP

(57) ABSTRACT

The subject invention relates to a multiple-allelic RT-real-time polymerase chain reaction (PCR) assay for coronaviruses including the SARS virus. Multiple target sequences within the SARS-CoV, S, E, M and N genes are identified. The use of the four different targets enhances the likelihood that the fundamental genetic drift of the virus will not lead to a false negative result. Multiplex assays format for the assay are envisioned. Thus, the present invention allows for early diagnosis of a SARS infection. The assay would be useful in the context of monitoring treatment regimens, screening potential anti SARS agents, and similar applications requiring qualitative and quantitative determinations.

6 Claims, 82 Drawing Sheets

Figure 1: **CLUSTAL W (1.81) multiple DNA sequence alignment of coronavirus *S* genes from strains isolated from different species**

```
CcoV        ATGATTGTGCTTACATTGTGCCTTTTCTTGTT---TTTGTACAGTAGTGTGAGCTGTACA
FcoV        ATGATTGTGCTCGTAACTTGCCTCTTGTTGTTATGTTCATACCACACAGTTTTGAGTACA
TGE         ATGAAAAAACTATTTGTGGTTTTGGTCGTAATGCCATTGATTTATGGAGACAATTTTCCT
PRCoV       ------------------------------------------------------------
HCoVOC43    ------------------------------------------------------------
PEDV        ------------------------------------------------------------
SARSUrba    ------------------------------------------------------------
SARSTor2    ------------------------------------------------------------
BcoV        ------------------------------------------------------------
HEV         ------------------------------------------------------------
MHV         ------------------------------------------------------------
RtCoV       ------------------------------------------------------------
IBV         ------------------------------------------------------------

CcoV        TCAAACAATGACTGTGTACAAGTTAATGTGACACAACTGCCTGGCAATGAAAATATTATC
FcoV        ACAAATAATGAATGCATACAAGTTAACGTAACACAATTGGCTGGCAATGAAAACCTTATC
TGE         TGTTCTAAATTGACTAATAGAACTATAGGCAACCAGTGGAATCTCATTGAAACCTTCCTT
PRCoV       ------------------------------------------------------------
HCoVOC43    ------------------------------------------------------------
PEDV        ----------------------------ATGAGGTCTTTAATTTACTTCTGGTTGCTCTT
SARSUrba    ------------------------------------------------------ATGTTT
SARSTor2    ------------------------------------------------------ATGTTT
BcoV        ---------------------------------------------ATGTTTTTGATACTT
HEV         ---------------------------------------------ATGTTTTTTATACTT
MHV         ---------------------------------------------ATGCTATTCGTGTTT
RtCoV       ---------------------------------------------ATGCTATTCGTGTTT
IBV         ------------------------------------------------------------

CcoV        AAAGATTTTCTATTTCAGAACTTTAAAGAAGAAGGAAGTTTAGTTGTTGGTGGTTATTAC
FcoV        AGAGATTTTCTGTTTAGTAACTTTAAAGAAGAAGGAAGTGTAGTTGTTGGTGGTTATTAC
TGE         CTAAACTATAGTAGTAGGTTACCACCTAATTCAGATGTGGTGTTAGGTGATTATTTTCCT
PRCoV       ------------------------------------------------------------
HCoVOC43    ------------------------------------------------------------
PEDV        ACCAGTACTTCCAACACTCAGCCTACCACAAGATGTCACTAGGTGCCAGTCTACTACTAA
SARSUrba    ATTTTCTTATTATTTCTTACTCTCACTAGTGGTAGTGACCTTGACCGGTGCACCACTTTT
SARSTor2    ATTTTCTTATTATTTCTTACTCTCACTAGTGGTAGTGACCTTGACCGGTGCACCACTTTT
BcoV        TTAATTTCCTTACCAATGGCTTTTGCTGTTATAGGAGATTTAAAGTGTACTACGGTTTCC
HEV         TTAATCTCCCTGCCTTCTGCTTTTGCAGTTATAGGGGATTTAAAGTGTACTACTTCATTA
MHV         TTAACCTTGTTGCCCTCTTCTCTAGGGTATATTGGTGATTTTAGATGTATCCAACTTGTA
RtCoV       TTAACCCTATTGCCCTCTTGTCTAGGGTATATTGGTGATTTTAGATGTATCAACCTTGTA
IBV         ------------------------------------------------------------

CcoV        CCCACAGAGGTGTGGTATAACTGTTCCACAACTCAACAAACTACCGCTTATAAGTATTTT
FcoV        CCTACAGAGGTGTGGTACAACTGCTCTAGAACAGCTCGAACTACTGCCTTTCAGTATTTT
TGE         ACTGTACAACCTTGGTTTAATTGCATTCGCAATGATAGTAATGACCTTTATGTTACACTG
PRCoV       ------------------------------------------------------------
HCoVOC43    ------------------------------------------------------------
PEDV        CTTTAGGCGGTTCTTTTCAA--AATTTAATGTTCAGGCACCTGCCGTCGTCGTTTTGGGT
SARSUrba    GA------------TGATGTTCAAGCTCCTA--ATTACACTCAACATACTTCAT----CT
SARSTor2    GA------------TGATGTTCAAGCTCCTA--ATTACACTCAACATACTTCAT----CT
BcoV        ATTAATGATGT---TGACACCGGTGCTCCCTCTATTAGCACTGATATTGTCGATGTTACT
HEV         ATTAATGACGT---TGACACTGGTGTGCCATCTATTAGCTCTGAAGTTGTTGATGTCACT
MHV         AATACCGACACCTCTAATGCCAGCGCTCCAAGCGTTAGTACAGAGGTAGTTGATGTTTCC
```

```
RtCoV       AACACCCGCATTTCTAATGCGCGCGCACCCAGTGTTAGCACAGAGGTAGTTGATGTTTCT
IBV         ------------------------------------------------------------

CcoV        AGTAATATACATGCATTTTATTTTGATATGGAAGCCATGGAGAATAGTACTGGCAATGCA
FcoV        AATAATATACATGCCTTTTATTTTGTTATGGAAGCCATGGAAAATAGCACTGGTAATGCA
TGE         GAAAATCTTAAAGCATTGTATTGGGATT---ATGCTACAGAAAATATCACTTGGAAT---
PRCoV       ------------------------------------------------------------
HCoVOC43    ------------------------------------------------------------
PEDV        GGTTACCTACCTAGTATGAACTCTTCTAGCTGGTACTGTGGCACAGGCATTGAAACTGCT
SARSUrba    ATGAG---GGGGGTTTACTATCCT---GATGAAATT--TTTAGATCAGACACTCTT----
SARSTor2    ATGAG---GGGGGTTTACTATCCT---GATGAAATT--TTTAGATCAGACACTCTT----
BcoV        AATGGTTTAGGTACTTATTATGTTTTAGATCGTGTGTATTTAAATACTACGTTGTTG---
HEV         AATGGTTTGGGGACTTTCTATGTTTTAGATCGTGTCTATTTAAATACCACATTGTTG---
MHV         AAAGGGATTGGTACTTATTATGTTTTAGATCGAGTCTATTTAAATGCCACACTATTG---
RtCoV       AAAGGTCTTGGTACATATTACGTTTTAGATCGTGTTTATTTAAATGCCACGTTATTG---
IBV         ------------------------------------------------------------

CcoV        CGTGGTAAACCTTTACTAGTACATGTTCATGGTAATCCTGTTAGTATCATTGTTTACATA
FcoV        CGTGGTAAACCATTATTATTTCATGTGCATGGTGAGCCTGTTAGTGTTATT------ATA
TGE         CACAGACAACGGTTAAACGTAGTCGTTAATGGATACCCATACTCCATCACAGTT---ACA
PRCoV       ------------------------------------------------------------
HCoVOC43    ------------------------------------------------------------
PEDV        AGTGGCGTTCATGGTATTTTTCTCAGCTACATCGATTCTGGTCAGGGCTTTGAGA--TTG
SARSUrba    -----TATTTA--ACTCAGGATTTATTTCTTC-CATTTTATTCTAATGTTACAGG--GTT
SARSTor2    -----TATTTA--ACTCAGGATTTATTTCTTC-CATTTTATTCTAATGTTACAGG--GTT
BcoV        CTTAATGGTTACTACCCTACTTCAGGTTCTACATATCGTAATATGGCACTGAAGG--GAA
HEV         CTCAATGGTTATTACCCAATTTCAGGTGCTACATTTCGTAATATGGCTCTGAAAG--GAA
MHV         CTTACTGGTTATTACCCTGTAGATGGGTCCATGTATAGAAACATGGCTCTAACGG--GAA
RtCoV       CTTACTGGTTACTACCCTGTAGATGGGTCCATGTATCGTAACATGGCTCTAATGG--GTA
IBV         ------------------------------------------------------------

CcoV        TCAGCTTATAGAGATGATGTGCAATTTAGGCCGCTTTTAAAGCATGGTTTATTGTGTATA
FcoV        TCGGCTTATAGGGATGATGTGCAACAAAGGCCCCTTTTAAAACATGGGTTAGTGTGCATA
TGE         ACAACCCGCAATTTTAAT-TCTGCTGAAGGTGCTATTATATGCATTTGTAAGGGCTCACC
PRCoV       ------------------------------------------------------------
HCoVOC43    ------------------------------------------------------------
PEDV        GCATTTCGCAAGAGCCGT-TTGATCCTAGTGGTTACCAGCTTTATTTACATAAGGCCACT
SARSUrba    TCATACTATTAATCATAC----GTTTGG--CAACCCTGTCAT-ACCTTTTAAGGATGGTA
SARSTor2    TCATACTATTAATCATAC----GTTTGG--CAACCCTGTCAT-ACCTTTTAAGGATGGTA
BcoV        CTTTACTATTGAGCAGACTATGGTTTAAACCACCTTTTCTTTCTGATTTTATTAATGGTA
HEV         CTCGATTATTGAGCACCTTGTGGTTTAAGCCGCCTTTTTTATCACCTTTTAATGATGGTA
MHV         TTAATACCATAAGCCTTAATTGGTACAAACCACCCTTTTTATCAGAGTTTAATGATGGCA
RtCoV       CTAATACCTTAAGCCTTAATTGGTTTGAACCGCCCTTTTTATCAGAGTTTAACGATGGCA
IBV         ------------------------------------------------------------

CcoV        ACTAAAAATGACACCGTTGACTATAATAGCTTTACAATTAACCAATGGCGAGACATATGT
FcoV        ACTAAAAATCGCCATATTAACTATGAACAATTCACCTCCAACCAGTGGAATTCCACATGT
TGE         ACCTACTACCACCACAGAATCTA-----GTTTGACTTGCAATTGGGGTAGTGAGTGCAGG
PRCoV       ------------------------------------------------------------
HCoVOC43    ------------------------------------------------------------
PEDV        AATGGTAACACTAATGCTATTGCACGACTGCGCATTTGCCAGTTTCCCGATAATAAAACA
SARSUrba    TTTA-TTTTGCTGCCACAGAGAAATCAAATGTTGTCCGTGGTTGGGTTTTTGGTTCTACC
SARSTor2    TTTA-TTTTGCTGCCACAGAGAAATCAAATGTTGTCCGTGGTTGGGTTTTTGGTTCTACC
BcoV        TTT----TTGCTAAGGTCAAAAATACCAAGGTTATTAAAAAGGGTGTAATGTATAGTGAG
HEV         TTT----TTGCCAAGGTTAAAAACAGCAGATTTTCTAAAGATGGTGTTATTTATAGTGAG
MHV         TAT----TTGCTAAGGTAAAGAACCTTAAAGCATCTTTGCCCAAAGATTCTATTTCATAT
RtCoV       TAT----ATGCTAAGGTAAAGAACCTCAAAGCATCTTTGCCCATAGGCTCGGCTTCATAC
IBV         ------------------------------------------------------------
```

```
CcoV        TTGGGTGACGACAGAAAAATACCATTCTCTGTAGTACCCACAGATAATGGTACGAAATTA
FcoV        ACGGGTGCTGACAGAAAAATTCCTTTCTCTGTCATACCCACGGACAATGGAACAAAAATC
TGE         TTAAACCATAAGTTCCCTATATGTCCTTCTAATTCAGAGGCAAATTGTGGTAATATGCTG
PRCoV       ------------------------------------------------------------
HCoVOC43    ------------------------------------------------------------
PEDV        TTGGGCCCTACTGTTAATGATGTTACAACAGGTCGTAACTGCCTATTCAACAAAGCCATT
SARSUrba    ATGAACAACA-AGTCACAGTCGGTGATTA--TTATTAACAATTCTACTAATGTTGTTATA
SARSTor2    ATGAACAACA-AGTCACAGTCGGTGATTA--TTATTAACAATTCTACTAATGTTGTTATA
BcoV        TTTCCTGCTATAACTATAGGTAGTACTT---TTGTAAATACATCCTATAGTGTGGTAGTA
HEV         TTTCCTGCTATTACTATAGGTAGTACTT---TTGTAAATACTTCCTATAGCATAGTAGTA
MHV         TTCCCTACTATAATTATAGGTAGTAATT---TTGTCACCACTTCCTATACTGTAGTATTG
RtCoV       TTTCCTACTATAATTATAGGTAGTAATT---TTGTTAATACTTCCTATACTGTAGTATTG
IBV         ------------------------------------------------------------

CcoV        TTTGGTCTTGAGTGGAATGATGACTATGTTACAGCCTATATTAGTGATGAGTCTCACCGT
FcoV        TATGGTCTTGAGTGGAATGATGACTTTGTTACAGCTTATATTAGTGGTCGTTCTTATCAC
TGE         TATGGCCTACAATGGTTTGCAGATGAGGTTGTTGCTTATTTACATGGTGCTAGTTACCGT
PRCoV       ------------------------------------------------------------
HCoVOC43    ------------------------------------------------------------
PEDV        CCAGCTTATATGCGTGATGGAAAAGATATTGTTGTCGGCATAACATGGGATAATGATCGT
SARSUrba    CGAGCATGTA------------ACTTTGAAT-------TGTGTGACAACCCTTTCTTTGC
SARSTor2    CGAGCATGTA------------ACTTTGAAT-------TGTGTGACAACCCTTTCTTTGC
BcoV        CAACCACATACTACCAATTTGGATAATAAATTACAAGGTCTCTTAGAGATCTCTGTTTGC
HEV         GAGCCTCATACCTCACTTATTAATGGTAATTTACAAGGTTTGTTGCAAATTTCTGTTTGT
MHV         GAACCGTATA------------ATGGTA-----------TAATTAT-GGCATCCATTTGC
RtCoV       GAACCATACA------------ATGGTA-----------TTATTAT-GGCATCTATTTGC
IBV         ------------------------------------------------------------

CcoV        TTGAATATCAATAATAATTGGTTTAACAATGTTACACTC--CTATACTCACGTACAAGCA
FcoV        TTGAACATCAATACTAATTGGTTTAACAATGTCACACTT--TTGTATTCACGCTCAAGCA
TGE         ATTAGTTTTGAAAATCAATGGTCTGGCACTGTCACATTTGGTGATATGCGTGCGACAACA
PRCoV       ------------------------------------------------------------
HCoVOC43    ------------------------------------------------------------
PEDV        GTCACTGTTTTTGCTGACAAGATCTATCATTTTTATCTT--AAAAATGATTGGTCCCGCG
SARSUrba    TGTTTCTAAACCCATGGGTACACAGACACATACTATGAT----ATTCGA----TAATGCA
SARSTor2    TGTTTCTAAACCCATGGGTACACAGACACATACTATGAT----ATTCGA----TAATGCA
BcoV        CAGTATACTATGTGCGAGTACCCACATACGATTTGTCATCCTAAGCTGGG---TAATAAA
HEV         CAATACACTATGTGTGAATACCCACATACTATTTGTCATCCTAATTTGGG---TAATCAA
MHV         CAGTATACCATTTGTCAACTACCGTACACGGATTGCAAACCGAATACGGGCGGTAATAAG
RtCoV       CAGTATACCATTTGTCAATTACCGCACACGGATTGCAAACCTAACACGGGCGGTAACACG
IBV         ------------------------------------------------------------

CcoV        CCGCCACGTGGCAACACA-GTGCTGCATATGTTTA---TCAAGGTGTTTCAAATTTTACT
FcoV        CTGCTACCTGGGAATACA-GTGCTGCATATGCTTA---CCAAGGTGTTTCTAACTTCACT
TGE         TTAGAAGTCGCTGGCACGCTTGTAGACCTTTGGTGGTTTAATCCTGTTTATGATGTCAGT
PRCoV       -------------------ATGAAAAAATTATTTG---TGGTCTTGGTTGTAATGCCATT
HCoVOC43    -------------------------ATGTT-TGTT-TTGCTTGTTGC--ATATGCCTTGT
PEDV        TTGCGACAAGATGTTACAATCGCAGAAGTTGTGCT-ATGCAATATGTTTATACACCTACC
SARSUrba    TTTAATTGCACTTTCGAGTACATATCTGATGCCTTTTCGCTTGATGTTTCAGAA-----A
SARSTor2    TTTAATTGCACTTTCGAGTACATATCTGATGCCTTTTCGCTTGATGTTTCAGAA-----A
BcoV        CG-CGTAGAACTATGGCATTGGGATACAGGTGTTGTTTCCTGTTTATATAAGCG-----T
HEV         CG-CATAGAATTATGGCATTATGACACAGATGTTGTTTCTTGTTTATACAGGCG-----T
MHV         TT-AATTGGCTTTTGGCACACAGAGCTAAAATCCCCTGTGTGCATTTTAAAGCG-----T
RtCoV       CT-AATTGGTTTTTGGCACACAGATTTAAGGCCTCCGGTGTGCATTTTAAAGCG-----T
IBV         ------------ATGTTGGTAACACCTCTTTTACTAGTGACTCTTTTGTGTGCACTATGT
                                                        *

CcoV        TATTACAAGTTAAATAAAACCGCTGGCTTAAAAAGCTATGAATTGTGTGAAGATTATG-A
FcoV        TATTACAAGTTAAATAACACCAATGGTCTAAAAACCTATGAATTATGTGAAGATTATG-A
```

```
TGE         TATTATAGGGTTAATAATAAAAATGGT------ACTACCGTAGTTTCCAATTGCACTG-A
PRCoV       GATTTATGGA-----GACAAGTTTCCT------ACTTCCGTAGTTTCCAATTGCACTG-A
HCoVOC43    TGCATATTGCTGGTTGTCAA-ACTACAAATGGGCTGAACACTAGTTACT--CTGTTTGCA
PEDV        TACTACATGCTTAATGTTACTAGTGCAGGTGAGGATGGCATTTATTATGAACCCTGTACA
SARSUrba    AGT----CAGGTAATTTTAAAC---ACTTACGAGAGTTTGTGTTTAAAAATAAAGATGGG
SARSTor2    AGT----CAGGTAATTTTAAAC---ACTTACGAGAGTTTGTGTTTAAAAATAAAGATGGG
BcoV        AATTTCACATATGATGTGAATGCTGATTACTTGTATTTCCATTTTTATCAAGAAGGTGGT
HEV         AATTTCACATATGATGTGAATGCTGATTATTTATATTTCACTTTTATCAGGAAGGTGGC
MHV         AATTTTACGTTTAATGTTAATGCCGAATGGCTTTATTTCATTTTTACCAGCAGGGTGGT
RtCoV       AATTTTACGTTTAATGTTAATGCCGAATGGCTTTATTTCATTTTTACCAGCAGGGTGGT
IBV         AGTGCTGTTTTGTATGACAGTAGTTCTTACGTTTACTACTACCAAAGTGCCTTCAGACCA
                                   *

CcoV        AT--ACTGCACTGGCTATGCAACCAATGTGTTTGCTCCGACATCAGGTGGTTATATACCT
FcoV        AC--ATTGCACTGGCTATGCTACCAATGTATTTGCTCCGACATCAGGTGGTTACATACCT
TGE         TC--AATGTGCTAGTTATGTGGCTAATGTTTTTACTACACAGCCAGGAGGTTTTATACCA
PRCoV       TC--AATGTGCTAGTTATGTGGCTAATGTTTTTACTATACTACCAGGAGGCTTTATACCA
HCoVOC43    AC-GGCTGTGTTGGTTATTCAGAAAATGTATTTGCTGTTGAGAGTGGTGGTTATATACCC
PEDV        GCTAATTGCACTGGTTACGCTGCCAATGTATTTGCCACTGATTCCAATGGCCATATACCA
SARSUrba    TTTCTCTATG-----TTTATAAGGGCTAT--------CAACCTATAGATGTAGTTCGTGA
SARSTor2    TTTCTCTATG-----TTTATAAGGGCTAT--------CAACCTATAGATGTAGTTCGTGA
BcoV        ACTTTTTATGCATATTTTACAGACACTGGTGTTGTTACTAAGTTTCTGTTTAATGTTTAT
HEV         ACTTTTTATGCATACTTTACAGATACTGGTTTTGTGACCAAGTTTCTGTTTAAGTTGTAT
MHV         ACTTTTTATGCGTATTATGCGGATGTTTCTTCTGCTACTACGTTTTTGTTTAGTATGTAT
RtCoV       ACTTTTTATGCGTATTATGCAGATGTTTCTTCTGCCACTACGTTTTTGTTTAGTTCGTAT
IBV         CCTAGTGGTTGGCATTTACAAGGGGGTGCTTATGCGGTAGTTAACATTTCTAGCGAATTT
                             *         *

CcoV        GATGGATTCAGTTTTAACAATTGGTTTATGCTTACAAACAGCTCCACTTTTGTTAGTGGC
FcoV        GATGGATTTAGTTTTAACAATTGGTTCTTGCTTACAAATAGTTCCACTTTTGTTAGTGGC
TGE         TCAGATTTTAGTTTTAATAATTGGTTCCTTCTAACTAATAGCTCCACGTTGGTTAGTGGT
PRCoV       TCAGATTTTAGTTTTAATAATTGGTTCCTCCTAACTAATAGCTCCACGTTGGTTAGTGGT
HCoVOC43    TCCGACTTTGCATTCAATAATTGGTTCCTTCTAACTAATACCTCATCTGTTGTAGATGGT
PEDV        GAAGGTTTTAGTTTTAATAATTGGTTTCTTTTATCCAATGACTCCACTTTGTTGCATGGT
SARSUrba    TCTACCTTCTGGTTTTAACACT-TTGAAACCTATTTTTAAGTTGCCTCTT----------
SARSTor2    TCTACCTTCTGGTTTTAACACT-TTGAAACCTATTTTTAAGTTGCCTCTT----------
BcoV        TTAGGCACGGTGCTTTCACATTATTATGTCCTGCCTTTGACTTGTTCT------------
HEV         TTAGGCACTGTGCTGTCACATTATTATGTTATGCCATTGACTTGTAAT------------
MHV         ATTGGTGATGTGTTAACACAATATTTTGTGTTGCCTTATATGTGTACTCTCACTACAACA
RtCoV       ATTGGTGCTGTGTTAACACAGTATTTTGTGTTGCCTTATATGTGTAGTCCCACTACCTCA
IBV         AATAATGCAGGCTCTTCATCAGGGTGTACTGTTGGTATTATTCATGGTGGTCGTGTTGTT
                                  *       *

CcoV        AGATTTGTAACAAATCAACCGCTGCTAGT--TAATTGCTTGTGGCCAGTGC--CCAGTTT
FcoV        AGGTTTGTAACAAATCAACCATTATTGAT--TAATTGCTTGTGGCCAGTGC--CCAGTTT
TGE         AAATTAGTTACCAAACAGCCGTTATTAGT--TAATTGCTTATGGCCAGTCC--CTAGCTT
PRCoV       AAATTAGTTACCAAACAGCCTCTATTAGT--TAATTGCTTATGGCCAGTCC--CTAGCTT
HCoVOC43    GTTGTGAGGAGTTTTCAGCCTTTGTTGCT--TAATTGCTTATGGTCTGTTT--CT--GGC
PEDV        AAAGTGGTTTCCAACCAACCCTTGTTGGT--CAATTGTCTTTTGGCCATTC--CTAAGAT
SARSUrba    GGTATTAACATTACAAATTTTAGAGCCATTCTTACAGCCTTTTCACC-TGC--TCAAGAC
SARSTor2    GGTATTAACATTACAAATTTTAGAGCCATTCTTACAGCCTTTTCACC-TGC--TCAAGAC
BcoV        AGTGCTATGACTTTAGAATATTGGGTTACACCTCTCACTTCTAAACAATAT--TTACTAG
HEV         AGCGCTTTATCTTTAGAATACTGGGTTACACCTCTCACTACTAGACAATTT--CTTCTAG
MHV         GGTGTCTTTTCACCGCAGTATTGGGTTACACCTCTTGTCAAGCGCCAATAT--TTATTTA
RtCoV       GGTGTTTCCTCACCGCAGTATTGGGTTACACCACTTGTTAAGCGCCAATAT--TTATTTA
IBV         AATGCTTCTTCTATAGCTATGACGGCACCGTCATCAGGTATGGCTTGGTCTAGCAGTCAG
                                                                  *

CcoV        TGGCGTCGCAGCACAAGAATT--TTGTTTTGAAGGTGCTCAGTTTAGCCAATGTAACGGT
FcoV        TGGTGTAGCAGCACAAGAATT--TTGTTTTGAAGGTGCACAGTTTAGCCAATGTAATGGT
TGE         TGAAGAAGCAGCTTCTACATT--TTGTTTTGAGGGTGCTGGCTTTGATCAATGTAATGGT
PRCoV       TGAAGAAGTAGCTTCTACATT--TTGTTTTGAAGGTGCTGACTTTGATCAATGTAATGGT
HCoVOC43    TTGCGGTTTACTACTGGTTTTGTCTATTTTAATGGTACTGGGAGAGGTGATTGTAAAGGT
```

```
PEDV       TTATGGACTAG-GCCAATTTT-TCTCATTCAATCACACGATGGATGGCGTTTGTAATGGA
SARSUrba   ATTTGGGGCAC-GTCAGC--TGCAGCCTATTTTGTTGGCTATTTAAAGCCAACTACATTT
SARSTor2   ATTTGGGGCAC-GTCAGC--TGCAGCCTATTTTGTTGGCTATTTAAAGCCAACTACATTT
BcoV       CTTTCAATCAA-GATGGTGTTATTTTTAATGCTGTTGATTGTAAGAGTGATTTTATGAGT
HEV        CCTTTGACCAG-GATGGTGTTTTATACCATGCTGTTGATTGTGCTAGTGATTTTATGAGT
MHV        ATTTTAATCAA-AAGGGTATTATTACTAGTGCTGTTGATTGTGCTAGTAGTTATACCAGC
RtCoV      ATTTTAACCAA-AAGGGTATTATTACTAGCGCTGTTGATTGTGCTAGTAGTTATACCAGT
IBV        TTTTGTACTGCACACTGTAATTTTTCAGATACTACAGTGTTTGTTACACATTGTTATAAA
                                   *                                   *

CcoV       GTTTCTTTAAATAATACAGTAGATGTTATTAGATTTAACCTTAATTTCACTACAGATGTA
FcoV       GTGTCTTTAAATAACACAGTGGATGTTATTAGATTCAACCTTAATTTCACTGCAGATGTA
TGE        GCTGTTTTAAATAATACTGTAGACGTCATTAGGTTCAACCTTAATTTTACTACAAATGTA
PRCoV      GCTGTTTTAAATAACACTGTAGACGTCATTAGGTTTAACCTTAATTTTACTACAAATGTA
HCoVOC43   TTTTCCTCAGATGTTTTGTCTGATGTCATACGTTACAACCTCAATTTTGAA------GAA
PEDV       GCTGCTGTGGATCGTGCCCCAGAGGCTCTGAGGTTTAATATTAATGACACCTC---CGTC
SARSUrba   ATGCTCAAGTATGATGAAAATGGTACAATCACAGATGCTGTTGATTGT-----------T
SARSTor2   ATGCTCAAGTATGATGAAAATGGTACAATCACAGATGCTGTTGATTGT-----------T
BcoV       GAGATTAAGTGTAAAACACTATCTATAGCACCATCTACTGGTGTTTATGAATTAAACGGT
HEV        GAGATTATGTGTAAAACTTCTTCAATTACACCACCTACTGGTGTTTATGAACTAAACGGT
MHV        GAAATAAAGTGTAAGACCCAAAGTATGAATCCCAATACGGGAGTTTATGATTTATCCGGT
RtCoV      GAAATAAAGTGTAAGACTCAAAGTATGAATCCCAATACGGGAGTCTATGATTTATCCGGT
IBV        CATGGTGGGTGTCCTTTAACTGGCATGCTTCAACAGAATCTTATACGT---------GTT
                       *

CcoV       CAATCTGGCATGGGTGCTACAGTATTTTCACTGAATACAACAGGCGGTGTCATTCTTGAG
FcoV       CAATCTGGTATGGGTGCTACAGTATTTTCACTGAATACAACAGGTGGTGTCATTCTTGAA
TGE        CAATCAGGTAAGGGTGCCACAGTGTTTTCATTGAACACAACGGGTGGTGTCACTCTTGAA
PRCoV      CAATCAGGTAAGGGTGCTACAGTGTTTTCATTGAACACAACGGGTGGTGTCACTCTTGAA
HCoVOC43   AACCTTAGACGTGGAACCATTTTGTTT------AAAACATCTTATGGTGTTGTTGTGTTT
PEDV       ATTCTTGCTGAAGGCTCAATTGTACTT------CATACTGCTTTAGGAACAAATCTTTCT
SARSUrba   CTCAAAATCCA-CTTGCTGAACTCAAATGCT---CTGTTAAGAGCTT---TGAGATTGAC
SARSTor2   CTCAAAATCCA-CTTGCTGAACTCAAATGCT---CTGTTAAGAGCTT---TGAGATTGAC
BcoV       TACACTGTTCAGCCAATTGCAGATGTTTACCGACGTATACCTAATCTTCCCGATTGTAAT
HEV        TACACAGTTCAACCTGTTGCCACTGTATATCGTAGAATACCTGATTTACCCAATTGCGAT
MHV        TACACCGTCCAACCTGTAGGATTAGTGTACCGGCGTGTTAGAAATTTGCCTGATTGTAAA
RtCoV      TACACCGTCCAACCTGTAGGACTAGTGTACCGGCGTGTTAGAAATTTGCCTGATTGTAAA
IBV        TCTGCTATGAAAAATGGCCAGCTTTTCTATAATTTAACAGTTAGTGTAGCTAAGTACCCT

CcoV       ATTTCTTGTTATAATGACACAGTGAGTGAGTCGAGT-TTCTACAGTTATGGTGAAATTCC
FcoV       ATTTCATGTTATAGTGACACAGTGAGTGAGTCTAGT-TCTTACAGTTATGGTGAAATCCC
TGE        ATTTCATGTTATA------CAGTGAGTGACTCGAGC-TTTTTCAGTTACGGTGAAATTCC
PRCoV      ATCTCATGTTATAATGATACAGTGAGTGATTCGAGC-TTTTCCAGTTACGGTGAAATTCC
HCoVOC43   TATTGTACCAACAACACTTTAGTTTC------AGGTGATGCTCACATACCATTTGGTACA
PEDV       TTTGTTTGCAGTAATTCCTCAGATCCTCATTTAGCCATCTTTGCCATACCTCTGGGTGCT
SARSUrba   AAAGGAATTTACCAGACCTCTAATTTCAGGGTTGTTCC-CTCAGGAGATGTTGTGAGATT
SARSTor2   AAAGGAATTTACCAGACCTCTAATTTCAGGGTTGTTCC-CTCAGGAGATGTTGTGAGATT
BcoV       ATAGAGGCTTGGCTTAATGATAAGTCGGTGCCCTCTCCATTAAATTGGGAACGTAAGACC
HEV        ATCGAAGCTTGGCTTAATTCTAAGACCGTTTCTTCGCCTCTTAATTGGGAACGTAAAATT
MHV        ATTGAGGAATGGCTAACTGCTAAGTCTGTACCTTCTCCTCTCAATTGGGAGCGCAAAACA
RtCoV      ATTGAGGAATGGTTGGCTGCTAACACAGTACCCTCTCCTCTCAATTGGGAGCGCAAAACA
IBV        ACTTTTAGATCATTTCAGTGTGTTAATAATTTAACATCCGTATATTTAAATGGTGATCTT

CcoV       ATTCGGCGTAACTGATG-GACCACGTTACTGTTATGTACTCT-ACAATGGCACAGCTCTT
FcoV       GTTCGGCATAACTGACG-GACCACGATACTGTTATGTACTTT-ACAATGGCACAGCTCTT
TGE        GTTCGGCGTAACTGATG-GACCACGGTACTGTTACGTACACT-ATAATGGCACAGCTCTT
PRCoV      GTTCGGCGTAACTAATG-GACCACGGTACTGTTACGTACTCT-ATAATGGCACAGCTCTT
HCoVOC43   GTTTTGGGCAATTTTT---ATTGCTTTGTAAATACTACTATTGGCAATGAAACTACGTCT
PEDV       ACTGAAGTACCCTACT---ATTGCTTTCTTAAAGTGGATACTTACAACTCCACTGTTTAT
SARSUrba   CCCTAATATTACAA-----ACTTGTGTCCTTTTGGAGAGGTTTTTAATGCTACTAAATTC
SARSTor2   CCCTAATATTACAA-----ACTTGTGTCCTTTTGGAGAGGTTTTTAATGCTACTAAATTC
```

```
BcoV        TTTTCAAATTGTAATTTTAATATGAGCAGCCTGATGTCTTTTATTCAGGCAGACTCATTT
HEV         TTTTCTAATTGTAATTTTAACATGGGCAGGCTGATGTCTTTTATTCAGGCTGACTCTTTT
MHV         TTTCAAAATTGTAACTTCGACCTGAGCAGTCTATTAAGATTTGTTCAGGCTGAGTCACTC
RtCoV       TTTCAAAATTGTAACTTCAACCTGAGCAGTCTATTAAGATTTGTTCAGGCTGAGTCACTC
IBV         GTTTACACCTCTAATGAGACCATAGATGTTACATCTGCAGGTGTTTATTTAAAGCTGGT
                                                         *    *

CcoV        AAGTATT-TAGGAACATTACCACCTAGTGTCAAGGAAATTGCTATTAGTAAGTGG-----
FcoV        AAATATT-TAGGAACATTACCACCCAGTGTAAAGGAAATTGCTATTAGTAAGTGG-----
TGE         AAGTATT-TAGGAACATTACCACCTAGTGTCAAGGAGATTGCTATTAGTAAGTGG-----
PRCoV       AAGTATC-TAGGAACATTACCACCTAGTGTCAAGGAGATTGCTATTAGTAAGTGG-----
HCoVOC43    GCTTTTG-TGGGTGCACTACCTAAGACAGTTCGTGAGTTTGTTATT-TCACGCACA----
PEDV        AAATTCT-TGGCTGTTTTACCTCCTACTGTCAGGGAAATTGTCATCACCAAGTAT-----
SARSUrba    CCTTCTG------TCTATGCATGGGAGAGAAAAAAAAT---TTCTAATTGTGTTGCT---
SARSTor2    CCTTCTG------TCTATGCATGGGAGAGAAAAAAAAT---TTCTAATTGTGTTGCT---
BcoV        ACTTGTAATAATATTGATGCTGCTAAGATATATGGTATGTGTTTTTCCAGCATAACTATA
HEV         GGTTGTAACAATATTGATGCTTCTCGCTTATATGGTATGTGTTTTGGTAGCATTACTATT
MHV         TCATGTAGTAATATAGATGCTTCCAAGGTTTATGGTATGTGCTTTGGTAGTATATCTATA
RtCoV       TCATGTAGTAATATAGATGCTTCCAAGGTTTATGGAATGTGCTTTGGTAGCATATCTATA
IBV         GGACCTA-TAACTTATAAAGTTATGAGAGAAGTTAAA---GCCCTGGCTTATTTT-----
                                                    *

CcoV        GGACATTTTTATATTAATGGTTACAATTTCTTTAGCACGTTTCCTATTGATTGTATAGCT
FcoV        GGCCATTTTTATATTAATGGTTACAATTTCTTTAGCACATTTCCTATTGGTTGTATATCT
TGE         GGCCATTTTTATATTAATGGTTACAATTTCTTTAGCACATTTCCTATTGATTGTATATCT
PRCoV       GGCCATTTTTATATTAATGGTTACAATTTCTTTAGCACATTTCCTATTGATTGTATATCT
HCoVOC43    GGACATTTTTATATTAATGGCTATCGCTATTTCACTTTAGGTAATGTAGAAGCCGT----
PEDV        GGTGATGTTTATGTCAATGGGTTTGGCTATTTGCATCTCGGTTTGTTGGATGCTGTCACA
SARSUrba    GATTACTCTGTGCTCTACAAC--TCAACATTTTTTTCAACCTTTAAGTGCTATGGCGTTT
SARSTor2    GATTACTCTGTGCTCTACAAC--TCAACATTTTTTTCAACCTTTAAGTGCTATGGCGTTT
BcoV        GATAAGTTTGCTATACCCAATGGTAGGAAGGTTGACCTACAATTGGGCAATTTGGGCTAT
HEV         GATAAGTTTGCTATACCCAATAGTAGAAAGGTTGATCTGCAAGTGGGTAAATCTGGTTAT
MHV         GACAAGTTTGCGATACCCAATAGACGCCGAGTTGATTTGCAGCTAGGCAACTCTGGGTTT
RtCoV       GATAAATTTGCAATACCCAACAGTCGCCCGTGTTGATCTTCAGCTAGGTAAATCGGGTCTT
IBV         GTTAATGGTACTGCACAAGATGTTATTTTGTGTGATGGATCACCTAGAGGCTTGTTAGCA
            *  *  *

CcoV        TTTAATTTAA------------CCACTGGTGCTAGTGGAGCAT-TTTGGACAATTGCTTA
FcoV        TTTAATTTAA------------CCACTGGTGTTAGTGGAGCTT-TTTGGACAATTGCTTA
TGE         TTTAATTTGA------------CCACTGGTGATAGTGACGTTT-TCTGGACAATAGCTTA
PRCoV       TTTAATTTGA------------CTACTGGTGATAGTGACGTCT-TCTGGACAATAGCTTA
HCoVOC43    --TAATTTCA------ATGTCACTACTGCAGAAACCACTGATT-TTTGTACTGTTGCGTT
PEDV        ATTAATTTCACTGGTCATGGCACTGACGATGACGTTTCAGGTT-TCTGGACCATAGCATC
SARSUrba    CTGC---CAC------------TAAGTTGAATGATCTTTGCTT-CTCCAATGTCTATGCA
SARSTor2    CTGC---CAC------------TAAGTTGAATGATCTTTGCTT-CTCCAATGTCTATGCA
BcoV        TTGCAGTCTT------------TTAACTATAGAATTGATACTA-CTGCTACAAGT-TGTC
HEV         TTACAATCTT------------TTAATTATAAGATTGACACTG-CTGTTAGCAGT-TGTC
MHV         TTGCAATCCT------------TTAATTACAAAATAGATACAA-GAGCTACTTCG-TGTC
RtCoV       TTGCAATCTT------------TTAATTATAAAATTGATACAA-GAGCGACCTCG-TGTC
IBV         TGCCAGTATA------------ATACTGGCAATTTTTCAGATGGCTTTTATCCTTTTACT
                                                               *

CcoV        TACG-TCGTACACAGAAGCATTAGTACAA-GTTGAAAACACAGCTATTAAAAAGGTGACG
FcoV        CACA-TCGTATACTGAAGCATTAGTACAA-GTTGAAAACACAGCTATTAAAAATGTGACG
TGE         CACA-TCGTACACTGAAGCATTAGTACAA-GTTGAAAACACAGCTATTACAAAGGTGACG
PRCoV       CACA-TCGTACACTGAAGCATTAGTACAA-GTTGAAAACACAGCTATTACAAATGTGACG
HCoVOC43    AGCT-TCTTATGCTGACGTTTTGGTTAAT-GTGTCACAAACCTCTATTGCTAATATAATT
PEDV        GACT-AATTTTGTTGATGCACTCATCGAG-GTTCAAGGAACTTCCATTCAGCGTATTCTT
SARSUrba    GATTCTTTTGTAGTCAAG--GGAGATGAT-GTAAG-ACAAATAGCGCCAGGACAAACTGG
SARSTor2    GATTCTTTTGTAGTCAAG--GGAGATGAT-GTAAG-ACAAATAGCGCCAGGACAAACTGG
BcoV        AGTTGTATTATAATTTACCTGCTGCTAAT-GTTTCTGTTAGCAGGTTTAATCCTTCTACT
HEV         AACTCTATTATAGTTTGCCTGCAGCAAAC-GTATCTGTCACTCATTATAATCCTTCATCT
MHV         AGCTCTATTATAGTCTTGCAAAAAATAAT-GTCACTGTCAATAACCATAACCCGTCCTCT
```

```
RtCoV      AGCTCTATTACAGTCTTGCACAAGATAAT-GTCACTGTCATTAACCACAACCCATCCTCC
IBV        AATAGTAGTTTAGTTAAGCAGAAGTTTATTGTCTATCGTGAAAATAGTGTTAATACTACT
                       *                         *    **

CcoV       TATT-GTAACAGTCAC--ATTAATAACATCAAATGTTCTCAACTTACTG----CTAATTT
FcoV       TATT-GTAACAGTCAC--ATTAATAACATTAAATGTTCTCAACTTACTG----CTAATTT
TGE        TATT-GTAATAGTCAC--GTTAATAACATTAAATGCTCTCAAATTACTG----CTAATTT
PRCoV      TATT-GTAATAGTTAT--GTTAATAACATTAAATGCTCTCAACTTACTG----CTAATTT
HCoVOC43   TATT-GCAACTCTGTT--ATTAACAGACTGAGATGTGACCAGTTGTCCT----TTGATGT
PEDV       TATT-GTGATGATCCT--GTTAGCCAACTCAAGTGTTCTCAGGTTGCTT----TTGACCT
SARSUrba   TGTT-ATTGCTGATTATAATT------ATAAATTGCCAGATGATTTCAT------GG---
SARSTor2   TGTT-ATTGCTGATTATAATT------ATAAATTGCCAGATGATTTCAT------GG---
BcoV       TGGA-ATAGGAGATTTGGTTTTACAGAACAATTTGTTTTTAAGCCTCAACCTGTAGGTGT
HEV        TGGA-ATAGAAGGTATGGGTTT----AATAATCAGAGTTTTGGTTCCAG-----AGG---
MHV        TGGA-ACAGGCGTTATGGGTTC----AATGATGTGGCTACATTTGGAAC-----TGG---
RtCoV      TGGA-ATAGGCGTTATGGATTT----AATGACGTGGCTACATTTCATAG-----TGG---
IBV        TGTACGTTACACAATTTCATTTTT--CATAATGAGACTGGCGCCAACCC-----------
           *                **          *    *

CcoV       GCAAAATGGTTTTTACCCTGTTG---CTTCAAGTGAAGTTGGTCTTGTCAATAAGAGTGT
FcoV       GAATAATGGATTTTATCCTGTTG---CTTCAAGTGAAGTAGGTTTCGTTAATAAGAGTGT
TGE        GAATAATGGATTTTATCCTGTTT---CTTCAAGTGAAGTTGGTCTTGTCAATAAGAGTGT
PRCoV      GAATAATGGATTTTATCCTGTTT---CTTCAAGTGAAGTTGGTTCTGTCAATAAGAGTGT
HCoVOC43   ACCAGATGGTTTTTATTCTACAA---GCCCTATTCAATCCGTTGAGCTACCTGTGTCTAT
PEDV       TGACGATGGTTTTTACCCCATCT---CTTCTAGA-AACCTTCTGAGTCACGAACAGCCAA
SARSUrba   --------GTTGTGTCCTTGCTTGGAATACTAGGAACATTGATGCTACTTCAACTGGTAA
SARSTor2   --------GTTGTGTCCTTGCTTGGAATACTAGGAACATTGATGCTACTTCAACTGGTAA
BcoV       TTTTACTCATCATGATGTTGTTT---ATGCACAACATTGTTTTAAAGCTCCCAAAAATTT
HEV        ------CCTTCATGATGCTGTTT---ATTCACAGCAATGTTTTAATACACCTAACACATA
MHV        ------TAAACATGACGTTGCTT---ATGCTGAGGCTTGTTTTACCGTGGGAGCATCATA
RtCoV      ------TGAACATGACGTTGCTT---ATGCAGAGGCATGTTTCACTGTTGGAGCTTCATA
IBV        ------TAATCCTAGTGGTGTTC---AGAATATTCAAACTTACCAAACAAAAACAGCTCA
                       *

CcoV       TGTGTTACTACCTAGTTTCTATTC---ACATACCAGTGTTAATATAACTATTGATCTTGG
FcoV       TGTGTTATTACCTAGCTTTTTCAC---ATACACCGCTGTCAATATAACCATTGATCTTGG
TGE        TGTGTTACTACCTAGCTTTTACAC---ACATACCATTGTTAACATAACTATTGGTCTTGG
PRCoV      TGTGTTACTACCTAGCTTTCTGAC---ACATACCATTGTTAACATAACTATTGGTCTTGG
HCoVOC43   TGTGTCGCTACCTGTTTATCATAA---ACATACGTTTATTGTGTTGTACGTTGACTTCAA
PEDV       TTTCTT-TTGTTACTTTGCCATCA---TTTAATGATCATTCTTTTGTTAAT--ATTACTG
SARSUrba   T-TATAATTATAAAT---ATAG--------------GTATCTTAGACATGGCAAGCTTAG
SARSTor2   T-TATAATTATAAAT---ATAG--------------GTATCTTAGACATGGCAAGCTTAG
BcoV       C-TGTCCGTGTAAATTGGATGG------GTCTTTGTGTGTAGGTAATGGTCCTGGTATAG
HEV        T-TGTCCTTGTAGA----ACAA------GTCA--ATGCATAGGTGGTG---CAGGCACAG
MHV        T-TGCCCTTGCGCGAACCCCAGCATAGTGTCGCCATGTACCACTGGAAAACCTAACTTTG
RtCoV      T-TGCCCTTGTGCGAAGCCCAGCACAGTCTATTCATGTGTCACAGGTAAACCTAAGTCTG
IBV        G-AGTGGTTATTATAATTTTAA------TTTTTCCTTTCTGAGTAGTTTTGTTTATAAGG
                   *

CcoV       TATGAAGCGTAGTG-TTACGGTCA--CCATAGCCTCACCATTAAGTAACATCACACTACC
FcoV       TATGAAGCTTAGTGGTTATGGTCAACCCATAGCCTCGACACTAAGTAACATCACACTACC
TGE        TATGAAGCGTAGTGGTTATGGTCAACCCATAGCCTCAACATTAAGTAACATCACACTACC
PRCoV      TATGAAGCGTAGTGGTTATGGTCAACCCATAGCCTCAACGCTAAGTAACATTACACTACC
HCoVOC43   ACCTCAGAGTGGCGGTGGCAAGTG--------------CTTTAACTGTTATCCTGCT---
PEDV       TCTCT------GCGGCTTTTGGTG--------------GTCTTAGTAGTGCCAATCT---
SARSUrba   GCCCTT-TGAGAGAGACATATCTAAT-----GTGCCTTTCT----------CCCCTGA--
SARSTor2   GCCCTT-TGAGAGAGACATATCTAAT-----GTGCCTTTCT----------CCCCTGA--
BcoV       ATGCTGGTTATAAAAATAGTGGTATAGGCACTTGTCCTGCA--GGTACTAATTATTTAAC
HEV        GAACTTGTCCTGTAGGCACCACTGTGCGCAAGTGTTTTGCT--G----CAGTTACAAAA-
MHV        CCAATTGCCCTACAGGCACCTCGAATCGTGAGTGCACTGTTATGCCATTGGCTAATAAT-
RtCoV      CTAATTGCCCAACAGGTACCTCGAATCGTGAGTGTAATGTTCAGGCTTCAGGTTTTAA--
IBV        AGTCTAATTTTATGTATGGATCTTAT-----------CACCCAAGTTGTAAATTTAGAC-
```

```
CcoV        AATGCAGGATAATAACATAGACGTGTACTGTATTCGTTCTAACCAATTCTCAGTTTATGT
FcoV        AATGCAGGATAACAATACTGATGTGTACTGTATTCGTTCTAACCAATTCTCAGTTTATGT
TGE         AATGCAGGATCACAACACCGATGTGTACTGTATTCGTTCTGACCAATTTTCAGTTTATGT
PRCoV       AATGCAGGATAACAACAACGATGTGTACTGTGTTCGTTCTGACCAATTTTCAGTTTATGT
HCoVOC43    --GGTGTTAATATTACACTGGCCAATTTT--AATGAAACTAAAGGGCCTT---TGTGTGT
PEDV        --CGT-TGCATCTGACACT----ACTATC--AATGGGTTTA---GTTCTT---TCTGTGT
SARSUrba    ------------TGGCAAACCTTGCACCCCACCTGCTCTTA---ATTGT------TATTG
SARSTor2    ------------TGGCAAACCTTGCACCCCACCTGCTCTTA---ATTGT------TATTG
BcoV        TTGCCATAATGCTGCCCAATGTGATTGTTTGTGCACTCCCG---ACCCCATTACATCTAA
HEV         ----------GCTACTAAGTGTACTTGCTGGTGTCAACCAG---ATCCTTCCACATATAA
MHV         ----------CAATTTAAGTGTGATTGCACTTGTAACCCTA---GTCC-------TCTAA
RtCoV       ------------GTCTAAGTGCGATTGCACATGTAACCCTA---GTCC-------TCTAA
IBV         ------------TAGAAACTATTAATAATGGCTTGTGGTTTA--ATTC------ACTTTC
                                                                       *

CcoV        TCATTCCACTTGCAAAAGTTCTTTATGGGATAACAATTTTAATTCAGCATGTACCGACGT
FcoV        TCATTCCACTTGCAAAAGTTCTTTATGGGACAATATTTTTAATCAAGACTGCACGGATGT
TGE         TCATTCTACTTGCAAAAGTGCTTTATGGGACAATATTTTTAAGCGAAACTGCACGGACGT
PRCoV       TCATTCTACTTGCAAAAGTGTTTTATGGGACAATGTTTTTAAGCGAAACTGCACGGACGT
HCoVOC43    TGACACATC-----ACACTTCACTACCAAATACGTTGCT-------GTTTATGCCAATGT
PEDV        TGACACTAG-----ACAATTTACCATTACACTGTTTTAT-------AATGTTACAAACAG
SARSUrba    GCCATTAAATGATTATG---GTTTTTACAC------CACTACTGGCATTGGCTACCAACC
SARSTor2    GCCATTAAATGATTATG---GTTTTTACAC------CACTACTGGCATTGGCTACCAACC
BcoV        ATCTACAGGGCCTTACAAGTGCCCCCAAACTAAATACTTAGTTGGCATAGGTGAGCACTG
HEV         AGGTGTAAACGCCTGGACTTGTCCGCAATCTAAAGTTTCTATACAACCAGGTCAGCATTG
MHV         CCACCTATGATCTTAGA--TGTCTCCAAGCAAGAAGCATGCTTGGCGTAGGTGATCATTG
RtCoV       CCACCTATGATCCTAGA--TGTCTTCAAGCGCGGAGCATGCTTGGCGTAGGTGATCATTG
IBV         AGTTTCAATTGCTTACGGTCCTCTTCAAGGTGGTTGCAA----GCAATCTGTCTTTAAAG
                                                                      *

CcoV        TT-TAGACGCCACAGCTGTTATAAAAACTGGTACTTGTC---CTTTCTCATTTGATAAAT
FcoV        TT-TAGAGGCTACAGCTGTTATAAAAACTGGTACTTGTC---CTTTCTCATTTGATAAAT
TGE         TT-TAGATGCCACAGCTGTTATAAAAACTGGTACTTGTC---CTTTCTCATTTGATAAAT
PRCoV       TT-TAGATGCCACAGCTGTTATAAAAACTGGTACTTGTC---CTTTCTCATTTGATAAAT
HCoVOC43    TGGTAGGTGGAGTGCTAGTATTA-ACACGGGAAATTGCC---CTTTTTCTTTTGGCAAAG
PEDV        TTAT-GGTTATGTGTCTAAATCACAGGATAGTAATTGTC---CTTTCACCTTGCAATCTG
SARSUrba    TT-ACAG------AGTTGTAGTACTTTCTTTTGA--------ACTTTTAAATGCACCGGC
SARSTor2    TT-ACAG------AGTTGTAGTACTTTCTTTTGA--------ACTTTTAAATGCACCGGC
BcoV        TT-CGGGTCTTGCTATTAAAAGTGATTATTGTGGAGGTA---ATCCTTGTACTTGCCAAC
HEV         CC-CTGGTTTGGGTCTTGTGGAGGATGATTGCTCTGGCA---ACCCTTGCACTTGTAAAC
MHV         TG-AAGGTCTAGGAGTTTTAGAAGATAAATGTGGTGGCAGCAACACCTGCAATTGTTCTG
RtCoV       TG-AAGGTCTAGGTATTTTAGAAGATAAATGTGGTGGCAGCAACATATGCAATTGTTCGG
IBV         GT--AGAGCAACTTGTTGTTATGCTTATTCATATGGAGG---------TCCTTCGCTGTG

CcoV        TGAATAATTACTTAACTTTTAACAAGTTCTGTTTGTCGTTGAATCCCGTTGGTGCCAACT
FcoV        TGAACAATTACTTGACTTTTAACAAGTTCTGTTTGTCGTTGAGTCCTGTTGGTGCTAATT
TGE         TGAACAATTACTTAACTTTTAACAAGTTCTGTTTGTCGTTGAGTCCTGTTGGTGCTAATT
PRCoV       TGAACAATTACTTAACTTTTAACAAGTTCTGTTTGTCGTTGAGTCCCGTTGGTGCTAATT
HCoVOC43    TTAATAACTTTGTTAAATTTGGCAGTGTATGTTTTTCGCTAAAGGATATACCCGGTGGTT
PEDV        TTAATGATTACCTGTCTTTTAGCAAATTTTGTGTTTCAACCAGCCTTTTGGCTGGTGCTT
SARSUrba    CACGG---TTTGTGGACCAAAAT-TATCCACTGACCTTATTAAGAACCAGTGTGTCAATT
SARSTor2    CACGG---TTTGTGGACCAAAAT-TATCCACTGACCTTATTAAGAACCAGTGTGTCAATT
BcoV        CACAAGCATTTTTGGGTTGGTCTGTTGACTCTTGTTTACAAGGGGATAGGTGTAATATTT
HEV         CACAGGCTTTCATAGGCTGGAGTTCAGAAACTTGTTTGCAAAATGGTAGGTGTAATATTT
MHV         CTCATGCCTTTGTTGGCTGGGCTAAGGATAGTTGCTTGGCTAATGGCCGCTGTCACATTT
RtCoV       CTGATGCCTTTGTTGGCTGGGCTATGGACAGCTGTCTATCTAATGCCCGCTGCCATATTT
IBV         TAAAGGTGTTTATTCAGGTGAGTTAGATCATAATTTTGAATGTGGACTGTTA-GTTTATG
                     *    *

CcoV        GTAAGTTAGATGTTGCCGCCCGTACAAGAACCAATGAGCAGGTTTTTGGAAGTT---TAT
FcoV        GCAAGTTTGATGTTGCTGCACGTACAAGAACCAATGAGCAGGTTGTTAGAAGTC---TAT
```

```
TGE        GTAAGTTTGATGTAGCTGCCCGTACAAGAACCAATGAGCAGGTTGTTAGAAGTT---TGT
PRCoV      GTAAGTTTGATGTAGCTGCCCGTACAAGAACCAATGATCAGGTTGTTAGAAGTT---TGT
HCoVOC43   GCGCAATGCCTATAGTGGCTAATTGGGCTTATAGTAAGTACTATACTATAGGCTCATTGT
PEDV       GTACCATAGATCTTTTTGGTTACCCTGCGTTCGGTAGTGGTGTTAAGTTGACGTCCCTTT
SARSUrba   TTAATTTTAATGGACTCACTGGTACTGGTGTGTTAACTCCTTCTTCAAAGAGAT---TTC
SARSTor2   TTAATTTTAATGGACTCACTGGTACTGGTGTGTTAACTCCTTCTTCAAAGAGAT---TTC
BcoV       TTGCTAATTTTATTTTTCATGATGTTAATAGTGGTACTACTTGTTCTACTGATT---TAC
HEV        TTGCTAATTTTATTCTGAATGATGTTAATAGCGGTACAACCTGTTCTACTGATT---TAC
MHV        TTAGTAATTTGATGTTAAATGGCATTAATAGTGGTACTACATGTTCCATGGATT---TGC
RtCoV      TTAGTAATTTGATGTTAAATGGCATTAATAGTGGTACTACATGTTCCACGGATT---TTC
IBV        TTACTAAGAGCGGTGGCTCTCGTATACAAACAGCCACTGAACCGCCAGTTATAA---CTC

CcoV       ATGTAATATATGAAGAAGGAGACAACATAGTGGGTGTACCGTCTGATAATAGTGGTTT-G
FcoV       ATGTAATATATGAAGAAGGAGACAACATAGTGGGTGTACCGTCTGATAATAGCGGTCT-G
TGE        ATGTAATATATGAAGAAGGAGACAACATAGTGGGTGTACCGTCTGATAATAGTGGTGT-G
PRCoV      ATGTAATATATGAAGAAGGAGACAGCATAGTTGGTGTACCGTCTGACAATAGTGGTTT-G
HCoVOC43   ATGTTTCTTGGAGTGATGGTGATGGAATTACTGGCGTCCCACAACCTGTTGAGGGTGTTA
PEDV       ATTTTCAATTCACAAAAGGTGAGTTGATTACTGGCACGCCTAAACCACTTGAAGGTATCA
SARSUrba   AACCATTT--CAACAATTTGGCCG-TGATGTTTCTG----ATTTCACTGATTCCGTTCGA
SARSTor2   AACCATTT--CAACAATTTGGCCG-TGATGTTTCTG----ATTTCACTGATTCCGTTCGA
BcoV       AAAAATCAAACACAGACATAATTCTTGGTGTTTGTGTTAATTATGATCTTTATGGTATTA
HEV        AACAGGGTAATACTATTATTACTACTGATGTTTGTGTTAATTATGACCTATATGGCATTA
MHV        AATTGCCTAATACTGAAGTGGTCACTGGCGTCTGCGTCAAATATGACCTCTACGGTATAA
RtCoV      AATTGCCTAATACGGAAGTGGTCACTGGCGTTTGTGTCAAGTATGACCTCTACGGTAGTA
IBV        AAAACAATTATAATAATATTACTTTAAATACTTGTGTTGATTATAATATATATGGCAGAA
           *                                                         *

CcoV       CACGATTTGTCAGTGTTGCACTTAGACTCTTGT-ACAGATTACAATATATATGGTAGAAC
FcoV       CACGATTTGTCTGTGCTACACCTAGACTCCTGT-ACAGATTACAATATATATGGTAGAAC
TGE        CACGATTTGTCAGTGCTACACCTAGATTCCTGC-ACAGATTACAATATATATGGTAGAAC
PRCoV      CACGATTTGTCAGTGCTACACCTAGATTCGTGC-ACAGATTACAATATATATGGTAGAAC
HCoVOC43   GTTCCTTTATGAATGTTACAT-TGGACAAATGT-ACTAAATATAATATTTATGATGTATC
PEDV       CAGACGTTTCTTTTATGACTC-TGGATGTGTGT-ACCAAGTATACTATCTATGGCTTTAA
SARSUrba   GATCCTAAAACATCT-----G--AAAT-----------ATTA-GACATTTCACCTTGCTC
SARSTor2   GATCCTAAAACATCT-----G--AAAT-----------ATTA-GACATTTCACCTTGCGC
BcoV       CAGGCCAAGGTATTTTTGTTG--AGGTTAATGCGACTTATTATAATAGTTGGCAGAACCT
HEV        CAGGCCAGGGCATACTTATAG--AAGTTAATGCCACTTATTATAATAGTTGGCAGAATCT
MHV        CAGGCCAAGGTATTTTTAAGG--AGGTTAAGGCTGACTATTATCATAGTTGGCAAAACCT
RtCoV      CAGGCCAAGGTGTTTTTAAGG--AGGTTAAGGCTGATTATTACAATAGTTGGCAGAACCT
IBV        CTGGCCAAGGTTTTATT--------ACTAATGTGACCGACTCAGCTGTTAGTTATAATTA
                                                  * *

CcoV       TGGTGTTGGTATTATTAGAAAAACTAACAGCACACTACTTAGTGGCTTATATT-ACACAT
FcoV       TGGTGTTGGTATTATTAGACGAACTAACAGTACGCTACTTAGTGGCTTATATT-ACACAT
TGE        TGGTGTTGGTATTATTAGACAAACTAACAGGACGCTACTTAGTGGCTTATATT-ACACAT
PRCoV      TGGTGTTGGTATTATTAGACAAACTAACAGGACGATACTTAGTGGCTTATATT-ACACAT
HCoVOC43   TGGTGTGGGTGTTATTCGCGTTAGCAATGACACCTTTCTTAATGGAATTACGT-ACACAT
PEDV       AGGTGAGGGTATTATTACCCTTACAAATTCTAGCATTTTGGCAGGTGTTTATT-ATACAT
SARSUrba   TTTTGGGGGTGTAAGTG-TAATTACACCTGGAACAAATGCTTCATCTGAAGTT-GCTGTT
SARSTor2   TTTTGGGGGTGTAAGTG-TAATTACACCTGGAACAAATGCTTCATCTGAAGTT-GCTGTT
BcoV       TTTATATGATTCTAATGGTAATCTCTATGGTTTTAGAGACTACTTAACAAACA-GAACTT
HEV        TCTTTATGATTCTAGTGGTAATCTCTATGGCTTTAGAGATTATTTATCAAATA-GAACTT
MHV        CTTATATGATGTTAATGGCAACTTAATCGGATTTCGCGATTTTGTTGCTAATA-AGAGTT
RtCoV      CTTATATGATGTTAATGGTAACTTAAATGGTTTCCGTGACATTGTTACCAATA-AGACTT
IBV        TCTAGCAGACGCAGGT-------TTGGCTATTTTAGATACATCTGGTTCCATAGACATCT
                *        *                                            *

CcoV       CACTATCAGGTGATTTGTTAGGTTTTAAAAAATGTTAGTGATGGTGTTGTCTACTCTGTAA
FcoV       CACTATCAGGTGATTTGTTAGGCTTTAAAAAATGTTAGTGATGGTGTCATTTATTCTGTGA
TGE        CACTATCAGGTGATTTGTTAGGTTTTAAAAAATGTTAGTGATGGTGTCATCTACTCTGTAA
PRCoV      CACTATCTGGTGATTTGTTAGGTTTTACAAATGTTAGTGATGGTGTTATCTACTCTGTAA
HCoVOC43   CAACTTCAGGTAACCTTCTGGGTTTTAAAGATGTTACTAAGGGCACCATCTACTCTATCA
```

```
PEDV        CTGATTCTGGACAGTTGTTAGCCTTTAAGAATGTCACTAGTGGTGCTGTTTATTCTGTCA
SARSUrba    CTATATCAAGATGTTA--ACTGCACTGATGTTTCTACAGCAATTCATGCAGATCAACTCA
SARSTor2    CTATATCAAGATGTTA--ACTGCACTGATGTTTCTACAGCAATTCATGCAGATCAACTCA
BcoV        TTATGATTCGTAGTTGCTATAGCGGTCGTGTTTCAGCGGCCTTTCATGCTAACTCTTCCG
HEV         TTCTTATTCGTAGCTGCTATAGTGGAAGAGTTTCAGCAGTTTTTCATGCTAACTCATCTG
MHV         ATACTATTCGAAGTTGCTATAGTGGGCGGGTCTCGGCTGCATATCATCAAGATGCACCAG
RtCoV       ATTTATTAAGAAGTTGCTATAGTGGGCGCGTTTCGGCTGCATATCATCAAGATGCACCTG
IBV         TTGTTGTACAAGGTGAATATGGTCTTAATTATTATAAGGTTAACCCTTGCGAAGATGTCA
                                                               *

CcoV        CGCCATGTGATGTAAGTGCACAAGCTGCTGT-TATTGATGGTGCCATAGTTGGAGCTATG
FcoV        CGCCATGTGATGTAAGCGCACAAGCGGCTGT-TATTGATGGTGCCATAGTTGGAGCTATG
TGE         CGCCATGTGATGTAAGCGCACAAGCAGCTGT-TATTGATGGTACCATAGTTGGGGCTATC
PRCoV       CGCCATGTGATGTTAGCGCACAAGCAGCTAT-TATTGATGGTACCATAGTTGGGGCTATC
HCoVOC43    CTCCTTGTAACCCACCAGATCAGCTTGTTGTTTATCAGCAA-GCTGTTGTTGGTGCTATG
PEDV        CGCCATGTTCTTTTTCAGAGCAGGCTGC-ATATGTTAATGATGATATAGTGGGTGTTATT
SARSUrba    CACCA-GCTT------------------GGCGCATATATTCTACTGGAAACAATG-TATT
SARSTor2    CACCA-GCTT------------------GGCGCATATATTCTACTGGAAACAATG-TATT
BcoV        AACCA-GCATTGCTATTTCGGAATATTAAATGCAATTACGTTTTTAATAATACTC-TTTC
HEV         AACCA-GCTTTGATGTTTCGTAATCTTAAATGCAGCCACGTTTTTAATAATACCA-TTTT
MHV         AACCA-GCGCTACTATATCGCAATTTAAAATGTGACTATGTCTTTAACAACAACA-TATC
RtCoV       AACCA-GCGCTACTATATCGCAATTTAAAATGTGATTATGTGTTTAATAACAACA-TATC
IBV         -ACCAGCAGTTTGTAGTTTCTGGTGGTAAATTAGTAGGTATTCTTACTTCACGTAATGAG
              **                                                     *

CcoV        ACTTCCATTAATAGTGAACTGTTAGGT--CTAACTCATTGGACAACAACACCTAATTTTT
FcoV        ACTTCCATTAACAGTGAACTGTTAGGT--CTAACACATTGGACAACGACACCTAATTTTT
TGE         ACTTCCATTAACAGTGAACTGTTAGGT--CTAACACATTGGACAACAACACCTAATTTTT
PRCoV       ACTTCCATTAACAGTGAATTGTTAGGT--CTAACACATTGGACAACAACACCTAATTTTT
HCoVOC43    TTGTCTGAAAATT-----TTACTAGTT--ACGGC---TTTTCTAATGTTGTAGAACTGCC
PEDV        TCT------AGTT-----TGTCTAACT--CCACT---TTTAACAATACTAGGGAGTTGCC
SARSUrba    CC---------------------------AGACTCAAGCAGGCTGTCTTAT-AGGAGCTG
SARSTor2    CC---------------------------AGACTCAAGCAGGCTGTCTTAT-AGGAGCTG
BcoV        ACGACAGCTGCAACCTATTAACTATTTTGATAGTTATCTTGGTTGTGTTGT-CAATGCTG
HEV         AAGACAAATACAGCTTGTTAACTATTTTGATAGTTACCTTGGTTGTGTTGT-TAATGCTT
MHV         CCGTGAGGAGACACCACTTAACTATTTCGATAGTTATCTTGGTTGTGTTGT-TAATGCTG
RtCoV       CCGTGAGGAGACACCACTTAACTATTTTGATAGTTATTTGGGTTGTGTTAT-TAATGCTG
IBV         AC---------TGGTTCTCAGCTTCTT-GAGAACCAGTTTTACATCAAAATCACTAATGG

CcoV        ATTACTACTCCATATATAATTATACAAATGTGATGAATCGTGGCACGGCAATTGA---TA
FcoV        ATTACTACTCTATATATAATTACACAAGTGAGAGGACTCGTGGCACTGCAATTGACAGTA
TGE         ATTACTACTCTATATATAATTACACAAATGATAGGACTCGTGGCACTGCAATTGACAGTA
PRCoV       ATTACTACTCTATATATAATTACACAAATGATAAGACTCGTGGCACTCCAATTGGCAGTA
HCoVOC43    GAAATTTTTCTATGCGT-------CCAATGGCAC-----------TTATAATTGC-----
PEDV        TGGTTTCTTCTACCATT-------CTAATGACGG-----------CTCCAATTGT-----
SARSUrba    AGCAT------GTCGACACTT---CTTATGAGTGCGACATTCCTATTGGAGCTGGCATTT
SARSTor2    AGCAT------GTCGACACTT---CTTATGAGTGCGACATTCCTATTGGAGCTGGCATTT
BcoV        ATAATAGTACTTCTAGTGTTG---TTCAAACATGTGATCTCACAGTAGGTAGTGGTTACT
HEV         ATAATAATACAGCTAGTGCTG---TAAGTACTTGTGATTTAACCGTTGGTAGCGGCTATT
MHV         ACAACTCAACTGAAGAAGCTG---TTGACGCGTGTGATTTGCGTATGGGTAGTGGCTTT
RtCoV       ATAACTCAACTGAGCAGTCTG---TTGACGCGTGTGATTTGCGTATGGGTAGTGGGCTTT
IBV         AACACGTCGTTTTAGACGTTC-TATTACTGAAAATG---------TTGCAAATTGCCCTT

CcoV        ATGATATTGATTGTGAACCTATCATAACATATTCTAATATAGGTGTTTGTAAAAATGGAG
FcoV        ACGATGTTGATTGTGAACCTGTCATAACCTATTCTAATATAGGTGTTTGTAAAAATGGTG
TGE         ATGATGTTGATTGTGAACCTGTCATAACCTATTCTAACATAGGTGTTTGTAAAAATGGTG
PRCoV       ATGACGTTGATTGTGAACCTGTCATAACCTATTCTAACATAGGTGTTTGTAAAAATGGTG
HCoVOC43    ---ACA--------GACGCTGTTTTAACTTATTCTAGTTTTGGCGTTTGTGCAGATGGTT
PEDV        ---ACA--------GAGCCTGTGTTGGTGTATAGTAACATAGGTGTTTGTAAATCTGGCA
SARSUrba    GTGCTAGTTACCATACAGTTTCTTTATTACGTAG---------TACTAGCCAAAAATCTA
SARSTor2    GTGCTAGTTACCATACAGTTTCTTTATTACGTAG---------TACTAGCCAAAAATCTA
```

```
BcoV            GTGTGGATTACTCTACAAAAAGACGAAGTCGTAGAGCGATTACCACTGGTTATCGGTTTA
HEV             GTGTTGATTATGTTACAGCACTTAGATCACGTAGATCTTTTACTACAGGTTATCGCTTTA
MHV             GTGTCAACTATTCAACGTCTCACCGCGCTCGCAGCTCTGTCAGCACGGGTTATAAATTAA
RtCoV           GTGTCAACTATTCAATCGCTCACCGTGCGCGCAGGTCTGTCAGTACGGGTTATAAATTAA
IBV             ATGTTAGTTATGGTAAGTTTTGTATAAAACCTGATGGCT----CAATTGCCACAATAGTA
                                                       *

CcoV            CTTTGGTTTTTATT--AACGTCACACATTCTG-ATGGAGACGTTCAACCAATTAGCACCG
FcoV            CTTTGGTTTTTATT--AACGTCACACATTCTG-ACGGAGACGTGCAACCAATTAGCACTG
TGE             CTTTTGTTTTTATT--AACGTCACACATTCTG-ATGGAGACGTGCAACCAATTAGCACTG
PRCoV           CTTTGGTTTTTATT--AACGTCACACATTCTG-ATGGAGACGTGCAACCAATTAGCACTG
HCoVOC43        CTATAATTGCTGTTCAACCACGTAATGTTTCATATGATAGTGTTTCAGCTATCGTCACAG
PEDV            GTATTGGCTATGTTCCATCTCAGTATGGCC---AAGTCAAGATTGCACCCACGGTTACTG
SARSUrba        ------TTGTGGCTTATACTATGTCTTTAGGTGCTGATAGTTC--AATTGCTTACTCTAA
SARSTor2        ------TTGTGGCTTATACTATGTCTTTAGGTGCTGATAGTTC--AATTGCTTACTCTAA
BcoV            CTAATTTTGAGCCATTTACTGTTAATTCAGTAAATGATAGTTTAGAACCTGTAGGTGGTT
HEV             CTAATTTTGAACCATTTGCCGCTAATTTGGTAAATGATAGTATAGAACCTGTTGGTGGTT
MHV             CTACTTTTGAACCATTTACAGTCCGCATTGTCAATGATAGTGTTGAGTCTGTTGATGGGT
RtCoV           CTACTTTTGAACCATTTACAGTCAGCATTGTCAATGATAGTGTTGAGTCTGTTGGTGGAT
IBV             ------------CCAAAACAATTGGAACAGTTTGTGGCACCTTT--ATTTAATGTTACTG
                                  *                *

CcoV            ---GTAATGTCACGATACCCACAAATTTTACTATATCTGTGCAAGTCGAATATATTCAGG
FcoV            ---GTAATGTCACGATACCTACAAATTTTACTATATCTGTGCAAGTTGAATACATGCAGG
TGE             ---GTAATGTCACGATACCTACAAACTTTACCATATCCGTGCAAGTCGAATATATTCAGG
PRCoV           ---GTAACGTCACGATACCTACTAACTTTACTATATCCGTGCAAGTCGAATACATTCAGG
HCoVOC43        ---CTAATTTGTCTATACCTTCCAATTGGACCACTTCGGTCCAGGTTGAGTATTTACAAA
PEDV            ---GGAATATTAGTATTCCCACCAACTTTAGTATGAGTATTAGAACAGAATATTTACAGC
SARSUrba        TA-ACACCATTGCTATACCTACTAACTTTTCAATTAGCATTACTACAGAAGTAATGCCTG
SARSTor2        TA-ACACCATTGCTATACCTACTAACTTTTCAATTAGCATTACTACAGAAGTAATGCCTG
BcoV            TGTATGAAATTCAAATACCTTCAGAGTTTACTATAGGTAATATGGAGGAGTTTATTCAAA
HEV             TGTATGAAATACAGATACCTTCAGAGTTTACCATTGGTAATTTAGAAGAGTTCATTCAAA
MHV             TATATGAGCTGCAAATACCAACCAACTTTACTATAGCTAGCCATCAGGAGTTCGTTCAAA
RtCoV           TATATGAGATGCAAATACCTACTAATTTTACTATAGCTAGCCATCAGGAGTTCATTCAAA
IBV             ---AAAATGTGCTCATACCTAACAGTTTCAACTTAACTGTTACAGATGAGTACATACAAA
                         *    ** **       *                    **     * *

CcoV            TTTACACTACACCAGTTTCAATAGACTGTGCAAGATACGTTTGCAATGGTAACCCAAGAT
FcoV            TTTACACTACACCAGTATCAATAGATTGTGCAAGATACGTTTGTAATGGTAACCCTAGAT
TGE             TTTACACTACACCAGTGTCAATAGACTGTTCAAGATATGTTTGTAATGGTAACCCTAGGT
PRCoV           TTTACACTACACCAGTGTCAATAGACTGTTCAAGATATGTTTGTAATGGCAACCCTAGGT
HCoVOC43        TTACAAGTACACCTATCGTAGTTGATTGCTCCACTTATGTTTGCAATGGTAATGTGCGCT
PEDV            TTTACAACACGCCTGTTAGTGTTGATTGTGCTACATATGTTTGTAATGGTAACTCTCGTT
SARSUrba        TTTCTATGGCTAAAACCTCCGTAGATTGTAATATGTACATCTGCGGAGATTCTACTGAAT
SARSTor2        TTTCTATGGCTAAAACCTCCGTAGATTGTAATATGTACATCTGCGGAGATTCTACTGAAT
BcoV            CAAGCTCTCCTAAAGTTACTATTGATTGTTCTGCTTTTGTCTGTGGTGATTATGCAGCAT
HEV             CGAGATCCCCTAAGGTTACTATAGACTGTGCTACATTTGTTTGTGGTGACTATGCAGCAT
MHV             CGAGGTCTCCAAAGGTTACTATAGACTGTGCTGCATTTGTCTGTGGTGGCCACACAGCAT
RtCoV           CGAGGTCTCCGAAGGTTACTATAGATTGTGCTGCATTTGTCTGTGGTGATTATACAGCGT
IBV             CGCGTATGGATAAGGTCCAAATTAATTGCCTGCAGTATGTTTGTGGCAGTTCTCTGGATT
                                     *  * **       *   * **                *

CcoV            GCAATAAGTTATTAACACAATACGTTTCTGCATGTCAAACTATTGAGCAAGCGCTTGCAA
FcoV            GTAACAAATTGTTAACACAATATGTGTCTGCATGTCAAACTATTGAACAAGCACTTGCAA
TGE             GTAACAAATTGTTAACACAATACGTTTCTGCATGTCAAACTATTGAGCAAGCACTTGCAA
PRCoV           GTAACAAACTGTTAACACAATACGTTTCTGCATGTCAAACTATTGAGCAAGCACTTGCAA
HCoVOC43        GTGTTGAATTGCTTAAGCAGTATACTTCTGCTTGTAAAACTATTGAAGACGCCTTAAGAA
PEDV            GTAAACAATTACTCACCCAGTACACTGCAGCATGTAAGACCATAGAGTCAGCATTACAAC
SARSUrba        GTGCTAATTTGCTTCTCCAATATGGTAGCTTTTGCACACAACTAAATCGTGCACTCTCAG
SARSTor2        GTGCTAATTTGCTTCTCCAATATGGTAGCTTTTGCACACAACTAAATCGTGCACTCTCAG
BcoV            GTAAATCACAGTTGGTTGAATATGGTAGCTTCTGTGACAATATTAATGCTATACTCACAG
HEV             GTAGACAACAGTTAGCTGAGTATGGTAGTTTTTGTGAGAACATTAATGCTATACTCACAG
MHV             GCCGTCAGCAGTTGGTTGAGTACGGCTCATTCTGTGATAATATTAATGCCATTCTTGGCG
```

```
RtCoV       GTAGACAACAGTTGGTTGATTATGGCTCTTTTTGTGATAATATTAATGCCATTCTTGGCG
IBV         GTAGAAAGTTGTTTCAACAATATGGGCCTGTTTGCGACAACATATTGTCTGTAGTAAATA
            *           *     * **          **        *           *

CcoV        TGGGTGCCAG---ACTTGAAAACATGGAGATTGATTCCATGTTATTTGTTTCGGAAAATG
FcoV        TGGGTGCCAG---ACTTGAAAACATGGAGGTTGATTCCATGTTGTTTGTCTCGGAAAATG
TGE         TGGGTGCCAG---ACTTGAAAACATGGAGGTTGATTCCATGTTGTTTGTTTCTGAAAATG
PRCoV       TGGGTGCCAG---ACTTGAAAACATGGAAGTTGATTCCATGTTATTTGTTTCTGAAAATG
HCoVOC43    ATAGCGCCAG---GCTGGAGTCTGCAGATGTTAGTGAGATGCTCACTTTGACAAGAAAG
PEDV        TCAGCGCTAG---GCTTGAGTCTGTTGAAGTTAACTCTATGCTTACCATTTCTGAAGAGG
SARSUrba    GTATTG-----CTGCTGAACAGGATCGCAACACACGTGAAGTGTTCGCTCAAGTCAAACA
SARSTor2    GTATTG-----CTGCTGAACAGGATCGCAACACACGTGAAGTGTTCGCTCAAGTCAAACA
BcoV        AAGTAAATGAACTACTTGACACTACACAGTTGCAAGT-AGCTAATAGTTTAATGAATGGT
HEV         AAGTAAATGAACTACTTGACACTACACAGTTGCAAGT-AGCTAATAGTTTAATGAATGGA
MHV         AGGTAAATAACCTCATAGATACTATGCAACTTCAAGT-TGCAAGTGCTTTAATCCAAGGT
RtCoV       AGGTGAATAACCTCATAGATACTATGCAATTACAAGT-TGCTAGTGCTCTGATCCAAGGT
IBV         GTGTTGGTCA---AAAAGAAGATATGGAACTTTTGAATTTCTATTCTTCTACTAAACCGG
                              *

CcoV        CCCTTA-AATTGGCATCTGTTGAAGCATTCAATAGTACGGAAAATTTAGACCCTATTTAT
FcoV        CCCTTA-AATTGGCATCTGTTGAGGCGTTCAATAGTACAGAAAATTTAGATCCTATTTAC
TGE         CCCTTA-AATTGGCATCTGTTGAAGCATTCAATAGTTCAGAAACTTTAGACCCTATTTAC
PRCoV       CCCTTA-AATTGGCTTCTGTCGAAGCATTCAATAGTTCAGAAACTTTAGATCCTATTTAC
HCoVOC43    CGTTTACACTT-GCTAATGTTAGT------AGTTTT---GGTGACTACAACCTTAGC---
PEDV        C-TTTACAGTTAGCTACCATCAGTTCGTTTAATGGT---GATGGATATAACTTTACT---
SARSUrba    AATGTACAAAACCCCAACTTTGAAA-------------TATTTTGGTGGTTTTAATT--
SARSTor2    AATGTACAAAACCCCAACTTTGAAA-------------TATTTTGGTGGTTTTAATT--
BcoV        GTCACTCTTAGCACTAAGCTTAAAGATGGCGTTAATTTCAATGTAGACGACATCAATT--
HEV         GTCACCCTTAGTACCAAGATTAAGGATGGCATTAATTTCAATGTTGACGATATCAACT--
MHV         GTCACGTTAAGCTCACGCTTATCGGATGGCATTGGTGGTCAAATAGATGATATTAATT--
RtCoV       GTCACGCTAAGTTCACGCTTGGCAGATGGCATCTCAGGTCAGATTGATGATATTAATT--
IBV         CTGGTTTTAATACACCAGTTCTTAG-------TAATGTTAGCACTGGTGAGTTTAATA--
                               *                                  *

CcoV        AAAGAATGGCCTAACATTGGTGGTTCTTGGCTAGGAGGTTTAAAAGATATATTGCCATCT
FcoV        AAAGAATGGCCTAGCATAGGTGGTTCTTGGCTAGGAGGTCTAAAAGATATACTACCGTCC
TGE         AAAGAATGGCCTAATATAGGTGGTTCTTGGCTAGAAGGTCTAAAATACATACTTCCGTCC
PRCoV       AAAGAATGGCCTAATATAGGTGGCTTTTGGCTAGAAGGTCTAAAATACATACTTCCGTCC
HCoVOC43    ----AGCGTCATA-----CCTAGCTTG--------------------------CCCACA
PEDV        ----AATGTGCTG-----GGTGCTTCCGTGTACGA------------------TCCTGCA
SARSUrba    ----TTTCACAAATATTACCTGACCCT--------------------CTAAAGCCAA---
SARSTor2    ----TTTCACAAATATTACCTGACCCT--------------------CTAAAGCCAA---
BcoV        ----TTTCCCCTGTATTAGGTTGTTTAGGAAGCGC------------TTGTAATAAAGTT
HEV         ----TCTCCCCTGTATTAGGTTGTTTAGGAAGCGA------------ATGTAATAGAGCT
MHV         ----TTAGTCCTCTGCTTGGTTGTTTAGGTTCTGA------------CTGTGGCGAAGTT
RtCoV       ----TTAGTCCTCTTCTAGGTTGCCTTGGCTCAGA------------TTGTAGCGAAGGC
IBV         ----TTTCTCTTCTGTTAACAAATCCT--------------------------AGTAGT

CcoV        CATAATAGCAAACGTAAGTACCGCTCGGCTATAGAAGACTTGCTTTTTGATAAGGTTGTA
FcoV        CATAATAGCAAACGTAAGTATGGTTCTGCTATAGAAGATTTGCTTTTTGATAAAGTTGTA
TGE         CATAATAGCAAACGTAAGTATCGTTCAGCTATAGAGGACTTGCTTTTTGATAAGGTTGTA
PRCoV       GATAATAGCAAACGTAAGTATCGTTCAGCTATAGAGGACTTGCTTTTTTCTAAGGTTGTA
HCoVOC43    AGTGGTAGTAGAGTGGCTGGTCGCAGTGCCATAGAAGACATACTTTTTAGCAAACTTGTT
PEDV        AGTGGCAGGGTGGTACAAAAAAGGTCTGTTATTGAAGACTTGCTTTTTAATAAAGTGGTT
SARSUrba    -CTAAGA---------------GGTCTTTTATTGAGGACTTGCTCTTTAATAAGGTGACA
SARSTor2    -CTAAGA---------------GGTCTTTTATTGAGGACTTGCTCTTTAATAAGGTGACA
BcoV        TCCAGCA-----------G----ATCTGCTATAGAGGATTTACTTTTTTCTAAAGTAAAG
HEV         TCCACTA-----------G----ATCTGCTATAGAGGATTTACTTTTTGATAAAGTAAAA
MHV         ACCATGGCAGCTCAAACCGGACGATCTGCTATAGAGGATGTATTATTTGACAAAGTCAAA
RtCoV       ACCAAGGCAGCGCAA---GGGCGATCTGCTATAGAGGATGTATTATTTGATAAGGTCAAA
IBV         CGTAGAA------------AGCGTTCTCTTATTGAAGACCTTCTATTTACAAGCGTTGAA
                                          ** ** **  *  * ***    *   *
```

```
CcoV       ACATCTGGCTTAGGTACAGTTGACGAAGATTACAAACGTTCTGCAGGTGGTTATGACA--
FcoV       ACATCTGGTTTAGGTACAGTTGATGAAGATTATAAACGTTGTACTGGTGGTTACGACA--
TGE        ACATCTGGTTTAGGTACAGTTGATGAAGATTATAAACGTTGTACAGGTGGTTATGACA--
PRCoV      ACATCTGGTTTAGGTACAGTTGATGAAGATTACAAACGTTGTACAGGTGGTTATGACA--
HCoVOC43   ACTTCTGGACTTGGCACTGTGGACGCAGACTACAAAAAGTGCACTAAGGGTCTTTCCA--
PEDV       ACTAATGGCCTTGGTACTGTTGATGAAGACTATAAGCGCTGTTCTAATGGTCGCTCTG--
SARSUrba   .CTCGCTGATGCTGGCTTCATGAA---GCAATATGGCGAATGCCTAGGTGATATTAATG--
SARSTor2   CTCGCTGATGCTGGCTTCATGAA---GCAATATGGCGAATGCCTAGGTGATATTAATG--
BcoV       TTATCTGATGTCGGTTTCGTTGA---GGCTTATAATAATTGTACTGGAGGTGCCGAAA--
HEV        TTGTCTGATGTCGGCTTTGTACA---GGCCTATAATAACTGCACTGGAGGTGCCGAAA--
MHV        CTCTCTGATGTTGGCTTTGTCGA---AGCATATAACAATTGCACTGGAGGCCAAGAAG--
RtCoV      CTCTCTGATGTTGGCTTTGTCGA---ATCATATAATAATTGCACTGGAGGTCAAGAAG--
IBV        TCTGTTGGACTACCAACAAATGA---CGCATATAAAAATTGCACTGCAGGACCTTTAGGC
                **                *        **        *         *

CcoV       ----TAGCTGACTTAGTGTGTGCACGATATTACAATGGCATCATGGTGCTACCTGGTGTA
FcoV       ----TAGCAGACTTGGTGTGTGCTCAATATTACAATGGCATCATGGTTCTACCAGGTGTA
TGE        ----TAGCTGACTTAGTATGTGCTCAATACTATAATGGCATCATGGTGCTACCTGGTGTG
PRCoV      ----TAGCTGACTTAGTATGTGCTCAATACTATAATGGCATTATGGTGCTACCTGGTGTG
HCoVOC43   ----TTGCTGACTTGGCTTGTGCTCAATATTATAATGGCATTATGGTTTTGCCTGGCGTC
PEDV       ----TGGCTGATCTAGTCTGTGCGCAGTATTACTCTGGTGTCATGGTACTACCTGGCGTT
SARSUrba   ----CTAGAGATCTCATTTGTGCGCAGAAGTTCAATGGACTTACAGTGTTGCCACCTCTG
SARSTor2   ----CTAGAGATCTCATTTGTGCGCAGAAGTTCAATGGACTTACAGTGTTGCCACCTCTG
BcoV       ----TTAGGGACCTCATTTGTGTGCAAAGTTATAATGGTATCAAAGTGTTGCCTCCACTG
HEV        ----TTAGGGATCTCATTTGTGTGCAAAGTTATAATGGTATCAAAGTGTTGCCTCCATTG
MHV        ----TTAGAGACCTACTTTGTGTGCAATCTTTTAATGGCATCAAAGTGCTACCGCCTGTG
RtCoV      ----TTAGAGACCTACTTTGTGTGCAATCTTTTAATGGCATTAAAGTGCTACCGCCTGTA
IBV        TTTTTAAGGACCTTGCGTGTGCTCGTGAATATAATGGTTTGCTTGTGTTGCCTCCTATC
                   **   *    ****  *      *     ***  *    **  * **     *

CcoV       GCTAATGATGACAAGATGACTATGTACACTGCATCTCTTACAGGTGGTATAACATTAGGT
FcoV       GCTAATGCTGACAAGATGACTATGTACACAGCATCACTTGCAGGTGGTATAACATTAGGT
TGE        GCTAATGCTGACAAAATGACTATGTACACAGCATCCCTTGCAGGTGGTATAACATTAGGT
PRCoV      GCTAATGCTGACAAAATGACTATGTACACAGCATCCCTCGCAGGTGGTATAACATTAGGT
HCoVOC43   GCTGATGCTGAACGAATGGCCATGTATACAGGTTCTTTAATTGGTGGAATTGCTTTAGGA
PEDV       GTTGACGCTGAGAAGCTTCACATGTACAGTGCGTCTCTCATAGGTGGTATGGCGCTAGGA
SARSUrba   CTCACTGATGATATGATTGCTGCCTACACTGCTGCTCTAGTTAGTGGTACTGCCACTGCT
SARSTor2   CTCACTGATGATATGATTGCTGCCTACACTGCTGCTCTAGTTAGTGGTACTGCCACTGCT
BcoV       CTCTCAGTAAATCAGATCAGTGGATACACTTTGGCTGCCACCTCTGCTAGTCTGTTTCCT
HEV        TTATCTGAAAATCAGATCAGTGGCTACACTTTGGCAGCCACCGCTGCTAGCTTATTCCCT
MHV        TTGTCTGAGAATCAAATTTCTGGTTATACAGCGGGAGCTACTGTATCTGCTATGTTCCC-
RtCoV      TTATCCGAGAGTCAAATCTCTGGTTATACAGCGGGAGCTACTGCATCTGCTATGTTCCCT
IBV        ATAACAGCAGAAATGCAAGCTTTGTATACTAGTTCTCTAGTAGCTTCTATGGCTTTTGGT
              *                 ** *

CcoV       GCACTTAGTGGTGGCGCAGTGGC---------TATACCTTTTGCAGTAGCAGTTCAGGCT
FcoV       GCACTTGGTGGTGGCGCCGTGGC---------TATACCTTTTGCAGTAGCAGTACAGGCT
TGE        GCACTTGGTGGAGGCGCCGTGGC---------TATACCTTTTGCAGTAGCAGTTCAGGCT
PRCoV      GCACTTGGTGGAGGCGCCGTGGC---------TATACCTTTTGCAGTAGCAGTTCAGGCT
HCoVOC43   GGTCTAACATCAG---CCGTTTC---------AATACCATTTTCATTAGCAATTCAGGCA
PEDV       GGTATAACTGCTG---CAGCGGC---------ATTGCCTTTTAGCTATGCTGTTCAAGCG
SARSUrba   GGATGGACATTTGGTGCTGGCGCTGCTCTTCAAATACCTTTTGCTATGCAAATGGCATAT
SARSTor2   GGATGGACATTTGGTGCTGGCGCTGCTCTTCAAATACCTTTTGCTATGCAAATGGCATAT
BcoV       CCTTTGTCAGCAGCAGTAGGTG------------TACCATTTTATTTAAATGTTCAGTAT
HEV        CCTTGGACAGCTGCAGCAGGTG------------TACCATTTTATTTAAATGTTCAGTAT
MHV        --ATGGTCTGCAGCTGCAGGTG------------TGCCATTTTCTTTAAGTGTTCAATAT
RtCoV      CCATGGTCTGCAGCTGCAGGTG------------TGCCATTTGCTTTAAGTGTTCAATAT
IBV        GGTATTACTGCAG---CTGGTGC---------TATACCTTTTGCCACACAACTGCAGGCT
                *     *                  *  **  ***          *

CcoV       AGACTTAATTATGTTGCTCTACAAACTGATGTATTGAACAAAAACCAACAAATCTTGGCT
FcoV       AGACTTAATTATGTTGCTCTACAAACTGATGTATTGAATAAAAACCAACAGATCCTGGCT
```

```
TGE          AGACTTAATTATGTTGCTCTACAAACTGATGTATTGAACAAAAACCAGCAGATTCTGGCT
PRCoV        AGACTTAATTATGTTGCTCTACAAACTGATGTATTGAACAAAAACCAGCAGATCCTGGCT
HCoVOC43     CGTTTAAATTATGTTGCATTGCAGACTGATGTTTTACAAGAAAATCAGAAAATTCTTGCT
PEDV         AGACTCAATTATCTTGCTTTACAGACGGATGTTCTACAGCGGAACCAGCAATTGCTTGCT
SARSUrba     AGGTTCAATGGCATTGGAGTTACCCAAAATGTTCTCTATGAGAACCAAAAACAAATCGCC
SARSTor2     AGGTTCAATGGCATTGGAGTTACCCAAAATGTTCTCTATGAGAACCAAAAACAAATCGCC
BcoV         CGTATTAATGGGATTGGTGTTACCATGGATGTGTTAAGTCAAAATCAAAAGCTTATTGCT
HEV          CGTATAAATGGGCTTGGCGTCACTATGGATGTGCTAAGTCAAAACCAAAAGCTTATTGCT
MHV          AGAATTAATGGTCTTGGTGTCACTATGAATGTTCTTAGTGAAAATCAGAAAATGATAGCA
RtCoV        AGAATTAATGGTCTTGGTGTCACTATGAATGTTCTTAGTGAAAACCAGAAAATGATAGCT
IBV          AGAATTAATCACTTGGGTATTACCCAGTCACTTTTGTTGAAGAATCAAGAAAAAATTGCT
              *  * ***    * *   *           *  *       ** **  *     * **

CcoV         AATGCTTTCAATCAAGCTATTGGTAACATTACACAGGCATTTGGTAAGGTTAATGACGCT
FcoV         AATGCTTTCAATCAAGCTATTGGTAACATTACACAGGCTTTTGGTAAGGTTAATGATGCT
TGE          AGTGCTTTCAATCAAGCTATTGGTAACATTACACAGTCATTTGGTAAGGTTAATGATGCT
PRCoV        AGTGCTTTTAATCAAGCTATTGGTAACATTACACAGTCATTTGGTAAGGTTAATGATGCT
HCoVOC43     GCATCTTTTAACAAAGCAATGACCAACATAGTAGATGCCTTTACTGGTGTTAATGATGCT
PEDV         GAGTCTTTTAACTCTGCTATTGGTAATATAACTTCAGCCTTTGAGAGTGTTAAAGAGGCT
SARSUrba     AACCAATTTAACAAGGCGATTAGTCAAAT-------------------------------
SARSTor2     AACCAATTTAACAAGGCGATTAGTCAAAT-------------------------------
BcoV         AATGCATTTAACAATGCTCTTGATGCTAT-------------------------------
HEV          AGTGCATTTAACAATGCTCTTGATGCTAT-------------------------------
MHV          AGTGCATTTAACAACGCGATAGGTGCTAT-------------------------------
RtCoV        AGTTCATTTAACAACGCGATAGGTGCTAT-------------------------------
IBV          GCTTCCTTTAATAAGGCCATTGGTCATAT-------------------------------
                   ** **    **  *       **

CcoV         ATACATCAAACATCAAAAGGTCTTGCTACTGTTGCTAAAGCATTGGCAAAGGTGCAAGAT
FcoV         ATACATCAAACATCACAAGGTCTTGCCACTGTTGCTAAAGCGTTGGCAAAAGTGCAAGAT
TGE          ATACATCAAACATCACGAGGTCTTGCTACTGTTGCTAAAGCATTGGCAAAAGTGCAAGAT
PRCoV        ATACATCAAACATCACGAGGTCTTACAACTGTTGCTAAAGCATTGGCAAAAGTGCAAGAT
HCoVOC43     ATTACACAAACTTCACAAGCCCTACAAACAGTTGCTACTGCACTTAACAAGATCCAGGAT
PEDV         ATTAGTCAAACTTCCAAGGGTTTGAACACTGTGGCTCATGCGCTTACTAAGGTTCAAGAG
SARSUrba     -----TCAAG------AATCACTTACAACAACATCAACTGCATTGGGCAAGCTGCAAGAC
SARSTor2     -----TCAAG------AATCACTTACAACAACATCAACTGCATTGGGCAAGCTGCAAGAC
BcoV         -----TCAGG------AAGGGTTTGATGCTACCAATTCTGCTTTAGTTAAAATTCAAGCT
HEV          -----CCAGG------AAGGGTTCGACGCAACCAATTCTGCTTTAGTTAAAATTCAGGCT
MHV          -----ACAGG------AAGGGTTTGCTGCAACCAATTCTGCCTTAGCAAAAATGCAGTTC
RtCoV        -----ACAGG------AAGGGTTCGATGCAACCAATTCTGCTTTAGCGAAAATTCAGTCC
IBV          -----GCAGG------AAGGTTTTAGAAGTACATCTCTAGCATTACAACAAATTCAAGAT
                   **              *                **  *     *  * **

CcoV         GTTGTTAACACGCAAGGTCAAGCTTTAAGCCACCTAACAGTACAATTGCAAAACAATTTT
FcoV         GTTGTCAACACACAAGGGCAAGCTTTAAGTCACCTTACAGTACAATTGCAAAATAATTTT
TGE          GTTGTCAACATACAAGGGCAAGCTTTAAGCCACCTAACAGTACAATTGCAAAATAATTTC
PRCoV        GTTGTCAACACACAAGGTCAAGCTTTAAGACACCTAACAGTACAATTGCAAAATAATTTC
HCoVOC43     GTTGTTAATCAACAAGGCAACTCATTGAACCATTTAACTTCTCAGTTGAGGCAGAATTTT
PEDV         GTTGTTAATTCGCAGGGTTCAGCTTTGAACCAACTTACCGTACAGCTGCAACACAACTTC
SARSUrba     GTTGTTAACCAGAATGCTCAAGCATTAAACACACTTGTTAAACAACTTAGCTCTAATTTT
SARSTor2     GTTGTTAACCAGAATGCTCAAGCATTAAACACACTTGTTAAACAACTTAGCTCTAATTTT
BcoV         GTTGTTAATGCAAATGCTGAAGCTCTTAATAACTTATTGCAACAACTCTCTAATAGATTT
HEV          GTTGTTAATGCAAATGCTGAAGCACTTAATAACTTATTGCAGCAACTCTCTAACAGATTT
MHV          GTTGTCAATGCAAATGCGGAAGCACTCAATAATTTATTAAACCAGCTTTCCAATAGGTTT
RtCoV        GTTGTCAACGCAAATGCAGAAGCACTCAATAACCTTTTGAATCAGCTTTCCAATAGGTTT
IBV          GTTGTTAGTAAACAGAGTGCTATTCTTACTGAGACTATGGCATCACTTAATAAAAATTTT
             ***** *      *           * *                  *       *  **

CcoV         CAAGCCATTAGCAGTTCTATTAGTGACATTTATAACAGGCTTGATGAATTGAGTGCTGAT
FcoV         CAAGCCATTAGTAGTTCTATTAGTGATATTTATAACAGGCTTGACGAACTGAGTGCTGAT
TGE          CAAGCCATTAGTAGTTCTATTAGTGACATTTATAATAGGCTTGACGAATTGAGTGCTGAT
PRCoV        CAAGCCATTAGTAGTTCTATTAGTGACATTTATAATAGGCTTGATGAATTGAGTGCTGAT
HCoVOC43     CAAGCTATCTCTAGCTCTATTCAGGCTATCTATGACAGACTTGACACTATTCAGGCTGAT
```

```
PEDV            CAAGCCATTTCTAGTTCTATTGATGACATTTATTCCCGACTGGACATTCTTTCAGCCGAT
SARSUrba        GGTGCAATTTCAAGTGTGCTAAATGATATCCTTTCGCGACTTGATAAAGTCGAGGCGGAG
SARSTor2        GGTGCAATTTCAAGTGTGCTAAATGATATCCTTTCGCGACTTGATAAAGTCGAGGCGGAG
BcoV            GGTGCTATAAGTTCTTCTTTACAAGAAATTCTATCTAGACTGGATGCTCTTGAAGCGCAA
HEV             GGTGCCATAAGTGCCTCTTTACAAGAAATTTTATCTCAGGCTCGATGCTCTTGAAGCGCAA
MHV             GGTGCAATTAGTGCTTCTTTACAAGAAATTCTATCTCGCCTAGATGCTCTTGAAGCTAAA
RtCoV           GGTGCAATTAGTGCTTCTTTACAGGAAATTCTATCTCGCCTCGATGCTCTTGAAGCGCAG
IBV             GGTGCTATTTCTTCTGTGATTCAAGAAATCTACCAGCAATTTGACGCCATACAAGCAAAT
                   ** **            *    *  **           * **      *    **  *

CcoV            GCACAAGTTGACAGGCTGATTACAGGACGACTTACAGCACTTAATGCATTTGTGTCTCAG
FcoV            GCACAAGTTGATAGGCTGATTACAGGTAGACTTACAGCACTTAATGCATTTGTGTCTCAG
TGE             GCACAAGTTGACAGGCTGATCACAGGAAGACTTACAGCACTTAATGCATTTGTGTCTCAG
PRCoV           GCACAAGTCGACAGGCTGATCACAGGAAGACTTACAGCACTTAATGCATTTGTGTCTCAG
HCoVOC43        CAACAAGTAGATAGGCTGATTACTGGTAGATTGGCTGCTTTGAATGTATTCGTTTCTCAT
PEDV            GTTCAGGTTGATCGTCTCATCACCGGCAGATTATCAGCACTTAATGCTTTTGTTGCCCAA
SARSUrba        GTACAAATTGACAGGTTAATTACAGGCAGACTTCAAAGCCTTCAAACCTATGTAACACAA
SARSTor2        GTACAAATTGACAGGTTAATTACAGGCAGACTTCAAAGCCTTCAAACCTATGTAACACAA
BcoV            GCTCAGATAGACAGACTTATTAATGGGCGTCTTACCGCTCTTAATGTTTATGTTTCTCAA
HEV             GCTCAGATAGACAGACTTATCAATGGGCGTCTCACCGCTCTTAATGCTTATGTTTCTCAG
MHV             GCTCAGATAGACCGTCTTATTAATGGCAGATTAACTGCACTTAATGCATATGTCTCTAAG
RtCoV           GCTCAGATAGACCGTCTTATTAATGGCAGATTAACTGCACTTAATGCATATGTCTCTAAG
IBV             GCTCAAGTGGATCGTCTTATAACTGGTAGATTGTCATCACTTTCTGTTTTAGCATCTGCT
                   **   * **   *  * ** *  **  *  *        *       *  *   *

CcoV            ACTTTAACCAGACAAGCAGAGGTTAGGGCTAGTAGACAACTTGCTAAAGACAAGGTTAAT
FcoV            ACTCTAACCAGACAAGCAGAGGTTAGGGCTAGTAGACAACTTGCCAAAGACAAGGTTAAT
TGE             ACTCTAACCAGACAAGCGGAGGTTAGGGCTAGTAGACAACTTGCCAAAGACAAGGTTAAT
PRCoV           ACTCTAACCAGACAAGCCGAGGTTAGGGCTAGTAGACAACTTGCTAAAGACAAGGTTAAT
HCoVOC43        ACATTGACTAAGTACACTGAAGTTCGTGCTTCCAGACAGCTTGCACAACAAAAAGTGAAT
PEDV            ACCCTCACTAAGTATACTGAGGTTCAGGCTAGCAGGAAGCTAGCACAGCAAAAGGTTAAT
SARSUrba        CAACTAATCAGGGCTGCTGAAATCAGGGCTTCTGCTAATCTTGCTGCTACTAAAATGTCT
SARSTor2        CAACTAATCAGGGCTGCTGAAATCAGGGCTTCTGCTAATCTTGCTGCTACTAAAATGTCT
BcoV            CAGCTTAGTGATTCTACACTAGTAAAATTTAGTGCAGCACAAGCTATGGAGAAGGTTAAT
HEV             CAGCTTAGTGATTCTACACTAGTAAAATTTAGTGCAGCACAAGCTATTGAGAAAGTTAAT
MHV             CAGCTGAGTGACATGACCCTTGTTAAGGTGAGTGCAGCCCAGGCTATAGAGAAAGTTAAT
RtCoV           CAGCTGAGCGACATGACCCTTATTAAGGTGAGTGCTGCCCAGGCTATAGAGAAAGTTAAT
IBV             AAGCAGGCGGAGTATATTAGAGTGTCACAACAGCGTGAGTTAGCTACTCAGAAAATTAAT
                                      *                    **        **  *   *

CcoV            GAATGCGTTAGGTCTCAATCCCAGAGATTTGGATTCTGTGGTA---ATGGTACACATTTG
FcoV            GAATGTGTTAGGTCTCAGTCTCAGAGATTCGGATTCTGTGGTA---ATGGTACACATTTG
TGE             GAATGCGTTAGGTCTCAGTCTCAGAGATTCGGATTCTGTGGTA---ATGGTACACATTTG
PRCoV           GAATGCGTTAGGTCTCAGTCTCAGAGATTCGGCTTCTGTGGTA---ATGGTACACATTTG
HCoVOC43        GAGTGTGTCAAATCCCAGTCTAAGCGTTATGGCTTCTGTGGAA---ATGGCACTCACATT
PEDV            GAGTGCGTCAAATCGCAATCTCAGCGTTACGGTTTTTGTGGTGGTGATGGCGAGCACATT
SARSUrba        GAGTGTGTTCTTGGACAATCAAAAAGAGTTGACTTTTGTGGAA---AGGGCTACCACCTT
SARSTor2        GAGTGTGTTCTTGGACAATCAAAAAGAGTTGACTTTTGTGGAA---AGGGCTACCACCTT
BcoV            GAATGTGTCAAAAGCCAATCATCTAGGATAAATTTTTGTGGTA---ATGGTAATCATATT
HEV             GAATGTGTTAAAAGCCAATCATCTAGGATAAATTTCTGTGGTA---ATGGTAATCATATT
MHV             GAGTGTGTTAAAAGCCAATCATCTAGGATAAATTTCTGTGGCA---ATGGCAATCATATA
RtCoV           GAGTGTGTTAAAAGCCAATCACCTAGGATAAATTTCTGTGGCA---ATGGCAATCATATA
IBV             GAGTGTGTTAAGTCACAGTCTATTAGGTACTCCTTTTGTGGTA---ATGGACGACATGTT
                ** ** **        ** **      *       ** *****     * **     **  *

CcoV            TTTTCACTTGCAAATGCGGCACCAAATGGCATGATTTTCTTTCACACAGTGCTATTACCA
FcoV            TTTTCACTAGCAAATGCAGCACCAAATGGCATGATTTTCTTTCATACAGTACTATTACCA
TGE             TTTTCACTCGCAAATGCAGCACCAAATGGCATGATTTTCTTTCACACAGTGCTATTACCA
PRCoV           TTTTCACTCGCAAATGCAGCACCAAATGGCATGATCTTCTTTCACACAGTGCTATTACCA
HCoVOC43        TTCTCAATTGTTAATGCTGCTCCTGAGGGGCTTGTTTTTCTCCACACTGTCTTGTTGCCG
PEDV            TTCTCTCTGGTACAGGCCGCACCTCAGGGCCTGCTGTTCTTACATACAGTACTTGTACCG
SARSUrba        ATGTCCTTCCCACAAGCAGCCCCGCATGGTGTTGTCTTCCTACATGTCACGTATGTGCCA
SARSTor2        ATGTCCTTCCCACAAGCAGCCCCGCATGGTGTTGTCTTCCTACATGTCACGTATGTGCCA
```

```
BcoV              ATATCATTAGTGCAGAATGCTCCATATGGTTTGTATTTATCCACTTTAGCTATGTCCCT
HEV               ATATCATTAGTACAGAATGCTCCATATGGTTTGTATTTATCCATTTTAGCTATGTCCCC
MHV               TTGTCATTAGTCCAGAATGCGCCTTATGGTTTATATTTATTCATTTCAGCTATGTGCCT
RtCoV             TTGTCATTAGTCCAGAATGCGCCTTACGGTTTATATTTATTCATTTCAGCTATGTGCCT
IBV               CTAACCATACCGCAAAATGCACCTAATGGTATAGTGTTTATACACTTTTCTTATACTCCA
                   *  *  *     *    ** **  * **  *    **  * **             **

CcoV              ACAGCTTATGAAACTGTGACGGCCTGGTCAGGTATTTGTGCGT---CAGATGGCAGTCGC
FcoV              ACAGCTTATGAAACTGTAACAGCTTGGTCAGGTATTTGTGCTT---CAGATGGCGATCGC
TGE               ACGGCTTATGAAACTGTGACTGCTTGGCCAGGTATTTGTGCTT---CAGATGGTGATCGC
PRCoV             ACGGCGTATGAAACTGTGACTGCTTGGTCAGGTATTTGTGCTT---TAGATGTTGATCGC
HCoVOC43          ACACAATATAAGGATGTTGAAGCGTGGTCTGGGTTGTGCGTTG---ATGGTACAAACGGT
PEDV              GGTGATTTTGTAAATGTTCTTGCCATCGCTGGCTTATGCGTTA---ATGGTGAAATTGCC
SARSUrba          TCCCAGGAGAGGAACTTCACCACAGCGCCAGCAATTTGTCATG---AAGGCAAAGCATAC
SARSTor2          TCCCAGGAGAGGAACTTCACCACAGCGCCAGCAATTTGTCATG---AAGGCAAAGCATAC
BcoV              ACTAAGTATGTCACTGCGAAGGTTAGTCCCGGTCTGTGCATTG---CTGGTGATAGAGGT
HEV               ACCAAGTATGTTACAGCAAAGGTTAGTCCTGGTTTGTGCATTG---CTGGCGATATAGGA
MHV               ACTTCCTTTACAACGGCAAATGTGAGTCCTGGGCTATGCATTT---CTGGTGATAGAGGA
RtCoV             ACATCCTTTACAACGGTAAATGTGAGTCCTGGACTATGCATTT---CTGGTGATAGAGGA
IBV               GATAGTTTTGTTAATGTTACTGCAATAGTGGGTTTTTGTGTAAAGCCAGCTAATGCTAGT
                                              *   * **          *

CcoV              ACTTTTGGACTTGTTGTTGAGGATGTCCAGCTGACGC-TATTTCGCAA-----TTTAGAT
FcoV              ACTTTCGGACTTGTCGTTAAAGATGTGCAGTTGACGT-TGTTTCGTAA-----TCTAGAT
TGE               ACTTTTGGACTTGTCGTTAAAGATGTCCAGTTGACTT-TGTTTCGTAA-----TCTAGAT
PRCoV             ACTTTTGGACTTGTCGTTAAAGATGTCCAGTTGACTT-TATTTCGTAA-----TCTAGAT
HCoVOC43          TATGTGTTGCGACAACCTAATCTTGCTCT--TTACAAAGAAGGCA---------ATTATT
PEDV              TTGACTCTACGTGAGCCTGGCTTAGTCTTGTTTACGCATGAACTTCAAACTTATACTGCG
SARSUrba          TTCCCT---------CGTGAAGGTGTTTTTGTGTTTAATG-------------GCACTT
SARSTor2          TTCCCT---------CGTGAAGGTGTTTTTGTGTTTAATG-------------GCACTT
BcoV              ATAGCC---------CCTAAGAGTGGTTATTTTGTTAATGTAA-----------ATAATA
HEV               ATATCG---------CCTAAGAGTGGTTATTTTATTAATGTAA-----------ATAATT
MHV               TTAGCA---------CCTAAAGCTGGATATTTTGTTCAAGATG-----------ATGGAG
RtCoV             TTAGCA---------CCTAAAGCTGGATATTTTGTTCAAGATC-----------ATGGAG
IBV               CAGTATGCAATAGTGCCCGCTAATGGTAGGGGTATTTTTATACAA---------GTTAAT
                                          *

CcoV              GAAAAATTTTATTTGACGCCCAGAACTATGTATCAGCCCAGAGTTGCAACTAGTTCTGAT
FcoV              GACAAGTTCTATTTGACCCCCAGAACTATGTATCAGCCTAGAGTTGCAACTAGTTCTGAT
TGE               GACAAGTTCTATTTGACCCCCAGAACTATGTATCAGCCTAGAGTTGCAACTAGTTCTGAC
PRCoV             GACAAGTTCTATTTGACACCCAGAACTATGTATCAGCCTAGAGTGGCAACTAGTTCTGAT
HCoVOC43          ATAGAAT-------CACATCTCGCATAATGTTTGAACCACGTATTCCTACCATGGCAGAT
PEDV              ACGGAATATTTTGTTTCATCGCGACGTATGTTTGAACCTAGAAAACCTACCGTTAGTGAT
SARSUrba          CTTGGTTTAT----TACACAGAGGAACTTCTTTTCTCCACAAATAATTACTACAGACAAT
SARSTor2          CTTGGTTTAT----TACACAGAGGAACTTCTTTTCTCCACAAATAATTACTACAGACAAT
BcoV              CTTGGATGTT----CACTGGTAGTGGTTATTACTACCCTGAACCCATAACTGGAAATAAT
HEV               CTTGGATGTT----CACTGGTAGTAGCTATTACTACCCTGAACCTATAACCCAAAATAAT
MHV               AGTGGAAGTT----CACAGGTAGTAATTATTATTACCCTGAACCCATTACAGATAAAAAT
RtCoV             AATGGAAGTT----CACAGGTAGCAATTATTACTACCCTGAATCCATTACAGATAAAAAC
IBV               GGTAGTTACTACATCACTGCACGAGATATGTATATGCCAAGAGCTATTACTGCAGGAGAT
                                  *     *       *     **          **        *

CcoV              TTTGTTCAAATAGAAGGCTGTGATGTGTTGTTTGTTAATGGAACTGTAATTGAATTGCCT
FcoV              TTTGTTCAAATTGAAGGGTGTGATGTGTTGTTTGTCAACGCGACTGTAATTGATTTGCCT
TGE               TTTGTTCAAATTGAAGGGTGCGATGTGCTGTTTGTTAATGCAACTGTAAGTGATTTGCCT
PRCoV             TTTGTTCAAATTGAAGGGTGCGATGTGCTGTTTGTTAATACAACTGTAAGTGATTTGCCT
HCoVOC43          TTTGTTCAAATTGAAAATTGCAATGTCACATTTGTTAACATTTCTCGCTCTGAGTTGCAA
PEDV              TTTGTTCAAATTGAGAGTTGTGTGGTCACCTATGTCAATCTGACTAGCGACCAGCTACCA
SARSUrba          ACATTTGTCTCAGGAAATTGTGATGTCGTTATTGGCATCATTAACAACACAGTTTATGAT
SARSTor2          ACATTTGTCTCAGGAAATTGTGATGTCGTTATTGGCATCATTAACAACACAGTTTATGAT
BcoV              GTTGTTGTTATGAGTACCTGTGCTGTTAACTATACTAAAGCGCCGGATGTAATGCTGAAC
HEV               GTTGTTGTGATGAGTACCTGTGCTGTTAATTATACTAAAGCACCGGATCTAATGCTGAAC
MHV               AGTGTCGTGATGAGTAGTTGCGCAGCAAACTACACAAAGGCACCTGAAGTTTTCTTGAAC
```

```
RtCoV       AGTGTCGTGATGAGTAGTTGCGCAGTAAACTACACAAAGGCACCTGAAGTTTTCTTGAAC
IBV         GTAGTTACGCTTACTTCTTGTCAAGCAAATTATGTAAGTGTAAATAAGACCGTCATTACT
                 *         **     *                 *

CcoV        AGTATCATA---CCTGACTATATCGATATTAATCAAACTGTTCAGGACATATTAGAAAAT
FcoV        AGTATTATA---CCTGACTATATTGACATTAATCAAACTGTTCAAGACATATTAGAAAAT
TGE         AGTATTATA---CCTGATTATATTGATATTAATCAGACTGTTCAAGACATATTAGAAAAT
PRCoV       AGTATTATA---CCTGATTATATTGATATTAATCAGACTGTTCAAGACATATTAGAAAAT
HCoVOC43    ACCATTGTG---CCAGAGTATATTGATGTTAATAAGACGCT--GCAAGAATTAAGTTACA
PEDV        GATGTAATC---CCAGATTACATCGATGTTAACAAAACACTTGATGAGATTTTAGCTTCT
SARSUrba    CCTCTGCAA---CCTGAGCTCGACTCATTCAAAGAAGAGCTGGACAAGTACTTCAAAAAT
SARSTor2    CCTCTGCAA---CCTGAGCTTGACTCATTCAAAGAAGAGCTGGACAAGTACTTCAAAAAT
BcoV        ATTTCAACA---CCCAACCTCCATGATTTTAAGGAAGAGTTGGATCAATGGTTTAAAAAC
HEV         ACATCGACA---CCCAACCTTCCTGACTTCAAGGAAGAATTGTATCAATGGTTTAAAAAC
MHV         ACTTCAATA---CCTAATCTACCCGACTTTAAGGAGGAGTTAGATAAATGGTTTAAAAAT
RtCoV       ACTTCAATA---ACTAATCTACCCGACTTTAAGGAGGAGTTAGATAAATGGTTTAAGAAT
IBV         ACATTCGTAGACAATGATGATTTTGATTTTAATGACGAATTGTCAAAATGGTGGAATGAT
                        *      * **  *     *    *     *    *

CcoV        TTCAGACCAAATTGGACTGTACCCGAGTTGCCACTTGACATTTTTCATGCAACCTACTTA
FcoV        TACAGACCAAACTGGACTGTACCTGAATTTACACTTGATATTTTCAACGCAACCTATTTA
TGE         TTTAGACCAAATTGGACTGTACCTGAGTTGACATTTGACATTTTTAACGCAACCTATTTA
PRCoV       TTTAGACCAAATTGGACTGTACCTGAGCTGACATTGGACGTTTTTAACGCAACCTATTTA
HCoVOC43    AATTG-CCAAATTACACTGTTCCAGACCTAGTTGTCGAACAGTACAACCAGACTATTTTG
PEDV        --CTG-CCCAATAGAACTGGTCCAAGTCTTCCCCTAGATGTTTTTAATGCCACTTATCTT
SARSUrba    CATACATCACCAGATGTTGATCT-TGGCGACATTTCAGGCA--TTAACGCTTCTGTCGTC
SARSTor2    CATACATCACCAGATGTTGATCT-TGGCGACATTTCAGGCA--TTAACGCTTCTGTCGTC
BcoV        CAAACATCAGTGGCACCAGATTTGTCACTTGATTATA------TAAATGTTACATTCTTG
HEV         CAATCTTCAGTGGCACCAGATTTGTCACTTGATTATA------TTAATGTTACGTTCTTG
MHV         CAGACGTCTATTGCGCCTGATTTATCTCTCGATTTCGAGAAATTAAACGTTACCCTCCTG
RtCoV       CAGACGTCTATTGTGCCTGATTTATCTTTCGATATCGGGAAATTAAATGTTACATTCCTT
IBV         -ACTAAGCATGAGCTACCAGACTTTGAC--AAATTCAATTA---CACAGTACCTATACTT
                 *                                          *     *

CcoV        AACCTGACTGGTGAAATTAATGACTTAGAATTTAGGTCAGAAAAGTTACATAACACCACA
FcoV        AATCTGACTGGTGAAATTGATGACTTAGAGTTTAGGTCAGAAAAGCTACATAACACTACA
TGE         AACCTGACTGGTGAAATTGATGACTTAGAATTTAGGTCAGAAAAGCTACATAACACCACT
PRCoV       AACCTGACTGGTGAAATTGATGACTTAGAGTTTAGGTCAGAAAAGCTACATAACACTACT
HCoVOC43    AATTTGACCAGTGAAATTAGCACCCTTGAAAATAAATCTGCGGAGCTTAATTACACTGTT
PEDV        AATCTTACTGGTGAAATTGCAGATCTAGAGCAGCGTTCAGAGTCTCTCCGTAATACTACA
SARSUrba    AACATTCAAAAGAAATTGACCGCCTCAATGAGG---------------------------
SARSTor2    AACATTCAAAAGAAATTGACCGCCTCAATGAGG---------------------------
BcoV        GACCTACAAGATGAAATGAATAGGTTACAGGAGG--------------------------
HEV         GACCTACAAGATGAAATGAATAGGTTACAAGAGG--------------------------
MHV         GACCTGACTGATGAGATGAACAGGATTCAGGATG--------------------------
RtCoV       GACCTGTCCTATGAGATGAACAGGATTCAGGATG--------------------------
IBV         GACATTGATAGTGAAATTGATCGTATTCAAGGCG--------------------------
              *  *      ** **        *  *

CcoV        GTAGAACTTGCTATTCTCATTGATAATATTAATAACACATTAGTCAATCTTGAATGGCTC
FcoV        GTAGAACTTGCCATTCTCATTGATAACATTAATAATACATTAGTCAATCTTGAATGGCTC
TGE         GTAGAACTTGCCATTCTCATTGACAACATTAACAATACATTAGTCAATCTTGAATGGCTC
PRCoV       GTAGAACTTGCCATTCTCATTGACAACATTAACAATACAGTAGTCAATCTTGAATGGCTT
HCoVOC43    CAAAAATTGCAAACTCTGATTGACAACATAAATAGCACATTAGTCGACTTAAAGTGGCTC
PEDV        GAAGAGCTCCGAAGTCTCATTAACAACATCAACAACACACTTGTTGACCTTGAGTGGCTC
SARSUrba    ---------------TCGCTAAAAATTTAAATGAATCACTCATTGACCTTCAAGAATTG
SARSTor2    ---------------TCGCTAAAAATTTAAATGAATCACTCATTGACCTTCAAGAATTG
BcoV        ---------------CAATAAAAGTTTTAAATCAGAGCTACATCAATCTCAAGGACATT
HEV         ---------------CTATAAAAGTTTTAAATCAGAGCTACATCAATCTCAAGGACATT
MHV         ---------------CAATTAAGAAGTTAAATGAGAGTTACATCAACCTCAAGGACGTT
RtCoV       ---------------CAATTAAGAATTTAAATGAGAGTTACATCAACCTCAAGGAAATT
IBV         ---------------TTATACAGGGTCTTAATGACTCTCTAATAGACCTTGAAAAACTT
                              *   * **         *   *    *    *
```

```
CcoV       AACAGAATTGAAACTTATGTAAAATGGCCTTGGTATGTTTGGCTACTAATTGGATTAGTA
FcoV       AATAGAATTGAAACTTATGTAAAATGGCCTTGGTATGTGTGGCTACTGATAGGTTTAGTA
TGE        AATAGAATTGAAACCTATGTAAAATGGCCTTGGTATGTGTGGCTACTAATAGGCTTAGTA
PRCoV      AATAGAATTGAAACTTATGTAAAATGGCCTTGGTATGTGTGGCTACTAATAGGCTTAGTA
HCoVOC43   AACCGGGTTGAGACTTACATCAAGTGGCCGTGGTGGGTGTGGTTGTGCATTTCAGTCGTG
PEDV       AACCGAGTTGAGACATACATCAAGTGGCCGTGGTGGGTTTGGTTGATCATTGTTATTGTT
SARSUrba   GGAAAATATGAGCAATATATTAAATGGCCTTGGTATGTTTGGCTCGGCTTCA---TTGCT
SARSTor2   GGAAAATATGAGCAATATATTAAATGGCCTTGGTATGTTTGGCTCGGCTTCA---TTGCT
BcoV       GGTACATATGAGTATTATGTAAAATGGCCTTGGTATGTATGGCTTTTAATTGGCTTTGCT
HEV        GGTACATATGAGTATTATGTGAAATGGCCTTGGTATGTATGGCTTTTAATTGGCCTTGCT
MHV        GGCACATATGAAATGTATGTGAAATGGCCTTGGTATGTGTGGTTGCTAATTGGATTAGCT
RtCoV      GGCACATATGAGATGTATGTGAAATGGCCTTGGTATGTTTGGCTGCTAATTGGATTAGCT
IBV        TCAATACTCAAAACTTATATTAAGTGGCCTTGGTATGTGTGGTTAGCCATAGCTTTTGCC
                   *   **  *  **  *****  ****    **  ***   *      *     *  *

CcoV       GTAATATTCTGCATACCCATATTGCTATTTTGTTGTTGTAGTACTGGTTGTTGTGGATGT
FcoV       GTAGTATTTTGCATACCATTACTGCTATTTTGCTGTTTTAGCACAGGTTGTTGTGGATGC
TGE        GTAATATTTTGCATACCATTACTGCTATTTTGCTGTTGTAGTACAGGTTGCTGTGGATGC
PRCoV      GTAATATTTTGCATACCATTACTGCTATTTTGCTGTTGTAGTACAGGTTGCTGTGGATGC
HCoVOC43   CTCATCTTTGTGGTGAGTATGTTGCTATTATGTTGTTGTTCTACTGGTTGCTGTGGCTTC
PEDV       CTCATCTTTGTTGTGTCATTACTAGTGTTCTGCTGCATTTCCACGGGTTGTTGTGGATGC
SARSUrba   GGACTAATTGCCATCGTCATGGTTACAATCTTGCTTTGTTGCATGACTAGTTGTTGCAGT
SARSTor2   GGACTAATTGCCATCGTCATGGTTACAATCTTGCTTTGTTGCATGACTAGTTGTTGCAGT
BcoV       GGTGTAGCTATGCTTGTTTTACTATTCTTCATATGCTGTTGTACAGGATGTGGGACTAGT
HEV        GGTGTAGCTATGCTTGTTTTACTATTCTTCATATGCTGCTGTACAGGATGTGGGACTAGT
MHV        GGTGTAGCTGTTTGTGTGTTGTTATTTTTCATATGTTGCTGCACGGGTTGTGGCTCATGT
RtCoV      GGTGTAGCTGTTTGTGTTTTGTTATTTTTTATATGTTGCTGCACAGGTTGTGGCTCTTGT
IBV        ACTATTATCTTCATCTTAATACTAGGATGGGTTTTCTTCATGACTGGTTGTTGTGGTTGT
                  *           *     *                *         *       *    *

CcoV       ATCGGGTGTTTAGGAAGCTGTTGTCATTCCATAT-GTAGTAGAGGCCA---ATTTGAAAG
FcoV       ATAGGTTGTTTAGGAAGTTGTTGTCACTCTATAT-GTAGTAGAAGACA---ATTTGAAAA
TGE        ATAGGTTGTTTAGGAAGTTGTTGTCACTCTATAT-GTAGTAGAAGACA---ATTTGAAAA
PRCoV      ATAGGTTGTTTAGGAAGTTGTTGTCACTCTATAT-TCAGTAGAAGACA---ATTTGAAAA
HCoVOC43   TTTAGTTGTTTTGCATCTTCTATTAGAGGTTGTT-GTGAATCAACTAA---ACTTCCTTA
PEDV       TGCGGTTGCTGCGGTGCTTGTTTTTCAGGTTGTT-GTAGGGGTCCTAG---ACTTCAACC
SARSUrba   TGCCTCAAGGGTGCATGCTCTTGTGGTTCTTGCT-GCAAGTTTGATGA---GGATGACTC
SARSTor2   TGCCTCAAGGGTGCATGCTCTTGTGGTTCTTGCT-GCAAGTTTGATGA---GGATGACTC
BcoV       TGTTTTAAGAT---ATG---TGGTGGTTGTTGTG-ATGATTATACTGG---ACACCAGG-
HEV        TGTTTTAAGAA---ATG---TGGCGGTTGTTGTG-ATGATTATACTGG---ACACCAGG-
MHV        TGTTTCAAGAA---GTG---TGGAAATTGTTGTG-ATGAGTGTGGAGG---ACACCAGGA
RtCoV      TGTTTTAAGAA---ATG---TGGAAATTGTTGTG-ATGAGTATGGAGG---ACGTCAGGC
IBV        TGTTGTGGATGC-TTTGGCATTATGCCTCTAATGAGTAAGTGTGGTAAGAAATCTTCTTA
                                                    *

CcoV       TTATGAACCTATTGAAAAAGTTCATGTTCACTGA--------------------------
FcoV       TTATGAACCAATTGAAAAAGTGCATGTCCACTAA--------------------------
TGE        TTACGAACCAATTGAAAAAGTGCACGTCCATTAA--------------------------
PRCoV      TTATGAACCTATTGAAAAAGTGCACGTCCATTAA--------------------------
HCoVOC43   TTACGACG---TTGAAAAGATCCACATACAGTAA--------------------------
PEDV       TTACGAAGCTTTTGAAAAGGTCCACGTGCAGTGA--------------------------
SARSUrba   TGAGCCAGTTCTCAAGGGTGTCAAATTACATTACACATAA--------------------
SARSTor2   TGAGCCAGTTCTCAAGGGTGTCAAATTACATTACACATAA--------------------
BcoV       -AGT-TAGTAAT-TAAAA-----CATCACATGACGACTAA--------------------
HEV        -AGT-TTGTAAT-CAAAA-----CTTCACATGACGATTAA--------------------
MHV        CAGTATTGTGATACATAATATTTCCTCTCATGAGGATTGA--------------------
RtCoV      AGGTATTGTGATACATAATATTTCCTCTCATGAGGATTGA--------------------
IBV        TTACACGACTTTTGATAACGATGTGGTAACTGAACAATACAGACCTAAAAAGTCTGTTTG
                   * *

CcoV       -
FcoV       -
```

| | |
|---|---|
| TGE | - |
| PRCoV | - |
| HCoVOC43 | - |
| PEDV | - |
| SARSUrba | - |
| SARSTor2 | - |
| BcoV | - |
| HEV | - |
| MHV | - |
| RtCoV | - |
| IBV | A |

**Figure 2: Phylogenetic Analysis of *S* Gene**
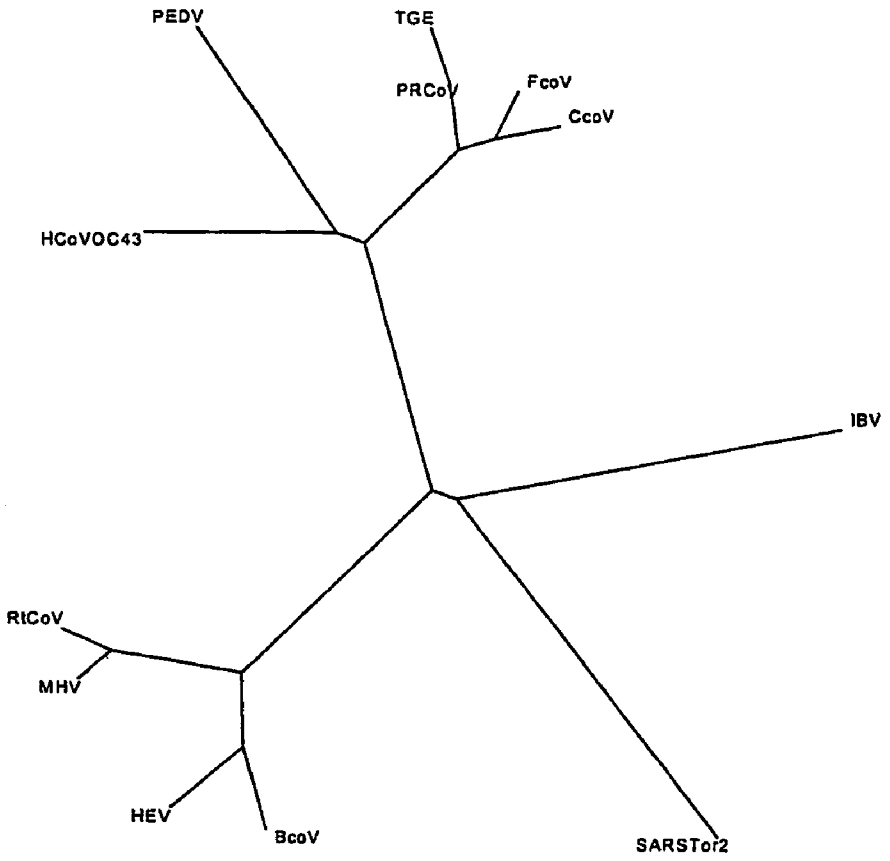

**<u>Figure 3</u>: Molecular Designs for SARS-Associated *S* Gene LK249 (Molecular Beacon) LK250 (Amplicon) and LK251 & LK252 (PCR Primers)**

| | |
|---|---|
| NOTE: | LK249 is a TET-molecular beacon, which recognizes the ***S* gene of coronavirus (SARS Tor2 and SARS urbani human pathogenic strains)**. It will be used in a real-time PCR diagnostic for the identification of **SARS-associated coronavirus RNA/DNA**. |

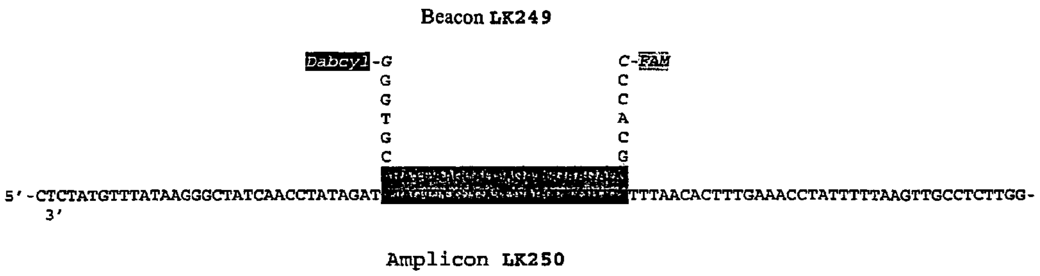

LK249

| | | |
|---|---|---|
| **A.** | Target recognition sequence: | **24 nucleotides (11 G/C)** |
| **B.** | Length of the arms: | **6 nucleotides (5 G/C)** |
| **C.** | Melting temperature of the beacon: | **dG = -2.37 dH = -46.3 dS = -135.9 Tm = 67.7 °C** |
| **D.** | Melting temperature of target: | **°C** |

---

<u>LK251</u> 5'-CTCTATGTTTATAAGGGCTATCAACC-3'

Length: 26 nucleotides (10 G/C)
*Tm*: °C
Position: (see alignment below)

<u>LK252</u> 5' –CCAAGAGGCAACTTAAAAATAGGTTTC- 3'

Length: 27 nucleotides (10 G/C)
*Tm*: °C
Position: (see alignment below)

<u>S-RT</u> 5'-AGGCTGTAAGAA-3'

Length: 14 nucleotides (6 G/C)
*Tm*: 47 °C
Position: (see alignment below)

<u>LK250 Amplicon (95 nucleotides)</u>

5' – CTCTATGTTTATAAGGGCTATCAACCTATAGATGTAGTTCGTGATCTA CCTTCTGGTTTTAACACTTTGAAACCTATTTTTAAGTTGCCTCTTGG -3'

DNA sequence alignment of complete S genes from corona virus strains

```
CcoV       ATGATTGTGCTTACATTGTGCCTTTTCTTGTT---TTTGTACAGTAGTGTGAGCTGTACA
FcoV       ATGATTGTGCTCGTAACTTGCCTCTTGTTGTTATGTTCATACCACACAGTTTTGAGTACA
TGE        ATGAAAAAACTATTTGTGGTTTTGGTCGTAATGCCATTGATTTATGGAGACAATTTTCCT
PRCoV      ------------------------------------------------------------
HCoVOC43   ------------------------------------------------------------
PEDV       ------------------------------------------------------------
SARSUrba   ------------------------------------------------------------
SARSTor2   ------------------------------------------------------------
BcoV       ------------------------------------------------------------
HEV        ------------------------------------------------------------
MHV        ------------------------------------------------------------
RtCoV      ------------------------------------------------------------
IBV        ------------------------------------------------------------

CcoV       TCAAACAATGACTGTGTACAAGTTAATGTGACACAACTGCCTGGCAATGAAAATATTATC
FcoV       ACAAATAATGAATGCATACAAGTTAACGTAACACAATTGGCTGGCAATGAAAACCTTATC
TGE        TGTTCTAAATTGACTAATAGAACTATAGGCAACCAGTGGAATCTCATTGAAACCTTCCTT
PRCoV      ------------------------------------------------------------
HCoVOC43   ------------------------------------------------------------
PEDV       ----------------------------ATGAGGTCTTTAATTTACTTCTGGTTGCTCTT
SARSUrba   ------------------------------------------------------ATGTTT
SARSTor2   ------------------------------------------------------ATGTTT
BcoV       ---------------------------------------------ATGTTTTTGATACTT
HEV        ---------------------------------------------ATGTTTTTTATACTT
MHV        ---------------------------------------------ATGCTATTCGTGTTT
RtCoV      ---------------------------------------------ATGCTATTCGTGTTT
IBV        ------------------------------------------------------------

CcoV       AAAGATTTTCTATTTCAGAACTTTAAAGAAGAAGGAAGTTTAGTTGTTGGTGGTTATTAC
FcoV       AGAGATTTTCTGTTTAGTAACTTTAAAGAAGAAGGAAGTGTAGTTGTTGGTGGTTATTAC
TGE        CTAAACTATAGTAGTAGGTTACCACCTAATTCAGATGTGGTGTTAGGTGATTATTTTCCT
PRCoV      ------------------------------------------------------------
HCoVOC43   ------------------------------------------------------------
PEDV       ACCAGTACTTCCAACACTCAGCCTACCACAAGATGTCACTAGGTGCCAGTCTACTACTAA
SARSUrba   ATTTTCTTATTATTTCTTACTCTCACTAGTGGTAGTGACCTTGACCGGTGCACCACTTTT
SARSTor2   ATTTTCTTATTATTTCTTACTCTCACTAGTGGTAGTGACCTTGACCGGTGCACCACTTTT
BcoV       TTAATTTCCTTACCAATGGCTTTTGCTGTTATAGGAGATTTAAAGTGTACTACGGTTTCC
HEV        TTAATCTCCCTGCCTTCTGCTTTTGCAGTTATAGGGGATTTAAAGTGTACTACTTCATTA
MHV        TTAACCTTGTTGCCCTCTTCTCTAGGGTATATTGGTGATTTTAGATGTATCCAACTTGTA
RtCoV      TTAACCCTATTGCCCTCTTGTCTAGGGTATATTGGTGATTTTAGATGTATCAACCTTGTA
IBV        ------------------------------------------------------------

CcoV       CCCACAGAGGTGTGGTATAACTGTTCCACAACTCAACAAACTACCGCTTATAAGTATTTT
FcoV       CCTACAGAGGTGTGGTACAACTGCTCTAGAACAGCTCGAACTACTGCCTTTCAGTATTTT
TGE        ACTGTACAACCTTGGTTTAATTGCATTCGCAATGATAGTAATGACCTTTATGTTACACTG
```

```
PRCoV       ------------------------------------------------------------
HCoVOC43    ------------------------------------------------------------
PEDV        CTTTAGGCGGTTCTTTTCAA--AATTTAATGTTCAGGCACCTGCCCGTCGTCGTTTTGGGT
SARSUrba    GA-----------TGATGTTCAAGCTCCTA--ATTACACTCAACATACTTCAT----CT
SARSTor2    GA-----------TGATGTTCAAGCTCCTA--ATTACACTCAACATACTTCAT----CT
BcoV        ATTAATGATGT---TGACACCGGTGCTCCCTCTATTAGCACTGATATTGTCGATGTTACT
HEV         ATTAATGACGT---TGACACTGGTGTGCCATCTATTAGCTCTGAAGTTGTTGATGTCACT
MHV         AATACCGACACCTCTAATGCCAGCGCTCCAAGCGTTAGTACAGAGGTAGTTGATGTTTCC
RtCoV       AACACCCGCATTTCTAATGCGCGCGCACCCAGTGTTAGCACAGAGGTAGTTGATGTTTCT
IBV         ------------------------------------------------------------

CcoV        AGTAATATACATGCATTTTATTTTGATATGGAAGCCATGGAGAATAGTACTGGCAATGCA
FcoV        AATAATATACATGCCTTTTATTTTGTTATGGAAGCCATGGAAAATAGCACTGGTAATGCA
TGE         GAAAATCTTAAAGCATTGTATTGGGATT---ATGCTACAGAAAATATCACTTGGAAT---
PRCoV       ------------------------------------------------------------
HCoVOC43    ------------------------------------------------------------
PEDV        GGTTACCTACCTAGTATGAACTCTTCTAGCTGGTACTGTGGCACAGGCATTGAAACTGCT
SARSUrba    ATGAG---GGGGGTTTACTATCCT---GATGAAATT--TTTAGATCAGACACTCTT----
SARSTor2    ATGAG---GGGGGTTTACTATCCT---GATGAAATT--TTTAGATCAGACACTCTT----
BcoV        AATGGTTTAGGTACTTATTATGTTTTAGATCGTGTGTATTTAAATACTACGTTGTTG---
HEV         AATGGTTTGGGGACTTTCTATGTTTTAGATCGTGTCTATTTAAATACCACATTGTTG---
MHV         AAAGGGATTGGTACTTATTATGTTTTAGATCGAGTCTATTTAAATGCCACACTATTG---
RtCoV       AAAGGTCTTGGTACATATTACGTTTTAGATCGTGTTTATTTAAATGCCACGTTATTG---
IBV         ------------------------------------------------------------

CcoV        CGTGGTAAACCTTTACTAGTACATGTTCATGGTAATCCTGTTAGTATCATTGTTTACATA
FcoV        CGTGGTAAACCATTATTATTTCATGTGCATGGTGAGCCTGTTAGTGTTATT------ATA
TGE         CACAGACAACGGTTAAACGTAGTCGTTAATGGATACCCATACTCCATCACAGTT---ACA
PRCoV       ------------------------------------------------------------
HCoVOC43    ------------------------------------------------------------
PEDV        AGTGGCGTTCATGGTATTTTTCTCAGCTACATCGATTCTGGTCAGGGCTTTGAGA--TTG
SARSUrba    -----TATTTA--ACTCAGGATTTATTTCTTC-CATTTTATTCTAATGTTACAGG--GTT
SARSTor2    -----TATTTA--ACTCAGGATTTATTTCTTC-CATTTTATTCTAATGTTACAGG--GTT
BcoV        CTTAATGGTTACTACCCTACTTCAGGTTCTACATATCGTAATATGGCACTGAAGG--GAA
HEV         CTCAATGGTTATTACCCAATTTCAGGTGCTACATTTCGTAATATGGCTCTGAAAG--GAA
MHV         CTTACTGGTTATTACCCTGTAGATGGGTCCATGTATAGAAACATGGCTCTAACGG--GAA
RtCoV       CTTACTGGTTACTACCCTGTAGATGGGTCCATGTATCGTAACATGGCTCTAATGG--GTA
IBV         ------------------------------------------------------------

CcoV        TCAGCTTATAGAGATGATGTGCAATTTAGGCCGCTTTTAAAGCATGGTTTATTGTGTATA
FcoV        TCGGCTTATAGGGATGATGTGCAACAAAGGCCCCTTTTAAAACATGGGTTAGTGTGCATA
TGE         ACAACCCGCAATTTTAAT-TCTGCTGAAGGTGCTATTATATGCATTTGTAAGGGCTCACC
PRCoV       ------------------------------------------------------------
HCoVOC43    ------------------------------------------------------------
PEDV        GCATTTCGCAAGAGCCGT-TTGATCCTAGTGGTTACCAGCTTTATTTACATAAGGCCACT
SARSUrba    TCATACTATTAATCATAC----GTTTGG--CAACCCTGTCAT-ACCTTTTAAGGATGGTA
SARSTor2    TCATACTATTAATCATAC----GTTTGG--CAACCCTGTCAT-ACCTTTTAAGGATGGTA
BcoV        CTTTACTATTGAGCAGACTATGGTTTAAACCACCTTTTCTTTCTGATTTTATTAATGGTA
HEV         CTCGATTATTGAGCACCTTGTGGTTTAAGCCGCCTTTTTTATCACCTTTTAATGATGGTA
MHV         TTAATACCATAAGCCTTAATTGGTACAAACCACCCTTTTTATCAGAGTTTAATGATGGCA
RtCoV       CTAATACCTTAAGCCTTAATTGGTTTGAACCGCCCTTTTTATCAGAGTTTAACGATGGCA
IBV         ------------------------------------------------------------

CcoV        ACTAAAAATGACACCGTTGACTATAATAGCTTTACAATTAACCAATGGCGAGACATATGT
FcoV        ACTAAAAATCGCCATATTAACTATGAACAATTCACCTCCAACCAGTGGAATTCCACATGT
TGE         ACCTACTACCACCACAGAATCTA-----GTTTGACTTGCAATTGGGGTAGTGAGTGCAGG
PRCoV       ------------------------------------------------------------
HCoVOC43    ------------------------------------------------------------
PEDV        AATGGTAACACTAATGCTATTGCACGACTGCGCATTTGCCAGTTTCCCGATAATAAAACA
```

```
SARSUrba    TTTA-TTTTGCTGCCACAGAGAAATCAAATGTTGTCCGTGGTTGGGTTTTTGGTTCTACC
SARSTor2    TTTA-TTTTGCTGCCACAGAGAAATCAAATGTTGTCCGTGGTTGGGTTTTTGGTTCTACC
BcoV        TTT----TTGCTAAGGTCAAAAATACCAAGGTTATTAAAAAGGGTGTAATGTATAGTGAG
HEV         TTT----TTGCCAAGGTTAAAAACAGCAGATTTTCTAAAGATGGTGTTATTTATAGTGAG
MHV         TAT----TTGCTAAGGTAAAGAACCTTAAAGCATCTTTGCCCAAAGATTCTATTTCATAT
RtCoV       TAT----ATGCTAAGGTAAAGAACCTCAAAGCATCTTTGCCCATAGGCTCGGCTTCATAC
IBV         ------------------------------------------------------------

CcoV        TTGGGTGACGACAGAAAAATACCATTCTCTGTAGTACCCACAGATAATGGTACGAAATTA
FcoV        ACGGGTGCTGACAGAAAAATTCCTTTCTCTGTCATACCCACGGACAATGGAACAAAAATC
TGE         TTAAACCATAAGTTCCCTATATGTCCTTCTAATTCAGAGGCAAATTGTGGTAATATGCTG
PRCoV       ------------------------------------------------------------
HCoVOC43    ------------------------------------------------------------
PEDV        TTGGGCCCTACTGTTAATGATGTTACAACAGGTCGTAACTGCCTATTCAACAAAGCCATT
SARSUrba    ATGAACAACA-AGTCACAGTCGGTGATTA--TTATTAACAATTCTACTAATGTTGTTATA
SARSTor2    ATGAACAACA-AGTCACAGTCGGTGATTA--TTATTAACAATTCTACTAATGTTGTTATA
BcoV        TTTCCTGCTATAACTATAGGTAGTACTT---TTGTAAATACATCCTATAGTGTGGTAGTA
HEV         TTTCCTGCTATTACTATAGGTAGTACTT---TTGTAAATACTTCCTATAGCATAGTAGTA
MHV         TTCCCTACTATAATTATAGGTAGTAATT---TTGTCACCACTTCCTATACTGTAGTATTG
RtCoV       TTTCCTACTATAATTATAGGTAGTAATT---TTGTTAATACTTCCTATACTGTAGTATTG
IBV         ------------------------------------------------------------

CcoV        TTTGGTCTTGAGTGGAATGATGACTATGTTACAGCCTATATTAGTGATGAGTCTCACCGT
FcoV        TATGGTCTTGAGTGGAATGATGACTTTGTTACAGCTTATATTAGTGGTCGTTCTTATCAC
TGE         TATGGCCTACAATGGTTTGCAGATGAGGTTGTTGCTTATTTACATGGTGCTAGTTACCGT
PRCoV       ------------------------------------------------------------
HCoVOC43    ------------------------------------------------------------
PEDV        CCAGCTTATATGCGTGATGGAAAAGATATTGTTGTCGGCATAACATGGGATAATGATCGT
SARSUrba    CGAGCATGTA------------ACTTTGAAT-------TGTGTGACAACCCTTTCTTTGC
SARSTor2    CGAGCATGTA------------ACTTTGAAT-------TGTGTGACAACCCTTTCTTTGC
BcoV        CAACCACATACTACCAATTTGGATAATAAATTACAAGGTCTCTTAGAGATCTCTGTTTGC
HEV         GAGCCTCATACCTCACTTATTAATGGTAATTTACAAGGTTTGTTGCAAATTTCTGTTTGT
MHV         GAACCGTATA------------ATGGTA-----------TAATTAT-GGCATCCATTTGC
RtCoV       GAACCATACA------------ATGGTA-----------TTATTAT-GGCATCTATTTGC
IBV         ------------------------------------------------------------

CcoV        TTGAATATCAATAATAATTGGTTTAACAATGTTACACTC--CTATACTCACGTACAAGCA
FcoV        TTGAACATCAATACTAATTGGTTTAACAATGTCACACTT--TTGTATTCACGCTCAAGCA
TGE         ATTAGTTTTGAAAATCAATGGTCTGGCACTGTCACATTTGGTGATATGCGTGCGACAACA
PRCoV       ------------------------------------------------------------
HCoVOC43    ------------------------------------------------------------
PEDV        GTCACTGTTTTTGCTGACAAGATCTATCATTTTTATCTT--AAAAATGATTGGTCCCGCG
SARSUrba    TGTTTCTAAACCCATGGGTACACAGACACATACTATGAT----ATTCGA----TAATGCA
SARSTor2    TGTTTCTAAACCCATGGGTACACAGACACATACTATGAT----ATTCGA----TAATGCA
BcoV        CAGTATACTATGTGCGAGTACCCACATACGATTTGTCATCCTAAGCTGGG---TAATAAA
HEV         CAATACACTATGTGTGAATACCCACATACTATTTGTCATCCTAATTTGGG---TAATCAA
MHV         CAGTATACCATTTGTCAACTACCGTACACGGATTGCAAACCGAATACGGGCGGTAATAAG
RtCoV       CAGTATACCATTTGTCAATTACCGCACACGGATTGCAAACCTAACACGGGCGGTAACACG
IBV         ------------------------------------------------------------

CcoV        CCGCCACGTGGCAACACA-GTGCTGCATATGTTTA---TCAAGGTGTTTCAAATTTTACT
FcoV        CTGCTACCTGGGAATACA-GTGCTGCATATGCTTA---CCAAGGTGTTTCTAACTTCACT
TGE         TTAGAAGTCGCTGGCACGCTTGTAGACCTTTGGTGGTTTAATCCTGTTTATGATGTCAGT
PRCoV       -------------------ATGAAAAAATTATTTG---TGGTCTTGGTTGTAATGCCATT
HCoVOC43    ----------------------ATGTT-TGTT-TTGCTTGTTGC--ATATGCCTTGT
PEDV        TTGCGACAAGATGTTACAATCGCAGAAGTTGTGCT-ATGCAATATGTTTATACACCTACC
SARSUrba    TTTAATTGCACTTTCGAGTACATATCTGATGCCTTTTCGCTTGATGTTTCAGAA-----A
SARSTor2    TTTAATTGCACTTTCGAGTACATATCTGATGCCTTTTCGCTTGATGTTTCAGAA-----A
BcoV        CG-CGTAGAACTATGGCATTGGGATACAGGTGTTGTTTCCTGTTTATATAAGCG-----T
```

```
HEV       CG-CATAGAATTATGGCATTATGACACAGATGTTGTTTCTTGTTTATACAGGCG-----T
MHV       TT-AATTGGCTTTTGGCACACAGAGCTAAAATCCCCTGTGTGCATTTTAAAGCG-----T
RtCoV     CT-AATTGGTTTTTGGCACACAGATTTAAGGCCTCCGGTGTGCATTTTAAAGCG-----T
IBV       ------------ATGTTGGTAACACCTCTTTTACTAGTGACTCTTTTGTGTGCACTATGT
                                                         *

CcoV      TATTACAAGTTAAATAAAACCGCTGGCTTAAAAAGCTATGAATTGTGTGAAGATTATG-A
FcoV      TATTACAAGTTAAATAACACCAATGGTCTAAAAACCTATGAATTATGTGAAGATTATG-A
TGE       TATTATAGGGTTAATAATAAAAATGGT------ACTACCGTAGTTTCCAATTGCACTG-A
PRCoV     GATTTATGGA-----GACAAGTTTCCT------ACTTCCGTAGTTTCCAATTGCACTG-A
HCoVOC43  TGCATATTGCTGGTTGTCAA-ACTACAAATGGGCTGAACACTAGTTACT--CTGTTTGCA
PEDV      TACTACATGCTTAATGTTACTAGTGCAGGTGAGGATGGCATTTATTATGAACCCTGTACA
SARSUrba  AGT----CAGGTAATTTTAAAC---ACTTACGAGAGTTTGTGTTTAAAAATAAAGATGGG
SARSTor2  AGT----CAGGTAATTTTAAAC---ACTTACGAGAGTTTGTGTTTAAAAATAAAGATGGG
BcoV      AATTTCACATATGATGTGAATGCTGATTACTTGTATTTCCATTTTTATCAAGAAGGTGGT
HEV       AATTTCACATATGATGTGAATGCTGATTATTTATATTTTCACTTTTATCAGGAAGGTGGC
MHV       AATTTTACGTTTAATGTTAATGCCGAATGGCTTTATTTTCATTTTTACCAGCAGGGTGGT
RtCoV     AATTTTACGTTTAATGTTAATGCCGAATGGCTTTATTTTCATTTTTACCAGCAGGGTGGT
IBV       AGTGCTGTTTTGTATGACAGTAGTTCTTACGTTTACTACTACCAAAGTGCCTTCAGACCA
                      *

CcoV      AT--ACTGCACTGGCTATGCAACCAATGTGTTTGCTCCGACATCAGGTG TA ATACCT
FcoV      AC--ATTGCACTGGCTATGCTACCAATGTATTTGCTCCGACATCAG TG TACATACCT
TGE       TC--AATGTGCTAGTTATGTGGCTAATGTTTTTACTACACAGCCAG AG TT ATACC
PRCoV     TC--AATGTGCTAGTTATGTGGCTAATGTTTTTACTATACTACCAG AG CTT ATACC
HCoVOC43  AC-GGCTGTGTTGGTTATTCAGAAAATGTATTTGCTGTTGAGAGTG TG TA ATACCC
PEDV      GCTAATTGCACTGGTTACGCTGCCAATGTATTTGCCACTGATTCCAATG CCA ATACCA
SARSUrba  TTTCTCTATG-----TTTATAAGGGCTAT--------CAACCTATA AT
SARSTor2  TTTCTCTATG-----TTTATAAGGGCTAT--------CAACCTATA AT
BcoV      ACTTTTTATGCATATTTTACAGACACTGGTGTTGTTACTAAGTTTCTGTT A GTT AT
HEV       ACTTTTTATGCATACTTTACAGATACTGGTTTTGTGACCAAGTTTCTGTT AG T AT
MHV       ACTTTTTATGCGTATTATGCGGATGTTTCTTCTGCTACTACGTTTTTGTT AT AT
RtCoV     ACTTTTTATGCGTATTATGCAGATGTTTCTTCTGCCACTACGTTTTTGTT AT
IBV       CCTAGTGGTTGGCATTTACAAGGGGGTGCTTATGCGGTAGTTAACATTTC CGAATTT
                          *        *
   LK251 5'-CTCTATG-----TTTATAAGGGCTAT--------CAACC-3'   LK249 BEACON
   >>>>>>>>>>>>>>>>>>>>>>>>>>>>>>>>>>>>>>>>>>>>>
CcoV      GA GGA CA T TAACAATTGGTTTATGCTTACAAACAGCTCCACTTTTGTTAGTGGC
FcoV      GA GGA TA T TAACAATTGGTTCTTGCTTACAAATAGTTCCACTTTTGTTAGTGGC
TGE       AGAT TA T TAATAATTGGTTCCTTCTAACTAATAGCTCCACGTTGGTTAGTGGT
PRCoV     AGAT TA T TAATAATTGGTTCCTCCTAACTAATAGCTCCACGTTGGTTAATGGT
HCoVOC43  T CGA TGCA CAATAATTGGTTCCTTCTAACTAATACCTCATCTGTTGTAGATGGT
PEDV      GAAGGT TA T TAATAATTGGTTTCTTTTATCCAATGACTCCACTTTGTTGCATGGT
SARSUrba  TTAA ACT-TTGAAACCTATTTTTAAGTTGCCTCTT----------
SARSTor2  TTAA ACT-TTGAAACCTATTTTTAAGTTGCCTCTT----------
BcoV      TAGG ACGGT C TTCA ATTATTATGTCCTGCCTTTGACTTGTTCT------------
HEV       TAGG ACTGT C GTCA ATTATTATGTTATGCCATTGACTTGTAAT------------
MHV       AT GGTGATGT T AACA AATATTTTGTGTTGCCTTATATGTGTACTCTCACTACAACA
RtCoV     AT GGTGCTGT AACA AGTATTTTGTGTTGCCTTATATGTGTAGTCCCACTACCTCA
IBV       AA AATGCAG C CTTCATCAGGGTGTACTGTTGGTATTATTCATGGTGGTCGTGTTGTT
                             *        *
                          3'-CTTTGGATAAAAATTCAACGGAGAA----------
                          <<<<<<<<<<<<<<<<<<<<<<<<<<<<<<<<<<<<<
CcoV      AGATTTGTAACAAATCAACCGCTGCTAGT--TAATTGCTTGTGGCCAGTGC--CCAGTTT
FcoV      AGGTTTGTAACAAATCAACCATTATTGAT--TAATTGCTTGTGGCCAGTGC--CCAGTTT
TGE       AAATTAGTTACCAAACAGCCGTTATTAGT--TAATTGCTTATGGCCAGTCC--CTAGCTT
PRCoV     AAATTAGTTACCAAACAGCCTCTATTAGT--TAATTGCTTATGGCCAGTCC--CTAGCTT
HCoVOC43  GTTGTGAGGAGTTTTCAGCCTTTGTTGCT--TAATTGCTTATGGTCTGTTT--CT--GGC
PEDV      AAAGTGGTTTCCAACCAACCCTTGTTGGT--CAATTGTCTTTTGGCCATTC--CTAAGAT
SARSUrba  GGTATTAACATTACAAATTTTAGAGCCATTCTTACAGCCTTTTCACC-TGC--TCAAGAC
SARSTor2  GGTATTAACATTACAAATTTTAGAGCCATTCTTACAGCCTTTTCACC-TGC--TCAAGAC
BcoV      AGTGCTATGACTTTAGAATATTGGGTTACACCTCTCACTTCTAAACAATAT--TTACTAG
```

```
HEV        AGCGCTTTATCTTTAGAATACTGGGTTACACCTCTCACTACTAGACAATTT--CTTCTAG
MHV        GGTGTCTTTTCACCGCAGTATTGGGTTACACCTCTTGTCAAGCGCCAATAT--TTATTTA
RtCoV      GGTGTTTCCTCACCGCAGTATTGGGTTACACCACTTGTTAAGCGCCAATAT--TTATTTA
IBV        AATGCTTCTTCTATAGCTATGACGGCACCGTCATCAGGTATGGCTTGGTCTAGCAGTCAG
                                                              *

           CC-5' LK252              3'-GTAAGAATGTCGGA-5' S-RT
           <<<<<<<<<<

CcoV       TGGCGTCGCAGCACAAGAATT--TTGTTTTGAAGGTGCTCAGTTTAGCCAATGTAACGGT
FcoV       TGGTGTAGCAGCACAAGAATT--TTGTTTTGAAGGTGCACAGTTTAGCCAATGTAATGGT
TGE        TGAAGAAGCAGCTTCTACATT--TTGTTTTGAGGGTGCTGGCTTTGATCAATGTAATGGT
PRCoV      TGAAGAAGTAGCTTCTACATT--TTGTTTTGAAGGTGCTGACTTTGATCAATGTAATGGT
HCoVOC43   TTGCGGTTTACTACTGGTTTTGTCTATTTTAATGGTACTGGGAGAGGTGATTGTAAAGGT
PEDV       TTATGGACTAG-GCCAATTTT-TCTCATTCAATCACACGATGGATGGCGTTTGTAATGGA
SARSUrba   ATTTGGGGCAC-GTCAGC--TGCAGCCTATTTTGTTGGCTATTTAAAGCCAACTACATTT
SARSTor2   ATTTGGGGCAC-GTCAGC--TGCAGCCTATTTTGTTGGCTATTTAAAGCCAACTACATTT
BcoV       CTTTCAATCAA-GATGGTGTTATTTTTAATGCTGTTGATTGTAAGAGTGATTTTATGAGT
HEV        CCTTTGACCAG-GATGGTGTTTTATACCATGCTGTTGATTGTGCTAGTGATTTTATGAGT
MHV        ATTTTAATCAA-AAGGGTATTATTACTAGTGCTGTTGATTGTGCTAGTAGTTATACCAGC
RtCoV      ATTTTAACCAA-AAGGGTATTATTACTAGCGCTGTTGATTGTGCTAGTAGTTATACCAGT
IBV        TTTTGTACTGCACACTGTAATTTTTCAGATACTACAGTGTTTGTTACACATTGTTATAAA
                     *                                 *

CcoV       GTTTCTTTAAATAATACAGTAGATGTTATTAGATTTAACCTTAATTTCACTACAGATGTA
FcoV       GTGTCTTTAAATAACACAGTGGATGTTATTAGATTCAACCTTAATTTCACTGCAGATGTA
TGE        GCTGTTTTAAATAATACTGTAGACGTCATTAGGTTCAACCTTAATTTTACTACAAATGTA
PRCoV      GCTGTTTTAAATAACACTGTAGACGTCATTAGGTTTAACCTTAATTTTACTACAAATGTA
HCoVOC43   TTTTCCTCAGATGTTTTGTCTGATGTCATACGTTACAACCTCAATTTTGAA------GAA
PEDV       GCTGCTGTGGATCGTGCCCCAGAGGCTCTGAGGTTTAATATTAATGACACCTC---CGTC
SARSUrba   ATGCTCAAGTATGATGAAAATGGTACAATCACAGATGCTGTTGATTGT----------T
SARSTor2   ATGCTCAAGTATGATGAAAATGGTACAATCACAGATGCTGTTGATTGT----------T
BcoV       GAGATTAAGTGTAAAACACTATCTATAGCACCATCTACTGGTGTTTATGAATTAAACGGT
HEV        GAGATTATGTGTAAAACTTCTTCAATTACACCACCTACTGGTGTTTATGAACTAAACGGT
MHV        GAAATAAAGTGTAAGACCCAAAGTATGAATCCCAATACGGGAGTTTATGATTTATCCGGT
RtCoV      GAAATAAAGTGTAAGACTCAAAGTATGAATCCCAATACGGGAGTCTATGATTTATCCGGT
IBV        CATGGTGGGTGTCCTTTAACTGGCATGCTTCAACAGAATCTTATACGT---------GTT
                  *

CcoV       CAATCTGGCATGGGTGCTACAGTATTTTCACTGAATACAACAGGCGGTGTCATTCTTGAG
FcoV       CAATCTGGTATGGGTGCTACAGTATTTTCACTGAATACAACAGGTGGTGTCATTCTTGAA
TGE        CAATCAGGTAAGGGTGCCACAGTGTTTTCATTGAACACAACGGGTGGTGTCACTCTTGAA
PRCoV      CAATCAGGTAAGGGTGCTACAGTGTTTTCATTGAACACAACGGGTGGTGTCACTCTTGAA
HCoVOC43   AACCTTAGACGTGGAACCATTTTGTTT------AAAACATCTTATGGTGTTGTTGTGTTT
PEDV       ATTCTTGCTGAAGGCTCAATTGTACTT------CATACTGCTTTAGGAACAAATCTTTCT
SARSUrba   CTCAAAATCCA-CTTGCTGAACTCAAATGCT---CTGTTAAGAGCTT---TGAGATTGAC
SARSTor2   CTCAAAATCCA-CTTGCTGAACTCAAATGCT---CTGTTAAGAGCTT---TGAGATTGAC
BcoV       TACACTGTTCAGCCAATTGCAGATGTTTACCGACGTATACCTAATCTTCCCGATTGTAAT
HEV        TACACAGTTCAACCTGTTGCCACTGTATATCGTAGAATACCTGATTTACCCAATTGCGAT
MHV        TACACCGTCCAACCTGTAGGATTAGTGTACCGGCGTGTTAGAAATTTGCCTGATTGTAAA
RtCoV      TACACCGTCCAACCTGTAGGACTAGTGTACCGGCGTGTTAGAAATTTGCCTGATTGTAAA
IBV        TCTGCTATGAAAAATGGCCAGCTTTTCTATAATTTAACAGTTAGTGTAGCTAAGTACCCT

CcoV       ATTTCTTGTTATAATGACACAGTGAGTGAGTCGAGT-TTCTACAGTTATGGTGAAATTCC
FcoV       ATTTCATGTTATAGTGACACAGTGAGTGAGTCTAGT-TCTTACAGTTATGGTGAAATCCC
TGE        ATTTCATGTTATA------CAGTGAGTGACTCGAGC-TTTTTCAGTTACGGTGAAATTCC
PRCoV      ATCTCATGTTATAATGATACAGTGAGTGATTCGAGC-TTTTCCAGTTACGGTGAAATTCC
HCoVOC43   TATTGTACCAACAACACTTTAGTTTC-----AGGTGATGCTCACATACCATTTGGTACA
PEDV       TTTGTTTGCAGTAATTCCTCAGATCCTCATTTAGCCATCTTTGCCATACCTCTGGGTGCT
SARSUrba   AAAGGAATTTACCAGACCTCTAATTTCAGGGTTGTTCC-CTCAGGAGATGTTGTGAGATT
SARSTor2   AAAGGAATTTACCAGACCTCTAATTTCAGGGTTGTTCC-CTCAGGAGATGTTGTGAGATT
BcoV       ATAGAGGCTTGGCTTAATGATAAGTCGGTGCCCTCTCCATTAAATTGGGAACGTAAGACC
HEV        ATCGAAGCTTGGCTTAATTCTAAGACCGTTTCTTCGCCTCTTAATTGGGAACGTAAAATT
```

```
MHV                 ATTGAGGAATGGCTAACTGCTAAGTCTGTACCTTCTCCTCTCAATTGGGAGCGCAAAACA
RtCoV               ATTGAGGAATGGTTGGCTGCTAACACAGTACCCTCTCCTCTCAATTGGGAGCGCAAAACA
IBV                 ACTTTTAGATCATTTCAGTGTGTTAATAATTTAACATCCGTATATTTAAATGGTGATCTT

CcoV                ATTCGGCGTAACTGATG-GACCACGTTACTGTTATGTACTCT-ACAATGGCACAGCTCTT
FcoV                GTTCGGCATAACTGACG-GACCACGATACTGTTATGTACTTT-ACAATGGCACAGCTCTT
TGE                 GTTCGGCGTAACTGATG-GACCACGGTACTGTTACGTACACT-ATAATGGCACAGCTCTT
PRCoV               GTTCGGCGTAACTAATG-GACCACGGTACTGTTACGTACTCT-ATAATGGCACAGCTCTT
HCoVOC43            GTTTTGGGCAATTTTT---ATTGCTTTGTAAATACTACTATTGGCAATGAAACTACGTCT
PEDV                ACTGAAGTACCCTACT---ATTGCTTTCTTAAAGTGGATACTTACAACTCCACTGTTTAT
SARSUrba            CCCTAATATTACAA-----ACTTGTGTCCTTTTGGAGAGGTTTTTAATGCTACTAAATTC
SARSTor2            CCCTAATATTACAA-----ACTTGTGTCCTTTTGGAGAGGTTTTTAATGCTACTAAATTC
BcoV                TTTTCAAATTGTAATTTTAATATGAGCAGCCTGATGTCTTTTATTCAGGCAGACTCATTT
HEV                 TTTTCTAATTGTAATTTTAACATGGGCAGGCTGATGTCTTTTATTCAGGCTGACTCTTTT
MHV                 TTTCAAAATTGTAACTTCGACCTGAGCAGTCTATTAAGATTTGTTCAGGCTGAGTCACTC
RtCoV               TTTCAAAATTGTAACTTCAACCTGAGCAGTCTATTAAGATTTGTTCAGGCTGAGTCACTC
IBV                 GTTTACACCTCTAATGAGACCATAGATGTTACATCTGCAGGTGTTTATTTTAAAGCTGGT
                                                             *    *

CcoV                AAGTATT-TAGGAACATTACCACCTAGTGTCAAGGAAATTGCTATTAGTAAGTGG-----
FcoV                AAATATT-TAGGAACATTACCACCCAGTGTAAAGGAAATTGCTATTAGTAAGTGG-----
TGE                 AAGTATT-TAGGAACATTACCACCTAGTGTCAAGGAGATTGCTATTAGTAAGTGG-----
PRCoV               AAGTATC-TAGGAACATTACCACCTAGTGTCAAGGAGATTGCTATTAGTAAGTGG-----
HCoVOC43            GCTTTTG-TGGGTGCACTACCTAAGACAGTTCGTGAGTTTGTTATT-TCACGCACA----
PEDV                AAATTCT-TGGCTGTTTTACCTCCTACTGTCAGGGAAATTGTCATCACCAAGTAT-----
SARSUrba            CCTTCTG------TCTATGCATGGGAGAGAAAAAAAAT---TTCTAATTGTGTTGCT---
SARSTor2            CCTTCTG------TCTATGCATGGGAGAGAAAAAAAAT---TTCTAATTGTGTTGCT---
BcoV                ACTTGTAATAATATTGATGCTGCTAAGATATATGGTATGTGTTTTTCCAGCATAACTATA
HEV                 GGTTGTAACAATATTGATGCTTCTCGCTTATATGGTATGTGTTTTGGTAGCATTACTATT
MHV                 TCATGTAGTAATATAGATGCTTCCAAGGTTTATGGTATGTGCTTTGGTAGTATATCTATA
RtCoV               TCATGTAGTAATATAGATGCTTCCAAGGTTTATGGAATGTGCTTTGGTAGCATATCTATA
IBV                 GGACCTA-TAACTTATAAAGTTATGAGAGAAGTTAAA---GCCCTGGCTTATTTT-----
                                                                *

CcoV                GGACATTTTTATATTAATGGTTACAATTTCTTTAGCACGTTTCCTATTGATTGTATAGCT
FcoV                GGCCATTTTTATATTAATGGTTACAATTTCTTTAGCACATTTCCTATTGGTTGTATATCT
TGE                 GGCCATTTTTATATTAATGGTTACAATTTCTTTAGCACATTTCCTATTGATTGTATATCT
PRCoV               GGCCATTTTTATATTAATGGTTACAATTTCTTTAGCACATTTCCTATTGATTGTATATCT
HCoVOC43            GGACATTTTTATATTAATGGCTATCGCTATTTCACTTTAGGTAATGTAGAAGCCGT----
PEDV                GGTGATGTTTATGTCAATGGGTTTGGCTATTTGCATCTCGGTTTGTTGGATGCTGTCACA
SARSUrba            GATTACTCTGTGCTCTACAAC--TCAACATTTTTTTCAACCTTTAAGTGCTATGGCGTTT
SARSTor2            GATTACTCTGTGCTCTACAAC--TCAACATTTTTTTCAACCTTTAAGTGCTATGGCGTTT
BcoV                GATAAGTTTGCTATACCCAATGGTAGGAAGGTTGACCTACAATTGGGCAATTTGGGCTAT
HEV                 GATAAGTTTGCTATACCCAATAGTAGAAAGGTTGATCTGCAAGTGGGTAAATCTGGTTAT
MHV                 GACAAGTTTGCGATACCCAATAGACGCCGAGTTGATTTGCAGCTAGGCAACTCTGGGTTT
RtCoV               GATAAATTTGCAATACCCAACAGTCGCCGTGTTGATCTTCAGCTAGGTAAATCGGGTCTT
IBV                 GTTAATGGTACTGCACAAGATGTTATTTTGTGTGATGGATCACCTAGAGGCTTGTTAGCA
                    *   *   *

CcoV                TTTAATTTAA------------CCACTGGTGCTAGTGGAGCAT-TTTGGACAATTGCTTA
FcoV                TTTAATTTAA------------CCACTGGTGTTAGTGGAGCTT-TTTGGACAATTGCTTA
TGE                 TTTAATTTGA------------CCACTGGTGATAGTGACGTTT-TCTGGACAATAGCTTA
PRCoV               TTTAATTTGA------------CTACTGGTGATAGTGACGTCT-TCTGGACAATAGCTTA
HCoVOC43            --TAATTTCA------ATGTCACTACTGCAGAAACCACTGATT-TTTGTACTGTTGCGTT
PEDV                ATTAATTTCACTGGTCATGGCACTGACGATGACGTTTCAGGTT-TCTGGACCATAGCATC
SARSUrba            CTGC---CAC------------TAAGTTGAATGATCTTTGCTT-CTCCAATGTCTATGCA
SARSTor2            CTGC---CAC------------TAAGTTGAATGATCTTTGCTT-CTCCAATGTCTATGCA
BcoV                TTGCAGTCTT------------TTAACTATAGAATTGATACTA-CTGCTACAAGT-TGTC
HEV                 TTACAATCTT------------TTAATTATAAGATTGACACTG-CTGTTAGCAGT-TGTC
MHV                 TTGCAATCCT------------TTAATTACAAAATAGATACAA-GAGCTACTTCG-TGTC
RtCoV               TTGCAATCTT------------TTAATTATAAAATTGATACAA-GAGCGACCTCG-TGTC
IBV                 TGCCAGTATA------------ATACTGGCAATTTTTCAGATGGCTTTTATCCTTTTACT
```

```
CcoV       TACG-TCGTACACAGAAGCATTAGTACAA-GTTGAAAACACAGCTATTAAAAAGGTGACG
FcoV       CACA-TCGTATACTGAAGCATTAGTACAA-GTTGAAAACACAGCTATTAAAAATGTGACG
TGE        CACA-TCGTACACTGAAGCATTAGTACAA-GTTGAAAACACAGCTATTACAAATGTGACG
PRCoV      CACA-TCGTACACTGAAGCATTAGTACAA-GTTGAAAACACAGCTATTACAAAGGTGACG
HCoVOC43   AGCT-TCTTATGCTGACGTTTTGGTTAAT-GTGTCACAAACCTCTATTGCTAATATAATT
PEDV       GACT-AATTTTGTTGATGCACTCATCGAG-GTTCAAGGAACTTCCATTCAGCGTATTCTT
SARSUrba   GATTCTTTTGTAGTCAAG--GGAGATGAT-GTAAG-ACAAATAGCGCCAGGACAAACTGG
SARSTor2   GATTCTTTTGTAGTCAAG--GGAGATGAT-GTAAG-ACAAATAGCGCCAGGACAAACTGG
BcoV       AGTTGTATTATAATTTACCTGCTGCTAAT-GTTTCTGTTAGCAGGTTTAATCCTTCTACT
HEV        AACTCTATTATAGTTTGCCTGCAGCAAAC-GTATCTGTCACTCATTATAATCCTTCATCT
MHV        AGCTCTATTATAGTCTTGCAAAAAATAAT-GTCACTGTCAATAACCATAACCCGTCCTCT
RtCoV      AGCTCTATTACAGTCTTGCACAAGATAAT-GTCACTGTCATTAACCACAACCCATCCTCC
IBV        AATAGTAGTTTAGTTAAGCAGAAGTTTATTGTCTATCGTGAAAATAGTGTTAATACTACT
                    *                    *   **

CcoV       TATT-GTAACAGTCAC--ATTAATAACATCAAATGTTCTCAACTTACTG----CTAATTT
FcoV       TATT-GTAACAGTCAC--ATTAATAACATTAAATGTTCTCAACTTACTG----CTAATTT
TGE        TATT-GTAATAGTCAC--GTTAATAACATTAAATGCTCTCAAATTACTG----CTAATTT
PRCoV      TATT-GTAATAGTTAT--GTTAATAACATTAAATGCTCTCAACTTACTG----CTAATTT
HCoVOC43   TATT-GCAACTCTGTT--ATTAACAGACTGAGATGTGACCAGTTGTCCT----TTGATGT
PEDV       TATT-GTGATGATCCT--GTTAGCCAACTCAAGTGTTCTCAGGTTGCTT----TTGACCT
SARSUrba   TGTT-ATTGCTGATTATAATT------ATAAATTGCCAGATGATTTCAT------GG---
SARSTor2   TGTT-ATTGCTGATTATAATT------ATAAATTGCCAGATGATTTCAT------GG---
BcoV       TGGA-ATAGGAGATTTGGTTTTACAGAACAATTTGTTTTTAAGCCTCAACCTGTAGGTGT
HEV        TGGA-ATAGAAGGTATGGGTTT----AATAATCAGAGTTTTGGTTCCAG-----AGG---
MHV        TGGA-ACAGGCGTTATGGGTTC----AATGATGTGGCTACATTTGGAAC-----TGG---
RtCoV      TGGA-ATAGGCGTTATGGATTT----AATGACGTGGCTACATTTCATAG-----TGG---
IBV        TGTACGTTACACAATTTCATTTTT--CATAATGAGACTGGCGCCAACCC-----------
           *                    **          *    *

CcoV       GCAAAATGGTTTTTACCCTGTTG---CTTCAAGTGAAGTTGGTCTTGTCAATAAGAGTGT
FcoV       GAATAATGGATTTTATCCTGTTG---CTTCAAGTGAAGTAGGTTTCGTTAATAAGAGTGT
TGE        GAATAATGGATTTTATCCTGTTT---CTTCAAGTGAAGTTGGTCTTGTCAATAAGAGTGT
PRCoV      GAATAATGGATTTTATCCTGTTT---CTTCAAGTGAAGTTGGTTCTGTCAATAAGAGTGT
HCoVOC43   ACCAGATGGTTTTTATTCTACAA---GCCCTATTCAATCCGTTGAGCTACCTGTGTCTAT
PEDV       TGACGATGGTTTTTACCCCATCT---CTTCTAGA-AACCTTCTGAGTCACGAACAGCCAA
SARSUrba   -------GTTGTGTCCTTGCTTGGAATACTAGGAACATTGATGCTACTTCAACTGGTAA
SARSTor2   -------GTTGTGTCCTTGCTTGGAATACTAGGAACATTGATGCTACTTCAACTGGTAA
BcoV       TTTACTCATCATGATGTTGTTT---ATGCACAACATTGTTTTAAAGCTCCCAAAAATTT
HEV        ------CCTTCATGATGCTGTTT---ATTCACAGCAATGTTTTAATACACCTAACACATA
MHV        ------TAAACATGACGTTGCTT---ATGCTGAGGCTTGTTTTACCGTGGGAGCATCATA
RtCoV      ------TGAACATGACGTTGCTT---ATGCAGAGGCATGTTTCACTGTTGGAGCTTCATA
IBV        ------TAATCCTAGTGGTGTTC---AGAATATTCAAACTTACCAAACAAAAACAGCTCA
                        *

CcoV       TGTGTTACTACCTAGTTTCTATTC---ACATACCAGTGTTAATATAACTATTGATCTTGG
FcoV       TGTGTTATTACCTAGCTTTTTCAC---ATACACCGCTGTCAATATAACCATTGATCTTGG
TGE        TGTGTTACTACCTAGCTTTTACAC---ACATACCATTGTTAACATAACTATTGGTCTTGG
PRCoV      TGTGTTACTACCTAGCTTTCTGAC---ACATACCATTGTTAACATAACTATTGGTCTTGG
HCoVOC43   TGTGTCGCTACCTGTTTATCATAA---ACATACGTTTATTGTGTTGTACGTTGACTTCAA
PEDV       TTTCTT-TTGTTACTTTGCCATCA---TTTAATGATCATTCTTTTGTTAAT--ATTACTG
SARSUrba   T-TATAATTATAAAT---ATAG-------------GTATCTTAGACATGGCAAGCTTAG
SARSTor2   T-TATAATTATAAAT---ATAG-------------GTATCTTAGACATGGCAAGCTTAG
BcoV       C-TGTCCGTGTAAATTGGATGG------GTCTTTGTGTGTAGGTAATGGTCCTGGTATAG
HEV        T-TGTCCTTGTAGA----ACAA------GTCA--ATGCATAGGTGTG---CAGGCACAG
MHV        T-TGCCCTTGCGCGAACCCCAGCATAGTGTCGCCATGTACCACTGGAAAACCTAACTTTG
RtCoV      T-TGCCCTTGTGCGAAGCCCAGCACAGTCTATTCATGTGTCACAGGTAAACCTAAGTCTG
IBV        G-AGTGGTTATTATAATTTTAA------TTTTTCCTTTCTGAGTAGTTTTGTTTATAAGG
                    *

CcoV       TATGAAGCGTAGTG-TTACGGTCA--CCATAGCCTCACCATTAAGTAACATCACACTACC
```

```
FcoV        TATGAAGCTTAGTGGTTATGGTCAACCCATAGCCTCGACACTAAGTAACATCACACTACC
TGE         TATGAAGCGTAGTGGTTATGGTCAACCCATAGCCTCAACATTAAGTAACATCACACTACC
PRCoV       TATGAAGCGTAGTGGTTATGGTCAACCCATAGCCTCAACGCTAAGTAACATTACACTACC
HCoVOC43    ACCTCAGAGTGGCGGTGGCAAGTG--------------CTTTAACTGTTATCCTGCT---
PEDV        TCTCT------GCGGCTTTTGGTG--------------GTCTTAGTAGTGCCAATCT---
SARSUrba    GCCCTT-TGAGAGAGACATATCTAAT-----GTGCCTTTCT----------CCCCTGA--
SARSTor2    GCCCTT-TGAGAGAGACATATCTAAT-----GTGCCTTTCT----------CCCCTGA--
BcoV        ATGCTGGTTATAAAAATAGTGGTATAGGCACTTGTCCTGCA--GGTACTAATTATTTAAC
HEV         GAACTTGTCCTGTAGGCACCACTGTGCGCAAGTGTTTTGCT--G----CAGTTACAAAA-
MHV         CCAATTGCCCTACAGGCACCTCGAATCGTGAGTGCACTGTTATGCCATTGGCTAATAAT-
RtCoV       CTAATTGCCCAACAGGTACCTCGAATCGTGAGTGTAATGTTCAGGCTTCAGGTTTTAA--
IBV         AGTCTAATTTTATGTATGGATCTTAT-----------CACCCAAGTTGTAAATTTAGAC-

CcoV        AATGCAGGATAATAACATAGACGTGTACTGTATTCGTTCTAACCAATTCTCAGTTTATGT
FcoV        AATGCAGGATAACAATACTGATGTGTACTGTATTCGTTCTAACCAATTCTCAGTTTATGT
TGE         AATGCAGGATCACAACACCGATGTGTACTGTATTCGTTCTGACCAATTTTCAGTTTATGT
PRCoV       AATGCAGGATAACAACAACGATGTGTACTGTGTTCGTTCTGACCAATTTTCAGTTTATGT
HCoVOC43    --GGTGTTAATATTACACTGGCCAATTTT--AATGAAACTAAAGGGCCTT---TGTGTGT
PEDV        --CGT-TGCATCTGACACT----ACTATC--AATGGGTTTA---GTTCTT---TCTGTGT
SARSUrba    ------------TGGCAAACCTTGCACCCCACCTGCTCTTA---ATTGT------TATTG
SARSTor2    ------------TGGCAAACCTTGCACCCCACCTGCTCTTA---ATTGT------TATTG
BcoV        TTGCCATAATGCTGCCCAATGTGATTGTTTGTGCACTCCCG---ACCCCATTACATCTAA
HEV         ----------GCTACTAAGTGTACTTGCTGGTGTCAACCAG---ATCCTTCCACATATAA
MHV         ----------CAATTTAAGTGTGATTGCACTTGTAACCCTA---GTCC-------TCTAA
RtCoV       ------------GTCTAAGTGCGATTGCACATGTAACCCTA---GTCC-------TCTAA
IBV         ------------TAGAAACTATTAATAATGGCTTGTGGTTTA--ATTC------ACTTTC
                                                                       *

CcoV        TCATTCCACTTGCAAAAGTTCTTTATGGGATAACAATTTTAATTCAGCATGTACCGACGT
FcoV        TCATTCCACTTGCAAAAGTTCTTTATGGGACAATATTTTTAATCAAGACTGCACGGATGT
TGE         TCATTCTACTTGCAAAAGTGCTTTATGGGACAATATTTTTAAGCGAAACTGCACGGACGT
PRCoV       TCATTCTACTTGCAAAAGTGTTTTATGGGACAATGTTTTTAAGCGAAACTGCACGGACGT
HCoVOC43    TGACACATC-----ACACTTCACTACCAAATACGTTGCT-------GTTTATGCCAATGT
PEDV        TGACACTAG-----ACAATTTACCATTACACTGTTTTAT-------AATGTTACAAACAG
SARSUrba    GCCATTAAATGATTATG---GTTTTTACAC------CACTACTGGCATTGGCTACCAACC
SARSTor2    GCCATTAAATGATTATG---GTTTTTACAC------CACTACTGGCATTGGCTACCAACC
BcoV        ATCTACAGGGCCTTACAAGTGCCCCCAAACTAAATACTTAGTTGGCATAGGTGAGCACTG
HEV         AGGTGTAAACGCCTGGACTTGTCCGCAATCTAAAGTTTCTATACAACCAGGTCAGCATTG
MHV         CCACCTATGATCTTAGA--TGTCTCCAAGCAAGAAGCATGCTTGGCGTAGGTGATCATTG
RtCoV       CCACCTATGATCCTAGA--TGTCTTCAAGCGCGGAGCATGCTTGGCGTAGGTGATCATTG
IBV         AGTTTCAATTGCTTACGGTCCTCTTCAAGGTGGTTGCAA----GCAATCTGTCTTTAAAG
                                                                     *

CcoV        TT-TAGACGCCACAGCTGTTATAAAAACTGGTACTTGTC---CTTTCTCATTTGATAAAT
FcoV        TT-TAGAGGCTACAGCTGTTATAAAAACTGGTACTTGTC---CTTTCTCATTTGATAAAT
TGE         TT-TAGATGCCACAGCTGTTATAAAAACTGGTACTTGTC---CTTTCTCATTTGATAAAT
PRCoV       TT-TAGATGCCACAGCTGTTATAAAAACTGGTACTTGTC---CTTTCTCATTTGATAAAT
HCoVOC43    TGGTAGGTGGAGTGCTAGTATTA-ACACGGGAAATTGCC---CTTTTTCTTTTGGCAAAG
PEDV        TTAT-GGTTATGTGTCTAAATCACAGGATAGTAATTGTC---CTTTCACCTTGCAATCTG
SARSUrba    TT-ACAG------AGTTGTAGTACTTTCTTTTGA--------ACTTTTAAATGCACCGGC
SARSTor2    TT-ACAG------AGTTGTAGTACTTTCTTTTGA--------ACTTTTAAATGCACCGGC
BcoV        TT-CGGGTCTTGCTATTAAAAGTGATTATTGTGGAGGTA---ATCCTTGTACTTGCCAAC
HEV         CC-CTGGTTTGGGTCTTGTGGAGGATGATTGCTCTGGCA---ACCCTTGCACTTGTAAAC
MHV         TG-AAGGTCTAGGAGTTTTAGAAGATAAATGTGGTGGCAGCAACACCTGCAATTGTTCTG
RtCoV       TG-AAGGTCTAGGTATTTTAGAAGATAAATGTGGTGGCAGCAACATATGCAATTGTTCGG
IBV         GT--AGAGCAACTTGTTGTTATGCTTATTCATATGGAGG---------TCCTTCGCTGTG

CcoV        TGAATAATTACTTAACTTTTAACAAGTTCTGTTTGTCGTTGAATCCCGTTGGTGCCAACT
FcoV        TGAACAATTACTTGACTTTTAACAAGTTCTGTTTGTCGTTGAGTCCTGTTGGTGCTAATT
TGE         TGAACAATTACTTAACTTTTAACAAGTTCTGTTTGTCGTTGAGTCCTGTTGGTGCTAATT
PRCoV       TGAACAATTACTTAACTTTTAACAAGTTCTGTTTGTCGTTGAGTCCCGTTGGTGCTAATT
```

```
HCoVOC43    TTAATAACTTTGTTAAATTTGGCAGTGTATGTTTTTCGCTAAAGGATATACCCGGTGGTT
PEDV        TTAATGATTACCTGTCTTTTAGCAAATTTTGTGTTTCAACCAGCCTTTTGGCTGGTGCTT
SARSUrba    CACGG---TTTGTGGACCAAAAT-TATCCACTGACCTTATTAAGAACCAGTGTGTCAATT
SARSTor2    CACGG---TTTGTGGACCAAAAT-TATCCACTGACCTTATTAAGAACCAGTGTGTCAATT
BcoV        CACAAGCATTTTTGGGTTGGTCTGTTGACTCTTGTTTACAAGGGGATAGGTGTAATATTT
HEV         CACAGGCTTTCATAGGCTGGAGTTCAGAAACTTGTTTGCAAAATGGTAGGTGTAATATTT
MHV         CTCATGCCTTTGTTGGCTGGGCTAAGGATAGTTGCTTGGCTAATGGCCGCTGTCACATTT
RtCoV       CTGATGCCTTTGTTGGCTGGGCTATGGACAGCTGTCTATCTAATGCCCGCTGCCATATTT
IBV         TAAAGGTGTTTATTCAGGTGAGTTAGATCATAATTTTGAATGTGGACTGTTA-GTTTATG
                      *    *

CcoV        GTAAGTTAGATGTTGCCGCCCGTACAAGAACCAATGAGCAGGTTTTTGGAAGTT---TAT
FcoV        GCAAGTTTGATGTTGCTGCACGTACAAGAACCAATGAGCAGGTTGTTAGAAGTC---TAT
TGE         GTAAGTTTGATGTAGCTGCCCGTACAAGAACCAATGAGCAGGTTGTTAGAAGTT---TGT
PRCoV       GTAAGTTTGATGTAGCTGCCCGTACAAGAACCAATGATCAGGTTGTTAGAAGTT---TGT
HCoVOC43    GCGCAATGCCTATAGTGGCTAATTGGGCTTATAGTAAGTACTATACTATAGGCTCATTGT
PEDV        GTACCATAGATCTTTTTGGTTACCCTGCGTTCGGTAGTGGTGTTAAGTTGACGTCCCTTT
SARSUrba    TTAATTTTAATGGACTCACTGGTACTGGTGTGTTAACTCCTTCTTCAAAGAGAT---TTC
SARSTor2    TTAATTTTAATGGACTCACTGGTACTGGTGTGTTAACTCCTTCTTCAAAGAGAT---TTC
BcoV        TTGCTAATTTTATTTTTCATGATGTTAATAGTGGTACTACTTGTTCTACTGATT---TAC
HEV         TTGCTAATTTTATTCTGAATGATGTTAATAGCGGTACAACCTGTTCTACTGATT---TAC
MHV         TTAGTAATTTGATGTTAAATGGCATTAATAGTGGTACTACATGTTCCATGGATT---TGC
RtCoV       TTAGTAATTTGATGTTAAATGGCATTAATAGTGGTACTACATGTTCCACGGATT---TTC
IBV         TTACTAAGAGCGGTGGCTCTCGTATACAAACAGCCACTGAACCGCCAGTTATAA---CTC

CcoV        ATGTAATATATGAAGAAGGAGACAACATAGTGGGTGTACCGTCTGATAATAGTGGTTT-G
FcoV        ATGTAATATATGAAGAAGGAGACAACATAGTGGGTGTACCGTCTGATAATAGCGGTCT-G
TGE         ATGTAATATATGAAGAAGGAGACAACATAGTGGGTGTACCGTCTGATAATAGTGGTGT-G
PRCoV       ATGTAATATATGAAGAAGGAGACAGCATAGTTGGTGTACCGTCTGACAATAGTGGTTT-G
HCoVOC43    ATGTTTCTTGGAGTGATGGTGATGGAATTACTGGCGTCCCACAACCTGTTGAGGGTGTTA
PEDV        ATTTTCAATTCACAAAAGGTGAGTTGATTACTGGCACGCCTAAACCACTTGAAGGTATCA
SARSUrba    AACCATTT--CAACAATTTGGCCG-TGATGTTTCTG----ATTTCACTGATTCCGTTCGA
SARSTor2    AACCATTT--CAACAATTTGGCCG-TGATGTTTCTG----ATTTCACTGATTCCGTTCGA
BcoV        AAAAATCAAACACAGACATAATTCTTGGTGTTTGTGTTAATTATGATCTTTATGGTATTA
HEV         AACAGGGTAATACTATTATTACTACTGATGTTTGTGTTAATTATGACCTATATGGCATTA
MHV         AATTGCCTAATACTGAAGTGGTCACTGGCGTCTGCGTCAAATATGACCTCTACGGTATAA
RtCoV       AATTGCCTAATACGGAAGTGGTCACTGGCGTTTGTGTCAAGTATGACCTCTACGGTAGTA
IBV         AAAACAATTATAATAATATTACTTTAAATACTTGTGTTGATTATAATATATATGGCAGAA
            *                                                          *

CcoV        CACGATTTGTCAGTGTTGCACTTAGACTCTTGT-ACAGATTACAATATATATGGTAGAAC
FcoV        CACGATTTGTCTGTGCTACACCTAGACTCCTGT-ACAGATTACAATATATATGGTAGAAC
TGE         CACGATTTGTCAGTGCTACACCTAGATTCCTGC-ACAGATTACAATATATATGGTAGAAC
PRCoV       CACGATTTGTCAGTGCTACACCTAGATTCGTGC-ACAGATTACAATATATATGGTAGAAC
HCoVOC43    GTTCCTTTATGAATGTTACAT-TGGACAAATGT-ACTAAATATAATATTTATGATGTATC
PEDV        CAGACGTTTCTTTTATGACTC-TGGATGTGTGT-ACCAAGTATACTATCTATGGCTTTAA
SARSUrba    GATCCTAAAACATCT-----G--AAAT-----------ATTA-GACATTTCACCTTGCTC
SARSTor2    GATCCTAAAACATCT-----G--AAAT-----------ATTA-GACATTTCACCTTGCGC
BcoV        CAGGCCAAGGTATTTTTGTTG--AGGTTAATGCGACTTATTATAATAGTTGGCAGAACCT
HEV         CAGGCCAGGGCATACTTATAG--AAGTTAATGCCACTTATTATAATAGTTGGCAGAATCT
MHV         CAGGCCAAGGTATTTTTAAGG--AGGTTAAGGCTGACTATTATCATAGTTGGCAAAACCT
RtCoV       CAGGCCAAGGTGTTTTTAAGG--AGGTTAAGGCTGATTATTACAATAGTTGGCAGAACCT
IBV         CTGGCCAAGGTTTTATT--------ACTAATGTGACCGACTCAGCTGTTAGTTATAATTA
                                                         *  *

CcoV        TGGTGTTGGTATTATTAGAAAAACTAACAGCACACTACTTAGTGGCTTATATT-ACACAT
FcoV        TGGTGTTGGTATTATTAGACGAACTAACAGTACGCTACTTAGTGGCTTATATT-ACACAT
TGE         TGGTGTTGGTATTATTAGACAAACTAACAGGACGCTACTTAGTGGCTTATATT-ACACAT
PRCoV       TGGTGTTGGTATTATTAGACAAACTAACAGGACGATACTTAGTGGCTTATATT-ACACAT
HCoVOC43    TGGTGTGGGTGTTATTCGCGTTAGCAATGACACCTTTCTTAATGGAATTACGT-ACACAT
PEDV        AGGTGAGGGTATTATTACCCTTACAAATTCTAGCATTTTGGCAGGTGTTTATT-ATACAT
SARSUrba    TTTTGGGGGTGTAAGTG-TAATTACACCTGGAACAAATGCTTCATCTGAAGTT-GCTGTT
```

```
SARSTor2    TTTTGGGGGTGTAAGTG-TAATTACACCTGGAACAAATGCTTCATCTGAAGTT-GCTGTT
BcoV        TTTATATGATTCTAATGGTAATCTCTATGGTTTTAGAGACTACTTAACAAACA-GAACTT
HEV         TCTTTATGATTCTAGTGGTAATCTCTATGGCTTTAGAGATTATTTATCAAATA-GAACTT
MHV         CTTATATGATGTTAATGGCAACTTAATCGGATTTCGCGATTTTGTTGCTAATA-AGAGTT
RtCoV       CTTATATGATGTTAATGGTAACTTAAATGGTTTCCGTGACATTGTTACCAATA-AGACTT
IBV         TCTAGCAGACGCAGGT-------TTGGCTATTTTAGATACATCTGGTTCCATAGACATCT
                    *        *                                            *

CcoV        CACTATCAGGTGATTTGTTAGGTTTTAAAAATGTTAGTGATGGTGTTGTCTACTCTGTAA
FcoV        CACTATCAGGTGATTTGTTAGGCTTTAAAAATGTTAGTGATGGTGTCATTTATTCTGTGA
TGE         CACTATCAGGTGATTTGTTAGGTTTTAAAAATGTTAGTGATGGTGTCATCTACTCTGTAA
PRCoV       CACTATCTGGTGATTTGTTAGGTTTTACAAATGTTAGTGATGGTGTTATCTACTCTGTAA
HCoVOC43    CAACTTCAGGTAACCTTCTGGGTTTTAAAGATGTTACTAAGGGCACCATCTACTCTATCA
PEDV        CTGATTCTGGACAGTTGTTAGCCTTTAAGAATGTCACTAGTGGTGCTGTTTATTCTGTCA
SARSUrba    CTATATCAAGATGTTA--ACTGCACTGATGTTTCTACAGCAATTCATGCAGATCAACTCA
SARSTor2    CTATATCAAGATGTTA--ACTGCACTGATGTTTCTACAGCAATTCATGCAGATCAACTCA
BcoV        TTATGATTCGTAGTTGCTATAGCGGTCGTGTTTCAGCGGCCTTTCATGCTAACTCTTCCG
HEV         TTCTTATTCGTAGCTGCTATAGTGGAAGAGTTTCAGCAGTTTTTCATGCTAACTCATCTG
MHV         ATACTATTCGAAGTTGCTATAGTGGGCGGGTCTCGGCTGCATATCATCAAGATGCACCAG
RtCoV       ATTTATTAAGAAGTTGCTATAGTGGGCGCGTTTCGGCTGCATATCATCAAGATGCACCTG
IBV         TTGTTGTACAAGGTGAATATGGTCTTAATTATTATAAGGTTAACCCTTGCGAAGATGTCA
                                                                       *

CcoV        CGCCATGTGATGTAAGTGCACAAGCTGCTGT-TATTGATGGTGCCATAGTTGGAGCTATG
FcoV        CGCCATGTGATGTAAGCGCACAAGCGGCTGT-TATTGATGGTGCCATAGTTGGAGCTATG
TGE         CGCCATGTGATGTAAGCGCACAAGCAGCTGT-TATTGATGGTACCATAGTTGGGGCTATC
PRCoV       CGCCATGTGATGTTAGCGCACAAGCAGCTAT-TATTGATGGTACCATAGTTGGGGCTATC
HCoVOC43    CTCCTTGTAACCCACCAGATCAGCTTGTTGTTTATCAGCAA-GCTGTTGTTGGTGCTATG
PEDV        CGCCATGTTCTTTTTCAGAGCAGGCTGC-ATATGTTAATGATGATATAGTGGGTGTTATT
SARSUrba    CACCA-GCTT-----------------GGCGCATATATTCTACTGGAAACAATG-TATT
SARSTor2    CACCA-GCTT-----------------GGCGCATATATTCTACTGGAAACAATG-TATT
BcoV        AACCA-GCATTGCTATTTCGGAATATTAAATGCAATTACGTTTTTAATAATACTC-TTTC
HEV         AACCA-GCTTTGATGTTTCGTAATCTTAAATGCAGCCACGTTTTTAATAATACCA-TTTT
MHV         AACCA-GCGCTACTATATCGCAATTTAAAATGTGACTATGTCTTTAACAACAACA-TATC
RtCoV       AACCA-GCGCTACTATATCGCAATTTAAAATGTGATTATGTGTTTAATAACAACA-TATC
IBV         -ACCAGCAGTTTGTAGTTTCTGGTGGTAAATTAGTAGGTATTCTTACTTCACGTAATGAG
                 **                                                    *

CcoV        ACTTCCATTAATAGTGAACTGTTAGGT--CTAACTCATTGGACAACAACACCTAATTTTT
FcoV        ACTTCCATTAACAGTGAACTGTTAGGT--CTAACACATTGGACAACGACACCTAATTTTT
TGE         ACTTCCATTAACAGTGAACTGTTAGGT--CTAACACATTGGACAACAACACCTAATTTTT
PRCoV       ACTTCCATTAACAGTGAATTGTTAGGT--CTAACACATTGGACAACAACACCTAATTTTT
HCoVOC43    TTGTCTGAAAATT-----TTACTAGTT--ACGGC---TTTTCTAATGTTGTAGAACTGCC
PEDV        TCT------AGTT-----TGTCTAACT--CCACT---TTTAACAATACTAGGGAGTTGCC
SARSUrba    CC-------------------------AGACTCAAGCAGGCTGTCTTAT-AGGAGCTG
SARSTor2    CC-------------------------AGACTCAAGCAGGCTGTCTTAT-AGGAGCTG
BcoV        ACGACAGCTGCAACCTATTAACTATTTTGATAGTTATCTTGGTTGTGTTGT-CAATGCTG
HEV         AAGACAAATACAGCTTGTTAACTATTTTGATAGTTACCTTGGTTGTGTTGT-TAATGCTT
MHV         CCGTGAGGAGACACCACTTAACTATTTCGATAGTTATCTTGGTTGTGTTGT-TAATGCTG
RtCoV       CCGTGAGGAGACACCACTTAACTATTTTGATAGTTATTTGGGTTGTGTTAT-TAATGCTG
IBV         AC--------TGGTTCTCAGCTTCTT-GAGAACCAGTTTTACATCAAAATCACTAATGG

CcoV        ATTACTACTCCATATATAATTATACAAATGTGATGAATCGTGGCACGGCAATTGA---TA
FcoV        ATTACTACTCTATATATAATTACACAAGTGAGAGGACTCGTGGCACTGCAATTGACAGTA
TGE         ATTACTACTCTATATATAATTACACAAATGATAGGACTCGTGGCACTGCAATTGACAGTA
PRCoV       ATTACTACTCTATATATAATTACACAAATGATAAGACTCGTGGCACTCCAATTGGCAGTA
HCoVOC43    GAAATTTTTCTATGCGT-------CCAATGGCAC----------TTATAATTGC-----
PEDV        TGGTTTCTTCTACCATT------CTAATGACGG----------CTCCAATTGT-----
SARSUrba    AGCAT------GTCGACACTT---CTTATGAGTGCGACATTCCTATTGGAGCTGGCATTT
SARSTor2    AGCAT------GTCGACACTT---CTTATGAGTGCGACATTCCTATTGGAGCTGGCATTT
BcoV        ATAATAGTACTTCTAGTGTTG---TTCAAACATGTGATCTCACAGTAGGTAGTGGTTACT
HEV         ATAATAATACAGCTAGTGCTG---TAAGTACTTGTGATTTAACCGTTGGTAGCGGCTATT
```

```
MHV                 ACAACTCAACTGAAGAAGCTG---TTGACGCGTGTGATTTGCGTATGGGTAGTGGGCTTT
RtCoV               ATAACTCAACTGAGCAGTCTG---TTGACGCGTGTGATTTGCGTATGGGTAGTGGGCTTT
IBV                 AACACGTCGTTTTAGACGTTC-TATTACTGAAAATG---------TTGCAAATTGCCCTT

CcoV                ATGATATTGATTGTGAACCTATCATAACATATTCTAATATAGGTGTTTGTAAAAATGGAG
FcoV                ACGATGTTGATTGTGAACCTGTCATAACCTATTCTAATATAGGTGTTTGTAAAAATGGTG
TGE                 ATGATGTTGATTGTGAACCTGTCATAACCTATTCTAACATAGGTGTTTGTAAAAATGGTG
PRCoV               ATGACGTTGATTGTGAACCTGTCATAACCTATTCTAACATAGGTGTTTGTAAAAATGGTG
HCoVOC43            ---ACA--------GACGCTGTTTTAACTTATTCTAGTTTTGGCGTTTGTGCAGATGGTT
PEDV                ---ACA--------GAGCCTGTGTTGGTGTATAGTAACATAGGTGTTTGTAAATCTGGCA
SARSUrba            GTGCTAGTTACCATACAGTTTCTTTATTACGTAG---------TACTAGCCAAAAATCTA
SARSTor2            GTGCTAGTTACCATACAGTTTCTTTATTACGTAG---------TACTAGCCAAAAATCTA
BcoV                GTGTGGATTACTCTACAAAAAGACGAAGTCGTAGAGCGATTACCACTGGTTATCGGTTTA
HEV                 GTGTTGATTATGTTACAGCACTTAGATCACGTAGATCTTTTACTACAGGTTATCGCTTTA
MHV                 GTGTCAACTATTCAACGTCTCACCGCGCTCGCAGCTCTGTCAGCACGGGTTATAAATTAA
RtCoV               GTGTCAACTATTCAATCGCTCACCGTGCGCGCAGGTCTGTCAGTACGGGTTATAAATTAA
IBV                 ATGTTAGTTATGGTAAGTTTTGTATAAAACCTGATGGCT----CAATTGCCACAATAGTA
                                                                    *

CcoV                CTTTGGTTTTTATT--AACGTCACACATTCTG-ATGGAGACGTTCAACCAATTAGCACCG
FcoV                CTTTGGTTTTTATT--AACGTCACACATTCTG-ACGGAGACGTGCAACCAATTAGCACTG
TGE                 CTTTTGTTTTTATT--AACGTCACACATTCTG-ATGGAGACGTGCAACCAATTAGCACTG
PRCoV               CTTTGGTTTTTATT--AACGTCACACATTCTG-ATGGAGACGTGCAACCAATTAGCACTG
HCoVOC43            CTATAATTGCTGTTCAACCACGTAATGTTTCATATGATAGTGTTTCAGCTATCGTCACAG
PEDV                GTATTGGCTATGTTCCATCTCAGTATGGCC---AAGTCAAGATTGCACCCACGGTTACTG
SARSUrba            ------TTGTGGCTTATACTATGTCTTTAGGTGCTGATAGTTC--AATTGCTTACTCTAA
SARSTor2            ------TTGTGGCTTATACTATGTCTTTAGGTGCTGATAGTTC--AATTGCTTACTCTAA
BcoV                CTAATTTTGAGCCATTTACTGTTAATTCAGTAAATGATAGTTTAGAACCTGTAGGTGGTT
HEV                 CTAATTTTGAACCATTTGCCGCTAATTTGGTAAATGATAGTATAGAACCTGTTGGTGGTT
MHV                 CTACTTTTGAACCATTTACAGTCCGCATTGTCAATGATAGTGTTGAGTCTGTTGATGGGT
RtCoV               CTACTTTTGAACCATTTACAGTCAGCATTGTCAATGATAGTGTTGAGTCTGTTGGTGGAT
IBV                 ------------CCAAAACAATTGGAACAGTTTGTGGCACCTTT--ATTTAATGTTACTG
                                      *                *

CcoV                ---GTAATGTCACGATACCCACAAATTTTACTATATCTGTGCAAGTCGAATATATTCAGG
FcoV                ---GTAATGTCACGATACCTACAAATTTTACTATATCTGTGCAAGTTGAATACATGCAGG
TGE                 ---GTAATGTCACGATACCTACAAACTTTACCATATCCGTGCAAGTCGAATATATTCAGG
PRCoV               ---GTAACGTCACGATACCTACTAACTTTACTATATCCGTGCAAGTCGAATACATTCAGG
HCoVOC43            ---CTAATTTGTCTATACCTTCCAATTGGACCACTTCGGTCCAGGTTGAGTATTTACAAA
PEDV                ---GGAATATTAGTATTCCCACCAACTTTAGTATGAGTATTAGAACAGAATATTTACAGC
SARSUrba            TA-ACACCATTGCTATACCTACTAACTTTTCAATTAGCATTACTACAGAAGTAATGCCTG
SARSTor2            TA-ACACCATTGCTATACCTACTAACTTTTCAATTAGCATTACTACAGAAGTAATGCCTG
BcoV                TGTATGAAATTCAAATACCTTCAGAGTTTACTATAGGTAATATGGAGGAGTTTATTCAAA
HEV                 TGTATGAAATACAGATACCTTCAGAGTTTACCATTGGTAATTTAGAAGAGTTCATTCAAA
MHV                 TATATGAGCTGCAAATACCAACCAACTTTACTATAGCTAGCCATCAGGAGTTCGTTCAAA
RtCoV               TATATGAGATGCAAATACCTACTAATTTTACTATAGCTAGCCATCAGGAGTTCATTCAAA
IBV                 ---AAAATGTGCTCATACCTAACAGTTTCAACTTAACTGTTACAGATGAGTACATACAAA
                             *    ** **       *                    **     * *

CcoV                TTTACACTACACCAGTTTCAATAGACTGTGCAAGATACGTTTGCAATGGTAACCCAAGAT
FcoV                TTTACACTACACCAGTATCAATAGATTGTGCAAGATACGTTTGTAATGGTAACCCTAGAT
TGE                 TTTACACTACACCAGTGTCAATAGACTGTTCAAGATATGTTTGTAATGGTAACCCTAGGT
PRCoV               TTTACACTACACCAGTGTCAATAGACTGTTCAAGATATGTTTGTAATGGCAACCCTAGGT
HCoVOC43            TTACAAGTACACCTATCGTAGTTGATTGCTCCACTTATGTTTGCAATGGTAATGTGCGCT
PEDV                TTTACAACACGCCTGTTAGTGTTGATTGTGCTACATATGTTTGTAATGGTAACTCTCGTT
SARSUrba            TTTCTATGGCTAAAACCTCCGTAGATTGTAATATGTACATCTGCGGAGATTCTACTGAAT
SARSTor2            TTTCTATGGCTAAAACCTCCGTAGATTGTAATATGTACATCTGCGGAGATTCTACTGAAT
BcoV                CAAGCTCTCCTAAAGTTACTATTGATTGTTCTGCTTTTGTCTGTGGTGATTATGCAGCAT
HEV                 CGAGATCCCCTAAGGTTACTATAGACTGTGCTACATTTGTTTGTGGTGACTATGCAGCAT
MHV                 CGAGGTCTCCAAAGGTTACTATAGACTGTGCTGCATTTGTCTGTGGTGGCCACACAGCAT
RtCoV               CGAGGTCTCCGAAGGTTACTATAGATTGTGCTGCATTTGTCTGTGGTGATTATACAGCGT
IBV                 CGCGTATGGATAAGGTCCAAATTAATTGCCTGCAGTATGTTTGTGGCAGTTCTCTGGATT
```

```
CcoV       GCAATAAGTTATTAACACAATACGTTTCTGCATGTCAAACTATTGAGCAAGCGCTTGCAA
FcoV       GTAACAAATTGTTAACACAATATGTGTCTGCATGTCAAACTATTGAACAAGCACTTGCAA
TGE        GTAACAAATTGTTAACACAATACGTTTCTGCATGTCAAACTATTGAGCAAGCACTTGCAA
PRCoV      GTAACAAACTGTTAACACAATACGTTTCTGCATGTCAAACTATTGAGCAAGCACTTGCAA
HCoVOC43   GTGTTGAATTGCTTAAGCAGTATACTTCTGCTTGTAAAACTATTGAAGACGCCTTAAGAA
PEDV       GTAAACAATTACTCACCCAGTACACTGCAGCATGTAAGACCATAGAGTCAGCATTACAAC
SARSUrba   GTGCTAATTTGCTTCTCCAATATGGTAGCTTTTGCACACAACTAAATCGTGCACTCTCAG
SARSTor2   GTGCTAATTTGCTTCTCCAATATGGTAGCTTTTGCACACAACTAAATCGTGCACTCTCAG
BcoV       GTAAATCACAGTTGGTTGAATATGGTAGCTTCTGTGACAATATTAATGCTATACTCACAG
HEV        GTAGACAACAGTTAGCTGAGTATGGTAGTTTTTGTGAGAACATTAATGCTATACTCACAG
MHV        GCCGTCAGCAGTTGGTTGAGTACGGCTCATTCTGTGATAATATTAATGCCATTCTTGGCG
RtCoV      GTAGACAACAGTTGGTTGATTATGGCTCTTTTTGTGATAATATTAATGCCATTCTTGGCG
IBV        GTAGAAAGTTGTTTCAACAATATGGGCCTGTTTGCGACAACATATTGTCTGTAGTAAATA
           *             *      *  **             **          *            *

CcoV       TGGGTGCCAG---ACTTGAAAACATGGAGATTGATTCCATGTTATTTGTTTCGGAAAATG
FcoV       TGGGTGCCAG---ACTTGAAAACATGGAGGTTGATTCCATGTTGTTTGTCTCGGAAAATG
TGE        TGGGTGCCAG---ACTTGAAAACATGGAGGTTGATTCCATGTTGTTTGTTTCTGAAAATG
PRCoV      TGGGTGCCAG---ACTTGAAAACATGGAAGTTGATTCCATGTTATTTGTTTCTGAAAATG
HCoVOC43   ATAGCGCCAG---GCTGGAGTCTGCAGATGTTAGTGAGATGCTCACTTTTGACAAGAAAG
PEDV       TCAGCGCTAG---GCTTGAGTCTGTTGAAGTTAACTCTATGCTTACCATTTCTGAAGAGG
SARSUrba   GTATTG-----CTGCTGAACAGGATCGCAACACACGTGAAGTGTTCGCTCAAGTCAAACA
SARSTor2   GTATTG-----CTGCTGAACAGGATCGCAACACACGTGAAGTGTTCGCTCAAGTCAAACA
BcoV       AAGTAAATGAACTACTTGACACTACACAGTTGCAAGT-AGCTAATAGTTTAATGAATGGT
HEV        AAGTAAATGAACTACTTGACACTACACAGTTGCAAGT-AGCTAATAGTTTAATGAATGGA
MHV        AGGTAAATAACCTCATAGATACTATGCAACTTCAAGT-TGCAAGTGCTTTAATCCAAGGT
RtCoV      AGGTGAATAACCTCATAGATACTATGCAATTACAAGT-TGCTAGTGCTCTGATCCAAGGT
IBV        GTGTTGGTCA---AAAAGAAGATATGGAACTTTTGAATTTCTATTCTTCTACTAAACCGG
                               *

CcoV       CCCTTA-AATTGGCATCTGTTGAAGCATTCAATAGTACGGAAAATTTAGACCCTATTTAT
FcoV       CCCTTA-AATTGGCATCTGTTGAGGCGTTCAATAGTACAGAAAATTTAGATCCTATTTAC
TGE        CCCTTA-AATTGGCATCTGTTGAAGCATTCAATAGTTCAGAAACTTTAGACCCTATTTAC
PRCoV      CCCTTA-AATTGGCTTCTGTCGAAGCATTCAATAGTTCAGAAACTTTAGATCCTATTTAC
HCoVOC43   CGTTTACACTT-GCTAATGTTAGT------AGTTTT---GGTGACTACAACCTTAGC---
PEDV       C-TTTACAGTTAGCTACCATCAGTTCGTTTAATGGT---GATGGATATAACTTTACT---
SARSUrba   AATGTACAAAACCCCAACTTTGAAA-------------TATTTTGGTGGTTTTAATT--
SARSTor2   AATGTACAAAACCCCAACTTTGAAA-------------TATTTTGGTGGTTTTAATT--
BcoV       GTCACTCTTAGCACTAAGCTTAAAGATGGCGTTAATTTCAATGTAGACGACATCAATT--
HEV        GTCACCCTTAGTACCAAGATTAAGGATGGCATTAATTTCAATGTTGACGATATCAACT--
MHV        GTCACGTTAAGCTCACGCTTATCGGATGGCATTGGTGGTCAAATAGATGATATTAATT--
RtCoV      GTCACGCTAAGTTCACGCTTGGCAGATGGCATCTCAGGTCAGATTGATGATATTAATT--
IBV        CTGGTTTTAATACACCAGTTCTTAG-------TAATGTTAGCACTGGTGAGTTTAATA--
                               *                                     *

CcoV       AAAGAATGGCCTAACATTGGTGGTTCTTGGCTAGGAGGTTTAAAAGATATATTGCCATCT
FcoV       AAAGAATGGCCTAGCATAGGTGGTTCTTGGCTAGGAGGTCTAAAAGATATACTACCGTCC
TGE        AAAGAATGGCCTAATATAGGTGGTTCTTGGCTAGAAGGTCTAAAATACATACTTCCGTCC
PRCoV      AAAGAATGGCCTAATATAGGTGGCTTTTGGCTAGAAGGTCTAAAATACATACTTCCGTCC
HCoVOC43   ----AGCGTCATA-----CCTAGCTTG--------------------------CCCACA
PEDV       ----AATGTGCTG-----GGTGCTTCCGTGTACGA------------------TCCTGCA
SARSUrba   ----TTTCACAAATATTACCTGACCCT--------------------CTAAAGCCAA---
SARSTor2   ----TTTCACAAATATTACCTGACCCT--------------------CTAAAGCCAA---
BcoV       ----TTTCCCCTGTATTAGGTTGTTTAGGAAGCGC------------TTGTAATAAAGTT
HEV        ----TCTCCCCTGTATTAGGTTGTTTAGGAAGCGA------------ATGTAATAGAGCT
MHV        ----TTAGTCCTCTGCTTGGTTGTTTAGGTTCTGA------------CTGTGGCGAAGTT
RtCoV      ----TTAGTCCTCTTCTAGGTTGCCTTGGCTCAGA------------TTGTAGCGAAGGC
IBV        ----TTTCTCTTCTGTTAACAAATCCT--------------------------AGTAGT

CcoV       CATAATAGCAAACGTAAGTACCGCTCGGCTATAGAAGACTTGCTTTTTGATAAGGTTGTA
```

```
FcoV            CATAATAGCAAACGTAAGTATGGTTCTGCTATAGAAGATTTGCTTTTTGATAAAGTTGTA
TGE             CATAATAGCAAACGTAAGTATCGTTCAGCTATAGAGGACTTGCTTTTTGATAAGGTTGTA
PRCoV           GATAATAGCAAACGTAAGTATCGTTCAGCTATAGAGGACTTGCTTTTTTCTAAGGTTGTA
HCoVOC43        AGTGGTAGTAGAGTGGCTGGTCGCAGTGCCATAGAAGACATACTTTTTAGCAAACTTGTT
PEDV            AGTGGCAGGGTGGTACAAAAAAGGTCTGTTATTGAAGACTTGCTTTTTAATAAAGTGGTT
SARSUrba        -CTAAGA---------------GGTCTTTTATTGAGGACTTGCTCTTTAATAAGGTGACA
SARSTor2        -CTAAGA---------------GGTCTTTTATTGAGGACTTGCTCTTTAATAAGGTGACA
BcoV            TCCAGCA-----------G----ATCTGCTATAGAGGATTTACTTTTTTCTAAAGTAAAG
HEV             TCCACTA-----------G----ATCTGCTATAGAGGATTTACTTTTTGATAAAGTAAAA
MHV             ACCATGGCAGCTCAAACCGGACGATCTGCTATAGAGGATGTATTATTTGACAAAGTCAAA
RtCoV           ACCAAGGCAGCGCAA---GGGCGATCTGCTATAGAGGATGTATTATTTGATAAGGTCAAA
IBV             CGTAGAA------------AGCGTTCTCTTATTGAAGACCTTCTATTTACAAGCGTTGAA
                                              ** ** **  *  * ***   *   *

CcoV            ACATCTGGCTTAGGTACAGTTGACGAAGATTACAAACGTTCTGCAGGTGGTTATGACA--
FcoV            ACATCTGGTTTAGGTACAGTTGATGAAGATTATAAACGTTGTACTGGTGGTTACGACA--
TGE             ACATCTGGTTTAGGTACAGTTGATGAAGATTATAAACGTTGTACAGGTGGTTATGACA--
PRCoV           ACATCTGGTTTAGGTACAGTTGATGAAGATTACAAACGTTGTACAGGTGGTTATGACA--
HCoVOC43        ACTTCTGGACTTGGCACTGTGGACGCAGACTACAAAAAGTGCACTAAGGGTCTTTCCA--
PEDV            ACTAATGGCCTTGGTACTGTTGATGAAGACTATAAGCGCTGTTCTAATGGTCGCTCTG--
SARSUrba        CTCGCTGATGCTGGCTTCATGAA---GCAATATGGCGAATGCCTAGGTGATATTAATG--
SARSTor2        CTCGCTGATGCTGGCTTCATGAA---GCAATATGGCGAATGCCTAGGTGATATTAATG--
BcoV            TTATCTGATGTCGGTTTCGTTGA---GGCTTATAATAATTGTACTGGAGGTGCCGAAA--
HEV             TTGTCTGATGTCGGCTTTGTACA---GGCCTATAATAACTGCACTGGAGGTGCCGAAA--
MHV             CTCTCTGATGTTGGCTTTGTCGA---AGCATATAACAATTGCACTGGAGGCCAAGAAG--
RtCoV           CTCTCTGATGTTGGCTTTGTCGA---ATCATATAATAATTGCACTGGAGGTCAAGAAG--
IBV             TCTGTTGGACTACCAACAAATGA---CGCATATAAAAATTGCACTGCAGGACCTTTAGGC
                     **               *       **       *        *

CcoV            ----TAGCTGACTTAGTGTGTGCACGATATTACAATGGCATCATGGTGCTACCTGGTGTA
FcoV            ----TAGCAGACTTGGTGTGTGCTCAATATTACAATGGCATCATGGTTCTACCAGGTGTA
TGE             ----TAGCTGACTTAGTATGTGCTCAATACTATAATGGCATCATGGTGCTACCTGGTGTG
PRCoV           ----TAGCTGACTTAGTATGTGCTCAATACTATAATGGCATTATGGTGCTACCTGGTGTG
HCoVOC43        ----TTGCTGACTTGGCTTGTGCTCAATATTATAATGGCATTATGGTTTTGCCTGGCGTC
PEDV            ----TGGCTGATCTAGTCTGTGCGCAGTATTACTCTGGTGTCATGGTACTACCTGGCGTT
SARSUrba        ----CTAGAGATCTCATTTGTGCGCAGAAGTTCAATGGACTTACAGTGTTGCCACCTCTG
SARSTor2        ----CTAGAGATCTCATTTGTGCGCAGAAGTTCAATGGACTTACAGTGTTGCCACCTCTG
BcoV            ----TTAGGGACCTCATTTGTGTGCAAAGTTATAATGGTATCAAAGTGTTGCCTCCACTG
HEV             ----TTAGGGATCTCATTTGTGTGCAAAGTTATAATGGTATCAAAGTGTTGCCTCCATTG
MHV             ----TTAGAGACCTACTTTGTGTGCAATCTTTTAATGGCATCAAAGTGCTACCGCCTGTG
RtCoV           ----TTAGAGACCTACTTTGTGTGCAATCTTTTAATGGCATTAAAGTGCTACCGCCTGTA
IBV             TTTTTTAAGGACCTTGCGTGTGCTCGTGAATATAATGGTTTGCTTGTGTTGCCTCCTATC
                         **  *    ****  *     *    ***  *    **  * **     *

CcoV            GCTAATGATGACAAGATGACTATGTACACTGCATCTCTTACAGGTGGTATAACATTAGGT
FcoV            GCTAATGCTGACAAGATGACTATGTACACAGCATCACTTGCAGGTGGTATAACATTAGGT
TGE             GCTAATGCTGACAAAATGACTATGTACACAGCATCCCTTGCAGGTGGTATAACATTAGGT
PRCoV           GCTAATGCTGACAAAATGACTATGTACACAGCATCCCTCGCAGGTGGTATAACATTAGGT
HCoVOC43        GCTGATGCTGAACGAATGGCCATGTATACAGGTTCTTTAATTGGTGGAATTGCTTTAGGA
PEDV            GTTGACGCTGAGAAGCTTCACATGTACAGTGCGTCTCTCATAGGTGGTATGGCGCTAGGA
SARSUrba        CTCACTGATGATATGATTGCTGCCTACACTGCTGCTCTAGTTAGTGGTACTGCCACTGCT
SARSTor2        CTCACTGATGATATGATTGCTGCCTACACTGCTGCTCTAGTTAGTGGTACTGCCACTGCT
BcoV            CTCTCAGTAAATCAGATCAGTGGATACACTTTGGCTGCCACCTCTGCTAGTCTGTTTCCT
HEV             TTATCTGAAAATCAGATCAGTGGCTACACTTTGGCAGCCACCGCTGCTAGCTTATTCCCT
MHV             TTGTCTGAGAATCAAATTTCTGGTTATACAGCGGGAGCTACTGTATCTGCTATGTTCCC-
RtCoV           TTATCCGAGAGTCAAATCTCTGGTTATACAGCGGGAGCTACTGCATCTGCTATGTTCCCT
IBV             ATAACAGCAGAAATGCAAGCTTTGTATACTAGTTCTCTAGTAGCTTCTATGGCTTTTGGT
                      *                 ** *

CcoV            GCACTTAGTGGTGGCGCAGTGGC---------TATACCTTTTGCAGTAGCAGTTCAGGCT
FcoV            GCACTTGGTGGTGGCGCCGTGGC---------TATACCTTTTGCAGTAGCAGTACAGGCT
TGE             GCACTTGGTGGAGGCGCCGTGGC---------TATACCTTTTGCAGTAGCAGTTCAGGCT
PRCoV           GCACTTGGTGGAGGCGCCGTGGC---------TATACCTTTTGCAGTAGCAGTTCAGGCT
```

```
HCoVOC43    GGTCTAACATCAG---CCGTTTC---------AATACCATTTTCATTAGCAATTCAGGCA
PEDV        GGTATAACTGCTG---CAGCGGC---------ATTGCCTTTTAGCTATGCTGTTCAAGCG
SARSUrba    GGATGGACATTTGGTGCTGGCGCTGCTCTTCAAATACCTTTTGCTATGCAAATGGCATAT
SARSTor2    GGATGGACATTTGGTGCTGGCGCTGCTCTTCAAATACCTTTTGCTATGCAAATGGCATAT
BcoV        CCTTTGTCAGCAGCAGTAGGTG-----------TACCATTTTATTTAAATGTTCAGTAT
HEV         CCTTGGACAGCTGCAGCAGGTG-----------TACCATTTTATTTAAATGTTCAGTAT
MHV         --ATGGTCTGCAGCTGCAGGTG-----------TGCCATTTTCTTTAAGTGTTCAATAT
RtCoV       CCATGGTCTGCAGCTGCAGGTG-----------TGCCATTTGCTTTAAGTGTTCAATAT
IBV         GGTATTACTGCAG---CTGGTGC---------TATACCTTTTGCCACACAACTGCAGGCT
                 *          *            * ** ***              *

CcoV        AGACTTAATTATGTTGCTCTACAAACTGATGTATTGAACAAAAACCAACAAATCTTGGCT
FcoV        AGACTTAATTATGTTGCTCTACAAACTGATGTATTGAATAAAAACCAACAGATCCTGGCT
TGE         AGACTTAATTATGTTGCTCTACAAACTGATGTATTGAACAAAAACCAGCAGATTCTGGCT
PRCoV       AGACTTAATTATGTTGCTCTACAAACTGATGTATTGAACAAAAACCAGCAGATCCTGGCT
HCoVOC43    CGTTTAAATTATGTTGCATTGCAGACTGATGTTTTACAAGAAAATCAGAAAATTCTTGCT
PEDV        AGACTCAATTATCTTGCTTTACAGACGGATGTTCTACAGCGGAACCAGCAATTGCTTGCT
SARSUrba    AGGTTCAATGGCATTGGAGTTACCCAAAATGTTCTCTATGAGAACCAAAAACAAATCGCC
SARSTor2    AGGTTCAATGGCATTGGAGTTACCCAAAATGTTCTCTATGAGAACCAAAAACAAATCGCC
BcoV        CGTATTAATGGGATTGGTGTTACCATGGATGTGTTAAGTCAAAATCAAAAGCTTATTGCT
HEV         CGTATAAATGGGCTTGGCGTCACTATGGATGTGCTAAGTCAAAACCAAAAGCTTATTGCT
MHV         AGAATTAATGGTCTTGGTGTCACTATGAATGTTCTTAGTGAAAATCAGAAAATGATAGCA
RtCoV       AGAATTAATGGTCTTGGTGTCACTATGAATGTTCTTAGTGAAAACCAGAAAATGATAGCT
IBV         AGAATTAATCACTTGGGTATTACCCAGTCACTTTTGTTGAAGAATCAAGAAAAAATTGCT
             *   *  ***       **   *         * *       ** **   *    * **

CcoV        AATGCTTTCAATCAAGCTATTGGTAACATTACACAGGCATTTGGTAAGGTTAATGACGCT
FcoV        AATGCTTTCAATCAAGCTATTGGTAACATTACACAGGCTTTTGGTAAGGTTAATGATGCT
TGE         AGTGCTTTCAATCAAGCTATTGGTAACATTACACAGTCATTTGGTAAGGTTAATGATGCT
PRCoV       AGTGCTTTTAATCAAGCTATTGGTAACATTACACAGTCATTTGGTAAGGTTAATGATGCT
HCoVOC43    GCATCTTTTAACAAAGCAATGACCAACATAGTAGATGCCTTTACTGGTGTTAATGATGCT
PEDV        GAGTCTTTTAACTCTGCTATTGGTAATATAACTTCAGCCTTTGAGAGTGTTAAAGAGGCT
SARSUrba    AACCAATTTAACAAGGCGATTAGTCAAAT-------------------------------
SARSTor2    AACCAATTTAACAAGGCGATTAGTCAAAT-------------------------------
BcoV        AATGCATTTAACAATGCTCTTGATGCTAT-------------------------------
HEV         AGTGCATTTAACAATGCTCTTGATGCTAT-------------------------------
MHV         AGTGCATTTAACAACGCGATAGGTGCTAT-------------------------------
RtCoV       AGTTCATTTAACAACGCGATAGGTGCTAT-------------------------------
IBV         GCTTCCTTTAATAAGGCCATTGGTCATAT-------------------------------
              ** **    ** **    **      **

CcoV        ATACATCAAACATCAAAAGGTCTTGCTACTGTTGCTAAAGCATTGGCAAAGGTGCAAGAT
FcoV        ATACATCAAACATCACAAGGTCTTGCCACTGTTGCTAAAGCGTTGGCAAAAGTGCAAGAT
TGE         ATACATCAAACATCACGAGGTCTTGCTACTGTTGCTAAAGCATTGGCAAAAGTGCAAGAT
PRCoV       ATACATCAAACATCACGAGGTCTTACAACTGTTGCTAAAGCATTGGCAAAAGTGCAAGAT
HCoVOC43    ATTACACAAACTTCACAAGCCCTACAAACAGTTGCTACTGCACTTAACAAGATCCAGGAT
PEDV        ATTAGTCAAACTTCCAAGGGTTTGAACACTGTGGCTCATGCGCTTACTAAGGTTCAAGAG
SARSUrba    -----TCAAG------AATCACTTACAACAACATCAACTGCATTGGGCAAGCTGCAAGAC
SARSTor2    -----TCAAG------AATCACTTACAACAACATCAACTGCATTGGGCAAGCTGCAAGAC
BcoV        -----TCAGG------AAGGGTTTGATGCTACCAATTCTGCTTTAGTTAAAATTCAAGCT
HEV         -----CCAGG------AAGGGTTCGACGCAACCAATTCTGCTTTAGTTAAAATTCAGGCT
MHV         -----ACAGG------AAGGGTTTGCTGCAACCAATTCTGCCTTAGCAAAAATGCAGTTC
RtCoV       -----ACAGG------AAGGGTTCGATGCAACCAATTCTGCTTTAGCGAAAATTCAGTCC
IBV         -----GCAGG------AAGGTTTTAGAAGTACATCTAGCATTACAACAAATTCAAGAT
                 **             *             ** *      *   * **

CcoV        GTTGTTAACACGCAAGGTCAAGCTTTAAGCCACCTAACAGTACAATTGCAAAACAATTTT
FcoV        GTTGTCAACACACAAGGGCAAGCTTTAAGTCACCTTACAGTACAATTGCAAAATAATTTT
TGE         GTTGTCAACATACAAGGGCAAGCTTTAAGCCACCTAACAGTACAATTGCAAAATAATTTC
PRCoV       GTTGTCAACACACAAGGTCAAGCTTTAAGACACCTAACAGTACAATTGCAAAATAATTTC
HCoVOC43    GTTGTTAATCAACAAGGCAACTCATTGAACCATTTAACTTCTCAGTTGAGGCAGAATTTT
PEDV        GTTGTTAATTCGCAGGGTTCAGCTTTGAACCAACTTACCGTACAGCTGCAACACAACTTC
SARSUrba    GTTGTTAACCAGAATGCTCAAGCATTAAACACACTTGTTAAACAACTTAGCTCTAATTTT
```

```
SARSTor2   GTTGTTAACCAGAATGCTCAAGCATTAAACACACTTGTTAAACAACTTAGCTCTAATTTT
BcoV       GTTGTTAATGCAAATGCTGAAGCTCTTAATAACTTATTGCAACAACTCTCTAATAGATTT
HEV        GTTGTTAATGCAAATGCTGAAGCACTTAATAACTTATTGCAGCAACTCTCTAACAGATTT
MHV        GTTGTCAATGCAAATGCGGAAGCACTCAATAATTTATTAAACCAGCTTTCCAATAGGTTT
RtCoV      GTTGTCAACGCAAATGCAGAAGCACTCAATAACCTTTTGAATCAGCTTTCCAATAGGTTT
IBV        GTTGTTAGTAAACAGAGTGCTATTCTTACTGAGACTATGGCATCACTTAATAAAAATTTT
           ***** *     *          * *                     *       *  **

CcoV       CAAGCCATTAGCAGTTCTATTAGTGACATTTATAACAGGCTTGATGAATTGAGTGCTGAT
FcoV       CAAGCCATTAGTAGTTCTATTAGTGATATTTATAACAGGCTTGACGAACTGAGTGCTGAT
TGE        CAAGCCATTAGTAGTTCTATTAGTGACATTTATAATAGGCTTGACGAATTGAGTGCTGAT
PRCoV      CAAGCCATTAGTAGTTCTATTAGTGACATTTATAATAGGCTTGATGAATTGAGTGCTGAT
HCoVOC43   CAAGCTATCTCTAGCTCTATTCAGGCTATCTATGACAGACTTGACACTATTCAGGCTGAT
PEDV       CAAGCCATTTCTAGTTCTATTGATGACATTTATTCCCGACTGGACATTCTTTCAGCCGAT
SARSUrba   GGTGCAATTTCAAGTGTGCTAAATGATATCCTTTCGCGACTTGATAAAGTCGAGGCGGAG
SARSTor2   GGTGCAATTTCAAGTGTGCTAAATGATATCCTTTCGCGACTTGATAAAGTCGAGGCGGAG
BcoV       GGTGCTATAAGTTCTTCTTTACAAGAAATTCTATCTAGACTGGATGCTCTTGAAGCGCAA
HEV        GGTGCCATAAGTGCCTCTTTACAAGAAATTTTATCCAGGCTCGATGCTCTTGAAGCTAAA
MHV        GGTGCAATTAGTGCTTCTTTACAAGAAATTCTATCTCGCCTAGATGCTCTTGAAGCGCAG
RtCoV      GGTGCAATTAGTGCTTCTTTACAGGAAATTCTATCTCGCCTCGATGCTCTTGAAGCTCAG
IBV        GGTGCTATTTCTTCTGTGATTCAAGAAATCTACCAGCAATTTGACGCCATACAAGCAAAT
              ** **             *    *  **          * **     *    **  *

CcoV       GCACAAGTTGACAGGCTGATTACAGGACGACTTACAGCACTTAATGCATTTGTGTCTCAG
FcoV       GCACAAGTTGATAGGCTGATTACAGGTAGACTTACAGCACTTAATGCATTTGTGTCTCAG
TGE        GCACAAGTTGACAGGCTGATCACAGGAAGACTTACAGCACTTAATGCATTTGTGTCTCAG
PRCoV      GCACAAGTCGACAGGCTGATCACAGGAAGACTTACAGCACTTAATGCATTTGTGTCTCAG
HCoVOC43   CAACAAGTAGATAGGCTGATTACTGGTAGATTGGCTGCTTTGAATGTATTCGTTTCTCAT
PEDV       GTTCAGGTTGATCGTCTCATCACCGGCAGATTATCAGCACTTAATGCTTTTGTTGCCCAA
SARSUrba   GTACAAATTGACAGGTTAATTACAGGCAGACTTCAAAGCCTTCAAACCTATGTAACACAA
SARSTor2   GTACAAATTGACAGGTTAATTACAGGCAGACTTCAAAGCCTTCAAACCTATGTAACACAA
BcoV       GCTCAGATAGACAGACTTATTAATGGGCGTCTTACCGCTCTTAATGTTTATGTTTCTCAA
HEV        GCTCAGATAGACAGACTTATCAATGGGCGTCTCACCGCTCTTAATGCTTATGTTTCTCAG
MHV        GCTCAGATAGACCGTCTTATTAATGGCAGATTAACTGCACTTAATGCATATGTCTCTAAG
RtCoV      GCTCAGATAGACCGTCTTATTAATGGCAGATTAACTGCACTTAATGCATATGTCTCTAAG
IBV        GCTCAAGTGGATCGTCTTATAACTGGTAGATTGTCATCACTTTCTGTTTTAGCATCTGCT
              **   * **   *   * ** *  **  *  *         *        *  *   *

CcoV       ACTTTAACCAGACAAGCAGAGGTTAGGGCTAGTAGACAACTTGCTAAAGACAAGGTTAAT
FcoV       ACTCTAACCAGACAAGCAGAGGTTAGGGCTAGTAGACAACTTGCCAAAGACAAGGTTAAT
TGE        ACTCTAACCAGACAAGCGGAGGTTAGGGCTAGTAGACAACTTGCCAAAGACAAGGTTAAT
PRCoV      ACTCTAACCAGACAAGCCGAGGTTAGGGCTAGTAGACAACTTGCTAAAGACAAGGTTAAT
HCoVOC43   ACATTGACTAAGTACACTGAAGTTCGTGCTTCCAGACAGCTTGCACAACAAAAAGTGAAT
PEDV       ACCCTCACTAAGTATACTGAGGTTCAGGCTAGCAGGAAGCTAGCACAGCAAAAGGTTAAT
SARSUrba   CAACTAATCAGGGCTGCTGAAATCAGGGCTTCTGCTAATCTTGCTGCTACTAAAATGTCT
SARSTor2   CAACTAATCAGGGCTGCTGAAATCAGGGCTTCTGCTAATCTTGCTGCTACTAAAATGTCT
BcoV       CAGCTTAGTGATTCTACACTAGTAAAATTTAGTGCAGCACAAGCTATGGAGAAGGTTAAT
HEV        CAGCTTAGTGATTCTACACTAGTAAAATTTAGTGCAGCACAAGCTATTGAGAAAGTTAAT
MHV        CAGCTGAGTGACATGACCCTTGTTAAGGTGAGTGCAGCCCAGGCTATAGAGAAAGTTAAT
RtCoV      CAGCTGAGCGACATGACCCTTATTAAGGTGAGTGCTGCCCAGGCTATAGAGAAAGTTAAT
IBV        AAGCAGGCGGAGTATATTAGAGTGTCACAACAGCGTGAGTTAGCTACTCAGAAAATTAAT
                               *               **        **  *   *

CcoV       GAATGCGTTAGGTCTCAATCCCAGAGATTTGGATTCTGTGGTA---ATGGTACACATTTG
FcoV       GAATGTGTTAGGTCTCAGTCTCAGAGATTCGGATTCTGTGGTA---ATGGTACACATTTG
TGE        GAATGCGTTAGGTCTCAGTCTCAGAGATTCGGATTCTGTGGTA---ATGGTACACATTTG
PRCoV      GAATGCGTTAGGTCTCAGTCTCAGAGATTCGGCTTCTGTGGTA---ATGGTACACATTTG
HCoVOC43   GAGTGTGTCAAATCCCAGTCTAAGCGTTATGGCTTCTGTGGAA---ATGGCACTCACATT
PEDV       GAGTGCGTCAAATCGCAATCTCAGCGTTACGGTTTTTGTGGTGGTGATGGCGAGCACATT
SARSUrba   GAGTGTGTTCTTGGACAATCAAAAAGAGTTGACTTTTGTGGAA---AGGGCTACCACCTT
SARSTor2   GAGTGTGTTCTTGGACAATCAAAAAGAGTTGACTTTTGTGGAA---AGGGCTACCACCTT
BcoV       GAATGTGTCAAAAGCCAATCATCTAGGATAAATTTTTGTGGTA---ATGGTAATCATATT
HEV        GAATGTGTTAAAAGCCAATCATCTAGGATAAATTTCTGTGGTA---ATGGTAATCATATT
```

```
MHV             GAGTGTGTTAAAAGCCAATCATCTAGGATAAATTTCTGTGGCA---ATGGCAATCATATA
RtCoV           GAGTGTGTTAAAAGCCAATCACCTAGGATAAATTTCTGTGGCA---ATGGCAATCATATA
IBV             GAGTGTGTTAAGTCACAGTCTATTAGGTACTCCTTTTGTGGTA---ATGGACGACATGTT
                ** ** **       ** **     *       ** *****     * **    **  *

CcoV            TTTTCACTTGCAAATGCGGCACCAAATGGCATGATTTTCTTTCACACAGTGCTATTACCA
FcoV            TTTTCACTAGCAAATGCAGCACCAAATGGCATGATTTTCTTTCATACAGTACTATTACCA
TGE             TTTTCACTCGCAAATGCAGCACCAAATGGCATGATTTTCTTTCACACAGTGCTATTACCA
PRCoV           TTTTCACTCGCAAATGCAGCACCAAATGGCATGATCTTCTTTCACACAGTGCTATTACCA
HCoVOC43        TTCTCAATTGTTAATGCTGCTCCTGAGGGGCTTGTTTTTCTCCACACTGTCTTGTTGCCG
PEDV            TTCTCTCTGGTACAGGCCGCACCTCAGGGCCTGCTGTTCTTACATACAGTACTTGTACCG
SARSUrba        ATGTCCTTCCCACAAGCAGCCCCGCATGGTGTTGTCTTCCTACATGTCACGTATGTGCCA
SARSTor2        ATGTCCTTCCCACAAGCAGCCCCGCATGGTGTTGTCTTCCTACATGTCACGTATGTGCCA
BcoV            ATATCATTAGTGCAGAATGCTCCATATGGTTTGTATTTTATCCACTTTAGCTATGTCCCT
HEV             ATATCATTAGTACAGAATGCTCCATATGGTTTGTATTTTATCCATTTTAGCTATGTCCCC
MHV             TTGTCATTAGTCCAGAATGCGCCTTATGGTTTATATTTTATTCATTTCAGCTATGTGCCT
RtCoV           TTGTCATTAGTCCAGAATGCGCCTTACGGTTTATATTTTATTCATTTCAGCTATGTGCCT
IBV             CTAACCATACCGCAAAATGCACCTAATGGTATAGTGTTTATACACTTTTCTTATACTCCA
                 *  *  *     *    ** **  * **  *    **  * **             **

CcoV            ACAGCTTATGAAACTGTGACGGCCTGGTCAGGTATTTGTGCGT---CAGATGGCAGTCGC
FcoV            ACAGCTTATGAAACTGTAACAGCTTGGTCAGGTATTTGTGCTT---CAGATGGCGATCGC
TGE             ACGGCTTATGAAACTGTGACTGCTTGGCCAGGTATTTGTGCTT---CAGATGGTGATCGC
PRCoV           ACGGCGTATGAAACTGTGACTGCTTGGTCAGGTATTTGTGCTT---TAGATGTTGATCGC
HCoVOC43        ACACAATATAAGGATGTTGAAGCGTGGTCTGGGTTGTGCGTTG---ATGGTACAAACGGT
PEDV            GGTGATTTTGTAAATGTTCTTGCCATCGCTGGCTTATGCGTTA---ATGGTGAAATTGCC
SARSUrba        TCCCAGGAGAGGAACTTCACCACAGCGCCAGCAATTTGTCATG---AAGGCAAAGCATAC
SARSTor2        TCCCAGGAGAGGAACTTCACCACAGCGCCAGCAATTTGTCATG---AAGGCAAAGCATAC
BcoV            ACTAAGTATGTCACTGCGAAGGTTAGTCCCGGTCTGTGCATTG---CTGGTGATAGAGGT
HEV             ACCAAGTATGTTACAGCAAAGGTTAGTCCTGGTTTGTGCATTG---CTGGCGATATAGGA
MHV             ACTTCCTTTACAACGGCAAATGTGAGTCCTGGGCTATGCATTT---CTGGTGATAGAGGA
RtCoV           ACATCCTTTACAACGGTAAATGTGAGTCCTGGACTATGCATTT---CTGGTGATAGAGGA
IBV             GATAGTTTTGTTAATGTTACTGCAATAGTGGGTTTTTGTGTAAAGCCAGCTAATGCTAGT
                                              *   * **          *

CcoV            ACTTTTGGACTTGTTGTTGAGGATGTCCAGCTGACGC-TATTTCGCAA-----TTTAGAT
FcoV            ACTTTCGGACTTGTCGTTAAAGATGTGCAGTTGACGT-TGTTTCGTAA-----TCTAGAT
TGE             ACTTTTGGACTTGTCGTTAAAGATGTCCAGTTGACTT-TGTTTCGTAA-----TCTAGAT
PRCoV           ACTTTTGGACTTGTCGTTAAAGATGTCCAGTTGACTT-TATTTCGTAA-----TCTAGAT
HCoVOC43        TATGTGTTGCGACAACCTAATCTTGCTCT--TTACAAAGAAGGCA---------ATTATT
PEDV            TTGACTCTACGTGAGCCTGGCTTAGTCTTGTTTACGCATGAACTTCAAACTTATACTGCG
SARSUrba        TTCCCT---------CGTGAAGGTGTTTTTGTGTTTAATG--------------GCACTT
SARSTor2        TTCCCT---------CGTGAAGGTGTTTTTGTGTTTAATG--------------GCACTT
BcoV            ATAGCC---------CCTAAGAGTGGTTATTTTGTTAATGTAA-----------ATAATA
HEV             ATATCG---------CCTAAGAGTGGTTATTTTATTAATGTAA-----------ATAATT
MHV             TTAGCA---------CCTAAAGCTGGATATTTTGTTCAAGATG-----------ATGGAG
RtCoV           TTAGCA---------CCTAAAGCTGGATATTTTGTTCAAGATC-----------ATGGAG
IBV             CAGTATGCAATAGTGCCCGCTAATGGTAGGGGTATTTTTATACAA---------GTTAAT
                                        *

CcoV            GAAAAATTTTATTTGACGCCCAGAACTATGTATCAGCCCAGAGTTGCAACTAGTTCTGAT
FcoV            GACAAGTTCTATTTGACCCCCAGAACTATGTATCAGCCTAGAGTTGCAACTAGTTCTGAT
TGE             GACAAGTTCTATTTGACCCCCAGAACTATGTATCAGCCTAGAGTTGCAACTAGTTCTGAC
PRCoV           GACAAGTTCTATTTGACACCCAGAACTATGTATCAGCCTAGAGTGGCAACTAGTTCTGAT
HCoVOC43        ATAGAAT-------CACATCTCGCATAATGTTTGAACCACGTATTCCTACCATGGCAGAT
PEDV            ACGGAATATTTTGTTTCATCGCGACGTATGTTTGAACCTAGAAAACCTACCGTTAGTGAT
SARSUrba        CTTGGTTTAT----TACACAGAGGAACTTCTTTTCTCCACAAATAATTACTACAGACAAT
SARSTor2        CTTGGTTTAT----TACACAGAGGAACTTCTTTTCTCCACAAATAATTACTACAGACAAT
BcoV            CTTGGATGTT----CACTGGTAGTGGTTATTACTACCCTGAACCCATAACTGGAAATAAT
HEV             CTTGGATGTT----CACTGGTAGTAGCTATTACTACCCTGAACCTATAACCCAAAATAAT
MHV             AGTGGAAGTT----CACAGGTAGTAATTATTATTACCCTGAACCCATTACAGATAAAAAT
RtCoV           AATGGAAGTT----CACAGGTAGCAATTATTACTACCCTGAATCCATTACAGATAAAAAC
IBV             GGTAGTTACTACATCACTGCACGAGATATGTATATGCCAAGAGCTATTACTGCAGGAGAT
```

```
CcoV          TTTGTTCAAATAGAAGGCTGTGATGTGTTGTTTGTTAATGGAACTGTAATTGAATTGCCT
FcoV          TTTGTTCAAATTGAAGGGTGTGATGTGTTGTTTGTCAACGCGACTGTAATTGATTTGCCT
TGE           TTTGTTCAAATTGAAGGGTGCGATGTGCTGTTTGTTAATGCAACTGTAAGTGATTTGCCT
PRCoV         TTTGTTCAAATTGAAGGGTGCGATGTGCTGTTTGTTAATACAACTGTAAGTGATTTGCCT
HCoVOC43      TTTGTTCAAATTGAAAATTGCAATGTCACATTTGTTAACATTTCTCGCTCTGAGTTGCAA
PEDV          TTTGTTCAAATTGAGAGTTGTGTGGTCACCTATGTCAATCTGACTAGCGACCAGCTACCA
SARSUrba      ACATTTGTCTCAGGAAATTGTGATGTCGTTATTGGCATCATTAACAACACAGTTTATGAT
SARSTor2      ACATTTGTCTCAGGAAATTGTGATGTCGTTATTGGCATCATTAACAACACAGTTTATGAT
BcoV          GTTGTTGTTATGAGTACCTGTGCTGTTAACTATACTAAAGCGCCGGATGTAATGCTGAAC
HEV           GTTGTTGTGATGAGTACCTGTGCTGTTAATTATACTAAAGCACCGGATCTAATGCTGAAC
MHV           AGTGTCGTGATGAGTAGTTGCGCAGCAAACTACACAAAGGCACCTGAAGTTTTCTTGAAC
RtCoV         AGTGTCGTGATGAGTAGTTGCGCAGTAAACTACACAAAGGCACCTGAAGTTTTCTTGAAC
IBV           GTAGTTACGCTTACTTCTTGTCAAGCAAATTATGTAAGTGTAAATAAGACCGTCATTACT
                  *              **   *           *

CcoV          AGTATCATA---CCTGACTATATCGATATTAATCAAACTGTTCAGGACATATTAGAAAAT
FcoV          AGTATTATA---CCTGACTATATTGACATTAATCAAACTGTTCAAGACATATTAGAAAAT
TGE           AGTATTATA---CCTGATTATATTGATATTAATCAGACTGTTCAAGACATATTAGAAAAT
PRCoV         AGTATTATA---CCTGATTATATTGATATTAATCAGACTGTTCAAGACATATTAGAAAAT
HCoVOC43      ACCATTGTG---CCAGAGTATATTGATGTTAATAAGACGCT--GCAAGAATTAAGTTACA
PEDV          GATGTAATC---CCAGATTACATCGATGTTAACAAAACACTTGATGAGATTTTAGCTTCT
SARSUrba      CCTCTGCAA---CCTGAGCTCGACTCATTCAAAGAAGAGCTGGACAAGTACTTCAAAAAT
SARSTor2      CCTCTGCAA---CCTGAGCTTGACTCATTCAAAGAAGAGCTGGACAAGTACTTCAAAAAT
BcoV          ATTTCAACA---CCCAACCTCCATGATTTTAAGGAAGAGTTGGATCAATGGTTTAAAAAC
HEV           ACATCGACA---CCCAACCTTCCTGACTTCAAGGAAGAATTGTATCAATGGTTTAAAAAC
MHV           ACTTCAATA---CCTAATCTACCCGACTTTAAGGAGGAGTTAGATAAATGGTTTAAAAAT
RtCoV         ACTTCAATA---ACTAATCTACCCGACTTTAAGGAGGAGTTAGATAAATGGTTTAAGAAT
IBV           ACATTCGTAGACAATGATGATTTTGATTTAATGACGAATTGTCAAAATGGTGGAATGAT
                               *          * **  *     *     *    *

CcoV          TTCAGACCAAATTGGACTGTACCCGAGTTGCCACTTGACATTTTTCATGCAACCTACTTA
FcoV          TACAGACCAAACTGGACTGTACCTGAATTTACACTTGATATTTTCAACGCAACCTATTTA
TGE           TTTAGACCAAATTGGACTGTACCTGAGTTGACATTTGACATTTTTAACGCAACCTATTTA
PRCoV         TTTAGACCAAATTGGACTGTACCTGAGCTGACATTGGACGTTTTTAACGCAACCTATTTA
HCoVOC43      AATTG-CCAAATTACACTGTTCCAGACCTAGTTGTCGAACAGTACAACCAGACTATTTTG
PEDV          --CTG-CCCAATAGAACTGGTCCAAGTCTTCCCCTAGATGTTTTTAATGCCACTTATCTT
SARSUrba      CATACATCACCAGATGTTGATCT-TGGCGACATTTCAGGCA--TTAACGCTTCTGTCGTC
SARSTor2      CATACATCACCAGATGTTGATCT-TGGCGACATTTCAGGCA--TTAACGCTTCTGTCGTC
BcoV          CAAACATCAGTGGCACCAGATTTGTCACTTGATTATA------TAAATGTTACATTCTTG
HEV           CAATCTTCAGTGGCACCAGATTTGTCACTTGATTATA------TTAATGTTACGTTCTTG
MHV           CAGACGTCTATTGCGCCTGATTTATCTCTCGATTTCGAGAAATTAAACGTTACCCTCCTG
RtCoV         CAGACGTCTATTGTGCCTGATTTATCTTTCGATATCGGGAAATTAAATGTTACATTCCTT
IBV           -ACTAAGCATGAGCTACCAGACTTTGAC--AAATTCAATTA---CACAGTACCTATACTT
                      *                                            *     *

CcoV          AACCTGACTGGTGAAATTAATGACTTAGAATTTAGGTCAGAAAAGTTACATAACACCACA
FcoV          AATCTGACTGGTGAAATTGATGACTTAGAGTTTAGGTCAGAAAAGCTACATAACACTACA
TGE           AACCTGACTGGTGAAATTGATGACTTAGAATTTAGGTCAGAAAAGCTACATAACACCACT
PRCoV         AACCTGACTGGTGAAATTGATGACTTAGAGTTTAGGTCAGAAAAGCTACATAACACTACT
HCoVOC43      AATTTGACCAGTGAAATTAGCACCCTTGAAAATAAATCTGCGGAGCTTAATTACACTGTT
PEDV          AATCTTACTGGTGAAATTGCAGATCTAGAGCAGCGTTCAGAGTCTCTCCGTAATACTACA
SARSUrba      AACATTCAAAAAGAAATTGACCGCCTCAATGAGG--------------------------
SARSTor2      AACATTCAAAAAGAAATTGACCGCCTCAATGAGG--------------------------
BcoV          GACCTACAAGATGAAATGAATAGGTTACAGGAGG--------------------------
HEV           GACCTACAAGATGAAATGAATAGGTTACAAGAGG--------------------------
MHV           GACCTGACTGATGAGATGAACAGGATTCAGGATG--------------------------
RtCoV         GACCTGTCCTATGAGATGAACAGGATTCAGGATG--------------------------
IBV           GACATTGATAGTGAAATTGATCGTATTCAAGGCG--------------------------
                *  *       ** **        *  *

CcoV          GTAGAACTTGCTATTCTCATTGATAATATTAATAACACATTAGTCAATCTTGAATGGCTC
```

```
FcoV            GTAGAACTTGCCATTCTCATTGATAACATTAATAATACATTAGTCAATCTTGAATGGCTC
TGE             GTAGAACTTGCCATTCTCATTGACAACATTAACAATACATTAGTCAATCTTGAATGGCTC
PRCoV           GTAGAACTTGCCATTCTCATTGACAACATTAACAATACAGTAGTCAATCTTGAATGGCTT
HCoVOC43        CAAAAATTGCAAACTCTGATTGACAACATAAATAGCACATTAGTCGACTTAAAGTGGCTC
PEDV            GAAGAGCTCCGAAGTCTCATTAACAACATCAACAACACACTTGTTGACCTTGAGTGGCTC
SARSUrba        ----------------TCGCTAAAAATTTAAATGAATCACTCATTGACCTTCAAGAATTG
SARSTor2        ----------------TCGCTAAAAATTTAAATGAATCACTCATTGACCTTCAAGAATTG
BcoV            ----------------CAATAAAAGTTTTAAATCAGAGCTACATCAATCTCAAGGACATT
HEV             ----------------CTATAAAAGTTTTAAATCAGAGCTACATCAATCTCAAGGACATT
MHV             ----------------CAATTAAGAAGTTAAATGAGAGTTACATCAACCTCAAGGACGTT
RtCoV           ----------------CAATTAAGAATTTAAATGAGAGTTACATCAACCTCAAGGAAATT
IBV             ----------------TTATACAGGGTCTTAATGACTCTCTAATAGACCTTGAAAAACTT
                                      *     * **           *  *  *  *     *

CcoV            AACAGAATTGAAACTTATGTAAAATGGCCTTGGTATGTTTGGCTACTAATTGGATTAGTA
FcoV            AATAGAATTGAAACTTATGTAAAATGGCCTTGGTATGTGTGGCTACTGATAGGTTTAGTA
TGE             AATAGAATTGAAACCTATGTAAAATGGCCTTGGTATGTGTGGCTACTAATAGGCTTAGTA
PRCoV           AATAGAATTGAAACTTATGTAAAATGGCCTTGGTATGTGTGGCTACTAATAGGCTTAGTA
HCoVOC43        AACCGGGTTGAGACTTACATCAAGTGGCCGTGGTGGGTGTGGTTGTGCATTTCAGTCGTG
PEDV            AACCGAGTTGAGACATACATCAAGTGGCCGTGGTGGGTTTGGTTGATCATTGTTATTGTT
SARSUrba        GGAAAATATGAGCAATATATTAAATGGCCTTGGTATGTTTGGCTCGGCTTCA---TTGCT
SARSTor2        GGAAAATATGAGCAATATATTAAATGGCCTTGGTATGTTTGGCTCGGCTTCA---TTGCT
BcoV            GGTACATATGAGTATTATGTAAAATGGCCTTGGTATGTATGGCTTTTAATTGGCTTTGCT
HEV             GGTACATATGAGTATTATGTGAAATGGCCTTGGTATGTATGGCTTTTAATTGGCCTTGCT
MHV             GGCACATATGAAATGTATGTGAAATGGCCTTGGTATGTGTGGTTGCTAATTGGATTAGCT
RtCoV           GGCACATATGAGATGTATGTGAAATGGCCTTGGTATGTTTGGCTGCTAATTGGATTAGCT
IBV             TCAATACTCAAAACTTATATTAAGTGGCCTTGGTATGTGTGGTTAGCCATAGCTTTTGCC
                          *    **  * ** ***** ****  ** *** *     *     * *

CcoV            GTAATATTCTGCATACCCATATTGCTATTTGTTGTTGTAGTACTGGTTGTTGTGGATGT
FcoV            GTAGTATTTTGCATACCATTACTGCTATTTGCTGTTTTAGCACAGGTTGTTGTGGATGT
TGE             GTAATATTTTGCATACCATTACTGCTATTTGCTGTTGTAGTACAGGTTGCTGTGGATGC
PRCoV           GTAATATTTTGCATACCATTACTGCTATTTGCTGTTGTAGTACAGGTTGCTGTGGATGC
HCoVOC43        CTCATCTTTGTGGTGAGTATGTTGCTATTATGTTGTTGTTCTACTGGTTGCTGTGGCTTC
PEDV            CTCATCTTTGTTGTGTCATTACTAGTGTTCTGCTGCATTTCCACGGGTTGTTGTGGATGC
SARSUrba        GGACTAATTGCCATCGTCATGGTTACAATCTTGCTTTGTTGCATGACTAGTTGTTGCAGT
SARSTor2        GGACTAATTGCCATCGTCATGGTTACAATCTTGCTTTGTTGCATGACTAGTTGTTGCAGT
BcoV            GGTGTAGCTATGCTTGTTTTACTATTCTTCATATGCTGTTGTACAGGATGTGGGACTAGT
HEV             GGTGTAGCTATGCTTGTTTTACTATTCTTCATATGCTGCTGTACAGGATGTGGGACTAGT
MHV             GGTGTAGCTGTTTGTGTGTTGTTATTTTTCATATGTTGCTGCACGGGTTGTGGCTCATGT
RtCoV           GGTGTAGCTGTTTGTGTTTTGTTATTTTTTATATGTTGCTGCACAGGTTGTGGCTCTTGT
IBV             ACTATTATCTTCATCTTAATACTAGGATGGGTTTTCTTCATGACTGGTTGTTGTGGTTGT
                    *              *  *                   *      *  *

CcoV            ATCGGGTGTTTAGGAAGCTGTTGTCATTCCATAT-GTAGTAGAGGCCA---ATTTGAAAG
FcoV            ATAGGTTGTTTAGGAAGTTGTTGTCACTCTATAT-GTAGTAGAAGACA---ATTTGAAAA
TGE             ATAGGTTGTTTAGGAAGTTGTTGTCACTCTATAT-GTAGTAGAAGACA---ATTTGAAAA
PRCoV           ATAGGTTGTTTAGGAAGTTGTTGTCACTCTATAT-TCAGTAGAAGACA---ATTTGAAAA
HCoVOC43        TTTAGTTGTTTTGCATCTTCTATTAGAGGTTGTT-GTGAATCAACTAA---ACTTCCTTA
PEDV            TGCGGTTGCTGCGGTGCTTGTTTTTCAGGTTGTT-GTAGGGGTCCTAG---ACTTCAACC
SARSUrba        TGCCTCAAGGGTGCATGCTCTTGTGGTTCTTGCT-GCAAGTTTGATGA---GGATGACTC
SARSTor2        TGCCTCAAGGGTGCATGCTCTTGTGGTTCTTGCT-GCAAGTTTGATGA---GGATGACTC
BcoV            TGTTTTAAGAT---ATG---TGGTGGTTGTTGTG-ATGATTATACTGG---ACACCAGG-
HEV             TGTTTTAAGAA---ATG---TGGCGGTTGTTGTG-ATGATTATACTGG---ACACCAGG-
MHV             TGTTTCAAGAA---GTG---TGGAAATTGTTGTG-ATGAGTGTGGAGG---ACACCAGGA
RtCoV           TGTTTTAAGAA---ATG---TGGAAATTGTTGTG-ATGAGTATGGAGG---ACGTCAGGC
IBV             TGTTGTGGATGC-TTTGGCATTATGCCTCTAATGAGTAAGTGTGGTAAGAAATCTTCTTA
                                    *

CcoV            TTATGAACCTATTGAAAAAGTTCATGTTCACTGA--------------------------
FcoV            TTATGAACCAATTGAAAAAGTGCATGTCCACTAA--------------------------
TGE             TTACGAACCAATTGAAAAAGTGCACGTCCATTAA--------------------------
PRCoV           TTATGAACCTATTGAAAAAGTGCACGTCCATTAA--------------------------
```

```
HCoVOC43     TTACGACG---TTGAAAAGATCCACATACAGTAA-------------------------
PEDV         TTACGAAGCTTTTGAAAAGGTCCACGTGCAGTGA-------------------------
SARSUrba     TGAGCCAGTTCTCAAGGGTGTCAAATTACATTACACATAA-------------------
SARSTor2     TGAGCCAGTTCTCAAGGGTGTCAAATTACATTACACATAA-------------------
BcoV         -AGT-TAGTAAT-TAAAA-----CATCACATGACGACTAA-------------------
HEV          -AGT-TTGTAAT-CAAAA-----CTTCACATGACGATTAA-------------------
MHV          CAGTATTGTGATACATAATATTTCCTCTCATGAGGATTGA-------------------
RtCoV        AGGTATTGTGATACATAATATTTCCTCTCATGAGGATTGA-------------------
IBV          TTACACGACTTTTGATAACGATGTGGTAACTGAACAATACAGACCTAAAAAGTCTGTTTG
                         *   *

CcoV         -
FcoV         -
TGE          -
PRCoV        -
HCoVOC43     -
PEDV         -
SARSUrba     -
SARSTor2     -
BcoV         -
HEV          -
MHV          -
RtCoV        -
IBV          A
```

Figure 4: List of Molecular Designs for S Gene

LK249 5'-FAM-CCCACGCCAGAAGGTAGATCACGAACTACACGTGGG-3'-Dubcyl

LK249.N 5'-FAM-GCCCACGCCAGAAGGTAGATCACGAACTACACGTGGGC-3'-Dubcyl

LK250

5'-CTCTATGTTTATAAGGGCTATCAACCTATAGATGTAGTTCGTGATCTA
CCTTCTGGTTTTAACACTTTGAAACCTATTTTTAAGTTGCCTCTTGG -3'

LK251 5'-CTCTATGTTTATAAGGGCTATCAACC-3'

LK251-T7 5'-TAATACGACTCACTATAGGCTCTATGTTTATAAGGGCTATCAACC-3'

LK252 5'-CCAAGAGGCAACTTAAAAATAGGTTTC- 3'

LK252-RT 5'- AGGCTGTAAGAACCAAGAGGCAACTTAAAAATAGGTTTC- 3'

S-RT 5'-AGGCTGTAAGAA-3'

Figure 5: **CLUSTAL W (1.81) multiple DNA sequence alignment of coronavirus *E* genes from strains isolated from different species**

```
SARS-Urb    ------------------------------------------------------------
SARS-Tor    ------------------------------------------------------------
HCoOC43     ------------------------------------------------------------
PEDV        ------------------------------------------------------------
TGE         ------------------------------------------------------------
PRCoV       ------------------------------------------------------------
CcoV        ------------------------------------------------------------
FcoV        ------------------------------------------------------------
MHV         ------------------------------------------------------------
RtCoV       ------------------------------------------------------------
BcoV        ------------------------------------------------------------
IBV         ATGAATTTATTGAATAAGTCGCTAGAGGAGAATGGAAGTTTTCTAACAGCGCTTTACATA

SARS-Urb    ----------ATGTACTCATTCGTTTCGGAAGAAACAGGTACGTTAATAGTTAATAGCGT
SARS-Tor    ----------ATGTACTCATTCGTTTCGGAAGAAACAGGTACGTTAATAGTTAATAGCGT
HCoOC43     ------------ATGTTCCTTAAGCTAGTGGATGATCA-TGCTTTGGTTGTTAATGTACT
PEDV        ---------------ATGCTACAATTAGTGAATGATAA-TGGTCTAGTAGTTAATGTTAT
TGE         ATGACGTTTCCTAGGGCATTGACTGTCATAGATGACAA-TGGAATGGTCATTAACATCAT
PRCoV       ATGACGTTTCCTAGGGCATTGACTGTCATAGATGACAA-CGGAATGGTCATTAGCATCAT
CcoV        ATGACGTTCCCTCGGGCATTGACTGTCATAGATGACAA-TGGAATGGTCATTAGTATCAT
FcoV        ATGACGTTCCCTAGGGCATTTACTATCATAGATGACCA-TGGCATGGTTGTTAGCGTCTT
MHV         ---------ATGTTTAATTTATTCCTTACAGATACAGTATGGTATGTGGGGCAG-ATTAT
RtCoV       ---------ATGTTTAATTTATTCCTTATAGACACAGTATGGTACGTGGGGCAG-ATTAT
BcoV        ---ATGTTTATGGCTGATGCTTATTTTGCAGACACTGTGTGGTATGTGGGGCAA-ATAAT
IBV         ATTGTAGGATTTTTAGCACTTTATCTTCTAGGTA--GAGCACTTCAAGCATTTGTACAGG
                                     *

SARS-Urb    ACTTCTTTTTCTTGCTTTCGTGGTATT-------CTTGCTAGTCACACTAGCCATCCTTA
SARS-Tor    ACTTCTTTTTCTTGCTTTCGTGGTATT-------CTTGCTAGTCACACTAGCCATCCTTA
HCoOC43     ACTCTGGTGTGTGGTGCTTATAGTGAT-------ACTACTAGTGTGTATTACAATAATTA
PEDV        ACTTTGGCTTTTCGTACTCTTTTTCCT-------GCTTATTATAAGCATTACCTTCGTCC
TGE         TTTCTGGTTCCTGTTGATAATTATATT-------GATATTACTTTCAATAGCATTGCTAA
PRCoV       TTTTTGGTTCCTGTTGATAATTATATT-------GATATTACTTTCAATAGCATTGCTAA
CcoV        TTTCTGGTTCCTGTTGATAATTATATT-------GATATTATTTTCAATAGCATTGCTAA
FcoV        CTTCTGGCTCCTGTTGATAATTATATT-------GATATTGTTTTCAATAGCATTGCTAA
MHV         TTTTATAGTCGCAGTGTGTTTGATGGT-------CACCATAATAGTGGTTGCCTTCCTTG
RtCoV       TTTTATAGTCGCAGTGTGTTTGATGGT-------CACCATAATTGTGGTTGCCTTCCTTG
BcoV        TTTTATAGTTGCCATTTGTTTATTGGT-------TATAATAGTTGTAGTGGCATTTTTGG
IBV         CTGCTGATGCTTGTTGTTTATTTTGGTATACATGGGTAGTAATTCCAGGAGCTAAGGGTA
                                *  *  *            *  *        *

SARS-Urb    CTGCGCTTCGATT---GTGTGCGTACTGCTGCAATATTGTTAACGTGAGTTTAGTAAAAC
SARS-Tor    CTGCGCTTCGATT---GTGTGCGTACTGCTGCAATATTGTTAACGTGAGTTTAGTAAAAC
HCoOC43     AACTAATTAAGCT---TTGTTTCACTTGCCATATGTTTTGTAATAGAACAGTTTATGGCC
PEDV        AATTGGTTAATCT---GTGCTTCACTTGTCACCGGTTGTGTAATAGCGCAGTTTATACAC
TGE         ATATAATTAAGCT---ATGCATGGTGTGTTGCAATTTAGGAAGGACAGTTATTATTGTTC
PRCoV       ATATAATTAAGCT---ATGCATGGTGTGTTGCAATTTAGGAAGGACAGTTATTATTGTTC
CcoV        ATATAATTAAGCT---ATGCATGGTATGTTGCAATTTAGGAAGAACAGTTATTATTGTTC
FcoV        ATGTTATTAAATT---GTGCATGGTATGTTGCAATTTGGGTAAGACTATTATAGTACTAC
MHV         CGTCTATCAAACT---TTGTATTCAACTTTGCGGTTTGTGTAATACTTTGTTGCTGTCTC
RtCoV       CGTCTATTAAACT---TTGTATTCAACTTTGCGGTTTGTGTAATACTTTGTTGCTGTCTC
BcoV        CAACTTTTAAATT---GTGTATTCAACTTTGCGGTATGTGTAATACCTTAGTACTGTCCC
IBV         CAGCCTTTGTATACAAGTATACATATGGTAGAAAACTTAACAATCCGGAATTAGAAGCAG
                  *          *                  *    *         *

SARS-Urb    CAACGGTTTACGTCTAC--TCGCGTG--TTAAAAATCTGAACTCTTCTGAAGGA------
SARS-Tor    CAACGGTTTACGTCTAC--TCGCGTG--TTAAAAATCTGAACTCTTCTGAAGGA------
```

```
HCoOC43      CCATTAAAAATGTGTA---CCACATT--TACCAATCATATATGCACATAGACCC-----T
PEDV         CTATAGGGCGCCTGTA---TAGAGTT--TATAAGTCTTACATGCGAATTGACCC-----C
TGE          CAGCGCAACATGCTTA---CGATGCC--TATAAGAATTTTATGCGAATTAAAGCAT--AC
PRCoV        CAGTGCAACATGCTTA---CGATGCC--TATAAGAATTTTATGCGAATTAAAGCAT--AC
CcoV         CAGCTCGACATGCCTA---TGATGCC--TATAAGAATTTTATGCAAATTAGAGCAT--AC
FcoV         CTGCACGCCATGCATA---TGATGCC--TATAAGACCTTTATGCAAACCAAGGCAT--AT
MHV          CTTCTATTTGTGTGTATAATAGGAGT--AAGCAGCTTTATAAGTATTATAATGAAGAAGT
RtCoV        CTTCTATTTATGTGTATAATAGGAGT--AAGCAGCTTTATAAGTATTATAATGAAGAAGT
BcoV         CTTCTATTTATGTGTTTAATAGAGGT--AGGCAGTTTTATGAGTTTTACAACGAT---GT
IBV          TTATTGTTAACGAGTTTCCTAAGAACGGTTGGAATAATAAAAATCCAGCAAATTTTCAAG
                             *                 *   *

SARS-Urb     GTTCCTGATCTTCTGGTCTAA---------------------------
SARS-Tor     GTTCCTGATCTTCTGGTCTAA---------------------------
HCoOC43      TTCCCTAAACGAGTTATTGATTTCTAA---------------------
PEDV         CTCCCCAGTACTGTTATTGACGTATAA---------------------
TGE          AACCCCGATGGAGCACTCCTTGCTTGA---------------------
PRCoV        AACCCTGATGGAGCACTCCTTGTTTGA---------------------
CcoV         AACCCTGATGAAGCACTCCTTGTTTGA---------------------
FcoV         AATCCCGACGAAGCATTTTTGGTTTGA---------------------
MHV          GAGACCGCCCCCGTTAGAGGTGGATGATATAATAATCCAAACATTATGA
RtCoV        GAGACCGCCCCCGTTAGAGGTGGATGATATAATAATCCAAACATTATGA
BcoV         AAAACCACCAGTTCTTGATGTGGATGACGTT-TAG-------------
IBV          ATGCCCAACGAGACAAATTGTACTCTTGA-------------------
                *
```

Figure 6: **Phylogenetic Analysis of *E* Gene**
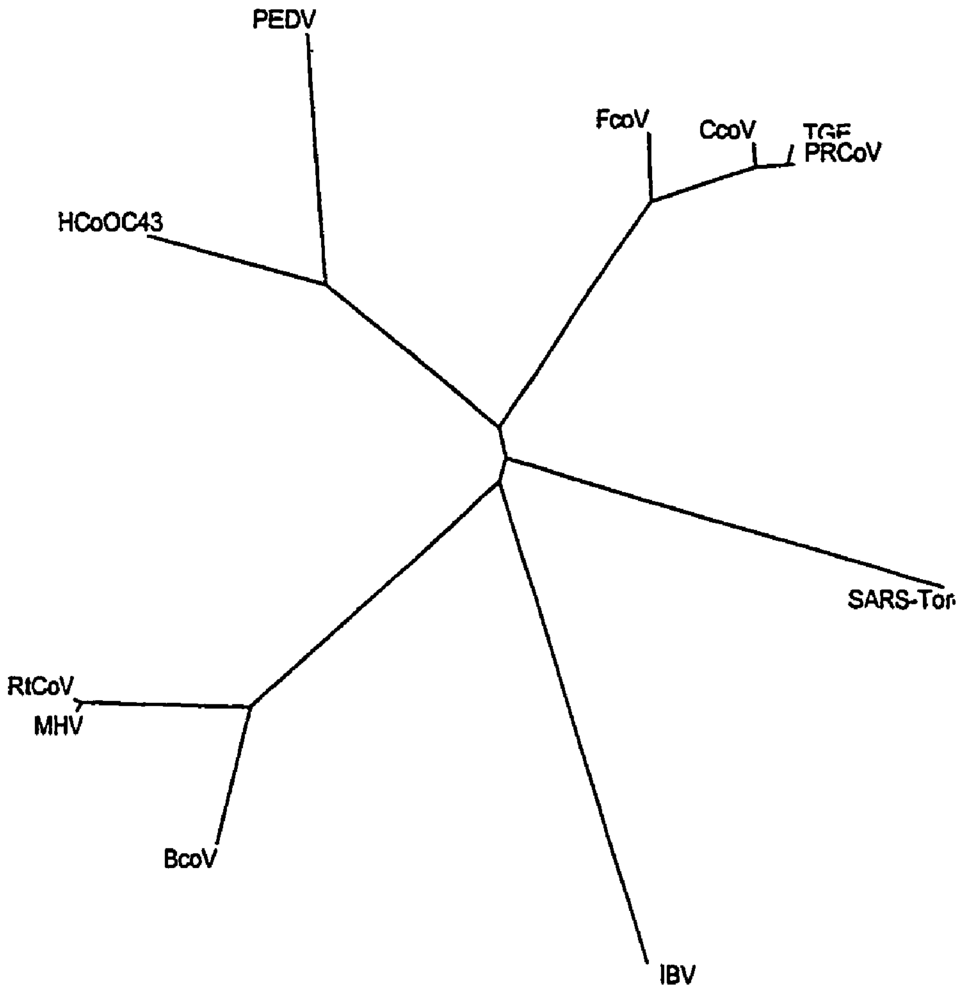

Figure 7: Molecular Designs for SARS-Associated *E* Gene

| | |
|---|---|
| NOTE: | LK253 is a TET-molecular beacon, which recognizes the *E* **gene of coronavirus (SARS Tor2 and SARS urbani human pathogenic strains)**. It will be used in a real-time PCR diagnostic for the identification of **SARS-associated coronavirus RNA/DNA**. |

Beacon LK253

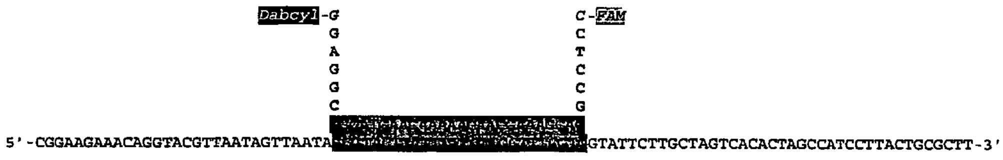

Amplicon LK254

LK253

| | | |
|---|---|---|
| **E.** | Target recognition sequence: | **26 nucleotides (11 G/C)** |
| **F.** | Length of the arms: | **6 nucleotides (5 G/C)** |
| **G.** | Melting temperature of the beacon: | **dG = -2.29 dH = -67.2 dS = -200.8 Tm = 61.5 °C** |
| **H.** | Melting temperature of target: | **°C** |

LK255 5'-CGGAAGAAACAGGTACGTTAATAG-3'

Length: 24 nucleotides (10 G/C)
*Tm*: °C
Position: (see alignment below)

LK256 5' –AAGCGCAGTAAGGATGGCTA-3'

Length: 20 nucleotides (10 G/C)
*Tm*: °C
Position: (see alignment below)

E-RT 5' –TATTGCAGCAGTAC-3'

Length: 14 nucleotides (10 G/C)
*Tm*: 47 °C
Position: (see alignment below)

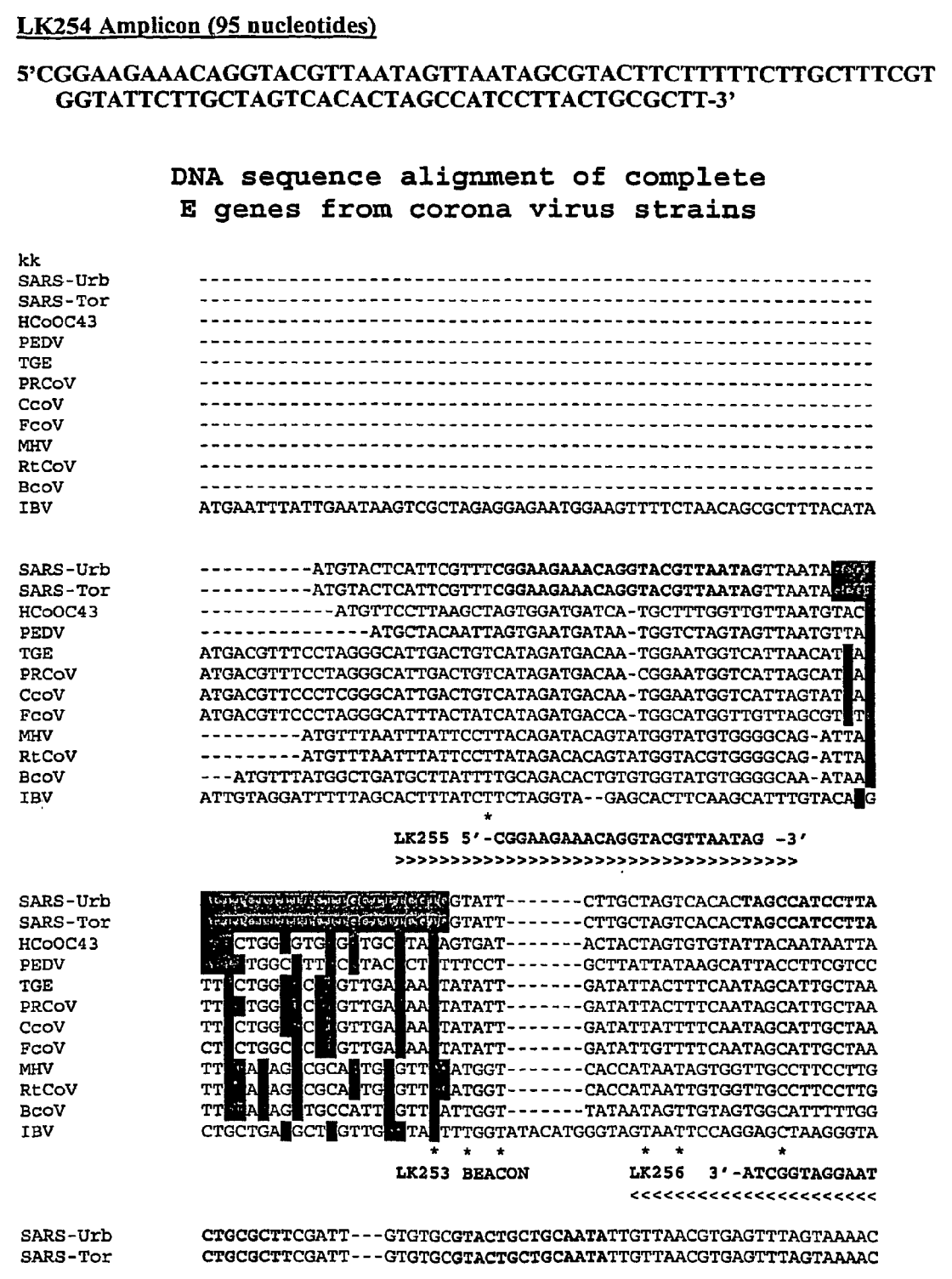

LK254 Amplicon (95 nucleotides)

5'CGGAAGAAACAGGTACGTTAATAGTTAATAGCGTACTTCTTTTTCTTGCTTTCGT GGTATTCTTGCTAGTCACACTAGCCATCCTTACTGCGCTT-3'

DNA sequence alignment of complete E genes from corona virus strains

```
kk
SARS-Urb   ------------------------------------------------------------
SARS-Tor   ------------------------------------------------------------
HCoOC43    ------------------------------------------------------------
PEDV       ------------------------------------------------------------
TGE        ------------------------------------------------------------
PRCoV      ------------------------------------------------------------
CcoV       ------------------------------------------------------------
FcoV       ------------------------------------------------------------
MHV        ------------------------------------------------------------
RtCoV      ------------------------------------------------------------
BcoV       ------------------------------------------------------------
IBV        ATGAATTTATTGAATAAGTCGCTAGAGGAGAATGGAAGTTTTCTAACAGCGCTTTACATA

SARS-Urb   ----------ATGTACTCATTCGTTTCGGAAGAAACAGGTACGTTAATAGTTAATA[illegible]
SARS-Tor   ----------ATGTACTCATTCGTTTCGGAAGAAACAGGTACGTTAATAGTTAATA[illegible]
HCoOC43    ------------ATGTTCCTTAAGCTAGTGGATGATCA-TGCTTTGGTTGTTAATGTAC
PEDV       ---------------ATGCTACAATTAGTGAATGATAA-TGGTCTAGTAGTTAATGTTA
TGE        ATGACGTTTCCTAGGGCATTGACTGTCATAGATGACAA-TGGAATGGTCATTAACAT A
PRCoV      ATGACGTTTCCTAGGGCATTGACTGTCATAGATGACAA-CGGAATGGTCATTAGCAT A
CcoV       ATGACGTTCCCTCGGGCATTGACTGTCATAGATGACAA-TGGAATGGTCATTAGTAT A
FcoV       ATGACGTTCCCTAGGGCATTTACTATCATAGATGACCA-TGGCATGGTTGTTAGCGT T
MHV        ---------ATGTTTAATTTATTCCTTACAGATACAGTATGGTATGTGGGGCAG-ATTA
RtCoV      ---------ATGTTTAATTTATTCCTTATAGACACAGTATGGTACGTGGGGCAG-ATTA
BcoV       ---ATGTTTATGGCTGATGCTTATTTTGCAGACACTGTGTGGTATGTGGGGCAA-ATAA
IBV        ATTGTAGGATTTTTAGCACTTTATCTTCTAGGTA--GAGCACTTCAAGCATTTGTACA G
                                           *
                               LK255 5'-CGGAAGAAACAGGTACGTTAATAG -3'
                               >>>>>>>>>>>>>>>>>>>>>>>>>>>>>>>>>>>>>>

SARS-Urb   [illegible]GTATT-------CTTGCTAGTCACACTAGCCATCCTTA
SARS-Tor   [illegible]GTATT-------CTTGCTAGTCACACTAGCCATCCTTA
HCoOC43      CTGG GTG G TGC TA AGTGAT-------ACTACTAGTGTGTATTACAATAATTA
PEDV          TGGC TT C TAC CT TTTCCT-------GCTTATTATAAGCATTACCTTCGTCC
TGE        TT CTGG  C  GTTGA AA TATATT-------GATATTACTTTCAATAGCATTGCTAA
PRCoV      TT  TGG  C  GTTGA AA TATATT-------GATATTACTTTCAATAGCATTGCTAA
CcoV       TT CTGG  C  GTTGA AA TATATT-------GATATTATTTTCAATAGCATTGCTAA
FcoV       CT CTGGC C  GTTGA AA TATATT-------GATATTGTTTTCAATAGCATTGCTAA
MHV        TT  A AG CGCA TG GTT  ATGGT-------CACCATAATAGTGGTTGCCTTCCTTG
RtCoV      TT  A AG CGCA TG GTT  ATGGT-------CACCATAATTGTGGTTGCCTTCCTTG
BcoV       TT  A AG TGCCATT GTT ATTGGT-------TATAATAGTTGTAGTGGCATTTTTGG
IBV        CTGCTGA GCT GTTG  TA TTTGGTATACATGGGTAGTAATTCCAGGAGCTAAGGGTA
                                  *  *  *          *  *        *
                               LK253 BEACON       LK256  3'-ATCGGTAGGAAT
                                                  <<<<<<<<<<<<<<<<<<<<<<<<

SARS-Urb   CTGCGCTTCGATT---GTGTGCGTACTGCTGCAATATTGTTAACGTGAGTTTAGTAAAAC
SARS-Tor   CTGCGCTTCGATT---GTGTGCGTACTGCTGCAATATTGTTAACGTGAGTTTAGTAAAAC
```

```
HCoOC43    AACTAATTAAGCT---TTGTTTCACTTGCCATATGTTTTGTAATAGAACAGTTTATGGCC
PEDV       AATTGGTTAATCT---GTGCTTCACTTGTCACCGGTTGTGTAATAGCGCAGTTTATACAC
TGE        ATATAATTAAGCT---ATGCATGGTGTGTTGCAATTTAGGAAGGACAGTTATTATTGTTC
PRCoV      ATATAATTAAGCT---ATGCATGGTGTGTTGCAATTTAGGAAGGACAGTTATTATTGTTC
CcoV       ATATAATTAAGCT---ATGCATGGTATGTTGCAATTTAGGAAGAACAGTTATTATTGTTC
FcoV       ATGTTATTAAATT---GTGCATGGTATGTTGCAATTTGGGTAAGACTATTATAGTACTAC
MHV        CGTCTATCAAACT---TTGTATTCAACTTTGCGGTTTGTGTAATACTTTGTTGCTGTCTC
RtCoV      CGTCTATTAAACT---TTGTATTCAACTTTGCGGTTTGTGTAATACTTTGTTGCTGTCTC
BcoV       CAACTTTTAAATT---GTGTATTCAACTTTGCGGTATGTGTAATACCTTAGTACTGTCCC
IBV        CAGCCTTTGTATACAAGTATACATATGGTAGAAAACTTAACAATCCGGAATTAGAAGCAG
                 *          *                  *    *         *
           GACGCGAA-5'        3'-CATGACGACGTTAT-5' E-RT
           <<<<<<<<<<


SARS-Urb   CAACGGTTTACGTCTAC--TCGCGTG--TTAAAAATCTGAACTCTTCTGAAGGA------
SARS-Tor   CAACGGTTTACGTCTAC--TCGCGTG--TTAAAAATCTGAACTCTTCTGAAGGA------
HCoOC43    CCATTAAAAATGTGTA---CCACATT--TACCAATCATATATGCACATAGACCC-----T
PEDV       CTATAGGGCGCCTGTA---TAGAGTT--TATAAGTCTTACATGCGAATTGACCC-----C
TGE        CAGCGCAACATGCTTA---CGATGCC--TATAAGAATTTTATGCGAATTAAAGCAT--AC
PRCoV      CAGTGCAACATGCTTA---CGATGCC--TATAAGAATTTTATGCGAATTAAAGCAT--AC
CcoV       CAGCTCGACATGCCTA---TGATGCC--TATAAGAATTTTATGCAAATTAGAGCAT--AC
FcoV       CTGCACGCCATGCATA---TGATGCC--TATAAGACCTTTATGCAAACCAAGGCAT--AT
MHV        CTTCTATTTGTGTGTATAATAGGAGT--AAGCAGCTTTATAAGTATTATAATGAAGAAGT
RtCoV      CTTCTATTTATGTGTATAATAGGAGT--AAGCAGCTTTATAAGTATTATAATGAAGAAGT
BcoV       CTTCTATTTATGTGTTTAATAGAGGT--AGGCAGTTTTATGAGTTTTACAACGAT---GT
IBV        TTATTGTTAACGAGTTTCCTAAGAACGGTTGGAATAATAAAAATCCAGCAAATTTTCAAG
                         *                 *    *

SARS-Urb   GTTCCTGATCTTCTGGTCTAA----------------------------
SARS-Tor   GTTCCTGATCTTCTGGTCTAA----------------------------
HCoOC43    TTCCCTAAACGAGTTATTGATTTCTAA----------------------
PEDV       CTCCCCAGTACTGTTATTGACGTATAA----------------------
TGE        AACCCCGATGGAGCACTCCTTGCTTGA----------------------
PRCoV      AACCCTGATGGAGCACTCCTTGTTTGA----------------------
CcoV       AACCCTGATGAAGCACTCCTTGTTTGA----------------------
FcoV       AATCCCGACGAAGCATTTTTGGTTTGA----------------------
MHV        GAGACCGCCCCCGTTAGAGGTGGATGATATAATAATCCAAACATTATGA
RtCoV      GAGACCGCCCCCGTTAGAGGTGGATGATATAATAATCCAAACATTATGA
BcoV       AAAACCACCAGTTCTTGATGTGGATGACGTT-TAG--------------
IBV        ATGCCCAACGAGACAAATTGTACTCTTGA--------------------
               *
```

**Figure 8: Molecular Designs for SARS-Associated *E* Gene**

LK253 5'-FAM-CCTCCGCACGAAAGCAAGAAAAAGAAGTACGCCGGAGG-3'-Dubcyl

LK253.N 5'-FAM-GCCTCCGCACGAAAGCAAGAAAAAGAAGTACGCCGGAGGC-3'-Dubcyl

LK254 5'-CGGAAGAAACAGGTACGTTAATAGTTAATAGCGTACTTCTTTTTC
TTGCTTTCGTGGTATTCTTGCTAGTCACACTAGCCATCCTTACTGCGCTT
-3'

LK255 5'- CGGAAGAAACAGGTACGTTAATAG -3'

LK255-T7 5'-TAATACGACTCACTATAGGCGGAAGAAACAGGTACGTTAATAG -3'

LK256 5'- AAGCGCAGTAAGGATGGCTA - 3'

LK256-RT 5'- TATTGCAGCAGTACAAGCGCAGTAAGGATGGCTA - 3'

E-RT 5' –TATTGCAGCAGTAC-3'

**Figure 9: DNA Sequence Alignment of Coronavirus *M* Genes Isolated from different Species**

```
TGE          ------------------------------------------------------------
PRCoV        ------------------------------------------------------------
CcoV         ------------------------------------------------------------
FCoV         ATGCATATGATGCCTATAAGACCTTTATGCAAACCAAGGCATATAATCCCGACGAAGCAT
HCoVOC43     ------------------------------------------------------------
PEDV         ------------------------------------------------------------
BCoV         ------------------------------------------------------------
HEV          ------------------------------------------------------------
MHV          ------------------------------------------------------------
RtCoV        ------------------------------------------------------------
SARS-Urb     ------------------------------------------------------------
SARS-Tor     ------------------------------------------------------------
IBV          ------------------------------------------------------------

TGE          ------------------------ATGAAGATTTTGTTAATATTAGCGTGTGTGATTGCA
PRCoV        ------------------------ATGAAGATTTTGTTGATATTAGCGTGTGCGATTGCA
CcoV         ---------------------ATGAAGAAAATTTTGTTTTTACTAGCGTGTGCAATTGCA
FCoV         TTTTGGTTTGAACTAAACAAAATGAAGTACATTTTGCTAATACTCGCGTGCATAATTGCA
HCoVOC43     ------------------------------------------------------------
PEDV         ------------------------------------------------------------
BCoV         ------------------------------------------------------------
HEV          ------------------------------------------------------------
MHV          ------------------------------------------------------------
RtCoV        ------------------------------------------------------------
SARS-Urb     ------------------------------------------------------------
SARS-Tor     ------------------------------------------------------------
IBV          ------------------------------------------------------------

TGE          TGCGCATGTGGAGAACGCTATTGTGCTATGAAATCCGATACAGATTTGTCATGTCGCAAT
PRCoV        TGCACATGTGGAGAACGCTATTGTGCTATGAAAGACGATACAGGTTTGTCATGTCGCAAT
CcoV         TGCGTCTATGGAGAACGCTATTGTGCCATGA---CTGAAAGTTCTACGTCATGTCGTAAT
FCoV         TGCGTTTATGGTGAACGCTACTGTGCCATGCAA---GACAGTGGCTTGCAGTGTATTAAT
HCoVOC43     ------------------------------------------------------------
PEDV         ------------------------------------------------------------
BCoV         --------------------------------------------------ATGAGTAGTG
HEV          --------------------------------------------------ATGAGTAGTC
MHV          --------------------------------------------------ATGACTAGTA
RtCoV        --------------------------------------------------ATGAGTAGTA
SARS-Urb     ------------------------------------------------------------
SARS-Tor     ------------------------------------------------------------
IBV          ------------------------------------------------------------

TGE          AGTACAGCGTCTGATTGTGAGTCA--TGCTTCAACGGAGGCGATCTTATTTGGCATCTTG
PRCoV        GGCACGGCGTCTGATTGTGAGTCA--TGCTTCAACAGAGGCGATCTTATTTGGCTTCTTG
CcoV         AGCACGGCTGGCAACTGTGCTTCA--TGCTTCGAAACAGGTGATCTTATTTGGCATCTTG
FCoV         GGCACAAATTCAAGATGTCAAACC--TGCTTTGAACGTGGTGATCTTATTTGGCATCTTG
HCoVOC43     --------------ATGTCAAATG---ACAATTGTACGGGTGACATTGTCACCCATTTGA
PEDV         --------------ATGTCTAACGGTTCTATTCCCGTTGATGAGGTGATTGAACACCTTA
BCoV         TAACT---ACACCAGCACCAGTTTACACCTGGACTGCTGATGAAGCTATTAAATTCCTAA
HEV          CAACT---ACACCAGTACCAGTTATTAGCTGGACTGCTGATGAAGCTATTAAATTCCTAA
MHV          CCACTCAGGCTCCACAGCCTGTTTATCAGTGGACGGCTGATGAGGCAATTCGATTCCTTA
RtCoV        CCACTCCAGCCCCCCAGACTGTCTATCAATGGACGGCCGATGTGGCAGTTCGATTCCTTA
SARS-Urb     --TTGCTTATCATGGCAGACAACGGTACTATTACCGTTGAGGAGCTTAAACAACTCCTGG
SARS-Tor     --TTGCTTATCATGGCAGACAACGGTACTATTACCGTTGAGGAGCTTAAACAACTCCTGG
```

```
IBV            -----ATGCCCAACGAGACAAATTGTACTCTTGACTTTGAACAGTCAGTTCAGCTTTTTA
                                                     *                  *

TGE            CAAACTGGAACTTCAGCTGGTCTATAATATTGATCGTTTTTATAACTGTGCTACAATATG
PRCoV          CAAACTGGAACTTCAGCTGGTCTATAATATTGATCATTTTTATTACTGTGCTACAATATG
CcoV           CAAACTGGAACTTCAGCTGGTCTGTAATATTGATCATTTTTATAACAGTGTTACAATATG
FCoV           CTAACTGGAACTTCAGCTGGTCTGTAATATTGATTGTTTTTATAACAGTGTTACAATATG
HCoVOC43       AGAATTGGAATTTTGGTTGGAATGTTATTCTAACCATATTCATTGTTATTCTTCAGTTTG
PEDV           GAAACTGGAATTTCACATGGAATATCATACTGACGATACTACTTGTAGTGCTTCAGTATG
BCoV           AGGAATGGAACTTTTCTTTGGGTATTATACTACTTTTTATTACAATCATATTGCAATTTG
HEV            AGGAATGGAATTTTTCTTTGGGTATAATAGTACTCTTTATCACAATCATACTTCAATTTG
MHV            AGGAATGGAATTTCTCTCTCGGCATTATACTACTTTTTGTTACTATCATACTACAGTTCG
RtCoV          AGGAATGGAACTTCTTGTTGGGCATTATACTACTCTTTATTACTATCATACTACAGTTCG
SARS-Urb       AACAATGGAACCTAGTAATAGGTTTCCTATTCCTAGCCTGGATTATGTTACTACAATTTG
SARS-Tor       AACAATGGAACCTAGTAATAGGTTTCCTATTCCTAGCCTGGATTATGTTACTACAATTTG
IBV            AAGAGTATAATTTATTTATAACTGCATTCTTGTTGTTCTTAACCATAATACTTCAGTATG
                  * *  **  *              *  *                 *  * ** *  *

TGE            GAAGACCTCAATTCAGCTGGTTCGTGTATGGCATTAAAATGCTTATAATGTGGCTATTAT
PRCoV          GAAGACCTCAATTCAGCTGGTTCGTGTATGGCATTAAAATGCTTATAATGTGGCTATTAT
CcoV           GAAGACCTCAATTTAGCTGGTTCGTGTGTGGCATTAAAATGCTTATTATGTGGCTGTTAT
FCoV           GCAGACCACAATTTAGCTGGCTCGTTTATGGCATTAAAATGCTGATCATGTGGCTATTAT
HCoVOC43       GACACTATAAATACTCCAGATTGTTTTATGGTTTGAAGATGCTTGTACTGTGGCTTCTTT
PEDV           GCCATTACAAGTACTCTGTGTTCTTGTATGGTGTCAAGATGGCTATTCTATGGATACTTT
BCoV           GATATACAAGTCGCAGTATGTTTGTTTATGTTATTAAGATGATCATTTTGTGGCTTATGT
HEV            GATATACAAGTCGCAGTATGTTTGTTTATGTTATTAAGATGGTTATTCTGTGGCTCATGT
MHV            GTTACACGAGCCGTAGCATGTTTGTTTATGTTGTGAAAATGATACTTTTGTGGCTTATGT
RtCoV          GTTACACGAGCCGTAGCATGTTTATATATGTTGTGAAAATGATAATCTTGTGGTTAATGT
SARS-Urb       CCTATTCTAATCGGAACAGGTTTTTGTACATAATAAAGCTTGTTTTCCTCTGGCTCTTGT
SARS-Tor       CCTATTCTAATCGGAACAGGTTTTTGTACATAATAAAGCTTGTTTTCCTCTGGCTCTTGT
IBV            GCTATGCAACAAGAAGTAAGGTTATTTATACACTGAAAATGATAGTGTTATGGTGCTTTT
                                    *  * *      * **  *     *  * ***     **

TGE            GGCCCGTTGTTTTGGCTCTTACGATTTTTAATGCATACTCGGAATACCAAGTGTCCAGAT
PRCoV          GGCCGATTGTTTTGGCTCTTACGATTTTTAATGCATACTCGGAATACCAAGTGTCCAGGT
CcoV           GGCCCATTGTTTTAGCTCTTACGATTTTTAATGCATACCTGGAATACCGAGTTTCCAGAT
FCoV           GGCCTATTGTTCTAGCGCTTACGATTTTTAATGCATACTCTGAGTACCAAGTTTCCAGAT
HCoVOC43       GGCCACTCGTACTTGCTTTGTCAATCTTTGACAC---CTGGGCTAATTGGGATTCTAATT
PEDV           GGCCTCTTGTGTTGGCACTGTCACTTTTTGACGCATGGGCTAGCTTCCAGGT---CAACT
BCoV           GGCCCCTTACTATCATCTTAACTATTTTCAAT------TGCGTGTAT---GCGTTGAATA
HEV            GGCCTCTTACTATAATTTTAACTATCTTCAAC------TGCGTATAC---GCGTTGAATA
MHV            GGCCACTAACTATTGTTTTGTGTATTTTTAAC------TGCGTCTAT---GCGCTAAATA
RtCoV          GGCCACTGACTATTGTTTTGTGTATTTTTAAT------TGCGTGTAT---GCGCTAAATA
SARS-Urb       GGCCAGTAACACTTGCTTGTTTTGTGCTTGCTG------CTGTCTACAGAAT---TAATT
SARS-Tor       GGCCAGTAACACTTGCTTGTTTTGTGCTTGCTG------CTGTCTACAGAAT---TAATT
IBV            GGCCCCTTAACATTGCAGTAGGTGTAATTTCA------TGTACATACC---CACCAAACA
               ****  *     *           *  *                            *

TGE            ATGTAATGTTCGGCTTTAGTATTGCAGGTGCAATTGTTACATTTGTACTCTGGATTATGT
PRCoV          ATGTAATGTTCGGCTTTAGTATTGCAGGTGCAATTGTTACATTTGTACTCTGGATTATGT
CcoV           ATGTAATGTTCGGCTTTAGTGTTGCAGGTGCAACTGTTACATTTATACTTTGGATTATGT
FCoV           ATGTAATGTTCGGCTTTAGTGTTGCAGGTGCAGTTGTAACGTTTGCACTTTGGATGATGT
HCoVOC43       GGGCCTTTGTTGCATTTAGCTTTTTTATGGCCGTATCAACACTCGTTATGTGGGTGATGT
PEDV           GGGTCTTTTTCGCTTTCAGCATCCTTATGGCTTGCATCACTCTTATGCTGTGGATAATGT
BCoV           ATGTGTATCTTGGCTTTTCTATAGTTTTCACTATAGTGGCCATTATCATGTGGATTGTGT
HEV            ATGTGTACCTTGGCTTCTCTATAGTTTTTACTATAGTGGCCATTATTATGTGGGTTGTTT
MHV            ATGTGTATCTTGGATTTTCTATAGTGTTTACTATAGTGTCCATTATAATGTGGATTATGT
RtCoV          ATGTGTATCTTGGATTTTCTATAGTGTTTACTATAGTGTCCATTGTAATGTGGATTATGT
SARS-Urb       GGGTGACTGGCGGGATTGCGATTGCAATGGCTTGTATTGTAGGCTTGATGTGGCTTAGCT
SARS-Tor       GGGTGACTGGCGGGATTGCGATTGCAATGGCTTGTATTGTAGGCTTGATGTGGCTTAGCT
IBV            CAGGAGGTCTTGTCGCAGCGATAATACTTACAGTGTTTGCGTGTCTGTCTTTTGTAGGTT
```

```
TGE             ATTTTGTAAGATCCATTCAGTTGTACAGAAGGACTAAGTCTTGGTGGTCTTTCAACCCTG
PRCoV           ATTTTGTAAGATCCATTCAGTTGTACAGAAGGACTAAGTCTTGGTGGTCCTTCAACCCTG
CcoV            ATTTTGTTAGATCCATTCAGTTATACAGAAGGACTAAGTCTTGGTGGTCTTTCAACCCTG
FCoV            ATTTTGTGAGATCTGTTCAGCTATATAGAAGAACCAAATCATGGTGGTCTTTTAATCCTG
HCoVOC43        ACTTCGCAAACAGTTTCAGACTTTTCCGACGTGCTCGAACTTTTTGGGCATGGAATCCTG
PEDV            ATTTTGTCAATAGCATTCGGTTGTGGCGCAGGACACATTCTTGGTGGTCTTTCAATCCTG
BCoV            ATTTTGTGAATAGTATCAGGTTGTTTATTAGAACTGGAAGTTGGTGGAGTTTCAACCCAG
HEV             ATTTTGTGAATAGTATCAGGTTGTTTATTAGAACTGGAAGTTGGTGGAGTTTCAACCCAG
MHV             ATTTTGTTAATAGCATCAGGTTGTTTATCAGGACTGGCAGCTGGTGGAGCTTCAACCCCG
RtCoV           ATTTTGTTAATAGCATAAGGTTGTTTATCAGGACTGGTAGCTGGTGGAGCTTCAACCCTG
SARS-Urb        ACTTCGTTGCTTCCTTCAGGCTGTTTGCTCGTACCCGCTCAATGTGGTCATTCAACCCAG
SARS-Tor        ACTTCGTTGCTTCCTTCAGGCTGTTTGCTCGTACCCGCTCAATGTGGTCATTCAACCCAG
IBV             ATTGGATCCAGAGTATTAGACTCTTTAAGCGGTGTAGGTCATGGTGGTCATTTAATCCAG
                * *            *     * *      *             ***   *  ** ** *

TGE             AAACTAAAGCAATTCTTTGCGTTAGTGCATTAGGAAGAAGCTATGTGCTTCCTCTCGAAG
PRCoV           AAACTAACGCAATTCTTTGCGTTAGTGCATTAGGAAGAAGCTATGTGCTTCCTCTCGAAG
CcoV            AAACTAGCGCAATTCTTTGCGTTAGTGCGTTAGGAAGAAGCTATGTGCTTCCTCTTGAAG
FCoV            AGACTAATGCAATTCTTTGTGTTAATGCATTGGGTAGAAGTTATGTGCTTCCCTTAGATG
HCoVOC43        AGGTTAATGCAATCACTGTCACAACCGTGTTGGGACAGACATACTATCAACCCATTCAAC
PEDV            AAACTGACGCGCTTCTCACTACTTCTGTGATGGGCCGACAGGTCTGCATTCCAGTGCTTG
BCoV            AAACAAACAACTTGATGTGTATAGATATGAAGGGAAGGATGTATGTTAGGCCGATAATTG
HEV             AAACAAACAACTTGATGTGTATAGATATGAAGGGAAGAATGTATGTTAGGCCGATTATTG
MHV             AAACAAACAACCTAATGTGTATAGATATGAAAGGTACTGTGTATGTTAGACCCATTATAG
RtCoV           AAACAAACAACCTAATGTGTATAGATGTGAAAGGTACTGTGTATGTTAGACCCATTATTG
SARS-Urb        AAACAAACATTCTTCTCAATGTGCCTCTCCGGGGGACAATTGTGACCAGACCGCTCATGG
SARS-Tor        AAACAAACATTCTTCTCAATGTGCCTCTCCGGGGGACAATTGTGACCAGACCGCTCATGG
IBV             AATCTAATGCCGTAGGTTCAATACTCCTAACTAATGGTCAACAATGTAATTTTGCTATAG
                *           *

TGE             GTGTG---CCAACTGGTGTCACTCTAACTTTGCTTTCAGGGAATTTGTACGCTGAAGGGT
PRCoV           GTGTG---CCAACTGGTGTCACTCTAACTTTGCTTTCAGGGAATTTGTACGCTGAAGGGT
CcoV            GTGTG---CCAACTGGTGTCACTCTAACATTGCTTTCAGGGAATTTGTGTGCTGAAGGGT
FCoV            GTACT---CCTACAGGTGTTACCCTTACTCTACTTTCAGGAAATCTATATGCTGAAGGTT
HCoVOC43        AAGCT---CCAACAGGCATTACTGTGACCTTGCTGAGCGGCGTGCTTTACGTTGACGGAC
PEDV            GAGCA---CCAACTGGTGTAACGCTAACACTCCTTAGTGGTACATTGCTTGTAGAGGGCT
BCoV            AGGAC---TACCATACCCTTACGGTCACAATAATACGTGGTCATCTTTACATGCAAGGTA
HEV             AGGAC---TACCACACCCTTACTGCCACAATAATACGTGGCCACCTCTACATCCAAGGTA
MHV             AGGAT---TACCATACACTAACAGCCACTATCATTCGTGGTCACCTCTATATGCAAGGTG
RtCoV           AAGAT---TACCATACACTAACAGCCACAAATGTACGTGGCCACCTTTATATGCAAGGTG
SARS-Urb        AAAGT---GAACTTGTCATTGGTGCTGTGATCATTCGTGGTCACTTGCGAATGGCCGGAC
SARS-Tor        AAAGT---GAACTTGTCATTGGTGCTGTGATCATTCGTGGTCACTTGCGAATGGCCGGAC
IBV             AGAGTGTGCCAATGGTGCTTTCTCCAATTATAAAGAATGGTGTTCTTTATTGTGAGGGTC
                                  *                   **     *          **

TGE             TCAAAATTGCAGGTGGTATGAACATCGACAATTTACCAAAATACGTAATGGTTGCATTAC
PRCoV           TCAAAATTGCAGGTGGTATGACCATCGACAATTTGCCAAAATACGTAATGGTTGCATTAC
CcoV            TCAAAATTGCAGGTGGTATGAACATCGACAATTTACCAAAATATGTAATGGTTGCATTAC
FCoV            TCAAAATGGCTGGTGGTTTAACCATCGAGCATTTGCCTAAATACGTCATGATTGCTACAC
HCoVOC43        ATAGATTGGCTTCAGGTGTTCAGGTTCATAACCTACCTGAATACATGACAGTTGCCGTGC
PEDV            ATAAGGTTGCTACTGGCGTACAGGTAAGTCAATTACCTAATTTCGTCACAGTCGCCAAGG
BCoV            TAAAACTAGGTACTGGCTATTCTTTGTCAGATTTGCCAGCTTATGTGACTGTTGCTAAGG
HEV             TAAAACTAGGTACTGGCTATTCTTTGTCAGATTTGCCTGCTTATGTGACCGTTGCTAAGG
MHV             TTAAGCTAGGCACTGGCTTCTCTTTGTCTGATTTGCCTGCTTATGTTACAGTTGCTAAGG
RtCoV           TTAAGCTAGGCACTGGCTTCTCTTTGTCTGATTTGCCCGCTTATGTTACAGTTGCTAAGG
SARS-Urb        ACCCCCTAGGGCGCTGTG---ACATTAAGGACCTGCCAAAAGAGATCACTGTGGCTACAT
SARS-Tor        ACTCCCTAGGGCGCTGTG---ACATTAAGGACCTGCCAAAAGAGATCACTGTGGCTACAT
IBV             AGTGGCTTGCTAAGTGTG---AACCAGACCACTTGCCTAAAGATATATTTGTTTGTACAC
                      * *      *              *  * **        *     *
```

```
TGE         CTAGCAGGACTATTGTCTACACAC--TTGTTGGCAAGAAGTTGAAAGCAAGTAGTGCGAC
PRCoV       CCAGCAGGACTATTGTTTACACAC--TTGTTGGCAAGAAGTTGAAAGCAAGTAGTGCGAC
CcoV        CTGTCAGAACCATAGTCTACACAC--TTGTTGGCAAGAAATTGAAAGCAAGTAGTGCAAC
FCoV        CTAGTAGAACCATCGTTTATACAT--TAGTTGGAAAACAATTAAAAGCAACTACTGCCAC
HCoVOC43    CGAGCACTACTATAATTTATAGTA--GAGTCGGAAGGTCCGTAAATTCACAAAATAGCAC
PEDV        CCACTACAACAATTGTCTACGGAC--GTGTTGGTCGTTCAGTCAATGCTTCATCTGGCAC
BCoV        T--CTCACACCTGCTCACGTATAA--GCGT-GGTTTTCTTGACAAGATAGGCGATACTAG
HEV         T--TACACACCTGTGCACATATAA--GCGT-GGTTTTCTTGATAGGATAGGCGATACTAG
MHV         T--GTCTCACCTTTGCACTTATAA--GCGC-GCATTCTTAGACAAGGTAGACGGTGTTAG
RtCoV       T--GTCGCACCTTTGCACTTATAA--GCGC-GCATTTTTAGACAAGGTTGACGGTGTTAG
SARS-Urb    C---ACGAACGCTTTCTTATTACA--AATTAGGAGCGTCGCAGCGTGTAGGCACTGATTC
SARS-Tor    C---ACGAACGCTTTCTTATTACA--AATTAGGAGCGTCGCAGCGTGTAGGCACTGATTC
IBV         CGGATAGACGTAATATCTACCGTATGGTGCAGAAATATACTGGTGACCAAAGCGGAAATA
                                              *

TGE         TGGATGGGCTTACTATGTAAAATCTAAAGCTGGTGATTACTCAACAGAGG---CAAGAAC
PRCoV       TGGATGGGCTTACTATGTAAAATCTAAAGCTGGTGATTACTCAACAGAGG---CAAGAAC
CcoV        AGGATGGGCTTACTATGTAAAGTCTAAAGCTGGTGATTACTCAACAGATG---CACGAAC
FCoV        AGGATGGGCTTACTACGTAAAATCTAAAGCTGGTGATTACTCAACAGAAG---CACGTAC
HCoVOC43    AGGCTGGGTTTTCTACGTACGAGTAAAACACGGTGATTTTTCTGCAGTGAGCTCTCCCAT
PEDV        TGGTTGGGCTTTCTATGTCCGGTCAAAACACGGCGACTATTCAGCTGTGAGTAATCCGAG
BCoV        TGGTTTTGCTGTTTATGTTAAGTCCAAAGTCGGTAATTACCGACTGCCATCAACCCAAAA
HEV         TGGTTTTGCTGTTTATGTTAAGTCCAAAGTCGGTAATTATCGATTGCCTTCAACCCATAA
MHV         CGGTTTTGCTGTTTATGTGAAGTCCAAGGTCGGAAATTACCGACTGCCCTCAAATAAACC
RtCoV       CGGTTTTGCTGTTTATGTGAAGTCCAAGGTCGGTAATTACCGACTGCCCTCAAATAAACC
SARS-Urb    AGGTTTTGCTGCATACAACCGCTACCGTATTGGAAACTATAAATTAAATACAGACCACGC
SARS-Tor    AGGTTTTGCTGCATACAACCGCTACCGTATTGGAAACTATAAATTAAATACAGACCACGC
IBV         AGAAAAGGTTTGCTACGTTTG-TCTATGCAAAGCAGTCAGTAGATACTGGCGAGCTAGAA
                 *   * *  **                *

TGE         TGATAATTTGAGTGAGCAAGAAAAATTATTACATATGGTATAA
PRCoV       TGATAATTTGAGTGAGCAAGAAAAATTATTACATATGGTATAA
CcoV        TGATAATTTGAGTGAGCATGAAAAATTATTACATATGGTATAA
FCoV        TGACAATTTGAGTGAACATGAAAAATTATTACATATGGTGTAA
HCoVOC43    GAGCAACATGACAGAAAACGAAAGATTGCTTCATTTTTTCTAA
PEDV        TGCGGTTCTCACAGATAGTGAGAAAGTGCTTCATTTAGTCTAA
BCoV        GGGTTCTGGCATGGACACCGCATTGTTGAGAAATAATATCTAA
HEV         GGGCTCAGGCATGGACACCGCATTGTTGAGAAATAATATCTAA
MHV         GAGT---GGCATGGACACCGCATTGTTGAGAATCTAA------
RtCoV       GAGT---GGCGCGGACACCGCATTGTTGAGAATCTAA------
SARS-Urb    CGGTAGCAACGACAATATTGCTTTGCTAGTACAGTAA------
SARS-Tor    CGGTAGCAACGACAATATTGCTTTGCTAGTACAGTAA------
IBV         AGTGTAGCAACAGGAGGAAGTAGTCTTTACACATAA-------
                             *    *    *
```

**Figure 10: Phylogenetic Analysis of *M* Gene**
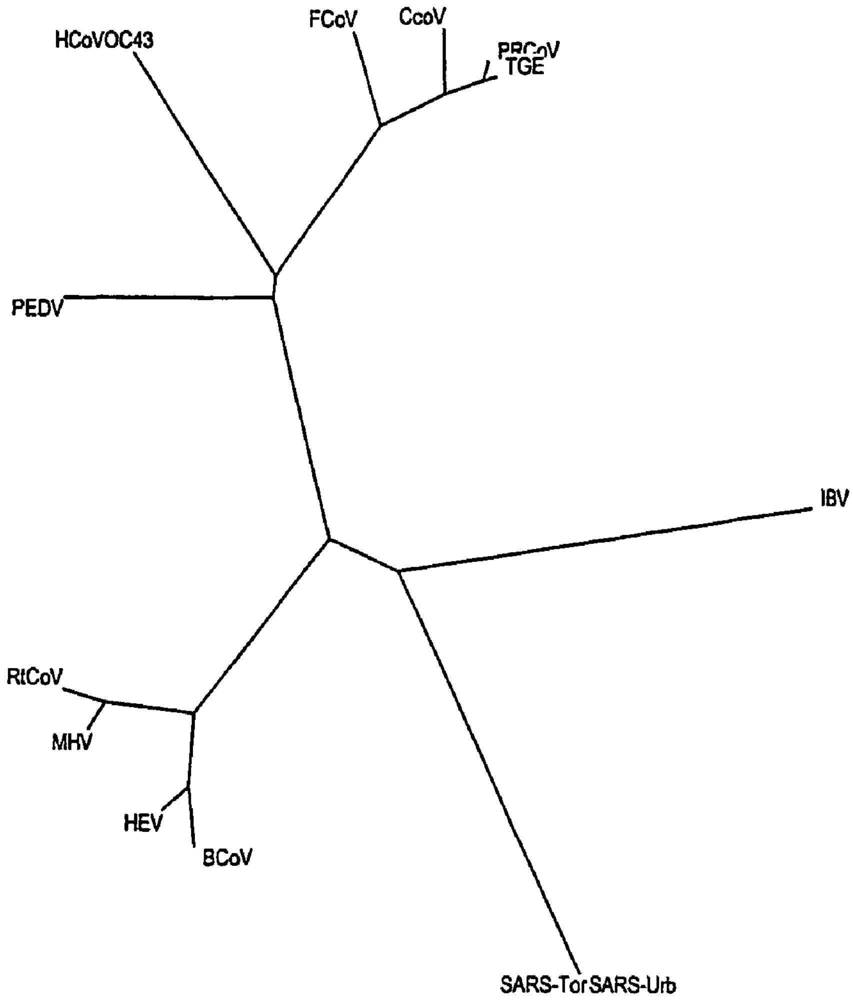

**Figure 11: Molecular Designs for SARS-Associated *M* Gene**

| | |
|---|---|
| NOTE: | LK257 is a TET-molecular beacon, which recognizes the ***M* gene of coronavirus (SARS Tor2 and SARS urbani human pathogenic strains)**. It will be used in a real-time PCR diagnostic for the identification of **SARS-associated coronavirus** RNA/DNA. |

Beacon LK257

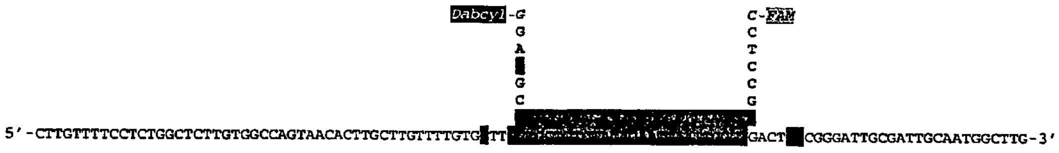

Amplicon LK258

LK257

| | | |
|---|---|---|
| I. | Target recognition sequence: | **26 nucleotides (11 G/C) + (3 nts arms G/C)** |
| J. | Length of the arms: | **6 nucleotides (5 G/C)** |
| K. | Melting temperature of the beacon: | **dG = -1.52 dH = -46.6 dS = -139.6 Tm = 60.7 °C** |
| L. | Melting temperature of target: | **°C (including 3 nts from the arms)** |

<u>LK259</u> 5'-CTTGTTTTCCTCTGGCTCTTG-3'

Length: 21 nucleotides (10 G/C)
*Tm*: °C
Position: (see alignment below)

<u>LK260</u> 5' –CAAGCCATTGCAATCGCAATC-3'

Length: 21 nucleotides (10 G/C)
*Tm*: °C
Position: (see alignment below)

<u>M-RT</u> 5'-AAGCAACGAAGTAG -3'

Length: 14 nucleotides (6 G/C)
*Tm*: 47 °C
Position: (see alignment below)

LK258 Amplicon (107 nucleotides)

5'–
CTTGTTTTCCTCTGGCTCTTGTGGCCAGTAACACTTGCTTGTTTTGTGCTTGCTGCTG
TCTACAGAATTAATTGGGTGACTGGCGGGATTGCGATTGCAATGGCTTG -3'

DNA sequence alignment of complete M genes from corona virus strains

```
TGE        ------------------------------------------------------------
PRCoV      ------------------------------------------------------------
CcoV       ------------------------------------------------------------
FCoV       ATGCATATGATGCCTATAAGACCTTTATGCAAACCAAGGCATATAATCCCGACGAAGCAT
HCoVOC43   ------------------------------------------------------------
PEDV       ------------------------------------------------------------
BCoV       ------------------------------------------------------------
HEV        ------------------------------------------------------------
MHV        ------------------------------------------------------------
RtCoV      ------------------------------------------------------------
SARS-Urb   ------------------------------------------------------------
SARS-Tor   ------------------------------------------------------------
IBV        ------------------------------------------------------------

TGE        ------------------------ATGAAGATTTTGTTAATATTAGCGTGTGTGATTGCA
PRCoV      ------------------------ATGAAGATTTTGTTGATATTAGCGTGTGCGATTGCA
CcoV       ---------------------ATGAAGAAAATTTTGTTTTTACTAGCGTGTGCAATTGCA
FCoV       TTTTGGTTTGAACTAAACAAAATGAAGTACATTTTGCTAATACTCGCGTGCATAATTGCA
HCoVOC43   ------------------------------------------------------------
PEDV       ------------------------------------------------------------
BCoV       ------------------------------------------------------------
HEV        ------------------------------------------------------------
MHV        ------------------------------------------------------------
RtCoV      ------------------------------------------------------------
SARS-Urb   ------------------------------------------------------------
SARS-Tor   ------------------------------------------------------------
IBV        ------------------------------------------------------------

TGE        TGCGCATGTGGAGAACGCTATTGTGCTATGAAATCCGATACAGATTTGTCATGTCGCAAT
PRCoV      TGCACATGTGGAGAACGCTATTGTGCTATGAAAGACGATACAGGTTTGTCATGTCGCAAT
CcoV       TGCGTCTATGGAGAACGCTATTGTGCCATGA---CTGAAAGTTCTACGTCATGTCGTAAT
FCoV       TGCGTTTATGGTGAACGCTACTGTGCCATGCAA---GACAGTGGCTTGCAGTGTATTAAT
HCoVOC43   ------------------------------------------------------------
PEDV       ------------------------------------------------------------
BCoV       --------------------------------------------------ATGAGTAGTG
HEV        --------------------------------------------------ATGAGTAGTC
MHV        --------------------------------------------------ATGACTAGTA
RtCoV      --------------------------------------------------ATGAGTAGTA
SARS-Urb   ------------------------------------------------------------
SARS-Tor   ------------------------------------------------------------
IBV        ------------------------------------------------------------

TGE        AGTACAGCGTCTGATTGTGAGTCA--TGCTTCAACGGAGGCGATCTTATTTGGCATCTTG
PRCoV      GGCACGGCGTCTGATTGTGAGTCA--TGCTTCAACAGAGGCGATCTTATTTGGCTTCTTG
```

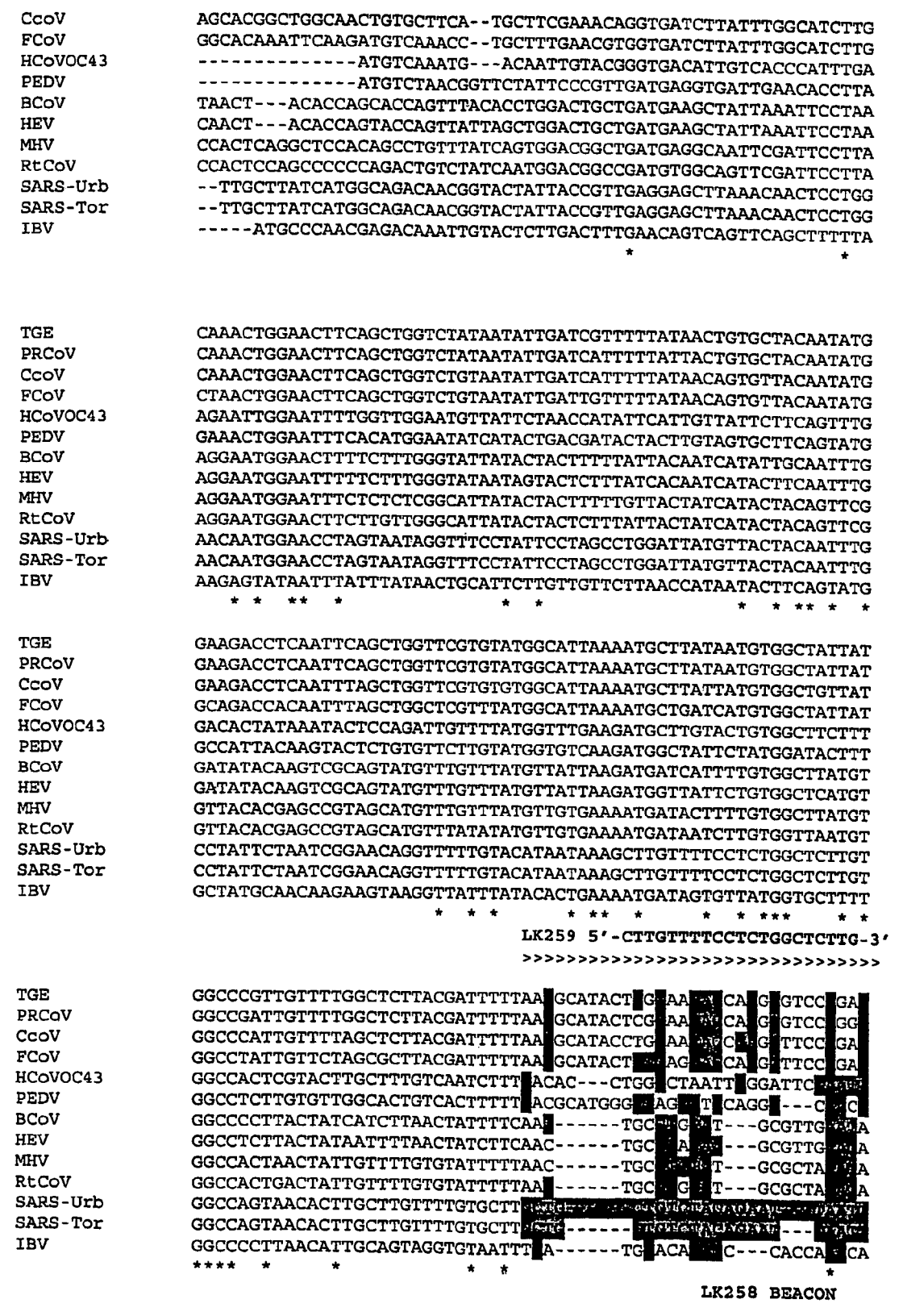

| | |
|---|---|
| CcoV | AGCACGGCTGGCAACTGTGCTTCA--TGCTTCGAAACAGGTGATCTTATTTGGCATCTTG |
| FCoV | GGCACAAATTCAAGATGTCAAACC--TGCTTTGAACGTGGTGATCTTATTTGGCATCTTG |
| HCoVOC43 | --------------ATGTCAAATG---ACAATTGTACGGGTGACATTGTCACCCATTTGA |
| PEDV | --------------ATGTCTAACGGTTCTATTCCCGTTGATGAGGTGATTGAACACCTTA |
| BCoV | TAACT---ACACCAGCACCAGTTTACACCTGGACTGCTGATGAAGCTATTAAATTCCTAA |
| HEV | CAACT---ACACCAGTACCAGTTATTAGCTGGACTGCTGATGAAGCTATTAAATTCCTAA |
| MHV | CCACTCAGGCTCCACAGCCTGTTTATCAGTGGACGGCTGATGAGGCAATTCGATTCCTTA |
| RtCoV | CCACTCCAGCCCCCCAGACTGTCTATCAATGGACGGCCGATGTGGCAGTTCGATTCCTTA |
| SARS-Urb | --TTGCTTATCATGGCAGACAACGGTACTATTACCGTTGAGGAGCTTAAACAACTCCTGG |
| SARS-Tor | --TTGCTTATCATGGCAGACAACGGTACTATTACCGTTGAGGAGCTTAAACAACTCCTGG |
| IBV | -----ATGCCCAACGAGACAAATTGTACTCTTGACTTTGAACAGTCAGTTCAGCTTTTTA |
| | * * |

| | |
|---|---|
| TGE | CAAACTGGAACTTCAGCTGGTCTATAATATTGATCGTTTTTATAACTGTGCTACAATATG |
| PRCoV | CAAACTGGAACTTCAGCTGGTCTATAATATTGATCATTTTTATTACTGTGCTACAATATG |
| CcoV | CAAACTGGAACTTCAGCTGGTCTGTAATATTGATCATTTTTATAACAGTGTTACAATATG |
| FCoV | CTAACTGGAACTTCAGCTGGTCTGTAATATTGATTGTTTTTATAACAGTGTTACAATATG |
| HCoVOC43 | AGAATTGGAATTTTGGTTGGAATGTTATTCTAACCATATTCATTGTTATTCTTCAGTTTG |
| PEDV | GAAACTGGAATTTCACATGGAATATCATACTGACGATACTACTTGTAGTGCTTCAGTATG |
| BCoV | AGGAATGGAACTTTTCTTTGGGTATTATACTACTTTTTATTACAATCATATTGCAATTTG |
| HEV | AGGAATGGAATTTTTCTTTGGGTATAATAGTACTCTTTATCACAATCATATTGCAATTTG |
| MHV | AGGAATGGAATTTCTCTCTCGGCATTATACTACTTTTTGTTACTATCATACTACAGTTCG |
| RtCoV | AGGAATGGAACTTCTTGTTGGGCATTATACTACTCTTTATTACTATCATACTACAGTTCG |
| SARS-Urb | AACAATGGAACCTAGTAATAGGTTTCCTATTCCTAGCCTGGATTATGTTACTACAATTTG |
| SARS-Tor | AACAATGGAACCTAGTAATAGGTTTCCTATTCCTAGCCTGGATTATGTTACTACAATTTG |
| IBV | AAGAGTATAATTTATTTATAACTGCATTCTTGTTGTTCTTAACCATAATACTTCAGTATG |
| | * * ** * * * * * ** * * |

| | |
|---|---|
| TGE | GAAGACCTCAATTCAGCTGGTTCGTGTATGGCATTAAAATGCTTATAATGTGGCTATTAT |
| PRCoV | GAAGACCTCAATTCAGCTGGTTCGTGTATGGCATTAAAATGCTTATAATGTGGCTATTAT |
| CcoV | GAAGACCTCAATTTAGCTGGTTCGTGTGTGGCATTAAAATGCTTATTATGTGGCTGTTAT |
| FCoV | GCAGACCACAATTTAGCTGGCTCGTTTATGGCATTAAAATGCTGATCATGTGGCTATTAT |
| HCoVOC43 | GACACTATAAATACTCCAGATTGTTTTATGGTTTGAAGATGCTTGTACTGTGGCTTCTTT |
| PEDV | GCCATTACAAGTACTCTGTGTTCTTGTATGGTGTCAAGATGGCTATTCTATGGATACTTT |
| BCoV | GATATACAAGTCGCAGTATGTTTGTTTATGTTATTAAGATGATCATTTTGTGGCTTATGT |
| HEV | GATATACAAGTCGCAGTATGTTTGTTTATGTTATTAAGATGGTTATTCTGTGGCTCATGT |
| MHV | GTTACACGAGCCGTAGCATGTTTGTTTATGTTGTGAAAATGATACTTTTGTGGCTTATGT |
| RtCoV | GTTACACGAGCCGTAGCATGTTTATATATGTTGTGAAAATGATAATCTTGTGGTTAATGT |
| SARS-Urb | CCTATTCTAATCGGAACAGGTTTTTGTACATAATAAAGCTTGTTTTCCTCTGGCTCTTGT |
| SARS-Tor | CCTATTCTAATCGGAACAGGTTTTTGTACATAATAAAGCTTGTTTTCCTCTGGCTCTTGT |
| IBV | GCTATGCAACAAGAAGTAAGGTTATTTATACACTGAAAATGATAGTGTTATGGTGCTTTT |
| | * * * * ** * * * *** * * |

LK259 5'-CTTGTTTTCCTCTGGCTCTTG-3'

>>>>>>>>>>>>>>>>>>>>>>>>>>>>>>>

| | |
|---|---|
| TGE | GGCCCGTTGTTTTGGCTCTTACGATTTTTAA[illegible]GCATACT[illegible]G[illegible]AA[illegible]CA[illegible]G[illegible]GTCC[illegible]GA[illegible] |
| PRCoV | GGCCGATTGTTTTGGCTCTTACGATTTTTAA[illegible]GCATACTCG[illegible]AA[illegible]CA[illegible]G[illegible]GTCC[illegible]GG[illegible] |
| CcoV | GGCCCATTGTTTTAGCTCTTACGATTTTTAA[illegible]GCATACCTG[illegible]AA[illegible]C[illegible]G[illegible]TTCC[illegible]GA[illegible] |
| FCoV | GGCCTATTGTTCTAGCGCTTACGATTTTTAA[illegible]GCATACT[illegible]AG[illegible]CA[illegible]G[illegible]TTCC[illegible]GA[illegible] |
| HCoVOC43 | GGCCACTCGTACTTGCTTTGTCAATCTTT[illegible]ACAC---CTGG[illegible]CTAATT[illegible]GGATTC[illegible] |
| PEDV | GGCCTCTTGTGTTGGCACTGTCACTTTTT[illegible]ACGCATGGG[illegible]AG[illegible]T[illegible]CAGG[illegible]---C[illegible]C[illegible] |
| BCoV | GGCCCCTTACTATCATCTTAACTATTTTCAA[illegible]------TGC[illegible]G[illegible]T---GCGTTG[illegible]A |
| HEV | GGCCTCTTACTATAATTTTAACTATCTTCAAC------TGC[illegible]A[illegible]---GCGTTG[illegible]A |
| MHV | GGCCACTAACTATTGTTTTGTGTATTTTTAAC------TGC[illegible]T---GCGCTA[illegible]A |
| RtCoV | GGCCACTGACTATTGTTTTGTGTATTTTTAA[illegible]------TGC[illegible]G[illegible]T---GCGCTA[illegible]A |
| SARS-Urb | GGCCAGTAACACTTGCTTGTTTTGTGCTT[illegible] |
| SARS-Tor | GGCCAGTAACACTTGCTTGTTTTGTGCTT[illegible]------[illegible]---[illegible] |
| IBV | GGCCCCTTAACATTGCAGTAGGTGTAATTT[illegible]A------TG[illegible]ACA[illegible]C---CACCA[illegible]CA |
| | **** * * * * * |

LK258 BEACON

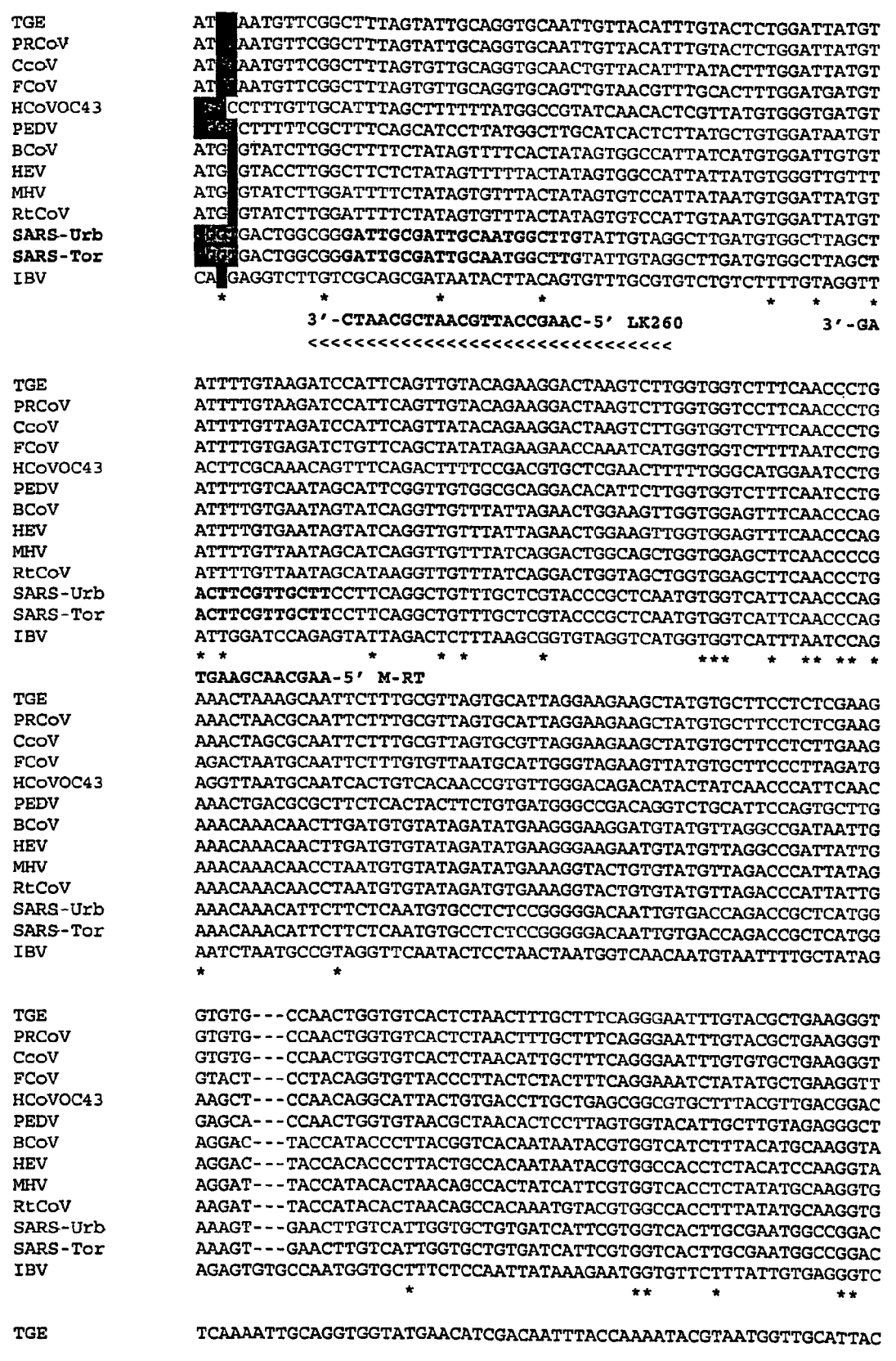

```
TGE         AT[illegible]AATGTTCGGCTTTAGTATTGCAGGTGCAATTGTTACATTTGTACTCTGGATTATGT
PRCoV       AT[illegible]AATGTTCGGCTTTAGTATTGCAGGTGCAATTGTTACATTTGTACTCTGGATTATGT
CcoV        AT[illegible]AATGTTCGGCTTTAGTGTTGCAGGTGCAACTGTTACATTTATACTTTGGATTATGT
FCoV        AT[illegible]AATGTTCGGCTTTAGTGTTGCAGGTGCAGTTGTAACGTTTGCACTTTGGATGATGT
HCoVOC43    [illegible]CCTTTGTTGCATTTAGCTTTTTTATGGCCGTATCAACACTCGTTATGTGGGTGATGT
PEDV        [illegible]CTTTTTCGCTTTCAGCATCCTTATGGCTTGCATCACTCTTATGCTGTGGATAATGT
BCoV        ATG[illegible]GTATCTTGGCTTTTCTATAGTTTTCACTATAGTGGCCATTATCATGTGGATTGTGT
HEV         ATG[illegible]GTACCTTGGCTTCTCTATAGTTTTTACTATAGTGGCCATTATTATGTGGGTTGTTT
MHV         ATG[illegible]GTATCTTGGATTTTCTATAGTGTTTACTATAGTGTCCATTATAATGTGGATTATGT
RtCoV       ATG[illegible]GTATCTTGGATTTTCTATAGTGTTTACTATAGTGTCCATTGTAATGTGGATTATGT
SARS-Urb    [illegible]GACTGGCGGATTGCGATTGCAATGGCTTGTATTGTAGGCTTGATGTGGCTTAGCT
SARS-Tor    [illegible]GACTGGCGGATTGCGATTGCAATGGCTTGTATTGTAGGCTTGATGTGGCTTAGCT
IBV         CA[illegible]GAGGTCTTGTCGCAGCGATAATACTTACAGTGTTTGCGTGTCTGTCTTTTGTAGGTT
              *        *         *        *                   *   *    *
                      3'-CTAACGCTAACGTTACCGAAC-5' LK260            3'-GA
                      <<<<<<<<<<<<<<<<<<<<<<<<<<<<<<<

TGE         ATTTTGTAAGATCCATTCAGTTGTACAGAAGGACTAAGTCTTGGTGGTCTTTCAACCCTG
PRCoV       ATTTTGTAAGATCCATTCAGTTGTACAGAAGGACTAAGTCTTGGTGGTCCTTCAACCCTG
CcoV        ATTTTGTTAGATCCATTCAGTTATACAGAAGGACTAAGTCTTGGTGGTCTTTCAACCCTG
FCoV        ATTTTGTGAGATCTGTTCAGCTATATAGAAGAACCAAATCATGGTGGTCTTTTAATCCTG
HCoVOC43    ACTTCGCAAACAGTTTCAGACTTTTCCGACGTGCTCGAACTTTTTGGCATGGAATCCTG
PEDV        ATTTTGTCAATAGCATTCGGTTGTGGCGCAGGACACATTCTTGGTGGTCTTTCAATCCTG
BCoV        ATTTTGTGAATAGTATCAGGTTGTTTATTAGAACTGGAAGTTGGTGGAGTTTCAACCCAG
HEV         ATTTTGTGAATAGTATCAGGTTGTTTATTAGAACTGGAAGTTGGTGGAGTTTCAACCCAG
MHV         ATTTTGTTAATAGCATCAGGTTGTTTATCAGGACTGGCAGCTGGTGGAGTTTCAACCCAG
RtCoV       ATTTTGTTAATAGCATAAGGTTGTTTATCAGGACTGGTAGCTGGTGGAGCTTCAACCCCG
SARS-Urb    ACTTCGTTGCTTCCTTCAGGCTGTTTGCTCGTACCCGCTCAATGTGGTCATTCAACCCTG
SARS-Tor    ACTTCGTTGCTTCCTTCAGGCTGTTTGCTCGTACCCGCTCAATGTGGTCATTCAACCCAG
IBV         ATTGGATCCAGAGTATTAGACTCTTTAAGCGGTGTAGGTCATGGTGGTCATTTAATCCAG
            * *            *     * *      *             ***   *  ** ** *
            TGAAGCAACGAA-5' M-RT
TGE         AAACTAAAGCAATTCTTTGCGTTAGTGCATTAGGAAGAAGCTATGTGCTTCCTCTCGAAG
PRCoV       AAACTAACGCAATTCTTTGCGTTAGTGCATTAGGAAGAAGCTATGTGCTTCCTCTCGAAG
CcoV        AAACTAGCGCAATTCTTTGCGTTAGTGCGTTAGGAAGAAGCTATGTGCTTCCTCTTGAAG
FCoV        AGACTAATGCAATTCTTTGTGTTAATGCATTGGGTAGAAGTTATGTGCTTCCCTTAGATG
HCoVOC43    AGGTTAATGCAATCACTGTCACAACCGTGTTGGGACAGACATACTATCAACCCATTCAAC
PEDV        AAACTGACGCGCTTCTCACTACTTCTGTGATGGGCCGACAGGTCTGCATTCCAGTGCTTG
BCoV        AAACAAACAACTTGATGTGTATAGATATGAAGGGAAGGATGTATGTTAGGCCGATAATTG
HEV         AAACAAACAACTTGATGTGTATAGATATGAAGGGAAGAATGTATGTTAGGCCGATTATTG
MHV         AAACAAACAACCTAATGTGTATAGATATGAAAGGTACTGTGTATGTTAGACCCATTATAG
RtCoV       AAACAAACAACCTAATGTGTATAGATGTGAAAGGTACTGTGTATGTTAGACCCATTATTG
SARS-Urb    AAACAAACATTCTTCTCAATGTGCCTCTCCGGGGGACAATTGTGACCAGACCGCTCATGG
SARS-Tor    AAACAAACATTCTTCTCAATGTGCCTCTCCGGGGGACAATTGTGACCAGACCGCTCATGG
IBV         AATCTAATGCCGTAGGTTCAATACTCCTAACTAATGGTCAACAATGTAATTTTGCTATAG
            *           *

TGE         GTGTG---CCAACTGGTGTCACTCTAACTTTGCTTTCAGGGAATTTGTACGCTGAAGGGT
PRCoV       GTGTG---CCAACTGGTGTCACTCTAACTTTGCTTTCAGGGAATTTGTACGCTGAAGGGT
CcoV        GTGTG---CCAACTGGTGTCACTCTAACATTGCTTTCAGGGAATTTGTGTGCTGAAGGGT
FCoV        GTACT---CCTACAGGTGTTACCCTTACTCTACTTTCAGGAAATCTATATGCTGAAGGTT
HCoVOC43    AAGCT---CCAACAGGCATTACTGTGACCTTGCTGAGCGGCGTGCTTTACGTTGACGGAC
PEDV        GAGCA---CCAACTGGTGTAACGCTAACACTCCTTAGTGGTACATTGCTTGTAGAGGGCT
BCoV        AGGAC---TACCATACCCTTACGGTCACAATAATACGTGGTCATCTTTACATGCAAGGTA
HEV         AGGAC---TACCACACCCTTACTGCCACAATAATACGTGGCCACCTCTACATCCAAGGTA
MHV         AGGAT---TACCATACACTAACAGCCACTATCATTCGTGGTCACCTCTATATGCAAGGTG
RtCoV       AAGAT---TACCATACACTAACAGCCACAAATGTACGTGGCCACCTTTATATGCAAGGTG
SARS-Urb    AAAGT---GAACTTGTCATTGGTGCTGTGATCATTCGTGGTCACTTGCGAATGGCCGGAC
SARS-Tor    AAAGT---GAACTTGTCATTGGTGCTGTGATCATTCGTGGTCACTTGCGAATGGCCGGAC
IBV         AGAGTGTGCCAATGGTGCTTTCTCCAATTATAAAGAATGGTGTTCTTTATTGTGAGGGTC
                               *                  **     *          **

TGE         TCAAAATTGCAGGTGGTATGAACATCGACAATTTACCAAAATACGTAATGGTTGCATTAC
```

```
PRCoV      TCAAAATTGCAGGTGGTATGACCATCGACAATTTGCCAAAATACGTAATGGTTGCATTAC
CcoV       TCAAAATTGCAGGTGGTATGAACATCGACAATTTACCAAAATATGTAATGGTTGCATTAC
FCoV       TCAAAATGGCTGGTGGTTTAACCATCGAGCATTTGCCTAAATACGTCATGATTGCTACAC
HCoVOC43   ATAGATTGGCTTCAGGTGTTCAGGTTCATAACCTACCTGAATACATGACAGTTGCCGTGC
PEDV       ATAAGGTTGCTACTGGCGTACAGGTAAGTCAATTACCTAATTTCGTCACAGTCGCCAAGG
BCoV       TAAAACTAGGTACTGGCTATTCTTTGTCAGATTTGCCAGCTTATGTGACTGTTGCTAAGG
HEV        TAAAACTAGGTACTGGCTATTCTTTGTCAGATTTGCCTGCTTATGTGACCGTTGCTAAGG
MHV        TTAAGCTAGGCACTGGCTTCTCTTTGTCTGATTTGCCTGCTTATGTTACAGTTGCTAAGG
RtCoV      TTAAGCTAGGCACTGGCTTCTCTTTGTCTGATTTGCCCGCTTATGTTACAGTTGCTAAGG
SARS-Urb   ACCCCCTAGGGCGCTGTG---ACATTAAGGACCTGCCAAAAGAGATCACTGTGGCTACAT
SARS-Tor   ACTCCCTAGGGCGCTGTG---ACATTAAGGACCTGCCAAAAGAGATCACTGTGGCTACAT
IBV        AGTGGCTTGCTAAGTGTG---AACCAGACCACTTGCCTAAAGATATATTTGTTTGTACAC
                 *  *    *          *   * **      *      *     *

TGE                    CTAGCAGGACTATTGTCTACACAC--TTGTTGGCAAGAAGTTGAAAGCAAGTAGTGCGAC
PRCoV                  CCAGCAGGACTATTGTTTACACAC--TTGTTGGCAAGAAGTTGAAAGCAAGTAGTGCGAC
CcoV                   CTGTCAGAACCATAGTCTACACAC--TTGTTGGCAAGAAATTGAAAGCAAGTAGTGCAAC
FCoV                   CTAGTAGAACCATCGTTTATACAT--TAGTTGGAAAACAATTAAAAGCAACTACTGCCAC
HCoVOC43               CGAGCACTACTATAATTTATAGTA--GAGTCGGAAGGTCCGTAAATTCACAAAATAGCAC
PEDV                   CCACTACAACAATTGTCTACGGAC--GTGTTGGTCGTTCAGTCAATGCTTCATCTGGCAC
BCoV                   T--CTCACACCTGCTCACGTATAA--GCGT-GGTTTTCTTGACAAGATAGGCGATACTAG
HEV                    T--TACACACCTGTGCACATATAA--GCGT-GGTTTTCTTGATAGGATAGGCGATACTAG
MHV                    T--GTCTCACCTTTGCACTTATAA--GCGC-GCATTCTTAGACAAGGTAGACGGTGTTAG
RtCoV                  T--GTCGCACCTTTGCACTTATAA--GCGC-GCATTTTAGACAAGGTTGACGGTGTTAG
SARS-Urb               C---ACGAACGCTTTCTTATTACA--AATTAGGAGCGTCGCAGCGTGTAGGCACTGATTC
SARS-Tor               C---ACGAACGCTTTCTTATTACA--AATTAGGAGCGTCGCAGCGTGTAGGCACTGATTC
IBV                    CGGATAGACGTAATATCTACCGTATGGTGCAGAAATATACTGGTGACCAAAGCGGAAATA
                                                                  *

TGE        TGGATGGGCTTACTATGTAAAATCTAAAGCTGGTGATTACTCAACAGAGG---CAAGAAC
PRCoV      TGGATGGGCTTACTATGTAAAATCTAAAGCTGGTGATTACTCAACAGAGG---CAAGAAC
CcoV       AGGATGGGCTTACTATGTAAAGTCTAAAGCTGGTGATTACTCAACAGATG---CACGAAC
FCoV       AGGATGGGCTTACTACGTAAAATCTAAAGCTGGTGATTACTCAACAGAAG---CACGTAC
HCoVOC43   AGGCTGGGTTTTCTACGTACGAGTAAAACACGGTGATTTTTCTGCAGTGAGCTCTCCCAT
PEDV       TGGTTGGGCTTTCTATGTCCGGTCAAAACACGGCGACTATTCAGCTGTGAGTAATCCGAG
BCoV       TGGTTTTGCTGTTTATGTTAAGTCCAAAGTCGGTAATTACCGACTGCCATCAACCCAAAA
HEV        TGGTTTTGCTGTTTATGTTAAGTCCAAAGTCGGTAATTATCGATTGCCTTCAACCCATAA
MHV        CGGTTTTGCTGTTTATGTGAAGTCCAAGGTCGGAAATTACCGACTGCCCTCAAATAAACC
RtCoV      CGGTTTTGCTGTTTATGTGAAGTCCAAGGTCGGTAATTACCGACTGCCCTCAAATAAACC
SARS-Urb   AGGTTTTGCTGCATACAACCGCTACCGTATTGGAAACTATAAATTAAATACAGACCACGC
SARS-Tor   AGGTTTTGCTGCATACAACCGCTACCGTATTGGAAACTATAAATTAAATACAGACCACGC
IBV        AGAAAAGGTTTGCTACGTTTG-TCTATGCAAAGCAGTCAGTAGATACTGGCGAGCTAGAA
                * *  * **   **               *

TGE        TGATAATTTGAGTGAGCAAGAAAAATTATTACATATGGTATAA
PRCoV      TGATAATTTGAGTGAGCAAGAAAAATTATTACATATGGTATAA
CcoV       TGATAATTTGAGTGAGCATGAAAAATTATTACATATGGTATAA
FCoV       TGACAATTTGAGTGAACATGAAAAATTATTACATATGGTGTAA
HCoVOC43   GAGCAACATGACAGAAAACGAAAGATTGCTTCATTTTTTCTAA
PEDV       TGCGGTTCTCACAGATAGTGAGAAAGTGCTTCATTTAGTCTAA
BCoV       GGGTTCTGGCATGGACACCGCATTGTTGAGAAATAATATCTAA
HEV        GGGCTCAGGCATGGACACCGCATTGTTGAGAAATAATATCTAA
MHV        GAGT---GGCATGGACACCGCATTGTTGAGAATCTAA------
RtCoV      GAGT---GGCGCGGACACCGCATTGTTGAGAATCTAA------
SARS-Urb   CGGTAGCAACGACAATATTGCTTTGCTAGTACAGTAA------
SARS-Tor   CGGTAGCAACGACAATATTGCTTTGCTAGTACAGTAA------
IBV        AGTGTAGCAACAGGAGGAAGTAGTCTTTACACATAA-------
                * *
```

**Figure 12: List of Molecular Designs for *M* Gene**

LK257 5'-FAM-CCTCCGACCCAATTAATTCTGTAGACAGCAGCCGGAGG-3'-Dubcyl

LK257.N 5'-FAM-GCCTCCGACCCAATTAATTCTGTAGACAGCAGCCGGAGGC-3'-Dubcyl

LK258

5'-CTTGTTTTCCTCTGGCTCTTGTGGCCAGTAACACTTGCTTGTTTTGTGCT
TGCTGCTGTCTACAGAATTAATTGGGTGACTGGCGGGATTGCGATTGCA
AT
GGCTTG-3'

LK259 5'- CTTGTTTTCCTCTGGCTCTTG -3'

5'- TAATACGACTCACTATAGGCTTGTTTTCCTCTGGCTCTTG -3'

LK260 5'- CAAGCCATTGCAATCGCAATC- 3'

LK260-RT 5'- AAGCAACGAAGTAGCAAGCCATTGCAATCGCAATC- 3'

M-RT 5'-AAGCAACGAAGTAG -3'

Figure 13: DNA Sequence Alignment of Coronavirus N Genes isolated from different Species

```
TGE        ------------------------------------------------------------
PRCoV      ------------------------------------------------------------
CcoV       ------------------------------------------------------------
FCoV       ------------------------------------------------------------
SARS-Urb   ---------------------ATGTCTGATAATGGACCCCAATCAAACCAACGTAGT
SARS-Tor   ---------------------ATGTCTGATAATGGACCCCAATCAAACCAACGTAGT
BcoV       ATGTCTTTTACTCCTGG-TAAGCAAT--CCAGTAGTAGAGCGTCCTTTGGAAATCGTTCT
HEV        ATGTCTTTCACTCCTGG-CAAGCAGT--CCAGCAGTAGAGCGTCCTCTGGAAATCGTTCT
MHV        ATGTCTTTTGTTCCTGGGCAAGAAAATGCCGGTAGCAGAAGCTCCTCTGGAAACCGCGCT
RtCoV      ATGTCTTTTGTTCCCGGACAAGAAAACGCCGGTAGCAGAAGCTCCTCTGGAAACCGCGCT
HCoVOC43   ------------------------------------------------------------
PEDV       ------------------------------------------------------------
IBV        ------------------------------------------------------------

TGE        ------------------------------ATGGCCAA-CCAGGGACAA--------
PRCoV      ------------------------------ATGGCCAA-CCAGGGACAA--------
CcoV       ------------------------------ATGGCCTC-TCAGGGACAA--------
FCoV       ------------------------------ATGGCCAC-ACAGGGACAA--------
SARS-Urb   GCCCCCCGCATTACATTTGGTGGACCCACAGATTCAACTGA--CAATAAC---------
SARS-Tor   GCCCCCCGCATTACATTTGGTGGACCCACAGATTCAACTGA--CAATAAC---------
BcoV       GGTAATGGCAT--CCTTAAGTGGGCCGATCAGTCCGACCAATCTAGAAATGT--------
HEV        GGTAATGGCAT--CCTTAAGTGGGCCGATCAGTCCGACCAGTCTAGAAATGT--------
MHV        GGTAATGGCAT--CCTCAAGAAGACCACTTGGGCTGACCAAACCGAGCG-----------
RtCoV      GGTAATGGAAT--CCTCAAGAAGACCACTTGGGCTGACCAAACCGAGCGCGGACAAAATA
HCoVOC43   ------------------------------------------------------------
PEDV       ------------------------------------------------------------
IBV        -----------------------------ATGGCAAGCGGTAAAGCAGC-------

TGE        -CGTGTCAGTTGGGGAGATGAATCTACCAAAACACGTGGTCGT-TCCAATTC---CCGTG
PRCoV      -CGTGTCAGTTGGGGGGATGAATCCACCAAAATACGTGGTCGC-TCCAATTC---CCGTG
CcoV       -CGTGTCAGTTGGGGAGATGAATCCACCAAGAGACGCGGTCGT-TCTAATTC---TCGTG
FCoV       -CGCGTCAACTGGGGAGATGAACCTTCCAAAAGACGTGGTCGT-TCTAACTC---TCGTG
SARS-Urb   -CAGAATGGAGGACGCAATGGGGCAAGGCCAAAACAGCGCCGA-CCCCAAGG----TTTA
SARS-Tor   -CAGAATGGAGGACGCAATGGGGCAAGGCCAAAACAGCGCCGA-CCCCAAGG----TTTA
BcoV       -TCAAACCAGGGGTAGAAGAGCTCAACCCAAGCAAACTGCTAC-TTCTCAGCTACCATCA
HEV        -TCAAACCAGGGGTAGAAGAGTTCAATCCAAGCAAACTGCTAC-TTCTCAGCAACCATCA
MHV        -TGGAAATAGAGGCAGAAGGAACCATCCCAAGCAGACTGCAAC-TACTCAGC--CCAATG
RtCoV      ATGGAAATAGAGGCAGAAGGAATCAGCCCAAGCAGACTGCAAC-TACTCAGC--CCAATA
HCoVOC43   ---------------ATGGCTACAGTCAAATGGGCTGATGCATCTGAACCACAACGTG
PEDV       ---------------------------------ATGGCTTCTGTCAGCTTTCAGG
IBV        -TGGAAAAACAGACGCCCCAGCGCCAGTCATTAAACTAGGAGGACCAAAACCACCTAAAG

TGE        GTCGGAAGAATAATAACATACC-TCTTTCATTCTTCAACCCCATAACCCTCCAACAAGGT
PRCoV      GTCGGAAGATTAATAACATACC-TCTTTCATTCTTCAACCCCATAACCCTCCAGCAAGGT
CcoV       GCCGGAAGAATAATGATATACC-TCTTTCATTCTTCAACCCCATTACCCTCGAGCAAGGA
FCoV       GTCGGAAGAATAATGATATACC-TTTGTCATTCTACAACCCCATTACCCTCGAACAAGGA
SARS-Urb   CCCAATAATACTGCG---------TCTTGGTTCACAGCTCTCACTCAGCATGGCAAGG--
SARS-Tor   CCCAATAATACTGCG---------TCTTGGTTCACAGCTCTCACTCAGCATGGCAAGG--
BcoV       GGAGGGAATGTTGTACCCTACTATTCTTGGTTCTCTGGAATTACTCAGTTTCAAAAAGGA
HEV        GGAGGGACTGTTGTACCCTACTATTCTTGGTTCTCTGGAATTACTCAGTTTCAAAAGGGA
MHV        CC-GGGAGTGTGGTTCCCCATTACTCTTGGTTTTCGGGCATCACCCAGTTTCAAAAGGGA
RtCoV      CC-GGGAGTGTGGTTCCCCATTACTCTTGGTTTTCGGGCATTACCCAATTCCAGAAGGGA
HCoVOC43   GTCGTCAGGGTAGAA---TACC-TTATTCTCTTTATAGCCCTTTGCTTGTTGATAGTG--
```

```
PEDV        ATCGTGGCCGCAAACGGGTGCCATTA-TCTCTCTATGCCCCTCTTAGGGTTACTAATGAC
IBV         TCGGTTCTTCTGGAAATGCA----TCTTGGTTTCAAGCAATAAAAGCCAAGAAGTTAAAT
                                     *   *

TGE         TCAAAATTTTGGAACTTATGTCCGAGAGACTTTGTACCCAAAGGAATAGGTAACAGGGAT
PRCoV       GCAAAATTTTGGAACTCATGTCCGAGAGATTTTGTACCCAAAGGAATAGGTAATAGGGAT
CcoV        TCAAAGTTTTGGGACTTATGTCCGAGAGACTTTGTACCCAAAGGAATAGGTAATAAGGAT
FCoV        TCTAAATTTTGGAATTTATGTCCGAGAGACCTTGTTCCCAAAGGAATAGGTAATAAGGAT
SARS-Urb    -AGGAACTTAGATTCCCTCGAGGCCAGGGCGTTCCAATCAACACCAATAGTGGTCCAGAT
SARS-Tor    -AGGAACTTAGATTCCCTCGAGGCCAGGGCGTTCCAATCAACACCAATAGTGGTCCAGAT
BcoV        AAGGAGTTTGAATTTGCAGAGGGACAAGGTGTGCCTATTGCACCAGGAGTCCCAGCTACT
HEV         AAGGAGTTTGAATTTGCAGAGGGACAAGGTGTGCCTATTGCACCAGGAGTCCCATCTACT
MHV         AAGGAGTTCCAGTTTGCACAAGGACAGGGAGTGCCTATTGCCAGTGGAATCCCCGCTTCA
RtCoV       AAAGAGTTCCAGTTTGCAGGTGGACAAGGAGTGCCTATTGCCAATGGAATCCCACCTTCT
HCoVOC43    -AACAACCTTGGAAGGTGATACCTCGTAATTTGGTACCCATCAACAAGAAAGACAAAAAT
PEDV        AAGCCCCTTTCTAAGGTACTTGCAAACAACGCTGTACCCACTAACAAGGGGAATAAGGAC
IBV         ACACCTCCGCCCAAGTTTGAAGGTAGCGGTGTTCCTGATAACGAAAACATTAAGCCAAGC

TGE         CAACAGATTGGTTATTGGAATAGACAAACTCG------CTATCGCATGGTGAAGGGCCAA
PRCoV       CAACAGATTGGTTATTGGAATAGACAAACTCG------CTATCGCATGGTGAAGGGCCAA
CcoV        CAACAAATTGGTTATTGGAACAGGCAAACCCG------TTATCGCATGGTGAAGGGTCGA
FCoV        CAACAAATTGGTTATTGGAATAGACAGATTCG------TTATCGTATTGTAAAAGGCCAG
SARS-Urb    GACCAAATTGGCTACTACCGAAGAGCTACCCGACGAGTTCGTGGT---GGTGACGGCAAA
SARS-Tor    GACCAAATTGGCTACTACCGAAGAGCTACCCGACGAGTTCGTGGT---GGTGACGGCAAA
BcoV        GAAGCTAAGGGGTACTGGTACAGACACAACAGACGTTCTTTTAAAACAGCCGATGGCAAC
HEV         GAAGCTAAGGGGTACTGGTACAGACACAACAGACGTTCTTTTAAAACAGCCGACGGCAAT
MHV         GAGCAAAAGGGATATTGGTATAGACACAACCGACGTTCTTTTAAAACACCTGATGGCCAG
RtCoV       GAGCAAAAGGGATATTGGTATAGACACAACCGTCGTTCTTTTAAAACACCTGATGGGCAG
HCoVOC43    AAGCTTATAGGCTATTGGAATGTTCAAAAACG------TTTCAGAACTAGAAAGGGCAAA
PEDV        CAGCAAATTGGGTACTGGAATGAGCAAATTCG------CTGGCGCATGCGCCGTGGTGAG
IBV         CAGCAACATGGATACTGGAGACGCCAAGCCAG------GTTTAAGCCAGGCAAAGGTGGA
              *         ** ** *             *                       **

TGE         CGTAAAGAGCTTCCTGAAAGGTGGTTCTTCTACTACTTAGGTACTGGACCTCATGCAGAT
PRCoV       CGTAAAGAGCTTCCTGAAAGGTGGTTCTTTTACTACTTAGGCACTGGACCTCATGCAGAT
CcoV        CGTAAAAATCTTCCTGAAAAGTGGTTCTTCTACTATTTAGGAACTGGACCTCATGCAGAT
FCoV        CGTAAGGAACTCGCTGAGAGGTGGTTCTTTTACTTCTTAGGTACAGGACCTCATGCTGAT
SARS-Urb    ATGAAAGAGCTCAGCCCCAGATGGTACTTCTATTACCTAGGAACTGGCCCAGAAGCTTCA
SARS-Tor    ATGAAAGAGCTCAGCCCCAGATGGTACTTCTATTACCTAGGAACTGGCCCAGAAGCTTCA
BcoV        CAGCGTCAACTGCTGCCACGATGGTATTTTTACTATCTTGGAACAGGACCGCATGCCAAA
HEV         CAGCGTCAACTGCTGCCACGATGGTACTTTTACTACCTGGGAACAGGACCGCATGCCAAA
MHV         CACAAGCAGCTACTGCCCAGATGGTATTTTTACTATCTTGGAACAGGGCCCCATGCTGGC
RtCoV       CAGAAGCAACTACTCCCCAGATGGTATTTTTACTATCTTGGGACGGGCCCCCATGCTGGA
HCoVOC43    CGGGTGGATTTGTCACCCAAGCTGCATTTTTATTATCTTGGCACAGGACCCCATAAAGAT
PEDV        CGAATTGAACAACCTTCCAATTGGCATTTCTACTACCTCGGAACAGGACCTCACGGCGAC
IBV         AGAAAACCAGTCCCAGATGCTTGGTACTTTTACTATACTGGAACAGGACCTGCCGCTGAC
                                     *   ** ** *     ** ** ** **

TGE         GCCAAATTTAAAGATAAATTAGATGGAGTTGTCTGGGTTGCCAAGGATGGTGCCATGAAC
PRCoV       GCCAAATTTAAAGATAAATTAGATGGAGTTGTCTGGGTTGCCAAGGATGGTGCCATGAAC
CcoV        GCCAAATTTAAGCAAAAATTAGATGGAGTTGTCTGGGTTGCTAGGGGAGATTCCATGACT
FCoV        GCTAAATTCAAAGACAAGATTGATGGAGTCTTCTGGGTTGCAAGGGATGGTGCCATGAAC
SARS-Urb    CTTCCCTACGGCGCTAACAAAGAAGGCATCGTATGGGTTGCAACTGAGGGAGCCTTGAAT
SARS-Tor    CTTCCCTACGGCGCTAACAAAGAAGGCATCGTATGGGTTGCAACTGAGGGAGCCTTGAAT
BcoV        GACCAGTATGGCACCGATATTGACGGAGTCTTCTGGGTCGCTAGTAACCAGGCTGATGTC
HEV         GACCAGTACGGCACCGACATTGACGGAGTCTTCTGGGTCGCTAGTAACCAGGCTGATATT
MHV         GCAGAGTATGGCGACGATATCGAAGGAGTTGTCTGGGTCGCAAGCCAACAGGCCGACACT
RtCoV       GCCAGTTTCGGAGACAGCATTGAGGGAGTCTTCTGGGTTGCAAATAGTCAGGCGGATACC
HCoVOC43    GCAAAATTTAGAGAGCGTGTTGAAGGTGTCGTCTGGGTTGCTGTTGATGGTGCTAAAACT
PEDV        CTCCGTTATAGGACTCGTACTGAGGGTGTTTTCTGGGTTGCTAAAGAAGGCGCAAAGACT
IBV         CTGAACTGGGGTGATACTCAAGATGGTATAGTGTGGGTTGCTGCTAAGGGTGCTGATACT
                *                ** **  *  * ***** **             *
```

```
TGE        AAACCAACCACGC---TTGGTAGTCGTGGTGCTAATA---ATGAATCCAAAGCTTTGAAA
PRCoV      AAACCAACCACGC---TTGGTAGTCGTGGTGCTAATA---ATGAATCCAAAGCTTTGAAA
CcoV       AAGCCAACAACTC---TTGGTACTCGTGGCACTAATA---ATGAATCAAAGGCTTTGAAA
FCoV       AAGCCCACAACGC---TTGGCACTCGTGGAACCAATA---ACGAATCCAAACCACTGAGA
SARS-Urb   ACACCCAAAGACCACATTGGCACCCGCAATCCTAATAACAATGCTGCCACCGTGCTACAA
SARS-Tor   ACACCCAAAGACCACATTGGCACCCGCAATCCTAATAACAATGCTGCCACCGTGCTACAA
BcoV       AATACCCCGGCTGACATTCTCGATCGGGACCCAAGTAGCGATGAGGCTATTCCGACTAGG
HEV        AATACCCCGGCTGACATTGTCGATCGGGATCCAAGTAGCGATGAGGCTATTCCGACTAGG
MHV        AAGACCACTGCCGATGTTGTTGAAAGGGACCCAAGCAGTCATGAGGCTATTCCTACTAGG
RtCoV      AACACCTCTGCTGACATTGTTGAAAGGGACCCAAGTAGCCATGAGGCTATTCCTACTAGG
HCoVOC43   GAACCTACAGGTTA---CGGTGTTAGGCGCAAGAATT----CAGAACCAGAGATACCACA
PEDV       GAACCCACTAATT---TGGGTGTCAGAAAGGCGTCTG----AAAAGCCAATCATTCCAAA
IBV        AAATCTAGATCCAATCAGGGTACAAGAGATCCTGATAA-GTTTGACCAATACCCACTACG
                        *                   *              *  *

TGE        TTCG---ATGGTAAAGTGCCAGGCGAA---TTTCAACTTGAAGTTAATCAATCAAGAGAC
PRCoV      TTCG---ATGGTAAAGTGCCAGGCGAA---TTTCAACTTGAAGTTAACCAGTCTAGGGAC
CcoV       TTCG---ATGTCAAAGTACCATCAGAA---TTTCACCTTGAAGTGAACCAATTAAGGGAC
FCoV       TTTG---ATGGTAAGATACCGCCACAG---TTTCAGCTTGAAGTGAACCGTTCTAGGAAC
SARS-Urb   CTTCCTCAAGGAACAACATTGCCAAAAGGCTTCTACGCAGAGGGAAGCAGAGGCGGCAGT
SARS-Tor   CTTCCTCAAGGAACAACATTGCCAAAAGGCTTCTACGCAGAGGGAAGCAGAGGCGGCAGT
BcoV       TTTCCGCCTGGCACGGTACTCCCTCAGGGTTACTATATTGAAGG---CTCAGGAAGGTCT
HEV        TTTCCGCCTGGCACGGTACTCCCTCAAGGTTACTATATTGAAGG---CTCAGGAAGGTCT
MHV        TTTGCGCCCGGCACGGTATTGCCTCAGGGCTTTTATGTAGAAGG---CTCGGGAAGGTCT
RtCoV      TTTGCGCCCGGTACGGTATTGCCTCAGGGTTTCTATGTTGAAGG---CTCGGGAAGGTCT
HCoVOC43   CTTC--AATCAAAAGCTCCCAAATGGTGTTACTGTTGTTGAAGAACCTGACTCCCGTGCT
PEDV       ATTC--TCTCAACAGCTCCCCAGTGTA---GTTGAGATTGTTGAACCTAACACACCTCCT
IBV        ATTC----TCGGATGGCGGACCTGATGGTAATTTCCGTTGGGACTTCATTCCCCTGAACC
                 *                                *

TGE        AATTCAAGGTCACGCTCTCAATCTAGATCTC------GGTCTAGAAATAGATCTCAATCT
PRCoV      AACTCAAGGTCACGCTCTCAATCTAGATCGC------GGTCTAGAAACAGATCTCAATCT
CcoV       AATTCAAGGTCTAGGTCTCAATCTAGATCTC------AGTCCAGAAATAGGTCTCAATCT
FCoV       AATTCAAGGTCTGGTTCTCAGTCTAGATCTG------TTTCAAGAAACAGATCTCAATCT
SARS-Urb   CAAGCCTCTTCTCGCTCCTCATCACGTAGTCGCGGTAATTCAAGAAATTCAACTCCTGGC
SARS-Tor   CAAGCCTCTTCTCGCTCCTCATCACGTAGTCGCGGTAATTCAAGAAATTCAACTCCTGGC
BcoV       GCTCCTAATTCCAGATCTACTTCACGCGCATCCAGTAGAGCCTCTAGTGCAGGATCGCGT
HEV        GCTCCTAATTCCAGATCTACTTCGCGTGCACCCAATAGAGCCCCTAGTGCAGGATCGCGT
MHV        GCACCTGCTAGTCGATCTGGTTCGCGGTCAC------AATCCCGTGGGCCAAATAATCGC
RtCoV      GCACCTGCTAGTCGATCTGGTTCGCGGTCAC------AATCCCGTGGGCCAAATAATCGC
HCoVOC43   CCTTCCCGGTCTCAGTCGAGGTCGCAGAGTCGCGGTCGTGGTGAATCCAAACCTCAATCT
PEDV       GCTTCACGTGCAAATTCGCGTAGCAGGAGTCGTGGCAATGGCAACAATAGGTCTAGATCT
IBV        GTGGTAGGAGTGGAAGATCAACAGCAGCTTCATCA-GCAGCAGCTAGTAGAGCACCATCA

TGE        AGAGGCAGGCAACAATTCAATAACAAGAAGGAT-------GACAGTGTAGAACAAGCTGT
PRCoV      AGAGGTAGGCAACAATCCAATAACAAGAAGGAT-------GACAGTGTAGAACAAGCTGT
CcoV       AGAGGAAGGCAACTATCCAATAATAAGAAGGAT-------GACAATGTTGAACAAGCTGT
FCoV       AGAGGAAGACACCATTCCAATAACCAGAA---T-------AATAATGTTGAGGATACAAT
SARS-Urb   AGCAGTAGGGAAATTCTCCTGCTCGAATGGCT-------AGCGGAGGTGGTGAAACTGC
SARS-Tor   AGCAGTAGGGAAATTCTCCTGCTCGAATGGCT-------AGCGGAGGTGGTGAAACTGC
BcoV       AG---TAGAGCCAATTCTGGCAACAGAACCCCT-------ACCTCTGGTGTAACACCTGA
HEV        AG---TAGAGCCAATTCTGGCAATAGAACCTCT-------ACCCCTGGTGTAACACCTGA
MHV        GC---TAGAAGCAGTTCCAACCAGCGCCAGCCT-------GCCTCTGCTGTAAAACCTGA
RtCoV      GC---TAGAAGCAGTTCCAACCAGCGCCAGCCT-------GCCTCTACTGTAAAACCTGA
HCoVOC43   CGGAATCCTTCAAGTGACAGAAACCATAACAGTCAG----GATGACATCATGAAGGCAGT
PEDV       CCAAGTAACAACAGAGGCAATAACCAGTCCCGTGGTAATTCACAGAATCGTGGAAATAAC
IBV        CG------TGAAGGTTCGCGTGGTCGTAGAAGT-------GATTCTGGAGATGACCTTAT
                                                     *

TGE        T---CTTGCCGCACTT-----AAAAAGTTAGGTGTTGACACAGAAAAACAACAGCA-ACG
```

```
PRCoV       T---CTTGCCGCACTT-----AAAAAGTTAGGTGTTTACACAGAAAAACAACAGCA-ACG
CcoV        T---CTTGCTGCACTC-----AAAAAGTTAGGTGTTGACACAGAAAAACAA---CA-AAG
FCoV        T---GTAGCCGTGCTT-----GAAAAATTAGGTGTT---ACTGACAAACAA-------AG
SARS-Urb    C---CTCGC-G--CTA-----TTGCTGCTAGAC-AGATTGAACCAGCTTGAGAGCA-AAG
SARS-Tor    C---CTCGC-G--CTA-----TTGCTGCTAGAC-AGATTGAACCAGCTTGAGAGCA-AAG
BcoV        T---ATGGCTG--ATC-----AAATTGCTAGTC-TTGTTCTGGCAAAACTTG-GCA-AGG
HEV         C---ATGGCTG--ATC-----AAATTGCTAGTC-TTGTTCTGGCAAAACTTG-GCA-AGG
MHV         C---ATGGCCG--AAG-----AAATTGCTGCTC-TTGTTTTGGCTAAGCTTG-GTA-AAG
RtCoV       T---ATGGCCG--AAG-----AAATTGCTGCTC-TTGTTTTGGCTAATCTAG-GCA-AAG
HCoVOC43    T---GCTGCGGCTCTT-----AAATCTTTAGGTTTTGACAAGCCTCAGGAAAAAGATAAA
PEDV        CAGGGTCGTGGAGCTTCTCAGAACAGAGGAGGCAATAATAATAACAATAACAAGTCTCGT
IBV         TGCTCGTGCAGCAAAG------ATAATCCAGGATCAGCAGAAAAAGGGCTCTCGCA--TT
                    *  *

TGE         CTCTCGTTCTAAATCTAAAG--AACGTAGTAACTCTAAGAC-AAGA--------GATACT
PRCoV       CTCTCGTTCTAAATCTAAAG--AACGTAGTAACTCTAAAAC-AAGA--------GATACT
CcoV        ATCTCGTTCCAAATCTAAGG--AACGTAGCAGCTCTAAGAC-AAGA--------GATACT
FCoV        GTCACGTTCTAAACCTAGAG--AACGTAGTGATTCCAAACC-TAGG--------GACACA
SARS-Urb    TTTCTGGTAAAGGCCAACAA-CAACAAGGCCAAACTGTCACTAAGA--------AATCTG
SARS-Tor    TTTCTGGTAAAGGCCAACAA-CAACAAGGCCAAACTGTCACTAAGA--------AATCTG
BcoV        ATGCCACTAAGCCACAGCAAGTAACTAAGC-AGACTGCCA--AAGA--------AATCAG
HEV         ATGCCACTAAGCCTCAGCAAGTAACTAAGC-AGACTGCCA--AAGA--------GGTCAG
MHV         ATGCCGGCCAGCCCAAGCAGGTAACTAAGC-AAAGCGCCA--AAGA--------AGTCAG
RtCoV       ATGCCGGACAGCCTAAGCAAGTAACTAAGC-AAAGTGCCA--AAGA--------AGTCAG
HCoVOC43    AAGTCAGCGAAAACGGGTAC--TCCTAAGCCTTCTCGTAATCAGAGT----CCTGCTTCT
PEDV        AACCAGTCCAATAACAGGAACCAGTCAAATGACCGTGGTGGTGTAACATCACGCGATGAT
IBV         ACCAAGGCAAAGGCAGATGA--AATGGCTCATCGCCGGTATTGCAAG----CGCACTATC

TGE         ACACCTAAGAATGAAAACAAACACACCTGGA---AGAGAACTGCAGGTAAA---GGTG--
PRCoV       ACGCCTAAGAATGAAAACAAACACACCTGGA---AGAGAACTGCAGGTAAA---GGTG--
CcoV        ACACCTAAGAATGAAAACAAACACACCTGGA---AGAGAACTGCAGGTAAA---GGTG--
FCoV        ACACCTAAGAATGCCAACAAACACACCTGGA---AGAAAACTGCAGGCAAG---GGAG--
SARS-Urb    CTGCTGAGGCATCTAAA-AAGCCTCGCCAAA---AACGTACTGCCACAAAAC--AGTACA
SARS-Tor    CTGCTGAGGCATCTAAA-AAGCCTCGCCAAA---AACGTACTGCCACAAAAC--AGTACA
BcoV        --ACAGAAAATTTTGAATAAGCCCCGCCAGA---AGAGGAGCCCCAATAAAC--AATGCA
HEV         --ACAGAAAATCTTGAATAAGCCCCGCCAGA---AGAGGAGCCCCAACAAAC--AATGCA
MHV         --GCAGAAAATTTTAACTAAGCCTCGTCAAA---AGAGGACTCCAAACAAGC--AGTGCC
RtCoV       --GCAGAAAATTTTAAATAAGCCTCGCCAAA---AGAGGACTCCAAACAAGC--AGTGCC
HCoVOC43    TCTCAAACTTCTGCCAAGAGTCTTGCTCGTTCTCAGAGTTCTGAAACAAAAG--AACAAA
PEDV        CTGGTGGCTGCTGTCAAGGATGCACTTAAATCTTTGGGTATTGGAGAAAATCCTGACAGG
IBV         CCACCTAATTATAGGGTTGATCAAGTGTTTGGTCCCCGTACTAAAGGTAAGG--AGGGGA
                                                            **

TGE         ---ATGTGACA---AGATTTTATGGAGCTAGAAGCAGTT--CAGCC-------AAT-TTT
PRCoV       ---ATGTGACA---AGATTTTATGGAGCTAGAAGCAGCT--CAGCC-------AAT-TTT
CcoV        ---ATGTGACA---AAATTTTATGGAGCTAGAAGTAGTT--CAGCC-------AAT-TTT
FCoV        ---ATGTGACA---ACTTTCTATGGTGCTAGAAGTAGTT--CAGCT-------AAC-TTT
SARS-Urb    A-CGTCACTCA---AGCATTTGGGAGACGTGGTCCAGAA--CAAACCCAAGGAAAT-TTC
SARS-Tor    A-CGTCACTCA---AGCATTTGGGAGACGTGGTCCAGAA--CAAACCCAAGGAAAT-TTC
BcoV        C-TGTTCAGCA---GTGTTTTGGGAAGAGAGGCCCCAAT--CAGA---------AT-TTT
HEV         C-TGTTCAGCA---GTGTTTTGGGAAGAGAGGCCCCAAT--CAGA---------AT-TTT
MHV         C-AGTGCAGCA---GTGTTTTGGGAAGAGAGGCCCTAAT--CAGA---------AC-TTT
RtCoV       C-AGTGCAGCA---GTGTTTTGGAAAGAGAGGCCCCAAT--CAGA---------AT-TTT
HCoVOC43    AGCATGAAATGC--AAAAGCCACGGTGGAAAAGACAGCC--TAATGATGATGTGACATCT
PEDV        CATAAGCAACAGCAGAAGCCTAAGCAGGAAAAGTCTGACAACAGCGGCAAAAATACACCT
IBV         A--TTTTGGTG-----ATGACAAGATGAATGAGGAAGGTATTAAGGATG----GGCGTGT
                                                      *
```

```
TGE         GGTGACACTGACCTCGTTGCCAAT----GGGAGCAGTGCCAAGCATTACCCACAACTGGC
PRCoV       GGTGACAGTGACCTCGTTGCCAAT----GGGAGCAGTGCCAAGCATTACCCACAATTGGC
CcoV        GGTGACAGCGATCTTGTTGCCAAT----GGGAACGGTGCCAAGCATTACCCACAACTGGC
FCoV        GGTGATAGTGATCTCGTTGCCAAT----GGTAACGCTGCCAAATGCTACCCTCAGATAGC
SARS-Urb    GGGGACCAAGACCTAATCAGACAA----GGAACTGATTACAAACATTGGCCGCAAATTGC
SARS-Tor    GGGGACCAAGACCTAATCAGACAA----GGAACTGATTACAAACATTGGCCGCAAATTGC
BcoV        GGTGGTGGAGAAATGTTAAAACTT----GGAACTAGTGACCCACAGTTCCCCATTCTTGC
HEV         GGTGGTGGAGAAATGTTAAAACTT----GGAACTAGTGACCCACAGTTCCCCATTCTTGC
MHV         GGAGGCTCTGAAATGTTAAAACTT----GGAACTAGTGATCCGCAGTTCCCCATTCTTGC
RtCoV       GGAGGCCCTGAAATGTTAAAACTT----GGAACTAGTGATCCACAGTTCCCCATTCTTGC
HCoVOC43    AATGTCACACAATGTTTTGGCCCC----AGAGACCTTGAC---CACAACTTTGGAAGTGC
PEDV        AAGAAGAACAAATCCAGGGCCACTTCGAAGGAACGTGACCTCAAAGACATCCCAGAGTGG
IBV         TACAGCAATGCTCAACCTAGTCCCT---AGCAGCCATGCT-----TGTCTTTTTGGAAGT
                                             *                            *

TGE         TGAATGTGTT-CCATCTGTGTC--TAGCATT----CT--GTTTGGAA-GCTATTGGACTT
PRCoV       TGAATGTGTT-CCATCTGTGTC--TAGCATT----TT--GTTTGGAA-GCTATTGGACTT
CcoV        TGAATGTGTT-CCATCTGTATC--TAGCATT----CT--GTTTGGAA-GCCATTGGACTG
FCoV        TGAATGTGTT-CCATCAGTGTC--TAGCATA----AT--CTTTGGCA-GTCAATGGTCTG
SARS-Urb    ACAATTTGCT-CCAAGTGCCTC--TGCA-------TT--CTTTGGAATGTCAC--GCATT
SARS-Tor    ACAATTTGCT-CCAAGTGCCTC--TGCA-------TT--CTTTGGAATGTCAC--GCATT
BcoV        AGAACTCGCA-CCCACAGCTGG--TGCGTTT----TT--CTTTGGATCAAGATTAGAGTT
HEV         AGAACTCGCA-CCCACAGCTGG--TGCGTTT----TT--CTTTGGATCAAGATTAGAGTT
MHV         AGAGTTGGCT-CCAACACCTAG--TGCCTTC----TT--CTTTGGATCTAAATTAGAATT
RtCoV       AGAGTTGGCC-CCAACACCTGG--TGCCTTC----TT--CTTTGGATCTAAATTAGAATT
HCoVOC43    AGGTGTTGTGGCCAATGGTGTT--AAAGCTAAAGGCT--ATCCACAATTTGCTGAGCTTG
PEDV        AGGAGAATTC-CCAAGGGCGAAAATAGCGTAGCAGCTTGCTTCGGACCCAGAGGGGGCTT
IBV         AGAGTGACACCCAAACTTCAAC--TAGATGG--GCTTCACTTGAGATTTGAATTTACTAC
                       *                        *   *

TGE         CAAAGGAA--GATGGCG----ACCAGATAGAAGTCAC----GTTCACACACAAATACC--
PRCoV       CAAAGGAA--GATGGCG----ACCAGATAGAAGTCAC----GTTCACACACAAATACC--
CcoV        CTAAGGAA--GATGGTG----ACCAGATTGAAGTCAC----ATTCACACACAAATACC--
FCoV        CTGAAGAA--GCTGGTG----ATCAAGTGAAAGTCAC----GCTCACTCACACCTACT--
SARS-Urb    GGCA-----------------------TGGAAGTCAC----ACCTTCGGGAACATG----
SARS-Tor    GGCA-----------------------TGGAAGTCAC----ACCTTCGGGAACATG----
BcoV        GGCCAAAG--TGCAGAA----TTTGTCTGGGAATCTTGACGAGCCCCAGAAGGATGTTTA
HEV         GGCCAAAG--TGCAGAA----TTTGTCTGGGAATCCTGACGAGCCCCAGAAGGATGTTTA
MHV         GGTCAAAA-----AGAA----CT---CTGGTGGTGCTGATGAACCCACCAAAGATGTTTA
RtCoV       GGTCAAAA-----AGAA----TT---CTGGTGGCGTTGATGAACCCACCAAAGATGTGTA
HCoVOC43    TGCCGTCA--ACAGCTGCTATGCTGTTTGATAGTCAC-ATTGTTTCCAAAGAGTCAGGCA
PEDV        CAAAAACTTTGGAGATGCGGAATTTGTCGAAAAAGGTGTTGATGCGTCAGGCTATGCTCA
IBV         TGTGGTCCCATGTGATGACCCGCAGTTTGATAATTATGTGAAAATTTGTGATCAGTGT--

TGE         --ACT-TGCCAAAGGATGA--TCCTA--AGACTGGACAATTCCTTCAGCAGATTAATGCC
PRCoV       --ACT-TGCCAAAGGATCA--TCCTA--AAACTGAACAATTCCTTCAGCAGATTAATGCC
CcoV        --ACT-TGCCAAAGGATGA--TCCTA--AGACTGGACAATTCCTTCAGCAGATTAATGCA
FCoV        --ACC-TGCCAAAGGATGA--TGCCA--AAACTAGTCAATTCCTAGAACAGATTGACGCT
SARS-Urb    ---GC-TGACTTATCATGG--AGCCATTAAATTGGATGACAAAGATCCACAATTCAAAGA
SARS-Tor    ---GC-TGACTTATCATGG--AGCCATTAAATTGGATGACAAAGATCCACAATTCAAAGA
BcoV        TGAAT-TGCGCTATAATGG--TGCAATTAGATTTGACAGTACACTTTCAGGTTTTGAGAC
HEV         TGAAT-TGCGCTATAATGG--CGCGATTAGATTTGACAGCACACTCTCAGGTTTTGAAAC
MHV         TGAAT-TGCAGTATTCAGG--TGCAATTAGATTTGATAGTACTCTACCCGGTTTTGAGAC
RtCoV       TGAGC-TGCAATATTCAGG--TGCAGTCAGATTTGATAGTACTCTACCTGGTTTTGAGAC
HCoVOC43    ACACTGTGGTCTTGACTTT--CACTACTAGAGT-GACTGTGCCCAAAGACCATCCACACT
PEDV        GATCGCCAGTTTAGCACCAAATGTTGCAGCATTGCTCTTTGGTGGTAATGTGGCTGTTCG
IBV         -GTCGATGGTGTAGGAACGCGTCCAA---AAGATGACGA-ACCAAAACCAAAGTCACGCT
                                          *

TGE         TATGCTCG--TCCATCAGAAGTGGCAAAAGAA--CAGAGA-AAAAGA-----AAATCTCG
PRCoV       TATGCTAG--CCCATCAGAATTGGCAAAAGAA--CAGAGA-AAAAGA-----AAGTCTCG
CcoV        TACGCCCG--TCCATCAGAGGTGGCTAAAGAA--CAGAGA-CAACGC-----AAAGCTCG
```

```
FCoV        TACAAGCG--ACCTTCTGAAGTGGCTAAGGAT--CAGAGG-CAAAGA-----AGATCCCG
SARS-Urb    CAACGTCA--TACTGCTGAACAAGCACATTGA--CGCATA-CAAAAC-----ATTCCCAC
SARS-Tor    CAACGTCA--TACTGCTGAACAAGCACATTGA--CGCATA-CAAAAC-----ATTCCCAC
BcoV        CATAATGA--AGGTGTTGAATGAGAATTTGAA--TGCATATCAACAA-----CA---AGA
HEV         CATTATGA--AGGTGCTTAACCAGAATTTGAA--TGCCTATCAACAT-----CAGGAAGA
MHV         TATCATGA--AAGTGTTGACTGAGAATTTGAA--TGCCTACCAGGAC-----CAAGCTGG
RtCoV       TATCATGA--AAGTGTTGAATGAGAATTTGAA--TGCCTACCAGAAT-----CAAGCTGG
HCoVOC43    TG-GGTAA--GTTTCTTGAGGAGTTAAATGCATTCACTAGAGAAATG-----CAACAACA
PEDV        TGAGCTAGCGGACTCTTACGAGATTACATACAACTATAAAATGACTGTGCCAAAGTCAGA
IBV         CAAGTTCAAGACCTGCTACAAGAGGAAATTCT--CCAGCGCCAAGACAACAGCGCCCAAA

TGE         TTCTAAATCTGCAGAAAGGTCAGAGCAAGATGTGGTACCTGATGCATTAATAGAA-AATT
PRCoV       TTCTAAATCTGCAGAAAGGTCAGAGCAAGAGGTGGTACCTGATTCATTAATAGAA-AACT
CcoV        TTCTAAATCTGTAGAAAGGGTAGAGCAAGAGGTTGTACCTGATGCATTAACAGAA-AATT
FCoV        TTCTAAGTCTGCTGATAAG---AAGCCTGAGGAGTTGTCTGTAACTCTTGTGGAG-GCAT
SARS-Urb    CAACAGAGCCTAAAAAGGACAAAAAGAAAAAGACTGATGAAGCTCAGCCTTTGCC-GCAG
SARS-Tor    CAACAGAGCCTAAAAAGGACAAAAAGAAAAAGACTGATGAAGCTCAGCCTTTGCC-GCAG
BcoV        TGGTATGATGAATATGAGTCCAAAACCACAGCGTCAGCGTGGTCAGAAG-------AATG
HEV         TGGGATGATGAATATTAGTCCTAAACCACAGCGGCAGCGTGGTCAGAAG-------AATG
MHV         TAGTGTAGATCTAGTGAGCCCAAAGCCTCCAAGAAGAGGTCGTAGACAGGCTCAA-GAAA
RtCoV       TGGTGCAGATGTAGTGAGCCCAAAGCCCCAAAGAAAGAGAGGGACGAAACAAACG-GCTC
HCoVOC43    TCCTCTTCTTAACCCTAGTGCACTAGAATTCAACCCATCTCAAACTTCACCTGCA-ACTG
PEDV        TCCAAATGTTGAGCTTCTTGTTTCACAGGTGGATGCATTTAAAACTGGGAATGCAAAACT
IBV         GAAGGAGAAAAAGCTAAAGAAGCAGGATGATGAAGCAGATAAAGCATTGACCTCAGATGA

TGE         ATACAGATGTGTTTGAT-GACACACAGGT-TGAGATAATTGATGAGGTA-ACGAACTAA-
PRCoV       ATACAGATGTGTTTGAT-GACACACAGGT-TGAGATGATTGACGAGGTA-ACGAACTAA-
CcoV        ACACAGATGTGTTTGAT-GACACACAGGT-TGAGATTATTGATGAGGTA-ACGAACTAA-
FCoV        ACACAGATGTGTTTGAT-GACACACAGGT-TGAGATGATTGATGAGGTT-ACGAACTAA-
SARS-Urb    AGACAAAAAGAAGCAGCCCACTGTGACTCT-TCTT---CCTGCGGCTGAC-ATG-GATGAT
SARS-Tor    AGACAAAAAGAAGCAGCCCACTGTGACTCT-TCTT---CCTGCGGCTGAC-ATG-GATGAT
BcoV        GACAAGGAGAAAATGAT-AATATAAGTGT-TGCAGCGCCTAAAAGCCGT-GTGCAGCAAA
HEV         GACAAGTAGAAAATGAT-AATGTAAGTGT-TGCAGCGCCTAAAAGCCGT-GTGCAGCAAA
MHV         AGAAAGATGAAGTAGAT-AATGTAAGCGT-TGCAAAGCCCAAAAGCTTG-GTGCAGCGAA
RtCoV       AGAAAGAAGAATTAGAT-AGTATAAGCGT-TGCAAAGCCCAAAAGTGCC-GTGCAGCGAA
HCoVOC43    CTGAACCAGTGCGTGAT-GAAGTTTCTAT-TGAAA--CTGACATAATTG-ATGAAGTAAA
PEDV        CCAGAGAAAGAAGGAAAAGAAGAACAAGCGTGAAACCACGCTGCAGCAGCATGAAGAGGC
IBV         GGAGAGGAACAATGCACAGCTGGAATTTTATGATGAGCCCAAGGTAATTAACTGGGGGGA
                *                             *

TGE         ------------------------------------------------------------
PRCoV       ------------------------------------------------------------
CcoV        ------------------------------------------------------------
FCoV        ------------------------------------------------------------
SARS-Urb    TTCTCCAGACAACTTCAAAATTCCATGAGTGGAGCTTCTGCTGATTCAACTCAGGCATAA
SARS-Tor    TTCTCCAGACAACTTCAAAATTCCATGAGTGGAGCTTCTGCTGATTCAACTCAGGCATAA
BcoV        ATAAGAGTAGAGAGTTGACTGCAGAGGACATCAGC--CTTCTTAAGAAGAT---GGATGA
HEV         ATAAGAGTAGAGAGTTGACAGCAGAGGACATCAGC--CTTCTTAAGAAGAT---GGATGA
MHV         ATGTAAGTAGAGAATTAACCCCCGAGGATCGTAGC--CTGCTGGCTCAGATCCTAGACGA
RtCoV       ATGTAAGCAGAGAATTAACCCCAGAGGATAGAAGC--CTGTTGGCGCAGATCCTAGATGA
HCoVOC43    CTAA--------------------------------------------------------
PEDV        CATCTACGATGATGTGGGTGCGCCATCTGATGTGACCCATGCCAATCTGGAATGGGACAC
IBV         TGCAGCTCTAGGAGAGAATGAACTTTGA--------------------------------

TGE         ------------------------------------------------------------
PRCoV       ------------------------------------------------------------
CcoV        ------------------------------------------------------------
FCoV        ------------------------------------------------------------
SARS-Urb    ------------------------------------------------------------
```

```
SARS-Tor     ------------------------------------------------------------
BcoV         --GCCCTATACTGAA----------GACACCTCAGAAATATAA-----------------
HEV          --GCCCTATACTGAA----------GATACCTCAGAAATATAA-----------------
MHV          TGGCGTTGTGCCAGATGGGTTGGAAGATGACTCTAATGTGTAA-----------------
RtCoV        TGGCGTTGTGCCTGATGGGTT---AGATGACTCTAATGTGTAA-----------------
HCoVOC43     ------------------------------------------------------------
PEDV         AGCTGTTGATGGTGGTGATACGGCCGTTGAAATTATCAACGAGATCTTCGATACAGGAAA
IBV          ------------------------------------------------------------

TGE          ----
PRCoV        ----
CcoV         ----
FCoV         ----
SARS-Urb     ----
SARS-Tor     ----
BcoV         ----
HEV          ----
MHV          ----
RtCoV        ----
HCoVOC43     ----
PEDV         TTAA
IBV          ----
```

**Figure 14: Phylogenetic Analysis of *N* Gene**
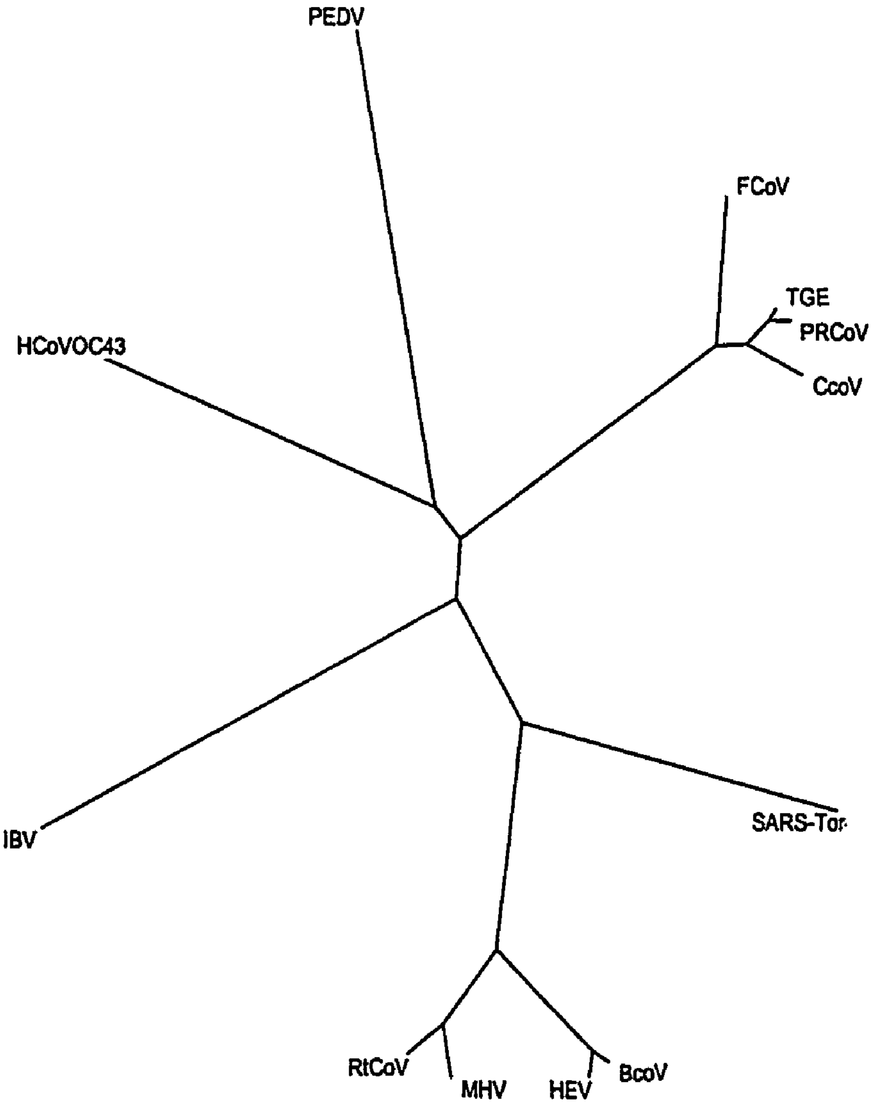

**Figure 15: Molecular Designs for SARS-Associated *N* Gene**
| | |
|---|---|
| **NOTE:** | LK261 is a TET-molecular beacon, which recognizes the *N* **gene of coronavirus (SARS Tor2 and SARS urbani human pathogenic strains).** It will be used in a real-time PCR diagnostic for the identification of **SARS-associated coronavirus** RNA/DNA. |
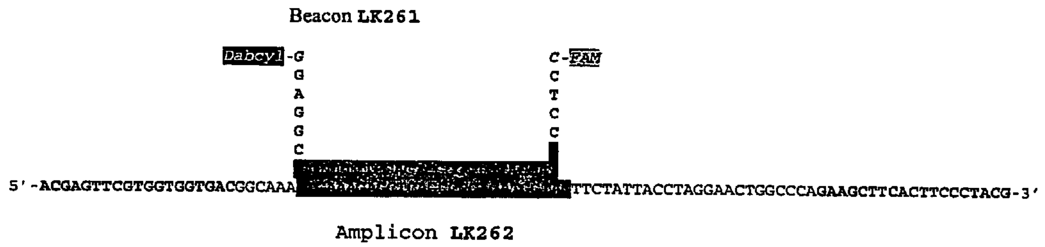

LK261

| | |
|---|---|
| M. Target recognition sequence: | 26 nucleotides (11 G/C) + (1 G/C arm) |
| N. Length of the arms: | 6 nucleotides (5 G/C) |
| O. Melting temperature of the beacon: | dG = -1.64 dH = -48.7 dS = -145.8 Tm = 61.0 °C |
| P. Melting temperature of target: | °C (including 1 nucleotide from the arms) |

---

<u>LK263</u> 5'-ACGAGTTCGTGGTGGTGAC-3'

Length: 19 nucleotides (11 G/C)
*Tm*: °C
Position: (see alignment below)

<u>LK264</u> 5' –CGTAGGGAAGTGAAGCTTC-3'

Length: 19 nucleotides (10 G/C)
*Tm*: °C
Position: (see alignment below)

<u>N-RT</u> 5' –GCCTTCTTTGTTAG-3'

Length: 14 nucleotides (6 G/C)
*Tm*: 47 °C
Position: (see alignment below)

<u>LK262 Amplicon (95 nucleotides)</u>

5'–
ACGAGTTCGTGGTGGTGACGGCAAAATGAAAGAGCTCAGCCCCAGATGGTAC
TTCTATTACCTAGGAACTGGCCCAGAAGCTTCACTTCCCTACG -3'

DNA sequence alignment of complete N genes from corona virus strains

```
TGE         ------------------------------------------------------------
PRCoV       ------------------------------------------------------------
CcoV        ------------------------------------------------------------
FCoV        ------------------------------------------------------------
SARS-Urb    ------------------------ATGTCTGATAATGGACCCCAATCAAACCAACGTAGT
SARS-Tor    ------------------------ATGTCTGATAATGGACCCCAATCAAACCAACGTAGT
BcoV        ATGTCTTTTACTCCTGG-TAAGCAAT--CCAGTAGTAGAGCGTCCTTTGGAAATCGTTCT
HEV         ATGTCTTTCACTCCTGG-CAAGCAGT--CCAGCAGTAGAGCGTCCTCTGGAAATCGTTCT
MHV         ATGTCTTTTGTTCCTGGGCAAGAAAATGCCGGTAGCAGAAGCTCCTCTGGAAACCGCGCT
RtCoV       ATGTCTTTTGTTCCCGGACAAGAAAACGCCGGTAGCAGAAGCTCCTCTGGAAACCGCGCT
HCoVOC43    ------------------------------------------------------------
PEDV        ------------------------------------------------------------
```

| | |
|---|---|
| IBV | ------------------------------------------------------------ |

| | |
|---|---|
| TGE | ---------------------------------ATGGCCAA-CCAGGGACAA-------- |
| PRCoV | ---------------------------------ATGGCCAA-CCAGGGACAA-------- |
| CcoV | ---------------------------------ATGGCCTC-TCAGGGACAA-------- |
| FCoV | ---------------------------------ATGGCCAC-ACAGGGACAA-------- |
| SARS-Urb | GCCCCCCGCATTACATTTGGTGGACCCACAGATTCAACTGA--CAATAAC---------- |
| SARS-Tor | GCCCCCCGCATTACATTTGGTGGACCCACAGATTCAACTGA--CAATAAC---------- |
| BcoV | GGTAATGGCAT--CCTTAAGTGGGCCGATCAGTCCGACCAATCTAGAAATGT-------- |
| HEV | GGTAATGGCAT--CCTTAAGTGGGCCGATCAGTCCGACCAGTCTAGAAATGT-------- |
| MHV | GGTAATGGCAT--CCTCAAGAAGACCACTTGGGCTGACCAAACCGAGCG----------- |
| RtCoV | GGTAATGGAAT--CCTCAAGAAGACCACTTGGGCTGACCAAACCGAGCGCGGACAAAATA |
| HCoVOC43 | ------------------------------------------------------------ |
| PEDV | ------------------------------------------------------------ |
| IBV | ---------------------------------ATGGCAAGCGGTAAAGCAGC------- |

| | |
|---|---|
| TGE | -CGTGTCAGTTGGGGAGATGAATCTACCAAAACACGTGGTCGT-TCCAATTC---CCGTG |
| PRCoV | -CGTGTCAGTTGGGGGGATGAATCCACCAAAATACGTGGTCGC-TCCAATTC---CCGTG |
| CcoV | -CGTGTCAGTTGGGGAGATGAATCCACCAAGAGACGCGGTCGT-TCTAATTC---TCGTG |
| FCoV | -CGCGTCAACTGGGGAGATGAACCTTCCAAAAGACGTGGTCGT-TCTAACTC---TCGTG |
| SARS-Urb | -CAGAATGGAGGACGCAATGGGGCAAGGCCAAAACAGCGCCGA-CCCCAAGG----TTTA |
| SARS-Tor | -CAGAATGGAGGACGCAATGGGGCAAGGCCAAAACAGCGCCGA-CCCCAAGG----TTTA |
| BcoV | -TCAAACCAGGGGTAGAAGAGCTCAACCCAAGCAAACTGCTAC-TTCTCAGCTACCATCA |
| HEV | -TCAAACCAGGGGTAGAAGAGTTCAATCCAAGCAAACTGCTAC-TTCTCAGCAACCATCA |
| MHV | -TGGAAATAGAGGCAGAAGGAACCATCCCAAGCAGACTGCAAC-TACTCAGC--CCAATG |
| RtCoV | ATGGAAATAGAGGCAGAAGGAATCAGCCCAAGCAGACTGCAAC-TACTCAGC--CCAATA |
| HCoVOC43 | -----------------ATGGCTACAGTCAAATGGGCTGATGCATCTGAACCACAACGTG |
| PEDV | -------------------------------------ATGGCTTCTGTCAGCTTTCAGG |
| IBV | -TGGAAAAAACAGACGCCCCAGCGCCAGTCATTAAACTAGGAGGACCAAAACCACCTAAAG |

| | |
|---|---|
| TGE | GTCGGAAGAATAATAACATACC-TCTTTCATTCTTCAACCCCATAACCCTCCAACAAGGT |
| PRCoV | GTCGGAAGATTAATAACATACC-TCTTTCATTCTTCAACCCCATAACCCTCCAGCAAGGT |
| CcoV | GCCGGAAGAATAATGATATACC-TCTTTCATTCTTCAACCCCATTACCCTCGAGCAAGGA |
| FCoV | GTCGGAAGAATAATGATATACC-TTTGTCATTCTACAACCCCATTACCCTCGAACAAGGA |
| SARS-Urb | CCCAATAATACTGCG---------TCTTGGTTCACAGCTCTCACTCAGCATGGCAAGG-- |
| SARS-Tor | CCCAATAATACTGCG---------TCTTGGTTCACAGCTCTCACTCAGCATGGCAAGG-- |
| BcoV | GGAGGGAATGTTGTACCCTACTATTCTTGGTTCTCTGGAATTACTCAGTTTCAAAAAGGA |
| HEV | GGAGGGACTGTTGTACCCTACTATTCTTGGTTCTCTGGAATTACTCAGTTTCAAAAGGGA |
| MHV | CC-GGGAGTGTGGTTCCCCATTACTCTTGGTTTTCGGGCATCACCCAGTTTCAAAAGGGA |
| RtCoV | CC-GGGAGTGTGGTTCCCCATTACTCTTGGTTTTCGGGCATTACCCAATTCCAGAAGGGA |
| HCoVOC43 | GTCGTCAGGGTAGAA---TACC-TTATTCTCTTTATAGCCCTTTGCTTGTTGATAGTG-- |
| PEDV | ATCGTGGCCGCAAACGGGTGCCATTA-TCTCTCTATGCCCCTCTTAGGGTTACTAATGAC |
| IBV | TCGGTTCTTCTGGAAATGCA----TCTTGGTTTCAAGCAATAAAAGCCAAGAAGTTAAAT |
| | * * |

| | |
|---|---|
| TGE | TCAAAATTTTGGAACTTATGTCCGAGAGACTTTGTACCCAAAGGAATAGGTAACAGGGAT |
| PRCoV | GCAAAATTTTGGAACTCATGTCCGAGAGATTTTGTACCCAAAGGAATAGGTAATAGGGAT |
| CcoV | TCAAAGTTTTGGGACTTATGTCCGAGAGACTTTGTACCCAAAGGAATAGGTAATAAGGAT |
| FCoV | TCTAAATTTTGGAATTTATGTCCGAGAGACCTTGTTCCCAAAGGAATAGGTAATAAGGAT |
| SARS-Urb | -AGGAACTTAGATTCCCTCGAGGCCAGGGCGTTCCAATCAACACCAATAGTGGTCCAGAT |
| SARS-Tor | -AGGAACTTAGATTCCCTCGAGGCCAGGGCGTTCCAATCAACACCAATAGTGGTCCAGAT |
| BcoV | AAGGAGTTTGAATTTGCAGAGGGACAAGGTGTGCCTATTGCACCAGGAGTCCCAGCTACT |
| HEV | AAGGAGTTTGAATTTGCAGAGGGACAAGGTGTGCCTATTGCACCAGGAGTCCCATCTACT |
| MHV | AAGGAGTTCCAGTTTGCACAAGGACAGGGAGTGCCTATTGCCAGTGGAATCCCCGCTTCA |
| RtCoV | AAAGAGTTCCAGTTTGCAGGTGGACAAGGAGTGCCTATTGCCAATGGAATCCCACCTTCT |
| HCoVOC43 | -AACAACCTTGGAAGGTGATACCTCGTAATTTGGTACCCATCAACAAGAAAGACAAAAAT |
| PEDV | AAGCCCCTTTCTAAGGTACTTGCAAACAACGCTGTACCCACTAACAAGGGGAATAAGGAC |
| IBV | ACACCTCCGCCCAAGTTTGAAGGTAGCGGTGTTCCTGATAACGAAAACATTAAGCCAAGC |

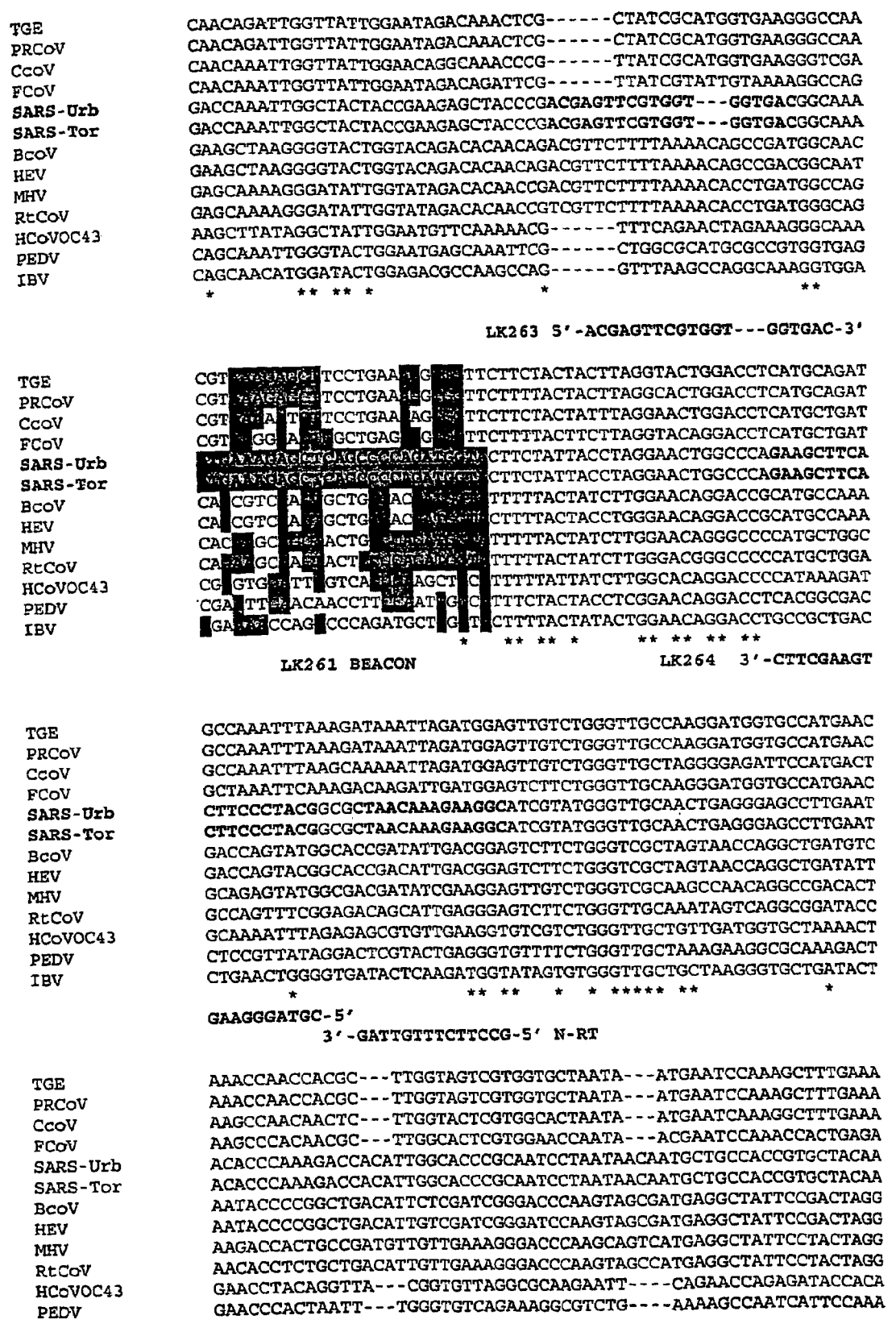

TGE CAACAGATTGGTTATTGGAATAGACAAACTCG------CTATCGCATGGTGAAGGGCCAA
PRCoV CAACAGATTGGTTATTGGAATAGACAAACTCG------CTATCGCATGGTGAAGGGCCAA
CcoV CAACAAATTGGTTATTGGAACAGGCAAACCCG------TTATCGCATGGTGAAGGGTCGA
FCoV CAACAAATTGGTTATTGGAATAGACAGATTCG------TTATCGTATTGTAAAAGGCCAG
SARS-Urb GACCAAATTGGCTACTACCGAAGAGCTACCCGACGAGTTCGTGGT---GGTGACGGCAAA
SARS-Tor GACCAAATTGGCTACTACCGAAGAGCTACCCGACGAGTTCGTGGT---GGTGACGGCAAA
BcoV GAAGCTAAGGGGTACTGGTACAGACACAACAGACGTTCTTTTAAAACAGCCGATGGCAAC
HEV GAAGCTAAGGGGTACTGGTACAGACACAACAGACGTTCTTTTAAAACAGCCGACGGCAAT
MHV GAGCAAAAGGGATATTGGTATAGACACAACCGACGTTCTTTTAAAACACCTGATGGCCAG
RtCoV GAGCAAAAGGGATATTGGTATAGACACAACCGTCGTTCTTTTAAAACACCTGATGGGCAG
HCoVOC43 AAGCTTATAGGCTATTGGAATGTTCAAAAACG------TTTCAGAACTAGAAAGGGCAAA
PEDV CAGCAAATTGGGTACTGGAATGAGCAAATTCG------CTGGCGCATGCGCCGTGGTGAG
IBV CAGCAACATGGATACTGGAGACGCCAAGCCAG------GTTTAAGCCAGGCAAAGGTGGA
*   * * **

LK263 5'-ACGAGTTCGTGGT---GGTGAC-3'

TGE CGT[illegible]TCCTGAA[illegible]G[illegible]TTCTTCTACTACTTAGGTACTGGACCTCATGCAGAT
PRCoV CGT[illegible]TCCTGAA[illegible]G[illegible]TTCTTTTACTACTTAGGCACTGGACCTCATGCAGAT
CcoV CGT[illegible]A[illegible]T[illegible]TCCTGAA[illegible]AG[illegible]TTCTTCTACTATTTAGGAACTGGACCTCATGCTGAT
FCoV CGT[illegible]GG[illegible]A[illegible]GCTGAG[illegible]G[illegible]TTCTTTTACTTCTTAGGTACAGGACCTCATGCTGAT
SARS-Urb [illegible]CTTCTATTACCTAGGAACTGGCCCAGAAGCTTCA
SARS-Tor [illegible]CTTCTATTACCTAGGAACTGGCCCAGAAGCTTCA
BcoV CA[illegible]CGTC[illegible]A[illegible]GCTG[illegible]AC[illegible]TTTTTACTATCTTGGAACAGGACCGCATGCCAAA
HEV CA[illegible]CGTC[illegible]A[illegible]GCTG[illegible]AC[illegible]CTTTTACTACCTGGGAACAGGACCGCATGCCAAA
MHV CAC[illegible]GC[illegible]ACTG[illegible]TTTTTACTATCTTGGAACAGGGCCCCATGCTGGC
RtCoV CA[illegible]GC[illegible]A[illegible]ACT[illegible]TTTTTACTATCTTGGGACGGGCCCCCATGCTGGA
HCoVOC43 CG[illegible]GTG[illegible]TT[illegible]GTCA[illegible]AGCT[illegible]C[illegible]TTTTTATTATCTTGGCACAGGACCCCATAAAGAT
PEDV CGA[illegible]TT[illegible]ACAACCTT[illegible]AT[illegible]G[illegible]C[illegible]TTTCTACTACCTCGGAACAGGACCTCACGGCGAC
IBV [illegible]GA[illegible]CCAG[illegible]CCCAGATGCT[illegible]G[illegible]T[illegible]CTTTTACTATACTGGAACAGGACCTGCCGCTGAC
*   *

LK261 BEACON LK264 3'-CTTCGAAGT

TGE GCCAAATTTAAAGATAAATTAGATGGAGTTGTCTGGGTTGCCAAGGATGGTGCCATGAAC
PRCoV GCCAAATTTAAAGATAAATTAGATGGAGTTGTCTGGGTTGCCAAGGATGGTGCCATGAAC
CcoV GCCAAATTTAAGCAAAAATTAGATGGAGTTGTCTGGGTTGCTAGGGGAGATTCCATGACT
FCoV GCTAAATTCAAAGACAAGATTGATGGAGTCTTCTGGGTTGCAAGGGATGGTGCCATGAAC
SARS-Urb CTTCCCTACGGCGCTAACAAAGAAGGCATCGTATGGGTTGCAACTGAGGGAGCCTTGAAT
SARS-Tor CTTCCCTACGGCGCTAACAAAGAAGGCATCGTATGGGTTGCAACTGAGGGAGCCTTGAAT
BcoV GACCAGTATGGCACCGATATTGACGGAGTCTTCTGGGTCGCTAGTAACCAGGCTGATGTC
HEV GACCAGTACGGCACCGACATTGACGGAGTCTTCTGGGTCGCTAGTAACCAGGCTGATATT
MHV GCAGAGTATGGCGACGATATCGAAGGAGTTGTCTGGGTCGCAAGCCAACAGGCCGACACT
RtCoV GCCAGTTTCGGAGACAGCATTGAGGGAGTCTTCTGGGTTGCAAATAGTCAGGCGGATACC
HCoVOC43 GCAAAATTTAGAGAGCGTGTTGAAGGTGTCGTCTGGGTTGCTGTTGATGGTGCTAAAACT
PEDV CTCCGTTATAGGACTCGTACTGAGGGTGTTTTCTGGGTTGCTAAAGAAGGCGCAAAGACT
IBV CTGAACTGGGGTGATACTCAAGATGGTATAGTGTGGGTTGCTGCTAAGGGTGCTGATACT
*   * * ***  *

GAAGGGATGC-5'
3'-GATTGTTTCTTCCG-5' N-RT

TGE AAACCAACCACGC---TTGGTAGTCGTGGTGCTAATA---ATGAATCCAAAGCTTTGAAA
PRCoV AAACCAACCACGC---TTGGTAGTCGTGGTGCTAATA---ATGAATCCAAAGCTTTGAAA
CcoV AAGCCAACAACTC---TTGGTACTCGTGGCACTAATA---ATGAATCAAAGGCTTTGAAA
FCoV AAGCCCACAACGC---TTGGCACTCGTGGAACCAATA---ACGAATCCAAACCACTGAGA
SARS-Urb ACACCCAAAGACCACATTGGCACCCGCAATCCTAATAACAATGCTGCCACCGTGCTACAA
SARS-Tor ACACCCAAAGACCACATTGGCACCCGCAATCCTAATAACAATGCTGCCACCGTGCTACAA
BcoV AATACCCCGGCTGACATTCTCGATCGGGACCCAAGTAGCGATGAGGCTATTCCGACTAGG
HEV AATACCCCGGCTGACATTGTCGATCGGGATCCAAGTAGCGATGAGGCTATTCCGACTAGG
MHV AAGACCACTGCCGATGTTGTTGAAAGGGACCCAAGCAGTCATGAGGCTATTCCTACTAGG
RtCoV AACACCTCTGCTGACATTGTTGAAAGGGACCCAAGTAGCCATGAGGCTATTCCTACTAGG
HCoVOC43 GAACCTACAGGTTA---CGGTGTTAGGCGCAAGAATT----CAGAACCAGAGATACCACA
PEDV GAACCCACTAATT---TGGGTGTCAGAAAGGCGTCTG----AAAAGCCAATCATTCCAAA

```
IBV          AAATCTAGATCCAATCAGGGTACAAGAGATCCTGATAA-GTTTGACCAATACCCACTACG
                 *                        *                         * *

TGE          TTCG---ATGGTAAAGTGCCAGGCGAA---TTTCAACTTGAAGTTAATCAATCAAGAGAC
PRCoV        TTCG---ATGGTAAAGTGCCAGGCGAA---TTTCAACTTGAAGTTAACCAGTCTAGGGAC
CcoV         TTCG---ATGTCAAAGTACCATCAGAA---TTTCACCTTGAAGTGAACCAATTAAGGGAC
FCoV         TTTG---ATGGTAAGATACCGCCACAG---TTTCAGCTTGAAGTGAACCGTTCTAGGAAC
SARS-Urb     CTTCCTCAAGGAACAACATTGCCAAAAGGCTTCTACGCAGAGGGAAGCAGAGGCGGCAGT
SARS-Tor     CTTCCTCAAGGAACAACATTGCCAAAAGGCTTCTACGCAGAGGGAAGCAGAGGCGGCAGT
BcoV         TTTCCGCCTGGCACGGTACTCCCTCAGGGTTACTATATTGAAGG---CTCAGGAAGGTCT
HEV          TTTCCGCCTGGCACGGTACTCCCTCAAGGTTACTATATTGAAGG---CTCAGGAAGGTCT
MHV          TTTGCGCCCGGCACGGTATTGCCTCAGGGCTTTTATGTAGAAGG---CTCGGGAAGGTCT
RtCoV        TTTGCGCCCGGTACGGTATTGCCTCAGGGTTTCTATGTTGAAGG---CTCGGGAAGGTCT
HCoVOC43     CTTC--AATCAAAAGCTCCCAAATGGTGTTACTGTTGTTGAAGAACCTGACTCCCGTGCT
PEDV         ATTC--TCTCAACAGCTCCCCAGTGTA---GTTGAGATTGTTGAACCTAACACACCTCCT
IBV          ATTC----TCGGATGGCGGACCTGATGGTAATTTCCGTTGGGACTTCATTCCCCTGAACC
              *                                         *

TGE          AATTCAAGGTCACGCTCTCAATCTAGATCTC------GGTCTAGAAATAGATCTCAATCT
PRCoV        AACTCAAGGTCACGCTCTCAATCTAGATCGC------GGTCTAGAAACAGATCTCAATCT
CcoV         AATTCAAGGTCTAGGTCTCAATCTAGATCTC------AGTCCAGAAATAGGTCTCAATCT
FCoV         AATTCAAGGTCTGGTTCTCAGTCTAGATCTG------TTTCAAGAAACAGATCTCAATCT
SARS-Urb     CAAGCCTCTTCTCGCTCCTCATCACGTAGTCGCGGTAATTCAAGAAATTCAACTCCTGGC
SARS-Tor     CAAGCCTCTTCTCGCTCCTCATCACGTAGTCGCGGTAATTCAAGAAATTCAACTCCTGGC
BcoV         GCTCCTAATTCCAGATCTACTTCACGCGCATCCAGTAGAGCCTCTAGTGCAGGATCGCGT
HEV          GCTCCTAATTCCAGATCTACTTCGCGTGCACCCAATAGAGCCCCTAGTGCAGGATCGCGT
MHV          GCACCTGCTAGTCGATCTGGTTCGCGGTCAC------AATCCCGTGGGCCAAATAATCGC
RtCoV        GCACCTGCTAGTCGATCTGGTTCGCGGTCAC------AATCCCGTGGGCCAAATAATCGC
HCoVOC43     CCTTCCCGGTCTCAGTCGAGGTCGCAGAGTCGCGGTCGTGGTGAATCCAAACCTCAATCT
PEDV         GCTTCACGTGCAAATTCGCGTAGCAGGAGTCGTGGCAATGGCAACAATAGGTCTAGATCT
IBV          GTGGTAGGAGTGGAAGATCAACAGCAGCTTCATCA-GCAGCAGCTAGTAGAGCACCATCA

TGE          AGAGGCAGGCAACAATTCAATAACAAGAAGGAT-------GACAGTGTAGAACAAGCTGT
PRCoV        AGAGGTAGGCAACAATCCAATAACAAGAAGGAT-------GACAGTGTAGAACAAGCTGT
CcoV         AGAGGAAGGCAACTATCCAATAATAAGAAGGAT-------GACAATGTTGAACAAGCTGT
FCoV         AGAGGAAGACACCATTCCAATAACCAGAA---T-------AATAATGTTGAGGATACAAT
SARS-Urb     AGCAGTAGGGGAAATTCTCCTGCTCGAATGGCT-------AGCGGAGGTGGTGAAACTGC
SARS-Tor     AGCAGTAGGGGAAATTCTCCTGCTCGAATGGCT-------AGCGGAGGTGGTGAAACTGC
BcoV         AG---TAGAGCCAATTCTGGCAACAGAACCCCT-------ACCTCTGGTGTAACACCTGA
HEV          AG---TAGAGCCAATTCTGGCAATAGAACCTCT-------ACCCCTGGTGTAACACCTGA
MHV          GC---TAGAAGCAGTTCCAACCAGCGCCAGCCT-------GCCTCTGCTGTAAAACCTGA
RtCoV        GC---TAGAAGCAGTTCCAACCAGCGCCAGCCT-------GCCTCTACTGTAAAACCTGA
HCoVOC43     CGGAATCCTTCAAGTGACAGAAACCATAACAGTCAG----GATGACATCATGAAGGCAGT
PEDV         CCAAGTAACAACAGAGGCAATAACCAGTCCCGTGGTAATTCACAGAATCGTGGAAATAAC
IBV          CG------TGAAGGTTCGCGTGGTCGTAGAAGT-------GATTCTGGAGATGACCTTAT
                                             *

TGE          T---CTTGCCGCACTT-----AAAAAGTTAGGTGTTGACACAGAAAAACAACAGCA-ACG
PRCoV        T---CTTGCCGCACTT-----AAAAAGTTAGGTGTTTACACAGAAAAACAACAGCA-ACG
CcoV         T---CTTGCTGCACTC-----AAAAAGTTAGGTGTTGACACAGAAAAACAA---CA-AAG
FCoV         T---GTAGCCGTGCTT-----GAAAAATTAGGTGTT---ACTGACAAACAA-------AG
SARS-Urb     C---CTCGC-G--CTA-----TTGCTGCTAGAC-AGATTGAACCAGCTTGAGAGCA-AAG
SARS-Tor     C---CTCGC-G--CTA-----TTGCTGCTAGAC-AGATTGAACCAGCTTGAGAGCA-AAG
BcoV         T---ATGGCTG--ATC-----AAATTGCTAGTC-TTGTTCTGGCAAAACTTG-GCA-AGG
HEV          C---ATGGCTG--ATC-----AAATTGCTAGTC-TTGTTCTGGCAAAACTTG-GCA-AGG
MHV          C---ATGGCCG--AAG-----AAATTGCTGCTC-TTGTTTTGGCTAAGCTTG-GTA-AAG
RtCoV        T---ATGGCCG--AAG-----AAATTGCTGCTC-TTGTTTTGGCTAATCTAG-GCA-AAG
HCoVOC43     T---GCTGCGGCTCTT-----AAATCTTTAGGTTTTGACAAGCCTCAGGAAAAAGATAAA
PEDV         CAGGGTCGTGGAGCTTCTCAGAACAGAGGAGGCAATAATAATAACAATAACAAGTCTCGT
IBV          TGCTCGTGCAGCAAAG------ATAATCCAGGATCAGCAGAAAAAGGGCTCTCGCA--TT
                     *   *
```

```
TGE        CTCTCGTTCTAAATCTAAAG--AACGTAGTAACTCTAAGAC-AAGA--------GATACT
PRCoV      CTCTCGTTCTAAATCTAAAG--AACGTAGTAACTCTAAAAC-AAGA--------GATACT
CcoV       ATCTCGTTCCAAATCTAAGG--AACGTAGCAGCTCTAAGAC-AAGA--------GATACT
FCoV       GTCACGTTCTAAACCTAGAG--AACGTAGTGATTCCAAACC-TAGG--------GACACA
SARS-Urb   TTTCTGGTAAAGGCCAACAA-CAACAAGGCCAAACTGTCACTAAGA--------AATCTG
SARS-Tor   TTTCTGGTAAAGGCCAACAA-CAACAAGGCCAAACTGTCACTAAGA--------AATCTG
BcoV       ATGCCACTAAGCCACAGCAAGTAACTAAGC-AGACTGCCA--AAGA--------AATCAG
HEV        ATGCCACTAAGCCTCAGCAAGTAACTAAGC-AGACTGCCA--AAGA--------GGTCAG
MHV        ATGCCGGCCAGCCCAAGCAGGTAACTAAGC-AAAGCGCCA--AAGA--------AGTCAG
RtCoV      ATGCCGGACAGCCTAAGCAAGTAACTAAGC-AAAGTGCCA--AAGA--------AGTCAG
HCoVOC43   AAGTCAGCGAAAACGGGTAC--TCCTAAGCCTTCTCGTAATCAGAGT----CCTGCTTCT
PEDV       AACCAGTCCAATAACAGGAACCAGTCAAATGACCGTGGTGGTGTAACATCACGCGATGAT
IBV        ACCAAGGCAAAGGCAGATGA--AATGGCTCATCGCCGGTATTGCAAG----CGCACTATC

TGE        ACACCTAAGAATGAAAACAAACACACCTGGA---AGAGAACTGCAGGTAAA---GGTG--
PRCoV      ACGCCTAAGAATGAAAACAAACACACCTGGA---AGAGAACTGCAGGTAAA---GGTG--
CcoV       ACACCTAAGAATGAAAACAAACACACCTGGA---AGAGAACTGCAGGTAAA---GGTG--
FCoV       ACACCTAAGAATGCCAACAAACACACCTGGA---AGAAAACTGCAGGCAAG---GGAG--
SARS-Urb   CTGCTGAGGCATCTAAA-AAGCCTCGCCAAA---AACGTACTGCCACAAAAC--AGTACA
SARS-Tor   CTGCTGAGGCATCTAAA-AAGCCTCGCCAAA---AACGTACTGCCACAAAAC--AGTACA
BcoV       --ACAGAAAATTTTGAATAAGCCCCGCCAGA---AGAGGAGCCCCAATAAAC--AATGCA
HEV        --ACAGAAAATCTTGAATAAGCCCCGCCAGA---AGAGGAGCCCCAACAAAC--AATGCA
MHV        --GCAGAAAATTTTAACTAAGCCTCGTCAAA---AGAGGACTCCAAACAAGC--AGTGCC
RtCoV      --GCAGAAAATTTTAAATAAGCCTCGCCAAA---AGAGGACTCCAAACAAGC--AGTGCC
HCoVOC43   TCTCAAACTTCTGCCAAGAGTCTTGCTCGTTCTCAGAGTTCTGAAACAAAAG--AACAAA
PEDV       CTGGTGGCTGCTGTCAAGGATGCACTTAAATCTTTGGGTATTGGAGAAAATCCTGACAGG
IBV        CCACCTAATTATAGGGTTGATCAAGTGTTTGGTCCCCGTACTAAAGGTAAGG--AGGGGA
                                                               **

TGE        ---ATGTGACA---AGATTTTATGGAGCTAGAAGCAGTT--CAGCC-------AAT-TTT
PRCoV      ---ATGTGACA---AGATTTTATGGAGCTAGAAGCAGCT--CAGCC-------AAT-TTT
CcoV       ---ATGTGACA---AAATTTTATGGAGCTAGAAGTAGTT--CAGCC-------AAT-TTT
FCoV       ---ATGTGACA---ACTTTCTATGGTGCTAGAAGTAGTT--CAGCT-------AAC-TTT
SARS-Urb   A-CGTCACTCA---AGCATTTGGGAGACGTGGTCCAGAA--CAAACCCAAGGAAAT-TTC
SARS-Tor   A-CGTCACTCA---AGCATTTGGGAGACGTGGTCCAGAA--CAAACCCAAGGAAAT-TTC
BcoV       C-TGTTCAGCA---GTGTTTTGGGAAGAGAGGCCCCAAT--CAGA---------AT-TTT
HEV        C-TGTTCAGCA---GTGTTTTGGGAAGAGAGGCCCCAAT--CAGA---------AT-TTT
MHV        C-AGTGCAGCA---GTGTTTTGGGAAGAGAGGCCCTAAT--CAGA---------AC-TTT
RtCoV      C-AGTGCAGCA---GTGTTTTGGAAAGAGAGGCCCCAAT--CAGA---------AT-TTT
HCoVOC43   AGCATGAAATGC--AAAAGCCACGGTGGAAAAGACAGCC--TAATGATGATGTGACATCT
PEDV       CATAAGCAACAGCAGAAGCCTAAGCAGGAAAAGTCTGACAACAGCGGCAAAAATACACCT
IBV        A--TTTTGGTG-----ATGACAAGATGAATGAGGAAGGTATTAAGGATG----GGCGTGT
                                                     *

TGE        GGTGACACTGACCTCGTTGCCAAT----GGGAGCAGTGCCAAGCATTACCCACAACTGGC
PRCoV      GGTGACAGTGACCTCGTTGCCAAT----GGGAGCAGTGCCAAGCATTACCCACAATTGGC
CcoV       GGTGACAGCGATCTTGTTGCCAAT----GGGAACGGTGCCAAGCATTACCCACAACTGGC
FCoV       GGTGATAGTGATCTCGTTGCCAAT----GGTAACGCTGCCAAATGCTACCCTCAGATAGC
SARS-Urb   GGGGACCAAGACCTAATCAGACAA----GGAACTGATTACAAACATTGGCCGCAAATTGC
SARS-Tor   GGGGACCAAGACCTAATCAGACAA----GGAACTGATTACAAACATTGGCCGCAAATTGC
BcoV       GGTGGTGGAGAAATGTTAAAACTT----GGAACTAGTGACCCACAGTTCCCCATTCTTGC
HEV        GGTGGTGGAGAAATGTTAAAACTT----GGAACTAGTGACCCACAGTTCCCCATTCTTGC
MHV        GGAGGCTCTGAAATGTTAAAACTT----GGAACTAGTGATCCGCAGTTCCCCATTCTTGC
RtCoV      GGAGGCCCTGAAATGTTAAAACTT----GGAACTAGTGATCCACAGTTCCCCATTCTTGC
HCoVOC43   AATGTCACACAATGTTTTGGCCCC----AGAGACCTTGAC---CACAACTTTGGAAGTGC
PEDV       AAGAAGAACAAATCCAGGGCCACTTCGAAGGAACGTGACCTCAAAGACATCCCAGAGTGG
IBV        TACAGCAATGCTCAACCTAGTCCCT---AGCAGCCATGCT-----TGTCTTTTTGGAAGT
                                    *                                *

TGE        TGAATGTGTT-CCATCTGTGTC--TAGCATT----CT--GTTTGGAA-GCTATTGGACTT
```

```
PRCoV       TGAATGTGTT-CCATCTGTGTC--TAGCATT----TT--GTTTGGAA-GCTATTGGACTT
CcoV        TGAATGTGTT-CCATCTGTATC--TAGCATT----CT--GTTTGGAA-GCCATTGGACTG
FCoV        TGAATGTGTT-CCATCAGTGTC--TAGCATA----AT--CTTTGGCA-GTCAATGGTCTG
SARS-Urb    ACAATTTGCT-CCAAGTGCCTC--TGCA-------TT--CTTTGGAATGTCAC--GCATT
SARS-Tor    ACAATTTGCT-CCAAGTGCCTC--TGCA-------TT--CTTTGGAATGTCAC--GCATT
BcoV        AGAACTCGCA-CCCACAGCTGG--TGCGTTT----TT--CTTTGGATCAAGATTAGAGTT
HEV         AGAACTCGCA-CCCACAGCTGG--TGCGTTT----TT--CTTTGGATCAAGATTAGAGTT
MHV         AGAGTTGGCT-CCAACACCTAG--TGCCTTC----TT--CTTTGGATCTAAATTAGAATT
RtCoV       AGAGTTGGCC-CCAACACCTGG--TGCCTTC----TT--CTTTGGATCTAAATTAGAATT
HCoVOC43    AGGTGTTGTGGCCAATGGTGTT--AAAGCTAAAGGCT--ATCCACAATTTGCTGAGCTTG
PEDV        AGGAGAATTC-CCAAGGGCGAAAATAGCGTAGCAGCTTGCTTCGGACCCAGAGGGGGCTT
IBV         AGAGTGACACCCAAACTTCAAC--TAGATGG--GCTTCACTTGAGATTTGAATTTACTAC
                     *                           *   *

TGE         CAAAGGAA--GATGGCG----ACCAGATAGAAGTCAC----GTTCACACACAAATACC--
PRCoV       CAAAGGAA--GATGGCG----ACCAGATAGAAGTCAC----GTTCACACACAAATACC--
CcoV        CTAAGGAA--GATGGTG----ACCAGATTGAAGTCAC----ATTCACACACAAATACC--
FCoV        CTGAAGAA--GCTGGTG----ATCAAGTGAAAGTCAC----GCTCACTCACACCTACT--
SARS-Urb    GGCA-----------------------TGGAAGTCAC----ACCTTCGGGAACATG----
SARS-Tor    GGCA-----------------------TGGAAGTCAC----ACCTTCGGGAACATG----
BcoV        GGCCAAAG--TGCAGAA----TTTGTCTGGGAATCTTGACGAGCCCCAGAAGGATGTTTA
HEV         GGCCAAAG--TGCAGAA----TTTGTCTGGGAATCCTGACGAGCCCCAGAAGGATGTTTA
MHV         GGTCAAAA-----AGAA----CT---CTGGTGGTGCTGATGAACCCACCAAAGATGTTTA
RtCoV       GGTCAAAA-----AGAA----TT---CTGGTGGCGTTGATGAACCCACCAAAGATGTGTA
HCoVOC43    TGCCGTCA--ACAGCTGCTATGCTGTTTGATAGTCAC-ATTGTTTCCAAAGAGTCAGGCA
PEDV        CAAAAACTTTGGAGATGCGGAATTTGTCGAAAAAGGTGTTGATGCGTCAGGCTATGCTCA
IBV         TGTGGTCCCATGTGATGACCCGCAGTTTGATAATTATGTGAAAATTTGTGATCAGTGT--

TGE         --ACT-TGCCAAAGGATGA--TCCTA--AGACTGGACAATTCCTTCAGCAGATTAATGCC
PRCoV       --ACT-TGCCAAAGGATCA--TCCTA--AAACTGAACAATTCCTTCAGCAGATTAATGCC
CcoV        --ACT-TGCCAAAGGATGA--TCCTA--AGACTGGACAATTCCTTCAGCAGATTAATGCA
FCoV        --ACC-TGCCAAAGGATGA--TGCCA--AAACTAGTCAATTCCTAGAACAGATTGACGCT
SARS-Urb    ---GC-TGACTTATCATGG--AGCCATTAAATTGGATGACAAAGATCCACAATTCAAAGA
SARS-Tor    ---GC-TGACTTATCATGG--AGCCATTAAATTGGATGACAAAGATCCACAATTCAAAGA
BcoV        TGAAT-TGCGCTATAATGG--TGCAATTAGATTTGACAGTACACTTTCAGGTTTTGAGAC
HEV         TGAAT-TGCGCTATAATGG--CGCGATTAGATTTGACAGCACACTCTCAGGTTTTGAAAC
MHV         TGAAT-TGCAGTATTCAGG--TGCAATTAGATTTGATAGTACTCTACCCGGTTTTGAGAC
RtCoV       TGAGC-TGCAATATTCAGG--TGCAGTCAGATTTGATAGTACTCTACCTGGTTTTGAGAC
HCoVOC43    ACACTGTGGTCTTGACTTT--CACTACTAGAGT-GACTGTGCCCAAAGACCATCCACACT
PEDV        GATCGCCAGTTTAGCACCAAATGTTGCAGCATTGCTCTTTGGTGGTAATGTGGCTGTTCG
IBV         -GTCGATGGTGTAGGAACGCGTCCAA---AAGATGACGA-ACCAAAACCAAAGTCACGCT
                                                           *

TGE         TATGCTCG--TCCATCAGAAGTGGCAAAAGAA--CAGAGA-AAAAGA-----AAATCTCG
PRCoV       TATGCTAG--CCCATCAGAATTGGCAAAAGAA--CAGAGA-AAAAGA-----AAGTCTCG
CcoV        TACGCCCG--TCCATCAGAGGTGGCTAAAGAA--CAGAGA-CAACGC-----AAAGCTCG
FCoV        TACAAGCG--ACCTTCTGAAGTGGCTAAGGAT--CAGAGG-CAAAGA-----AGATCCCG
SARS-Urb    CAACGTCA--TACTGCTGAACAAGCACATTGA--CGCATA-CAAAAC-----ATTCCCAC
SARS-Tor    CAACGTCA--TACTGCTGAACAAGCACATTGA--CGCATA-CAAAAC-----ATTCCCAC
BcoV        CATAATGA--AGGTGTTGAATGAGAATTTGAA--TGCATATCAACAA-----CA---AGA
HEV         CATTATGA--AGGTGCTTAACCAGAATTTGAA--TGCCTATCAACAT-----CAGGAAGA
MHV         TATCATGA--AAGTGTTGACTGAGAATTTGAA--TGCCTACCAGGAC-----CAAGCTGG
RtCoV       TATCATGA--AAGTGTTGAATGAGAATTTGAA--TGCCTACCAGAAT-----CAAGCTGG
HCoVOC43    TG-GGTAA--GTTTCTTGAGGAGTTAAATGCATTCACTAGAGAAATG-----CAACAACA
PEDV        TGAGCTAGCGGACTCTTACGAGATTACATACAACTATAAAATGACTGTGCCAAAGTCAGA
IBV         CAAGTTCAAGACCTGCTACAAGAGGAAATTCT--CCAGCGCCAAGACAACAGCGCCCAAA

TGE         TTCTAAATCTGCAGAAAGGTCAGAGCAAGATGTGGTACCTGATGCATTAATAGAA-AATT
PRCoV       TTCTAAATCTGCAGAAAGGTCAGAGCAAGAGGTGGTACCTGATTCATTAATAGAA-AACT
CcoV        TTCTAAATCTGTAGAAAGGGTAGAGCAAGAGGTTGTACCTGATGCATTAACAGAA-AATT
```

```
FCoV          TTCTAAGTCTGCTGATAAG---AAGCCTGAGGAGTTGTCTGTAACTCTTGTGGAG-GCAT
SARS-Urb      CAACAGAGCCTAAAAAGGACAAAAAGAAAAAGACTGATGAAGCTCAGCCTTTGCC-GCAG
SARS-Tor      CAACAGAGCCTAAAAAGGACAAAAAGAAAAAGACTGATGAAGCTCAGCCTTTGCC-GCAG
BcoV          TGGTATGATGAATATGAGTCCAAAACCACAGCGTCAGCGTGGTCAGAAG-------AATG
HEV           TGGGATGATGAATATTAGTCCTAAACCACAGCGGCAGCGTGGTCAGAAG-------AATG
MHV           TAGTGTAGATCTAGTGAGCCCAAAGCCTCCAAGAAGAGGTCGTAGACAGGCTCAA-GAAA
RtCoV         TGGTGCAGATGTAGTGAGCCCAAAGCCCCAAAGAAAGAGAGGGACGAAACAAACG-GCTC
HCoVOC43      TCCTCTTCTTAACCCTAGTGCACTAGAATTCAACCCATCTCAAACTTCACCTGCA-ACTG
PEDV          TCCAAATGTTGAGCTTCTTGTTTCACAGGTGGATGCATTTAAAACTGGGAATGCAAAACT
IBV           GAAGGAGAAAAAGCTAAAGAAGCAGGATGATGAAGCAGATAAAGCATTGACCTCAGATGA

TGE           ATACAGATGTGTTTGAT-GACACACAGGT-TGAGATAATTGATGAGGTA-ACGAACTAA-
PRCoV         ATACAGATGTGTTTGAT-GACACACAGGT-TGAGATGATTGACGAGGTA-ACGAACTAA-
CcoV          ACACAGATGTGTTTGAT-GACACACAGGT-TGAGATTATTGATGAGGTA-ACGAACTAA-
FCoV          ACACAGATGTGTTTGAT-GACACACAGGT-TGAGATGATTGATGAGGTT-ACGAACTAA-
SARS-Urb      AGACAAAAGAAGCAGCCCACTGTGACTCT-TCTT---CCTGCGGCTGAC-ATG-GATGAT
SARS-Tor      AGACAAAAGAAGCAGCCCACTGTGACTCT-TCTT---CCTGCGGCTGAC-ATG-GATGAT
BcoV          GACAAGGAGAAAATGAT-AATATAAGTGT-TGCAGCGCCTAAAAGCCGT-GTGCAGCAAA
HEV           GACAAGTAGAAAATGAT-AATGTAAGTGT-TGCAGCGCCTAAAAGCCGT-GTGCAGCAAA
MHV           AGAAAGATGAAGTAGAT-AATGTAAGCGT-TGCAAAGCCCAAAAGCTTG-GTGCAGCGAA
RtCoV         AGAAAGAAGAATTAGAT-AGTATAAGCGT-TGCAAAGCCCAAAAGTGCC-GTGCAGCGAA
HCoVOC43      CTGAACCAGTGCGTGAT-GAAGTTTCTAT-TGAAA--CTGACATAATTG-ATGAAGTAAA
PEDV          CCAGAGAAAGAAGGAAAAGAAGAACAAGCGTGAAACCACGCTGCAGCAGCATGAAGAGGC
IBV           GGAGAGGAACAATGCACAGCTGGAATTTTATGATGAGCCCAAGGTAATTAACTGGGGGA
                   *                            *

TGE           ------------------------------------------------------------
PRCoV         ------------------------------------------------------------
CcoV          ------------------------------------------------------------
FCoV          ------------------------------------------------------------
SARS-Urb      TTCTCCAGACAACTTCAAAATTCCATGAGTGGAGCTTCTGCTGATTCAACTCAGGCATAA
SARS-Tor      TTCTCCAGACAACTTCAAAATTCCATGAGTGGAGCTTCTGCTGATTCAACTCAGGCATAA
BcoV          ATAAGAGTAGAGAGTTGACTGCAGAGGACATCAGC--CTTCTTAAGAAGAT---GGATGA
HEV           ATAAGAGTAGAGAGTTGACAGCAGAGGACATCAGC--CTTCTTAAGAAGAT---GGATGA
MHV           ATGTAAGTAGAGAATTAACCCCCGAGGATCGTAGC--CTGCTGGCTCAGATCCTAGACGA
RtCoV         ATGTAAGCAGAGAATTAACCCCAGAGGATAGAAGC--CTGTTGGCGCAGATCCTAGATGA
HCoVOC43      CTAA--------------------------------------------------------
PEDV          CATCTACGATGATGTGGGTGCGCCATCTGATGTGACCCATGCCAATCTGGAATGGGACAC
IBV           TGCAGCTCTAGGAGAGAATGAACTTTGA--------------------------------

TGE           ------------------------------------------------------------
PRCoV         ------------------------------------------------------------
CcoV          ------------------------------------------------------------
FCoV          ------------------------------------------------------------
SARS-Urb      ------------------------------------------------------------
SARS-Tor      ------------------------------------------------------------
BcoV          --GCCCTATACTGAA----------GACACCTCAGAAATATAA-----------------
HEV           --GCCCTATACTGAA----------GATACCTCAGAAATATAA-----------------
MHV           TGGCGTTGTGCCAGATGGGTTGGAAGATGACTCTAATGTGTAA-----------------
RtCoV         TGGCGTTGTGCCTGATGGGTT---AGATGACTCTAATGTGTAA-----------------
HCoVOC43      ------------------------------------------------------------
PEDV          AGCTGTTGATGGTGGTGATACGGCCGTTGAAATTATCAACGAGATCTTCGATACAGGAAA
IBV           ------------------------------------------------------------

TGE           ----
PRCoV         ----
CcoV          ----
FCoV          ----
SARS-Urb      ----
SARS-Tor      ----
```

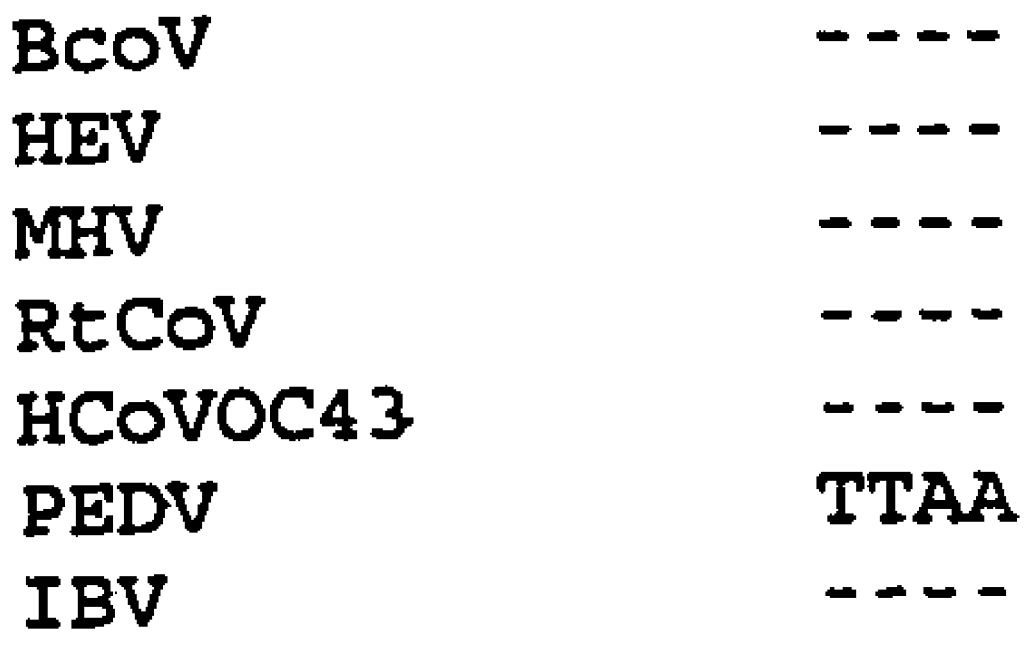

| | |
|---|---|
| BcoV | ---- |
| HEV | ---- |
| MHV | ---- |
| RtCoV | ---- |
| HCoVOC43 | ---- |
| PEDV | TTAA |
| IBV | ---- |

**Figure 16: List of Molecular Designs for *N* Gene**

LK261 5'-FAM-CCTCCGTACCATCTGGGGCTGAGCTCTTTCATCGGAGG-3'-Dubcyl

LK261.N 5'-FAM-GCCTCCGTACCATCTGGGGCTGAGCTCTTTCATCGGAGGC-3'-Dubcyl

LK262

5'-ACGAGTTCGTGGTGGTGACGGCAAAATGAAAGAGCTCAGCCCCAGAT GGTACTTCTATTACCTAGGAACTGGCCCAGAAGCTTCACTTCCCTACG-3'

LK263 5'- ACGAGTTCGTGGTGGTGAC -3'

LK263-T7 5'-TAATACGACTCACTATAGGACGAGTTCGTGGTGGTGAC -3'

LK264 5'- CGTAGGGAAGTGAAGCTTC- 3'

LK264-RT 5'- GCCTTCTTTGTTAGCGTAGGGAAGTGAAGCTTC- 3'

N-RT 5' –GCCTTCTTTGTTAG-3'

Figure 17: Molecular Designs for Internal Positive Control (IPC)

| | |
|---|---|
| **NOTE:** | LK265 is a TET-molecular beacon, which recognizes an artificial target (scrambled amplicon from S, E M and N genes of **coronavirus (SARS-associated coronavirus Tor2 and SARS strains)**. It will be used as an internal positive control (IPC) in a real-time PCR diagnostic for the identification of **SARS-associated coronavirus** RNA/DNA. |

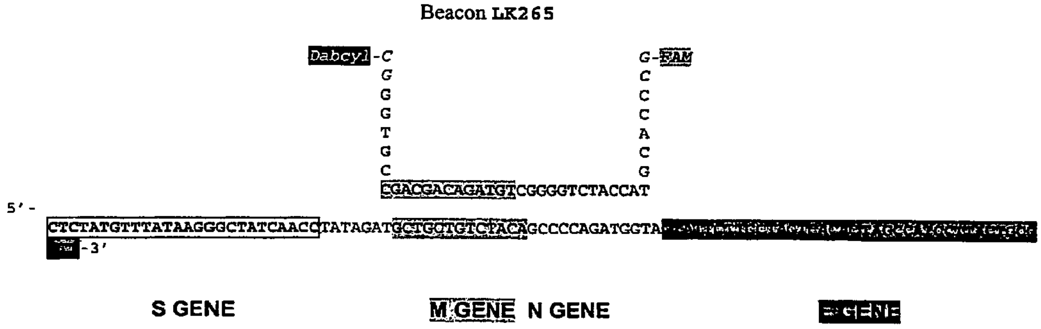

Amplicon LK266 (S, M, N and E hybrid)

LK249

| | | |
|---|---|---|
| **Q.** | Target recognition sequence: | **24 nucleotides (11 G/C)** |
| **R.** | Length of the arms: | **6 nucleotides (5 G/C)** |
| **S.** | Melting temperature of the beacon: | **dG = -2.37 dH = -46.3 dS = -135.9 Tm = 67.7 °C** |
| **T.** | Melting temperature of target: | **°C** |

LK251 5'-CTCTATGTTTATAAGGGCTATCAACC-3'

Length: 26 nucleotides (10 G/C)
*Tm*: °C
Position: (see alignment below)

LK256 5' -AAGCGCAGTAAGGATGGCTA-3'

Length: 20 nucleotides (10 G/C)
*Tm*: °C
Position: (see alignment below)

LK266 Amplicon (98 nucleotides)

5'-
CTCTATGTTTATAAGGGCTATCAACCTATAGATGCTGCTGTCTACAGCCCCAGA
TGGTAGTATTCTTGCTAGTCACACTAGCCATCCTTACTGCGCTT-3'

Figure 18: List of Molecular Designs for IPC

LK265 Dubcyl 5'-FAM-GCCCACGTACCATCTGGGGCTGTAGACAGCAGCCGTGGGC-3'-

LK266

5'-CTCTATGTTTATAAGGGCTATCAACCTATAGATGCTGCTGTCTACAGC
CCCAGATGGTAGTATTCTTGCTAGTCACACTAGCCATCCTTACTGCGCTT
-3'

LK251 5'-CTCTATGTTTATAAGGGCTATCAACC-3'

LK251-T7 5'-TAATACGACTCACTATAGGCTCTATGTTTATAAGGGCTATCAACC-3'

LK256 5'- AAGCGCAGTAAGGATGGCTA - 3'

LK256-RT 5'- TATTGCAGCAGTACAAGCGCAGTAAGGATGGCTA - 3'

E-RT 5' –TATTGCAGCAGTAC-3'

Figure 19: Molecular Beacon Melting Curves
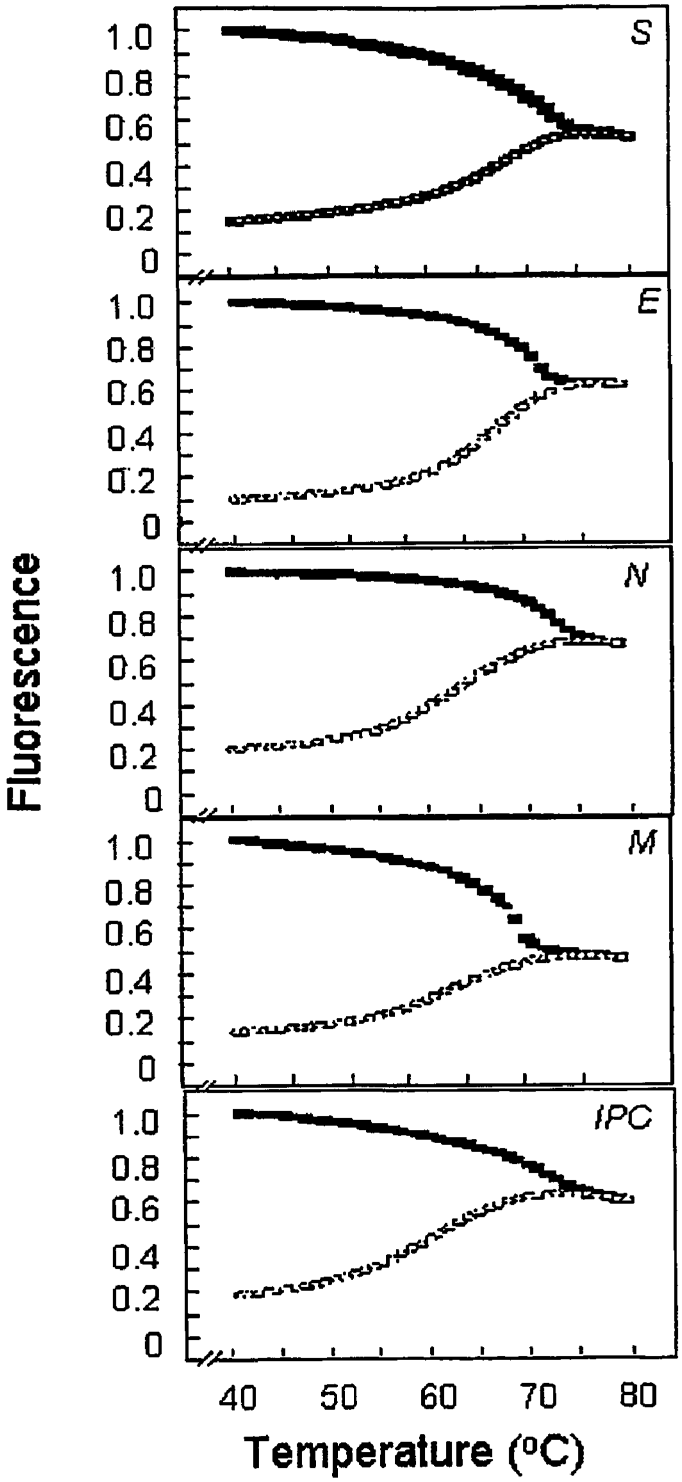

Figure 20: Uniplex Real-time PCR Amplifications (Serial Dilutions-Dynamic Range)
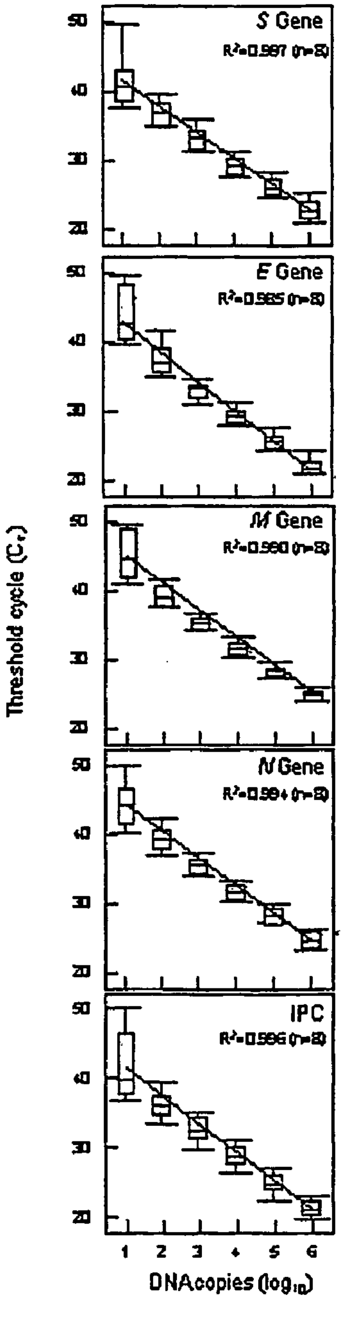

MULTI-ALLELIC DETECTION OF SARS-ASSOCIATED CORONAVIRUS

This application is the national stage filing of International Application No. PCT/US/2004/026380, filed Aug. 13, 2004 and claims the benefit thereof. The International Application is based on U.S. Provisional Application No. 60/576,314, filed Jun. 3, 2004 and U.S. Provisional Application No. 60/496,995, filed Aug. 22, 2003.

BACKGROUND OF THE INVENTION

1. Field of Invention

This invention is directed to methods for the detection and/or quantitation of the SARS virus, reagents and test kits containing the same for use in the method.

2. Background of the Invention

Severe acute respiratory syndrome (SARS) is one of the most recent emerging infectious diseases. The cause of SARS has been identified as a new coronavirus—a virus within the family Coronaviridae—designated as the “SARS coronavirus” (SARS-CoV) [1, 2] by the World Health Organization, following assessment of causation according to Koch’s postulates, including monkey inoculation [3]. The coronaviruses are enveloped positive single-stranded RNA viruses with genomes approximately 30 kb in length—the largest of any of the RNA viruses—that replicate in the cytoplasm of host cells without going through DNA intermediates. Coronaviruses have been reported to cause common colds in humans, and to cause respiratory, enteric, and neurological diseases, as well as hepatitis, in animals. Human coronaviruses are usually difficult to culture in vitro, whereas most animal coronaviruses and SARS-CoV can easily be cultured in Vero E6 cells [4]. There are three groups of coronaviruses: Groups 1 and 2 encompass mammalian viruses, whereas Group 3 encompasses avian viruses. Within each group, the coronaviruses are classified into distinct species according to host range, antigenic relationships, and genomic organization. Human coronaviruses (HCoVs) were previously reported to belong in Group 1 (HCoV-229E) and Group 2 (HCoV-OC43), and are responsible for mild respiratory illnesses.

Recently, two independent groups, one at the British Columbia Cancer Agency (BCCA) in Canada [5] (Tor2 isolate), and the other at the Centers for Disease Control and Prevention (CDCP) in the United States [6] (Urbani isolate), were first to obtain full genomic sequences of SARS-CoV. Phylogenetic analyses, based on the genome sequences, revealed that both isolates were distantly related to previously characterized coronaviruses, including the two previously isolated nonpathogenic human coronaviruses strains, HCoV-C43 and HCoV-229E. The genome of the Tor2 CoV isolate is 29,751 nucleotides long, and the genome of the Urbani CoV isolate is 29,727 nucleotides long, and their sequences differ at only 24 nucleotide positions. The genomic organization of both isolates is characteristic of coronaviruses having the following typical gene order: 5'-replicase (rep), spike (S), envelope (E), membrane (M), and nucleocapsid (N). The SARS-CoV rep gene, which is approximately 20,000 nucleotides long, is predicted to encode two polyproteins (ORF1a and ORF1b) that undergo proteolytic processing, resulting in several nonstructural proteins. There are four genes downstream of rep that encode the structural proteins S, E, M, and N.

The genome of SARS-CoV has several distinct genomic characteristics that distinguish it from other coronavirus isolates and that could be of biological significance. The gene encoding hemagglutinin-esterase, which is present between ORF1a and S in Group 2 coronaviruses (and in some Group 3 coronaviruses) is absent, and so is the short anchor of the S protein. Furthermore, the short anchor of the S protein, the specific number and location of the small ORFs, and the presence of only one copy of $PLP^{PRO}$ provide a combination of genetic features that readily distinguish SARS-CoV isolates from previously the described coronaviruses [5, 6]. There are several publications that describe reverse-transcriptase polymerase chain reaction assays (RT-PCR assays) for the detection of SARS-CoV.

Perris et al. [2] developed as RT-PCR assay that identifies the virus from nasopharyngeal aspiration samples obtained from patients infected with SARS-CoA. Total RNA from clinical samples is reverse transcribed in the presence of random hexamers, and the resulting cDNA is amplified with primers 5'-TACACACCTCAGCGTTG-3' (SEQ ID NO: 86) and 5'-CACGAACGTGACGAAT-3' (SEQ ID NO: 87). To determine the genetic sequence of an unknown RNA virus, they perform a random RT-PCR assay. Total RNA from virus-infected fetal rhesus kidney cells were isolated, reverse transcribed with primer 5'-GCCGGAGCTCTGCAGAATTCNNNNNN-3' (SEQ ID NO: 88), and the resulting cDNA was amplified with primer 5'-GCCGGAGCTCTGCAGAATTC-3' (SEQ ID NO: 89).

Ksiazek et al. [1] developed a reverse transcription and real-time PCR assay to identify SARS-CoV. Oligonucleotide primers used for amplification and sequencing of the SARS-related coronavirus were designed from alignments in open reading frame 1b of the coronavirus polymerase gene sequences. They used the primer pair IN-2 (+) 5'-GGGTTGGGACTATCCTAAGTGTGA-3' (SEQ ID NO: 90) and IN-4 (−) 5'-TAACACACAACICCATCATCA-3' (SEQ ID NO: 91), which was previously designed to hybridize to conserved regions of the open reading frame 1b (ORF1b), in order to achieve broad reactivity with coronavirus/genus. These primers were used to amplify DNA from SARS isolates, and the amplicon sequences obtained were used to design SARS-specific primers Cor-p-F2 (+) 5'-CTAACATGCRRAGGATAATGG-3' (SEQ ID NO: 92), Cor-p-F3 (+) 5'GCCTCTCTTGTTCTTGCTCGC-3' (SEQ ID NO: 94), which were used in turn to test patient specimens. Drosten et al. [4] used a PCR-based random-amplification procedure to genetically characterized a 300-nucleotide-long SARS-CoV genomic segment. On the basis of the sequence that was obtained, conventional real-time PCR assays for specific detection SARS-CoV ORF1b were established. Poon et al. [7] developed an RT-real-time-PCR assay. Total RNA isolated from stool specimens from SARS-CoV-infected individuals is reverse transcribed with random hexamers and resulting can is amplified with primers coro3 5'-TACACACCTCAGCGTTG-3' (SEQ ID NO: 86) and CORO4 5'-CACGAACGTGACGAAT-3' (SEQ ID NO: 87), which recognize a region of the viral polymerase gene. It is important to note that these authors acknowledges in their publication that the primers that they use in their assay can cross-react with the nonpathogenic human coronavirus strain HCoV-OC43.

SARS-specific PCR priers and diagnostic procedures were developed in several World Health Organization laboratories for the amplification of a region of the open reading frame 1b of the SARS-CoV polymerase gene sequence. These primers are currently being assessed to determine their relative performance and sensitivity with difference specimens obtained at different times over the course of illness. Lipkin and Breise have announced they develop a PCR-based SARS diagnostic that detects a SARS-CoV gene that is present in multiple copies, but no further information is available in the literature.

Problems with the prior art that the current invention is designed to solve. The main problems with current molecular diagnostic assays are: a) failure to consider the intrinsically polymorphic nature of coronaviruses, including the current SARS-CoV strains originated from the Tor2 and Urbani isolates—the ability of the virus to mutate and recombine during the period of time it is within the infected individual, and during horizontal transmission; and b) failure to account for the possibility of continuous and/or multiple introduction of non non-genetically identical SARS-CoV strains into the human population.

A characteristic of RNA viruses is their high rate of genetic mutation, which leads to evolution of new viral strains, and is well-established mechanism by which viruses escape the immune system. Coronaviruses, including SARS-CoA, are quite sloppy when it comes to replicating their genetic material, producing one error for every 10,000 nucleotides that they copy, which is roughly the same error rate as occurs during the replication of human immunodeficiency virus, HIV-1. Coronavirus RNA polymerase sometimes jumps between multiple copies of the viral genome that are present in an infected cell. Therefore, each new genome is actually copied from several templates, reducing the chance that any given mutation will become well established in the viral population. Moreover, if one of these jumps is imprecise, a whole chunk of genome can get skipped, resulting in the deletion of part of an important gene. The consequences can be dramatic, particularly if the change affects the protein spikes that enable the virus to bind to the surface of the host's cells. For example, in 1984 a new respiratory sickness appeared in European pig farms. It turned out to be a deletion mutant of a coronavirus that previously had infected piglets' stomachs 8. It possessed an altered spike protein that enabled the virus to infect a different cell type. Although the new disease was not generally lethal, it has since spread worldwide, and has complicated the diagnosis of the gut disease. Another example is the recent introduction of SARS-CoV into the human population. It is likely that a genetic deletion may have helped the SARS virus strains to make the transition from its animal reservoir to humans. Genetics analyses of the viral strains found in animals for sale in the Southern Chinese markets indicated that these SARS strains lacked 29 nucleotides in the gene encoding a protein of unknown function and the protein product of this gene is attached to the inside of the virus's coat protein. Furthermore, in a recent publication, full genome sequences of 14 isolates from SARS-CoV-infected patients in Singapore, Toronto, China and Hong Kong were compared, and 14 mutations were revealed 9. In one respect, this finding may be viewed as indicating that SARS virus fails to mutate; however, this virus has so far encountered little resistance from it new human hosts, and there has, therefore, been little selective pressure to cause new mutants to be retained. SARS-CoV will probably not remain as stable as it has been so far. Our immune systems could force changes, similar to the changes that frequently occur in flu viruses. In summary, we deem it prudent to develop a new SARS-CoV diagnostic assay that accounts for the genetically polymorphic nature of coronaviruses, including SARS-CoV.

SUMMARY OF THE INVENTION

The present invention includes a molecular-beacon-based multi-allelic RT-real-time-PCR assay for the detection of and discrimination between SARS-associated and other coronavirus isolates in clinical samples. The main elements of the assay design are: a) mismatch-tolerant molecular beacons; b) four sets of PCR primers for four different viral genes, and four different molecular beacons (each labeled with the same fluorophore, and each specific for a different SARS-CoV gene); c) an exogenous RNA standard that is added to the sample that can be reverse-transcribed and amplified by one of the primer sets; and d) a fifth molecular beacon that is labeled with a different fluorophore that is specific for the exogenous RNA standard. The assay further includes RNA isolation from clinical samples (blood, tissue, sputum, nasopharyngeal aspiration samples, and others), reverse transcription, PCR amplification and simultaneous automated implicit detection in a spectrofluorometric thermal cycler that measures the fluorescence intensity of each color during the annealing phase of each thermal cycle.

Multiple target sequences within the SARS-CoV S, E, M and N genes (Urbani and Tor2 strains) were identified. The S, M, and E genes encode structural proteins that are present on the outside of the virus, whereas the N gene encodes a structural protein that is required for viral RNA packaging inside the virion. The principle underlying the selection of four target sequences that uniquely identify SARS-CoV (rather than only one target sequence) is that the use of four different targets enhances the likelihood that the fundamental genetic drift of the virus will not lead to a false negative result—that is, one has better chance of hitting a moving target with a shotgun than with a rifle. Thus, by detecting four different target alleles in the same assay tube, and by using a single-fluorophore detection system, the design of the assay significantly minimizes the likelihood of missing the presence of the SARS-CoV in a clinical sample due to the continuous viral evolution of the viral sequence. Moreover, by simultaneously detecting four different target sequences in the same assay tube, the intrinsic sensitivity of the assay is enhanced.

In order to identify the best target sequences within each viral gene that discriminate the SARS-Urbani and SARS-Tor2 strains from other nonpathogenic human and animal coronavirus strains, we used DNA alignments and phylogenetic analysis of available coronavirus gene sequences deposited in GenBank. DNA sequences of SARS-CoV genes were compared with those from reference viruses representing each species in the three known groups of coronaviruses [group 1 (G1): human coronavirus 229E (HCoV-229E), af304460; porcine epidemic diarrhea virus (PEDV), af353511; transmissible gastroenteritis virus (TGEV), aj271965; canine coronavirus (CCoV), d13096; feline coronavirus (FCoV), ay204704; porcine respiratory coronavirus (PRCoV), z24675;—Group 2 (G2): bovine coronavirus (BCoV), af220295; murine hepatitis virus (MHV), af201929; human coronavirus OC43 (HCoV-OC43), m76373; porcine hemagglutinating encephalomyelitis virus (HEV), ay078417; rat coronavirus (RtCoV), af207551; and—Group 3 (G3): infectious bronchitis virus (IBV), m95169]. Sequence alignments were performed by CLUSTALW, which is a multiple sequence alignment tool that is commonly used in the bioinformatics community. It produces global multiple sequence alignments through three major phases: a) pairwise alignment, b) guide-tree construction, and c) multiple alignment. The guide tree generated by CLUSTALW is an estimate of relationships between sequences that are much like those shown by phylogenetic trees.

The criteria for selecting SARS-CoV gene-specific PCR primers were based on: a) the identification of genomic regions in SARS-CoV that, as a result of an examination of the sequence alignments, showed the highest genetic distance between SARS-CoV and other coronavirus strains; b) selection of primer sequences for amplification of the SARS-CoV targets that form primer-target hybrids whose theoretical melting temperature maximizes the ability of the primer to bind to the target even if nucleotide substitutions are present (mismatch tolerance), and yet enable all of the primers to hybridize to their targets at the same temperature in a multiplex assay ($T_m$ approximately 60° C.); and c) selection of primer sequences that enable the amplicons containing each of the four target sequences to be approximately the same (relatively short) length (approximately 100 nucleotides long).

The criteria for selecting the molecular beacon probe sequences, and their arm sequences, were based on: a) the identification of approximately 30-nucleotide-long regions in SARS-CoV (within the amplicons to be generated) that, as a result of an examination of the sequence alignments, showed the highest genetic distance between SARS-CoV and other coronavirus strains (with special emphasis on probe target sequences that encompass gaps or deletions in the SARS-CoV sequence compared to the sequence of other coronaviruses); b) selection of probe sequences that form probe-target hybrids whose theoretical melting temperature maximizes the ability of the probe to bind to the target sequence even if nucleotide substitutions are present (mismatch tolerance), and yet enable all of the probes to hybridize to their targets at the same temperature in a multiplex assay (Tm approximately 63° C.); and c) selection of arm sequences that provide the same degree of stability for the stem hybrids of all of the molecular beacon probes (stem $T_m$ of approximately 70° C.).

The assays described herein can be performed in either a heterogeneous or homogeneous format. The reagents needed for performance of the assay can be supplied in a kit format. The kit contains the detectants necessary for measuring two or more of the coronavirus genes S, E, M and N. It is recommended that the kit also contain an internal standard IPC. The reagents including the detectants can be separately packaged in individual containers. The kits may also contain a substrate including reaction tubes for performing an assay for a given sample. The kit may also contain additional reagents for performing amplification reactions including PCR and also for sample pretreatment including those reagent necessary to release and/or purify the coronavirus.

When there is a need to perform two or more different assays on the same sample, most of the time in a single vessel and at about the same time, a multiplex format can be utilized. Such formats are known in the art. Multiplex assays are typically used to determine simultaneously the presence or concentratin of more than one molecule in the sample being analyzed, or alternatively, several characteristics of a single molecule.

BRIEF DESCRIPTION OF THE DRAWINGS

FIG. 1 shows the DNA Sequence Alignment of Coronavirus S Genes isolated from different species (SEQ ID NOS 1-13, respectively in order of appearance).

FIG. 2 shows the Phylogenetic Analysis of S Gene.

FIG. 3 shows molecular designs for SARS-Associated S Gene. The oligonucleotides shown are SEQ ID NOS 14-18, and 15, respectively in order of appearance. The sequences in the alignment are SEQ ID NOS 1-13, and the three primers shown above the alignment are SEQ ID NOS 16-18, all respectively in order of appearance.

FIG. 4 lists Molecular Designs for S Gene (SEQ ID NO: 14, 19, 15, 16, 20, 17, 21, and 18, respectively in order of appearance).

FIG. 5 shows the DNA Sequence Alignment of Coronavirus E Genes isolated from different Species (SEQ ID NOS 22-33, respectively in order of appearance).

FIG. 6 shows the phylogenetic analysis of E Gene.

FIG. 7 shows molecular designs for SARS-Associated E Gene. The oligonucleotides shown are SEQ ID NOS 34-38, and 35, respectively in order of appearance. The sequences in the alignments are SEQ ID NOS 22-33, and the three primers shown above the alignment are SEQ ID NOS 36-38, all respectively in order of appearance.

FIG. 8 shows molecular designs for SARS-Associated E Gene (SEQ ID NOS 34, 39, 35, 36, 40, 37, 41, and 38, respectively in order of appearance).

FIG. 9 shows the DNA Sequence Alignment of Coronavirus M Genes isolate from difference species (SEQ ID NOS 42-54, respectively in order of appearance).

FIG. 10 shows the phylogenetic analysis of M Gene

FIG. 11 shows the molecular designs for SARS-Associated M Gene. The oligonucleotides shown are SEQ ID NOS 55-59, and 56, respectively in order of appearance. The sequences in the alignment are SEQ ID NOS 42-54, and the three primers shown above the alignment are SEQ ID NOS 57-59, all respectively in order of appearance.

FIG. 12 lists molecular designs for M Gene (SEQ ID NOS 55, 60, 56, 57, 61, 58, 62, and 59, respectively in order of appearance).

FIG. 13 shows the DNA Sequence Alignment of Coronavirus N Genes isolate from difference species (SEQ ID NOS 63-75, respectively in order of appearance).

FIG. 14 shows the phylogenetic analysis of N Gene.

FIG. 15 shows the molecular designs for SARS-Associated N Gene. The oligonucleotides shown are SEQ ID NOS 76-80, and 77, respectively in order of appearance. The sequences shown in the alignment are SEQ ID NOS 63-75, and the three primers shown above the alignment are SEQ ID NOS 78-80, all respectively in order of appearance.

FIG. 16 list molecular designs for N Gene (SEQ ID NOS 76, 81, 77, 78, 82, 79, 83, and 80, respectively in order of appearance).

FIG. 17 shows molecular designs for Internal Positive Control (IPC). The oligonucleotides shown are SEQ ID NOS 84, 85, 16, 37, and 85, respectively in order of appearance.

FIG. 18 lists molecular designs for IPC (SEQ ID NOS 84, 85, 16, 20, 37, 41, and 38, respectively in order of appearance).

FIG. 19 shows Molecular Beacon Melting Curves.

FIG. 20 shows Uniplex Real-time PCR Amplifications (Serial Dilutions-Dynamic Range).

DETAIL DESCRIPTION OF THE INVENTION

The general steps for the assay involve the performance of the following steps:

Step 1. An RNA standard that can be reverse-transcribed and amplified by one of the primer sets is added to each sample prior to isolation of RNA from the sample. RNA is then extracted from each clinical sample (nasopharyngeal aspirations, stool samples, or whole blood, obtained from patients suspected of being infected with SARS-CoV). RNA is then purified, using a QIAamp Viral RNA Kit (Qiagen, Inc., Valencia, Calif.), according to the manufacturer's instructions.

Step 2. The isolated RNA obtained from each clinical sample is then reverse transcribed with four target-specific primers (S Gene, S-RT 5'-AGGCTGTAAGAA-3' (SEQ ID NO: 18); E-Gene, E-RT 5'-TATTGCAGCAGTAC-3' (SEQ ID NO: 38); M Gene, M-RT 5'-AAGCAACGAAGTAG-3' (SEQ ID NO: 59); N Gene, N-RT 5'-GCCTTCTTGTTAG-3' (SEQ ID NO: 80; Internal Positive Control, E-RT 5'-TATTGCAGCAGTAC-3' (SEQ ID NO: 38)). Reverse transcription with SARS-CoV Viral RNA from patient samples is performed by adding 20 μL viral RNA to a mixture of 0.125 μM of (each) gene-specific primer and incubating at 80° C. for 5 minutes to denature secondary structures. The tubes are then immediately placed on ice for at least 2 minutes. Reverse transcription reactions consist of PCR buffer II (Applied Biosystems), 3 mM $MgCl_2$, 0.5 mM (each) dNTP, 10 mM dithiothreitoal, 20 Units riboneclease inhibitor (Roche Molecular Biochemicals, Indianapolis, IN) and 80 Units Superscript II Ribonuclease H-reverse transcriptase (GibcoBRL) in a final volume of 40 μL. The reactions are then incubated at 42° C. for 50 minutes, followed by inactivation at 70° C. for 15 minutes.

Step 3. Real-time PCR amplification of SARS-CoV cDNA is performed using four primer pairs and five molecular beacons in the same reaction, one primer pair for each viral gene (amplification of the internal positive control is enabled by one of the primer pairs that was designed to enable the amplification of one of the for the viral gene targets). Each PCR reaction consists of 20 μL of cDNA products, 1× PCR buffer II (Applied Biosystems), 3.5 mM $MgCl_2$, 0.5 mM (each) dNTP, 0.4 μM of each primer, and 2.5 Units of AmpliTaq Gold DNA polymerase (Applied Biosystems) in a final volume of 50 μL. Fifty cycles of amplification (94° C. for 15 seconds, 53° C. for 30 seconds, and 72° C for 30 seconds) are performed in an 7700 Prism spectrofluorometric thermal cycler (Applied Biosystems). For quantitative measurements, duplicates of six-fold serial dilutions ($10^6$ to 10 copies) of RNA standards are used as quantitative controls along with the samples being tested for a given experimental run. Viral RNA copy number for each clinical sample is calculated by interpolation of the experimentally determined threshold cycle for the test specimen onto a standard regression curve obtained from the control RNA standards (the logarithm of the number of genomic copies present in the clinical sample is inversely proportional to the observed threshold cycle).

Explanation of how the invention solves the problems of the prior art.

The main problem with the prior art is its failure to consider the intrinsically polymorphic nature of coronaviruses and to account for the possibility of continuous and/or multiple introductions of non non-genetically identical SARS-CoV strains into the human population. The present invention solves these problems by using multiple genetic sequences as targets (the S, E, M, and N genes). The primary principle of using four different genetic targets to identify SARS-CoV is to evade the fundamental genetic drift of the virus. Thus, by using four molecular beacons, each specific for a different amplified SARS-CoV target, and each labeled with same colored fluorophore, the likelihood of not detecting SARS-CoV due to continuous evolutionary changes in the virus is minimized. Furthermore, the assay design includes the presence of an internal positive control RNA, the reverse transcription and PCR amplification of which generates a signal in a different color, thus assuring that if there is an unexpected problem with RNA isolation, reverse transcription, or target amplification, the absence of the control signal will indicate that a problem occurred.

Summary of the features of other SARS nucleic acid assays and description of the differences between those assays and the current invention. As outlined in the previous sections, there are five SARS nucleic acid assays: an RT-PCR assay published by Perris et al. [2], an RT-real-time-PCR assay published by Ksiazek et al. [1], a similar RT-real-time-PCR assay published by Drosten et al. [4], another RT-real-time-PCR assay published by Poon et al. [7], and a PCR-based SARS diagnostic assay developed by Lipkin and Briese—no publication is available describing this assay. All of the published assays use RNA extracted from clinical samples. In addition, all of the published assays initiate reverse transcription of SARS-CoV RNA with random primers, and all of the published assays generate cDNA with primers previously designed to enable the amplification of conserved regions of open reading frame 1b (ORF1b), in order to achieve broad reactivity with the coronavirus genus. The present invention differs from these inventions in many different ways. The present assay uses four different targets instead of one and it has an internal positive RNA control (artificial RNA molecule) that can be reverse-transcribed and amplified with primers designed for the viral genes (it possesses a unique target recognition sequence for detection by a unique molecular beacon). This RNA molecule serves as a control for RNA isolation, reverse transcription, and PCR amplification. The present uses real-time PCR for nucleic acid amplification and molecular beacons for real-time detection. The present employs a dual-color detection scheme, a yellow signal (tetrachlorofluorescein) for all four SARS-CoV targets and a green signal (fluorescein) indicating that the internal positive control has been isolated, reverse transcribed, and PCR amplified.

Another important aspect of our invention, which is not an aspect of the published assays, is the construction of four viral RNA targets that contain gene-specific reverse transcription sequences built in to their 3' ends. Collectively, these molecules serve as SARS-specific positive controls. All of the present designs are thermodynamically compatible to work together in a five-amplicon multiplex assay.

Also multiplex polymerase chain reaction (mPCR) are envisioned. It is a procedure for simultaneously performing PCR on greater than two different sequences. A mPCR reaction comprises: treating said extracted DNA to form single stranded complementary strands, adding a plurality of labelled paired oligonucleotide primers, each paired primer specific for a different short tandem repeat sequence, one primer of each pair substantially complementary to a part of the sequence in the sense strand and the other primer of each pair substantially complementary to a different part of the same sequence in the complementary antisense strand, annealing the plurality of paired primers to their complementary sequences, simultaneously extending said plurality of annealed primers from the 3' terminus of each primer to synthesize an extension product complementary to the strands annealed to each primer, said extension products, after separation from their complement, serving as templates for the synthesis of an extension product for the other primer of each pair, separating said extension products from said templates to produce single stranded molecules, amplifying said single stranded molecules by repeating at least once said annealing, extending and separating steps.

Lower stringent conditions are routinely used to accommodate the capture of multiple target sequences that contain variations in their nucleic acid sequences. The stringency is reduced by either powering the temperature of hybridization and wash or by modification of the buffer. When the stringent conditions are reduced and the target nucleic acid sequence is very similar to nucleic acid sequences of another genus specificity of the capture probe for the target genus can be lost.

When multiple capture probes are used and are selected to compatible to variations in the target nucleic acid sequences, the specificity under high stringent conditions can be regained. The blending of multiple probes permits a single positive response for the presence of a group of target organisms.

In a multiplex assay, numerous conditions of interest are simultaneously examined. Multiplex analysis relies on the ability to sort sample components or the data associated therewith, during or after the assay is completed.

EXAMPLES

Example 1

Design of SARS-CoV-Specific Molecular Beacons, and Primers for Reverse Transcription and for PCR Purpose: The overall rationale in the design of molecular beacons and oligonucleotides for our SARS assay is to construct mismatch-tolerant molecular beacons that are thermodynamically compatible to work in a five-amplicon multiplex assay.

Design: The molecular beacons were designed so that they are able to hybridize to their targets at the annealing temperature of the PCR, while unbound molecular beacons remain in the closed conformation. These basic aspects were achieved by using coronavirus gene-specific multiple alignments and thermodynamic considerations to select the target sequences, the identity and length of the PCR primers, the identity and length of the probe sequences (target recognition sequences), and the length of the arm sequences.

Materials: In order to theoretically calculate the melting temperatures of the PCR primers and the probe-target hybrids, was used the Oligo Toolkit that is available on the internet. The melting temperatures and secondary structure predictions of the molecular beacons were calculated by using the DNA folding program developed by Michael Zuker that is available on the internet.

Results: The theoretical melting temperatures of the PCR primers was about 60° C.; the $T_m$ of the reverse transcription primers was 47° C.; the $T_m$ of the probe-target hybrid was about 63° C.; and the $T_m$ of the stem hybrids of the molecular beacons was about 70° C.

Conclusion: The mismatch-tolerant molecular beacons that are thermodynamically compatible are designed to work in a final five-amplicon multiplex SARS-CoV assay.

See the following Figures: The molecular designs for the S gene target of the SARS-CoV assay are described in detail in FIGS. 1-4; for the E gene target see FIGS. 5-8; for the M gene target, see FIGS. 9-12; for the N gene target, see FIGS. 13-16; and for the Internal Positive Control (IPC), see FIGS. 17 and 18.

Example 2

Experimental Characterization of the Molecular Beacons and the Molecular Beacon-target Complexes Purpose: The overall rationale of these experiments is to evaluate the thermodynamic properties of the constructed molecular beacons prior to carrying out real-time PCR experiments.

Design: For each molecular beacon, we have determined two melting curves—one for beacon alone, and one for the beacon-target complex—by using the ABI Prism 7700 spectrofluorometric thermal cycler.

Materials: For each molecular beacon, melting curves were obtained by preparing two tubes containing 50 µL of 200 nM molecular beacon dissolved in 3.5 mM $MgCl_2$ and 10 mM Tris-HCl, pH 8.0, and by adding a complementary oligonucleotide target to one of the tubes at a final concentration of 400 nM.

The fluorescence of each solution was determined as a function of temperature, using a thermal cycler with the capacity to monitor fluorescence. Temperature was decreased linearly with time from 80° C. to 10° C. in 1° C. steps; with each holding period lasting one minute, and fluorescence intensity was measured during each hold.

Results: The theoretical melting temperature of the PCR primers was 60° C. ±2° C.; the theoretical $T_m$ of the reverse transcription primers was 47±2° C.; the theoretical $T_m$ of the probe target-hybrids was about 63±3° C.; and the theoretical $T_m$ of the stem hybrid of the molecular beacons was 70±2° C.

Conclusion: The designed mismatch-tolerant molecular beacons was determined to correctly recognize their DNA targets, and to be thermodynamically compatible to work together in a five-amplicon multiplex SARS-CoV assay.

Figures: The melting curves of the molecular beacons and the molecular beacon-target hybrids are shown in FIG. 19.

Example 3

Uniplex SARS-CoV Viral and IPC PCR Amplifications, Using SYBR Green to Detect the Amplicons Purpose: The overall rationale of these experiments is to evaluate the PCR primers and PCR conditions.

Design: For each SARS-CoV gene-specific and IPC amplification, a synthetic target DNA was used. PCR reactions were performed using a spectrofluorometric thermal cycler (Cepheid).

Materials: The PCR protocols are shown in the following exhibits:

for S Gene:

(A) SYBR Green-based Detection of S Gene Amplicon (LK250) of SARS-associated CoV

| Mixture | Per reaction |
|---|---|
| $dH_20$ | 15 µl |
| 10X PCR Buffer (10X) | 2.5 µl |
| $MgCl_2$ (25 mM) | 4.0 µl |
| Plat Taq DNA Pol (5 $U\mu l^{-1}$) | 0.3 µl |
| dNTP (25 mM) | 0.3 µl |
| LK251 (10 pmole/µl) | 0.5 µl |
| LK252 (10 pmole/µl) | 0.5 µl |
| Sybr Green DNA (25X) | 1.0 µl |
| Target DNA | 1.0 µl |
| TOTAL | 25.0 µl |

Smart Cycler (Cepheid)

DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

(B) Molecular-beacon-based Detection of S Gene Amplicon (LK250) of SARS-associated CoV

| Mixture | Per reaction |
|---|---|
| $dH_20$ | 15.75 μl |
| 10X PCR Buffer (10X) | 2.5 μl |
| $MgCl_2$ (25 mM) | 4.0 μl |
| Plat Taq DNA Pol (5 $U\mu l^{-1}$) | 0.3 μl |
| dNTP (25 mM) | 0.3 μl |
| LK251 (10 pmole/μl) | 0.5 μl |
| LK252 (10 pmole/μl) | 0.5 μl |
| LK249 Beacon (10 pmole/μl) | 0.25 μl |
| Target DNA | 1.0 μl |
| TOTAL | 25.0 μl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

(C) SYBR Green-based Detection of S Gene Amplicon (T7- and RT-Amplicon)

| Mixture | Per reaction |
|---|---|
| $dH_20$ | 15 μl |
| 10X PCR Buffer (10X) | 2.5 μl |
| $MgCl_2$ (25 mM) | 4.0 μl |
| Plat Taq DNA Pol (5 $U\mu l^{-1}$) | 0.3 μl |
| dNTP (25 mM) | 0.3 μl |
| LK251-T7 (10 pmole/μl) | 0.5 μl |
| LK252-RT (10 pmole/μl) | 0.5 μl |
| Sybr Green DNA (25X) | 1.0 μl |
| Target DNA | 1.0 μl |
| TOTAL | 25.0 μl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

for the E Gene:

(A) SYBR Green-based Detection of E Gene Amplicon (LK254) of SARS-associated

| Mixture | Per reaction |
|---|---|
| $dH_20$ | 15 μl |
| 10X PCR Buffer (10X) | 2.5 μl |
| $MgCl_2$ (25 mM) | 4.0 μl |
| Plat Taq DNA Pol (5 $U\mu l^{-1}$) | 0.3 μl |
| dNTP (25 mM) | 0.3 μl |
| LK255 (10 pmole/μl) | 0.5 μl |
| LK256 (10 pmole/μl) | 0.5 μl |
| Sybr Green DNA (25X) | 1.0 μl |
| Target DNA | 1.0 μl |
| TOTAL | 25.0 μl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

(B) Molecular-beacon-based Detection of E Gene Amplicon (LK254) of SARS-associated CoV

| Mixture | Per reaction |
|---|---|
| $dH_20$ | 15.75 μl |
| 10X PCR Buffer (10X) | 2.5 μl |
| $MgCl_2$ (25 mM) | 4.0 μl |
| Plat Taq DNA Pol (5 $U\mu l^{-1}$) | 0.3 μl |
| dNTP (25 mM) | 0.3 μl |
| LK255 (10 pmole/μl) | 0.5 μl |
| LK256 (10 pmole/μl) | 0.5 μl |
| LK253 Beacon (10 pmole/μl) | 0.25 μl |
| Target DNA | 1.0 μl |
| TOTAL | 25.0 μl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

(C) SYBR Green-based Detection of E Gene Amplicon (T7- and RT-Amplicon)

| Mixture | Per reaction |
|---|---|
| $dH_20$ | 15 µl |
| 10X PCR Buffer (10X) | 2.5 µl |
| $MgCl_2$ (25 mM) | 4.0 µl |
| Plat Taq DNA Pol (5 $U\mu l^{-1}$) | 0.3 µl |
| dNTP (25 mM) | 0.3 µl |
| LK255-T7 (10 pmole/µl) | 0.5 µl |
| LK256-RT (10 pmole/µl) | 0.5 µl |
| Sybr Green DNA (25X) | 1.0 µl |
| Target DNA | 1.0 µl |
| TOTAL | 25.0 µl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

for the M Gene (A) SYBR Green-based Detection of M Gene Amplicon (LK258) of SARS-associated CoV

| Mixture | Per reaction |
|---|---|
| $dH_20$ | 15 µl |
| 10X PCR Buffer (10X) | 2.5 µl |
| $MgCl_2$ (25 mM) | 4.0 µl |
| Plat Taq DNA Pol (5 $U\mu l^{-1}$) | 0.3 µl |
| dNTP (25 mM) | 0.3 µl |
| LK259 (10 pmole/µl) | 0.5 µl |
| LK260 (10 pmole/µl) | 0.5 µl |
| Sybr Green DNA (25X) | 1.0 µl |
| Target DNA | 1.0 µl |
| TOTAL | 25.0 µl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

(B) Molecular-beacon-based Detection of M Gene Amplicon (LK258) of SARS-associated CoV

| Mixture | Per reaction |
|---|---|
| $dH_20$ | 15.75 µl |
| 10X PCR Buffer (10X) | 2.5 µl |
| $MgCl_2$ (25 mM) | 4.0 µl |
| Plat Taq DNA Pol (5 $U\mu l^{-1}$) | 0.3 µl |
| dNTP (25 mM) | 0.3 µl |
| LK259 (10 pmole/µl) | 0.5 µl |
| LK260 (10 pmole/µl) | 0.5 µl |
| LK257 Beacon (10 pmole/µl) | 0.25 µl |
| Target DNA | 1.0 µl |
| TOTAL | 25.0 µl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

(C) SYBR Green-based Detection of M Gene Amplicon (T7- and RT-Amplicon)

| Mixture | Per reaction |
|---|---|
| $dH_20$ | 15 µl |
| 10X PCR Buffer (10X) | 2.5 µl |
| $MgCl_2$ (25 mM) | 4.0 µl |
| Plat Taq DNA Pol (5 $U\mu l^{-1}$) | 0.3 µl |
| dNTP (25 mM) | 0.3 µl |
| LK259-T7 (10 pmole/µl) | 0.5 µl |
| LK260-RT (10 pmole/µl) | 0.5 µl |
| Sybr Green DNA (25X) | 1.0 µl |
| Target DNA | 1.0 µl |
| TOTAL | 25.0 µl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

for the N Gene:

(A) SYBR Green-based Detection of N Gene Amplicon (LK262) of SARS-associated CoV

| Mixture | Per reaction |
|---|---|
| $dH_20$ | 15 µl |
| 10X PCR Buffer (10X) | 2.5 µl |
| $MgCl_2$ (25 mM) | 4.0 µl |
| Plat Taq DNA Pol (5 $U\mu l^{-1}$) | 0.3 µl |
| dNTP (25 mM) | 0.3 µl |
| LK263 (10 pmole/µl) | 0.5 µl |
| LK264 (10 pmole/µl) | 0.5 µl |
| Sybr Green DNA (25X) | 1.0 µl |
| Target DNA | 1.0 µl |
| TOTAL | 25.0 µl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

(B) Molecular-beacon-based Detection of N Gene Amplicon (LK262) of SARS-associated CoV

| Mixture | Per reaction |
|---|---|
| $dH_20$ | 15.75 µl |
| 10X PCR Buffer (10X) | 2.5 µl |
| $MgCl_2$ (25 mM) | 4.0 µl |
| Plat Taq DNA Pol (5 $U\mu l^{-1}$) | 0.3 µl |
| dNTP (25 mM) | 0.3 µl |
| LK263 (10 pmole/µl) | 0.5 µl |
| LK264 (10 pmole/µl) | 0.5 µl |
| LK261 Beacon (10 pmole/µl) | 0.25 µl |
| Target DNA | 1.0 µl |
| TOTAL | 25.0 µl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

(C) SYBR Green-based Detection of N Gene Amplicon (T7- and RT-Amplicon)

| Mixture | Per reaction |
|---|---|
| $dH_20$ | 15 µl |
| 10X PCR Buffer (10X) | 2.5 µl |
| $MgCl_2$ (25 mM) | 4.0 µl |
| Plat Taq DNA Pol (5 $U\mu l^{-1}$) | 0.3 µl |
| dNTP (25 mM) | 0.3 µl |
| LK263-T7 (10 pmole/µl) | 0.5 µl |
| LK264-RT (10 pmole/µl) | 0.5 µl |
| Sybr Green DNA (25X) | 1.0 µl |
| Target DNA | 1.0 µl |
| TOTAL | 25.0 µl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

and for Internal Positive Control (IPC)

(A) SYBR Green-based Detection of Internal Positive Control (LK266)

| Mixture | Per reaction |
|---|---|
| $dH_20$ | 15 µl |
| 10X PCR Buffer (10X) | 2.5 µl |
| $MgCl_2$ (25 mM) | 4.0 µl |
| Plat Taq DNA Pol (5 $U\mu l^{-1}$) | 0.3 µl |
| dNTP (25 mM) | 0.3 µl |
| LK251 (10 pmole/µl) | 0.5 µl |
| LK256 (10 pmole/µl) | 0.5 µl |
| Sybr Green DNA (25X) | 1.0 µl |
| Target DNA | 1.0 µl |
| TOTAL | 25.0 µl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

(B) Molecular-beacon-based Detection of Internal Positive Control (LK266)

| Mixture | Per reaction |
|---|---|
| $dH_20$ | 15.75 µl |
| 10X PCR Buffer (10X) | 2.5 µl |
| $MgCl_2$ (25 mM) | 4.0 µl |
| Plat Taq DNA Pol (5 $U\mu l^{-1}$) | 0.3 µl |
| dNTP (25 mM) | 0.3 µl |
| LK251 (10 pmole/µl) | 0.5 µl |
| LK256 (10 pmole/µl) | 0.5 µl |
| LK265 Beacon (10 pmole/µl) | 0.25 µl |
| Target DNA | 1.0 µl |
| TOTAL | 25.0 µl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

(C) SYBR Green-based Detection of Internal Positive Control (T7- and RT-Amplicon)

| Mixture | Per reaction |
|---|---|
| $dH_20$ | 15 µl |
| 10X PCR Buffer (10X) | 2.5 µl |
| $MgCl_2$ (25 mM) | 4.0 µl |
| Plat Taq DNA Pol (5 $U\mu l^{-1}$) | 0.3 µl |
| dNTP (25 mM) | 0.3 µl |
| LK251-T7 (10 pmole/µl) | 0.5 µl |
| LK256-RT (10 pmole/µl) | 0.5 µl |
| Sybr Green DNA (25X) | 1.0 µl |
| Target DNA | 1.0 µl |
| TOTAL | 25.0 µl |

Smart Cycler (Cepheid)
DNA Denaturation & Enzyme Activation

| | | |
|---|---|---|
| Cycles: | 1 | |
| Target Temperature (° C.): | 95 | 120 sec |

Primary Amplification

| | | | |
|---|---|---|---|
| Cycles: | 35 | | |
| Denaturation: | 95° C. | 15 sec | |
| Annealing: | 53° C. | 15 sec | Spectra ON |
| Extension: | 72° C. | 15 sec | |

Results: Real-time PCR amplification curves were consistent with the presence or absence of target DNA and the amplicons that were synthesized in the PCR reactions had the correct lengths.

Conclusion: The synthesized primers work well under uniform PCR conditions.

Example 4

Uniplex SARS-CoV Viral and IPC PCR Amplifications, Using Gene-specific Molecular Beacons Purpose: The overall rationale of these experiments is to evaluate the molecular beacons, using the uniform PCR condition established in the tests with the PCR primers.

Design: For each SARS-CoV gene-specific and IPC amplification, a synthetic target DNA and molecular beacon are used. PCR reactions were performed using the spectrofluorometric thermal cycler (Cepheid). For each assay, utilized target dilutions are performed to establish the linearity and the dynamic range of the molecular beacon-based real-time PCR assays.

Materials: The PCR protocols are shown above in Example 3 for the S Gene, E gene, M Gene, N Gene, and the Internal Positive Control (IPC).

Results: Real-time PCR amplification curves were consistent with the presence or absence of target DNA.

Conclusion: The SARS-CoV-specific and IPC-specific molecular beacons work well in under uniform PCR conditions. See FIG. 20 Exhibit 25).

Example 5

Uniplex SARS-CoV Viral and IPC PCR Amplifications Using Bacteriophage T7 RNA Polymerase and Reverse Transcriptase Target PCR Primers Purpose: The overall rationale of these experiments is for each of the five amplicons (SARS-CoV S, E, M, and N genes and IPC) to produce dsDNA molecules that contain a bacteriophage T7 promoter target recognition sequence at their 5' ends and the gene-specific reverse transcriptase primer-binding site at their 3' ends. The synthesized amplicons are used for in vitro RNA production. The synthesized RNA molecules have the specific reverse transcriptase primer-binding site at their 3' ends.

Design: For each SARS-CoV gene-specific and IPC amplification, a synthetic target DNA and bacteriophage T7-RT-PCR primers are used. PCR reactions were performed using the spectrofluorometric thermal cycler (Cepheid), using SYBR green to detect the amplicons.

Materials: The PCR protocols are shown in Example 3.

Results: Real-time PCR amplification curves are consistent with the presence or absence of target DNA and the amplicons synthesized in the PCR reactions had the correct lengths.

Conclusion: SARS-CoV-specific bacteriophage T7-RT amplicons were generated for use as templates for in vitro RNA transcription, in order to produce the target RNAs that will be used to qualify the PCR assays. See FIG. 20.

Example 6

In vitro RNA Transcription of SARS-CoV- and IPC-specific RNA Molecules

Purpose: The overall rationale for these experiments is to produce RNA molecules containing the specific reverse transaction primer-binding site at their 3' ends.

Design: For each SARS-CoV gene-specific and IPC amplification, a T7-RT-PCR dsDNA amplicon (generated from Experiment 5) is used.

Materials: RNA transcripts corresponding to the four SARS-CoV-specific and IPC alleles were prepared by in vitro transcription of PCR products that contain the T7 RNA polymerase promoter site, by using a MEGAscript T7 kit (Ambion, Houston, Tex.).

Results: RNA molecules had the correct lengths, based on 8% polyacrylamide gel electrophoretic analysis of the product strands.

Conclusion: SARS-CoV-specific T7-RT amplicons were generated to be used for in vitro RNA transcription.

Example 7

Uniplex SARS-CoV-specific and IPC-specific RNA Reverse Transcription and Molecular Beacon-based Real-time PCR Purpose: The overall rationale of these experiments is to test whether the RNA molecules containing the specific reverse transcription primer-binding site at their 3' ends can be reverse transcribed and the generated cDNA can be amplified and detected by real-time PCR.

Design: For each SARS-CoV gene-specific and IPC amplification, a T7-RT-PCR dsDNA amplicon (generated from Experiment 5) is used.

Materials: Reverse transcription with viral and IPC RNA was performed by adding 20 μL of SARS-CoV-specific and IPC-specific RNA to 0.125 μM of SARS-CoV-specific and IPC-specific primers and incubated at 80° C. for 5 minutes. The PCR-tubes were then immediately placed on ice for at least 2 minutes. the reverse transcriptase reactions contained PCR buffer II (Applied Biosystems), 3 mM $MgCl_2$, 0.5 mM of each dNTP (GibcoBRL), 10 mM dithiothreitol, 20 Units ribonuclease inhibitor (Roche Molecular Biochemicals) and 80 Units SuperScript II RNase H-reverse transcriptase (GibcoBRL) in a final volume of 40 μL. The reactions were incubated at 42° C. for 50 minutes, followed by inactivation at 70° C. for 15 minutes. Real-time PCR of cDNA, using 10 μL cDNA, 1× PCR buffer, 3.5 mM $MgCl_2$, 0.5 mM of each dNTP, 0.4 μM of each molecular beacon, 0.4 μM of each PCR primer, and 2.5 Units AmpliTaq Gold DNA polymerase in a final volume of 50 μL. 35 cycles of amplification (94° C. for 15 sec, 53° C. for 30 sec, and 72° C. for 30 sec) were performed in a 7700 Prism spectrofluorometric thermal cycler (Applied Biosystems).

Results: SARS-CoV-specific and IPC-specific RNA molecules can be reverse transcribed, and the generated cDNA can be amplified and detected by SARS-CoV-specific and IPC-specific molecular-beacons in real-time PCR assays.

Conclusion: SARS-CoV-specific RNA molecules can be used as controls in the final assay.

Example 8

Multiplex SARS-CoV-specific and IPC-specific RNA Reverse Transcription and Molecular Beacon-based Real-time PCR Purpose: The overall rationale of this experiment is to multiplex the uniplex SARS-CoV-specific and IPC-specific RT-PCR reactions in a multiplex RT-PCR reaction.

Design: All five RT-PCR reactions are incorporated into one.

Materials: Identical to Experiment 7, with the exception that all five RT primers, four sets of PCR primers, and five molecular beacons are used in a single RT-PCR reaction Results: SARS-CoV-specific and IPC-specific RNA molecules can be reverse transcribed and generate cDNA, and can then be amplified and detected by SARS-CoV-specific and IPC-specific molecular beacons in a real-time PCR assay.

Conclusion: SARS-CoV-specific RNA molecules can be used as controls in a multiplex assay.

Example 9

Evaluate the Complete SARS-CoV Assay Using Clinical Samples

Purpose: The overall rationale of these experiments is to evaluate the SARS-CoV assay using real samples (isolated SARS-CoV from cultures, primary patient isolates from saliva, and whole blood and stool specimens).

Design: Identical to Experiment 8.

Materials: Identical to Experiment 8.

Results: SARS-CoV assay detects SARS-CoV and discriminates between SARS-CoV and other non-pathogenic coronaviruses.

Conclusion: SARS-CoV assay detects SARS RNA extracted from cultured SARS strains and primary isolates.

Example 10

Clinical Evaluation 64 samples collected from 23 individuals who were clinically diagnosed to have SARS based on CDC, WHO and Health Canada case definitions.

The sample types included: bronchial lavage and sputnum (pre-mortem samples) as well as lung, liver, small and large bowel, and spleen tissue (post mortem).

65 samples from 15 patients served as controls. 26 were bone marrow samples sent for routing pathogen screening. 39 were post mortem organ samples from 10 patients who died during the outbreak but whose deaths were attributed to other causes including congestive heart failure, cerebrovascular accidents, atherosclerotic heart disease, chronic obstructive pulmonary disease, invasive Group A streptococcal infection, amiodorone pulmonary toxicity, and pulmonary fibrosis.

All samples were blindl assayed by using the developed assay (using all four genes: S, E, M, N) and the specificity was 100%.

1. Ksiazek, T. G., et al. A novel coronavirus associated with severe acute respiratory syndrome, N. Engl J Med, 2003, 348(20): p. 1953-66.
2. Peiris, J. S., et al., Coronavirus as a possible cause of severe acute respiratory syndrome, Lancet, 2003, 361 (9366): p, 1319-25.
3. Munch, R., Robert Koch. Microbes Infect, 2003. 5(1): p. 69-74.
4. Drosten, C., et al., Identification of a novel coronavirus in patients with severe acute respiratory syndrome, N Engl J Med, 2003, 348(20): p. 1967-76.
5. Marra, M. A., et al., The Genome sequence of the SARS-associated coronavirus, Science, 2003, 300(5624): p. 1399-404.
6. Rota, P. A., et al., Characterization of a novel coronavirus associated with severe acute respiratory syndrome, Science, 2003, 300(5624): p. 1394-9.
7. Poon, L. L., et al., Rapid diagnosis of a coronavirus associated with severe acute respiratory syndrome (SARS), Clin Chem, 2003, 49(^Pt 1): p. 953-5.
8. Penaert, M., P. Callebaut, and J. Vergote, Isolation of a porcine respiratory, non-enteric coronavirus related to transmissible gastroenteritis, Vet. Q. 1986. 8(3): p. 257-61.
9. Ruan, Y. J., et al., Comparative full-length genome sequence analysis of 14 SARS coronavirus isolates and common mutations associated with putative origins of infection Lancet, 2003, 31(9371): p. 1779-85.

The content of each of the document identified above and cited in the specification documents is expressly incorporated herein by reference.

The invention claimed is:

1. A molecular-beacon-based multi-allelic real-time reverse transcription polymerase chain reaction (RT-PCR) multiplex assay for a Sever Acute Respiratory Syndrome (SARS) virus comprising:

(1) obtaining a sample;

(2) isolating RNA from the sample;

(3) placing the isolated RNA in a tube along with primers specific for spike (S), envelope (E), membrane (M), and nucleocapsid (N) genes of the SARS virus, wherein the S primer includes SEQ ID NO:18, the E primer includes SEQ ID NO:38, the M primer includes SEQ ID NO:59, and the N primer includes SEQ ID NO:80, (4) reverse transcribing the isolated RNA in the presence of a reverse transcriptase to form a cDNA unique for each of the S, E, M and N SARS viral genes, (5) real-time amplifying the SARS cDNA in the presence of four distinct types of molecular beacons, each labeled with the same fluorophore and specific for a different SARS coronavirus (CoV) gene selected from S, E, M and N viral genes, and four S, E, M and N gene-specific primer pairs, wherein the molecular beacons are:

for S gene:

LK249 5'-FAM-CCCACGCCAGAAGGTAGATCAC-GAACTACACGTGGG-3'-Dubcyl (SEQ ID NO:14);

for E gene:

LK253 5'-FAM-CCTCCGCACGAAAGCAAGAAAAA-GAAGTACGCCGGAGG-3'-Dubcyl (SEQ ID NO:34);

for M gene:

LK257 5'-FAM-CCTCCGACCCAATTAATTCTGTA-GACAGCAGCCGGAGG-3'-Dubcyl (SEQ ID NO:55); and for N gene:

LK261 5'-FAM-CCTCCGTACCATCTGGGGCT-GAGCTCTTFCATCGGAGG-3'-Dubcyl (SEQ ID NO:76);

wherein the S, E, M and N gene-specific primer pairs are:

for S gene

LK251 5'-CTCTATGTTTATAAGGGCTATCAACC-3' (SEQ ID NO:16)

LK252 5'-CCAAGAGGCAACTTAAAAATAGGTTTC-3' (SEQ ID NO:17);

for E gene

LK255 5'-CGGAAGAAACAGGTACGTTAATAG-3' (SEQ ID NO:36)

LK256 5'-AAGCGCAGTAAGGATGGCTA-3' (SEQ ID NO:37);

for M gene

LK259 5'-CTTGTTTTCCTCTGGCTCTTG-3' (SEQ ID NO:57)

LK260 5'-CAAGCCATTGCAATCGCAATC-3' (SEQ ID NO:58); and for N gene

LK263 5'-ACGAGTTCGTGGTGGTGAC-3' (SEQ ID NO:78)

LK264 5'-CGTAGGGAAGTGAAGCTTC-3' (SEQ ID NO:79); and (6) measuring fluorescence, which is a collective measure of the presence of the SARS virus.

2. The assay of claim 1 wherein the SARS virus is SARS-CoV.

3. The assay of claim 1, wherein step (3) further comprises a RNA internal positive control (IPC) and step (5) further comprises IPC-specific primers and a fifth molecular beacon that is specific for the IPC and labeled with a different fluorophore, which can be distinguished from the SARS-CoV gene-specific molecular beacon fluorophore, and wherein step (6) further includes a measurement of fluorescence at a wavelength unique for the fifth molecular beacon.

4. The assay of claim 1 wherein the sample source includes blood, tissue, sputum, or nasopharyngeal aspirations.

5. The assay of claim 1 wherein the measuring step includes simultaneous automated amplicon detection in a spectrofluorometric thermal cycler that measures the fluorescence intensity of each color during the annealing phase of each thermal cycle.

6. The assay of claim 3 wherein the IPC-specific primers are included in step (5) and have the following sequences: SEQ ID NO:16 and SEQ ID NO:37.

* * * * *

SEQUENCE LISTING

```
<160> NUMBER OF SEQ ID NOS: 94

<210> SEQ ID NO 1
<211> LENGTH: 4356
<212> TYPE: DNA
<213> ORGANISM: Canine coronavirus

<400> SEQUENCE: 1

atgattgtgc ttacattgtg ccttttcttg tttttgtaca gtagtgtgag ctgtacatca     60

aacaatgact gtgtacaagt taatgtgaca caactgcctg gcaatgaaaa tattatcaaa    120

gattttctat ttcagaactt taaagaagaa ggaagtttag ttgttggtgg ttattacccc    180

acagaggtgt ggtataactg ttccacaact caacaaacta ccgcttataa gtattttagt    240

aatatacatg cattttattt tgatatggaa gccatggaga atagtactgg caatgcacgt    300

ggtaaacctt tactagtaca tgttcatggt aatcctgtta gtatcattgt ttacatatca    360

gcttatagag atgatgtgca atttaggccg cttttaaagc atggtttatt gtgtataact    420

aaaaatgaca ccgttgacta taatagcttt acaattaacc aatggcgaga catatgtttg    480

ggtgacgaca gaaaaatacc attctctgta gtacccacag ataatggtac gaaattattt    540

ggtcttgagt ggaatgatga ctatgttaca gcctatatta gtgatgagtc tcaccgtttg    600

aatatcaata ataattggtt taacaatgtt acactcctat actcacgtac aagcaccgcc    660

acgtggcaac acagtgctgc atatgtttat caaggtgttt caaattttac ttattacaag    720

ttaaataaaa ccgctggctt aaaaagctat gaattgtgtg aagattatga atactgcact    780

ggctatgcaa ccaatgtgtt tgctccgaca tcaggtggtt atatacctga tggattcagt    840

tttaacaatt ggtttatgct tacaaacagc tccacttttg ttagtggcag atttgtaaca    900

aatcaaccgc tgctagttaa ttgcttgtgg ccagtgccca gttttggcgt cgcagcacaa    960

gaattttgtt ttgaaggtgc tcagtttagc caatgtaacg gtgtttcttt aaataataca   1020

gtagatgtta ttagatttaa ccttaatttc actacagatg tacaatctgg catgggtgct   1080

acagtatttt cactgaatac aacaggcggt gtcattcttg agatttcttg ttataatgac   1140

acagtgagtg agtcgagttt ctacagttat ggtgaaattc cattcggcgt aactgatgga   1200

ccacgttact gttatgtact ctacaatggc acagctctta agtatttagg aacattacca   1260

cctagtgtca aggaaattgc tattagtaag tggggacatt tttatattaa tggttacaat   1320

ttctttagca cgtttcctat tgattgtata gcttttaatt taaccactgg tgctagtgga   1380
```

-continued

```
gcattttgga caattgctta tacgtcgtac acagaagcat tagtacaagt tgaaaacaca   1440
gctattaaaa aggtgacgta ttgtaacagt cacattaata acatcaaatg ttctcaactt   1500
actgctaatt tgcaaaatgg tttttaccct gttgcttcaa gtgaagttgg tcttgtcaat   1560
aagagtgttg tgttactacc tagtttctat tcacatacca gtgttaatat aactattgat   1620
cttggtatga agcgtagtgt tacggtcacc atagcctcac cattaagtaa catcacacta   1680
ccaatgcagg ataataacat agacgtgtac tgtattcgtt ctaaccaatt ctcagtttat   1740
gttcattcca cttgcaaaag ttctttatgg gataacaatt ttaattcagc atgtaccgac   1800
gttttagacg ccacagctgt tataaaaact ggtacttgtc ctttctcatt tgataaattg   1860
aataattact taacttttaa caagttctgt ttgtcgttga atcccgttgg tgccaactgt   1920
aagttagatg ttgccgcccg tacaagaacc aatgagcagg tttttggaag tttatatgta   1980
atatatgaag aaggagacaa catagtgggt gtaccgtctg ataatagtgg tttgcacgat   2040
ttgtcagtgt tgcacttaga ctcttgtaca gattacaata tatatggtag aactggtgtt   2100
ggtattatta gaaaaactaa cagcacacta cttagtggct tatattacac atcactatca   2160
ggtgatttgt taggttttaa aaatgttagt gatggtgttg tctactctgt aacgccatgt   2220
gatgtaagtg cacaagctgc tgttattgat ggtgccatag ttggagctat gacttccatt   2280
aatagtgaac tgttaggtct aactcattgg acaacaacac ctaattttta ttactactcc   2340
atatataatt atacaaatgt gatgaatcgt ggcacggcaa ttgataatga tattgattgt   2400
gaacctatca taacatattc taatataggt gtttgtaaaa atggagcttt ggttttttatt  2460
aacgtcacac attctgatgg agacgttcaa ccaattagca ccggtaatgt cacgataccc   2520
acaaatttta ctatatctgt gcaagtcgaa tatattcagg tttacactac accagtttca   2580
atagactgtg caagatacgt ttgcaatggt aacccaagat gcaataagtt attaacacaa   2640
tacgtttctg catgtcaaac tattgagcaa gcgcttgcaa tgggtgccag acttgaaaac   2700
atggagattg attccatgtt atttgtttcg gaaaatgccc ttaaattggc atctgttgaa   2760
gcattcaata gtacggaaaa tttagaccct atttataaag aatggcctaa cattggtggt   2820
tcttggctag gaggtttaaa agatatattg ccatctcata atagcaaacg taagtaccgc   2880
tcggctatag aagacttgct tttgataag gttgtaacat ctggcttagg tacagttgac   2940
gaagattaca aacgttctgc aggtggttat gacatagctg acttagtgtg tgcacgatat   3000
tacaatggca tcatggtgct acctggtgta gctaatgatg acaagatgac tatgtacact   3060
gcatctctta caggtggtat aacattaggt gcacttagtg gtggcgcagt ggctatacct   3120
tttgcagtag cagttcaggc tagacttaat tatgttgctc tacaaactga tgtattgaac   3180
aaaaaccaac aaatcttggc taatgctttc aatcaagcta ttggtaacat tacacaggca   3240
tttggtaagg ttaatgacgc tatacatcaa acatcaaaag gtcttgctac tgttgctaaa   3300
gcattggcaa aggtgcaaga tgttgttaac acgcaaggtc aagctttaag ccacctaaca   3360
gtacaattgc aaaacaattt tcaagccatt agcagttcta ttagtgacat ttataacagg   3420
cttgatgaat tgagtgctga tgcacaagtt gacaggctga ttacaggacg acttacagca   3480
cttaatgcat ttgtgtctca gactttaacc agacaagcag aggttagggc tagtagacaa   3540
cttgctaaag acaaggttaa tgaatgcgtt aggtctcaat cccagagatt tggattctgt   3600
ggtaatggta cacatttgtt ttcacttgca aatgcggcac caaatggcat gattttcttt   3660
cacacagtgc tattaccaac agcttatgaa actgtgacgg cctggtcagg tatttgtgcg   3720
```

-continued

```
tcagatggca gtcgcacttt tggacttgtt gttgaggatg tccagctgac gctatttcgc   3780

aatttagatg aaaaatttta tttgacgccc agaactatgt atcagcccag agttgcaact   3840

agttctgatt ttgttcaaat agaaggctgt gatgtgttgt ttgttaatgg aactgtaatt   3900

gaattgccta gtatcatacc tgactatatc gatattaatc aaactgttca ggacatatta   3960

gaaaatttca gaccaaattg gactgtaccc gagttgccac ttgacatttt tcatgcaacc   4020

tacttaaacc tgactggtga aattaatgac ttagaattta ggtcagaaaa gttacataac   4080

accacagtag aacttgctat tctcattgat aatattaata acacattagt caatcttgaa   4140

tggctcaaca gaattgaaac ttatgtaaaa tggccttggt atgtttggct actaattgga   4200

ttagtagtaa tattctgcat acccatattg ctattttgtt gttgtagtac tggttgttgt   4260

ggatgtatcg ggtgtttagg aagctgttgt cattccatat gtagtagagg ccaatttgaa   4320

agttatgaac ctattgaaaa agttcatgtt cactga                             4356
```

<210> SEQ ID NO 2
<211> LENGTH: 4359
<212> TYPE: DNA
<213> ORGANISM: Feline coronavirus

<400> SEQUENCE: 2

```
atgattgtgc tcgtaacttg cctcttgttg ttatgttcat accacacagt tttgagtaca     60

acaaataatg aatgcataca agttaacgta acacaattgg ctggcaatga aaaccttatc    120

agagattttc tgtttagtaa ctttaaagaa gaaggaagtg tagttgttgg tggttattac    180

cctacagagg tgtggtacaa ctgctctaga acagctcgaa ctactgcctt tcagtatttt    240

aataatatac atgcctttta ttttgttatg gaagccatgg aaaatagcac tggtaatgca    300

cgtggtaaac cattattatt tcatgtgcat ggtgagcctg ttagtgttat tatatcggct    360

tatagggatg atgtgcaaca aaggcccctt ttaaaacatg ggttagtgtg cataactaaa    420

aatcgccata ttaactatga acaattcacc tccaaccagt ggaattccac atgtacgggt    480

gctgacagaa aaattccttt ctctgtcata cccacggaca atggaacaaa aatctatggt    540

cttgagtgga atgatgactt tgttacagct tatattagtg gtcgttctta tcacttgaac    600

atcaatacta attggtttaa caatgtcaca cttttgtatt cacgctcaag cactgctacc    660

tgggaataca gtgctgcata tgcttaccaa ggtgtttcta acttcactta ttacaagtta    720

aataacacca atggtctaaa aacctatgaa ttatgtgaag attatgaaca ttgcactggc    780

tatgctacca atgtatttgc tccgacatca ggtggttaca tacctgatgg atttagtttt    840

aacaattggt tcttgcttac aaatagttcc actttttgtta gtggcaggtt tgtaacaaat    900

caaccattat tgattaattg cttgtggcca gtgcccagtt ttggtgtagc agcacaagaa    960

ttttgttttg aaggtgcaca gtttagccaa tgtaatggtg tgtctttaaa taacacagtg   1020

gatgttatta gattcaacct taatttcact gcagatgtac aatctggtat gggtgctaca   1080

gtattttcac tgaatacaac aggtggtgtc attcttgaaa tttcatgtta tagtgacaca   1140

gtgagtgagt ctagttctta cagttatggt gaaatcccgt tcggcataac tgacggacca   1200

cgatactgtt atgtacttta caatggcaca gctcttaaat atttaggaac attaccaccc   1260

agtgtaaagg aaattgctat tagtaagtgg ggccattttt atattaatgg ttacaatttc   1320

tttagcacat ttcctattgg ttgtatatct tttaatttaa ccactggtgt tagtggagct   1380

ttttggacaa ttgcttacac atcgtatact gaagcattag tacaagttga aaacacagct   1440

attaaaaatg tgacgtattg taacagtcac attaataaca ttaaatgttc tcaacttact   1500
```

-continued

```
gctaatttga ataatggatt ttatcctgtt gcttcaagtg aagtaggttt cgttaataag   1560
agtgttgtgt tattacctag ctttttcaca tacaccgctg tcaatataac cattgatctt   1620
ggtatgaagc ttagtggtta tggtcaaccc atagcctcga cactaagtaa catcacacta   1680
ccaatgcagg ataacaatac tgatgtgtac tgtattcgtt ctaaccaatt ctcagtttat   1740
gttcattcca cttgcaaaag ttctttatgg gacaatattt ttaatcaaga ctgcacggat   1800
gttttagagg ctacagctgt tataaaaact ggtacttgtc ctttctcatt tgataaattg   1860
aacaattact tgacttttaa caagttctgt ttgtcgttga gtcctgttgg tgctaattgc   1920
aagtttgatg ttgctgcacg tacaagaacc aatgagcagg ttgttagaag tctatatgta   1980
atatatgaag aaggagacaa catagtgggt gtaccgtctg ataatagcgg tctgcacgat   2040
ttgtctgtgc tacacctaga ctcctgtaca gattacaata tatatggtag aactggtgtt   2100
ggtattatta gacgaactaa cagtacgcta cttagtggct tatattacac atcactatca   2160
ggtgatttgt taggctttaa aaatgttagt gatggtgtca tttattctgt gacgccatgt   2220
gatgtaagcg cacaagcggc tgttattgat ggtgccatag ttggagctat gacttccatt   2280
aacagtgaac tgttaggtct aacacattgg acaacgacac ctaattttta ttactactct   2340
atatataatt acacaagtga gaggactcgt ggcactgcaa ttgacagtaa cgatgttgat   2400
tgtgaacctg tcataaccta ttctaatata ggtgtttgta aaaatggtgc tttggttttt   2460
attaacgtca cacattctga cggagacgtg caaccaatta gcactggtaa tgtcacgata   2520
cctacaaatt ttactatatc tgtgcaagtt gaatacatgc aggtttacac tacaccagta   2580
tcaatagatt gtgcaagata cgtttgtaat ggtaacccta gatgtaacaa attgttaaca   2640
caatatgtgt ctgcatgtca aactattgaa caagcacttg caatgggtgc cagacttgaa   2700
aacatggagg ttgattccat gttgtttgtc tcggaaaatg cccttaaatt ggcatctgtt   2760
gaggcgttca atagtacaga aaatttagat cctatttaca aagaatggcc tagcataggt   2820
ggttcttggc taggaggtct aaaagatata ctaccgtccc ataatagcaa acgtaagtat   2880
ggttctgcta tagaagattt gctttttgat aaagttgtaa catctggttt aggtacagtt   2940
gatgaagatt ataaacgttg tactggtggt tacgacatag cagacttggt gtgtgctcaa   3000
tattacaatg gcatcatggt tctaccaggt gtagctaatg ctgacaagat gactatgtac   3060
acagcatcac ttgcaggtgg tataacatta ggtgcacttg gtggtggcgc cgtggctata   3120
ccttttgcag tagcagtaca ggctagactt aattatgttg ctctacaaac tgatgtattg   3180
aataaaaacc aacagatcct ggctaatgct ttcaatcaag ctattggtaa cattacacag   3240
gcttttggta aggttaatga tgctatacat caaacatcac aaggtcttgc cactgttgct   3300
aaagcgttgg caaaagtgca agatgttgtc aacacacaag ggcaagcttt aagtcacctt   3360
acagtacaat tgcaaaataa ttttcaagcc attagtagtt ctattagtga tatttataac   3420
aggcttgacg aactgagtgc tgatgcacaa gttgataggc tgattacagg tagacttaca   3480
gcacttaatg catttgtgtc tcagactcta accagacaag cagaggttag ggctagtaga   3540
caacttgcca aagacaaggt taatgaatgt gttaggtctc agtctcagag attcggattc   3600
tgtggtaatg gtacacattt gttttcacta gcaaatgcag caccaaatgg catgattttc   3660
tttcatacag tactattacc aacagcttat gaaactgtaa cagcttggtc aggtatttgt   3720
gcttcagatg gcgatcgcac tttcggactt gtcgttaaag atgtgcagtt gacgttgttt   3780
cgtaatctag atgacaagtt ctatttgacc cccagaacta tgtatcagcc tagagttgca   3840
```

-continued

```
actagttctg attttgttca aattgaaggg tgtgatgtgt tgtttgtcaa cgcgactgta   3900

attgatttgc ctagtattat acctgactat attgacatta atcaaactgt tcaagacata   3960

ttagaaaatt acagaccaaa ctggactgta cctgaattta cacttgatat tttcaacgca   4020

acctatttaa atctgactgg tgaaattgat gacttagagt ttaggtcaga aaagctacat   4080

aacactacag tagaacttgc cattctcatt gataacatta ataatacatt agtcaatctt   4140

gaatggctca atagaattga aacttatgta aaatggcctt ggtatgtgtg gctactgata   4200

ggtttagtag tagtattttg cataccatta ctgctatttt gctgttttag cacaggttgt   4260

tgtggatgca taggttgttt aggaagttgt tgtcactcta tatgtagtag aagacaattt   4320

gaaaattatg aaccaattga aaaagtgcat gtccactaa                           4359
```

<210> SEQ ID NO 3
<211> LENGTH: 4344
<212> TYPE: DNA
<213> ORGANISM: Transmissible gastroenteritis virus

<400> SEQUENCE: 3

```
atgaaaaaac tatttgtggt tttggtcgta atgccattga tttatggaga caattttcct     60

tgttctaaat tgactaatag aactataggc aaccagtgga atctcattga aaccttcctt    120

ctaaactata gtagtaggtt accacctaat tcagatgtgg tgttaggtga ttattttcct    180

actgtacaac cttggtttaa ttgcattcgc aatgatagta atgaccttta tgttacactg    240

gaaaatctta aagcattgta ttgggattat gctacagaaa atatcacttg gaatcacaga    300

caacggttaa acgtagtcgt taatggatac ccatactcca tcacagttac aacaacccgc    360

aattttaatt ctgctgaagg tgctattata tgcatttgta agggctcacc acctactacc    420

accacagaat ctagtttgac ttgcaattgg ggtagtgagt gcaggttaaa ccataagttc    480

cctatatgtc cttctaattc agaggcaaat tgtggtaata tgctgtatgg cctacaatgg    540

tttgcagatg aggttgttgc ttatttacat ggtgctagtt accgtattag ttttgaaaat    600

caatggtctg gcactgtcac atttggtgat atgcgtgcga caacattaga agtcgctggc    660

acgcttgtag acctttggtg gtttaatcct gtttatgatg tcagttatta tagggttaat    720

aataaaaatg gtactaccgt agtttccaat tgcactgatc aatgtgctag ttatgtggct    780

aatgttttta ctacacagcc aggaggtttt ataccatcag attttagttt taataattgg    840

ttccttctaa ctaatagctc cacgttggtt agtggtaaat tagttaccaa acagccgtta    900

ttagttaatt gcttatggcc agtccctagc tttgaagaag cagcttctac attttgtttt    960

gagggtgctg gctttgatca atgtaatggt gctgttttaa ataatactgt agacgtcatt   1020

aggttcaacc ttaattttac tacaaatgta caatcaggta agggtgccac agtgttttca   1080

ttgaacacaa cgggtggtgt cactcttgaa atttcatgtt atacagtgag tgactcgagc   1140

tttttcagtt acggtgaaat tccgttcggc gtaactgatg gaccacggta ctgttacgta   1200

cactataatg gcacagctct taagtattta ggaacattac cacctagtgt caaggagatt   1260

gctattagta agtggggcca tttttatatt aatggttaca atttctttag cacatttcct   1320

attgattgta tatcttttaa tttgaccact ggtgatagtg acgttttctg gacaatagct   1380

tacacatcgt acactgaagc attagtacaa gttgaaaaca cagctattac aaaggtgacg   1440

tattgtaata gtcacgttaa taacattaaa tgctctcaaa ttactgctaa tttgaataat   1500

ggattttatc ctgtttcttc aagtgaagtt ggtcttgtca ataagagtgt tgtgttacta   1560

cctagctttt acacacatac cattgttaac ataactattg gtcttggtat gaagcgtagt   1620
```

-continued

```
ggttatggtc aacccatagc ctcaacatta agtaacatca cactaccaat gcaggatcac   1680
aacaccgatg tgtactgtat tcgttctgac caattttcag tttatgttca ttctacttgc   1740
aaaagtgctt tatgggacaa tatttttaag cgaaactgca cggacgtttt agatgccaca   1800
gctgttataa aaactggtac ttgtcctttc tcatttgata aattgaacaa ttacttaact   1860
tttaacaagt tctgtttgtc gttgagtcct gttggtgcta attgtaagtt tgatgtagct   1920
gcccgtacaa gaaccaatga gcaggttgtt agaagtttgt atgtaatata tgaagaagga   1980
gacaacatag tgggtgtacc gtctgataat agtggtgtgc acgatttgtc agtgctacac   2040
ctagattcct gcacagatta caatatatat ggtagaactg gtgttggtat tattagacaa   2100
actaacagga cgctacttag tggcttatat tacacatcac tatcaggtga tttgttaggt   2160
tttaaaaatg ttagtgatgg tgtcatctac tctgtaacgc catgtgatgt aagcgcacaa   2220
gcagctgtta ttgatggtac catagttggg gctatcactt ccattaacag tgaactgtta   2280
ggtctaacac attggacaac aacacctaat ttttattact actctatata taattacaca   2340
aatgatagga ctcgtggcac tgcaattgac agtaatgatg ttgattgtga acctgtcata   2400
acctattcta acataggtgt ttgtaaaaat ggtgcttttg tttttattaa cgtcacacat   2460
tctgatggag acgtgcaacc aattagcact ggtaatgtca cgatacctac aaactttacc   2520
atatccgtgc aagtcgaata tattcaggtt tacactacac cagtgtcaat agactgttca   2580
agatatgttt gtaatggtaa ccctaggtgt aacaaattgt taacacaata cgtttctgca   2640
tgtcaaacta ttgagcaagc acttgcaatg ggtgccagac ttgaaaacat ggaggttgat   2700
tccatgttgt ttgtttctga aaatgccctt aaattggcat ctgttgaagc attcaatagt   2760
tcagaaactt tagaccctat ttacaaagaa tggcctaata taggtggttc ttggctagaa   2820
ggtctaaaat acatacttcc gtcccataat agcaaacgta agtatcgttc agctatagag   2880
gacttgcttt ttgataaggt tgtaacatct ggtttaggta cagttgatga agattataaa   2940
cgttgtacag gtggttatga catagctgac ttagtatgtg ctcaatacta taatggcatc   3000
atggtgctac ctggtgtggc taatgctgac aaaatgacta tgtacacagc atcccttgca   3060
ggtggtataa cattaggtgc acttggtgga ggcgccgtgg ctataccttt tgcagtagca   3120
gttcaggcta gacttaatta tgttgctcta caaactgatg tattgaacaa aaaccagcag   3180
attctggcta gtgctttcaa tcaagctatt ggtaacatta cacagtcatt tggtaaggtt   3240
aatgatgcta tacatcaaac atcacgaggt cttgctactg ttgctaaagc attggcaaaa   3300
gtgcaagatg ttgtcaacat acaagggcaa gctttaagcc acctaacagt acaattgcaa   3360
aataatttcc aagccattag tagttctatt agtgacattt ataataggct tgacgaattg   3420
agtgctgatg cacaagttga caggctgatc acaggaagac ttacagcact taatgcattt   3480
gtgtctcaga ctctaaccag acaagcggag gttagggcta gtagacaact tgccaaagac   3540
aaggttaatg aatgcgttag gtctcagtct cagagattcg gattctgtgg taatggtaca   3600
catttgtttt cactcgcaaa tgcagcacca aatggcatga ttttctttca cacagtgcta   3660
ttaccaacgg cttatgaaac tgtgactgct tggccaggta tttgtgcttc agatggtgat   3720
cgcacttttg gacttgtcgt taaagatgtc cagttgactt tgtttcgtaa tctagatgac   3780
aagttctatt tgacccccag aactatgtat cagcctagag ttgcaactag ttctgacttt   3840
gttcaaattg aagggtgcga tgtgctgttt gttaatgcaa ctgtaagtga tttgcctagt   3900
attatacctg attatattga tattaatcag actgttcaag acatattaga aaattttaga   3960
```

-continued ccaaattgga ctgtacctga gttgacattt gacattttta acgcaaccta tttaaacctg 4020
actggtgaaa ttgatgactt agaatttagg tcagaaaagc tacataacac cactgtagaa 4080
cttgccattc tcattgacaa cattaacaat acattagtca atcttgaatg gctcaataga 4140
attgaaacct atgtaaaatg gccttggtat gtgtggctac taataggctt agtagtaata 4200
ttttgcatac cattactgct attttgctgt tgtagtacag gttgctgtgg atgcataggt 4260
tgtttaggaa gttgttgtca ctctatatgt agtagaagac aatttgaaaa ttacgaacca 4320
attgaaaaag tgcacgtcca ttaa 4344

<210> SEQ ID NO 4
<211> LENGTH: 3678
<212> TYPE: DNA
<213> ORGANISM: Porcine respiratory coronavirus

<400> SEQUENCE: 4
atgaaaaaat tatttgtggt cttggttgta atgccattga tttatggaga caagtttcct 60
acttccgtag tttccaattg cactgatcaa tgtgctagtt atgtggctaa tgtttttact 120
atactaccag gaggctttat accatcagat tttagtttta ataattggtt cctcctaact 180
aatagctcca cgttggttaa tggtaaatta gttaccaaac agcctctatt agttaattgc 240
ttatggccag tccctagctt tgaagaagta gcttctacat tttgttttga aggtgctgac 300
tttgatcaat gtaatggtgc tgttttaaat aacactgtag acgtcattag gtttaacctt 360
aattttacta caaatgtaca atcaggtaag ggtgctacag tgttttcatt gaacacaacg 420
ggtggtgtca ctcttgaaat ctcatgttat aatgatacag tgagtgattc gagcttttcc 480
agttacggtg aaattccgtt cggcgtaact aatggaccac ggtactgtta cgtactctat 540
aatggcacag ctcttaagta tctaggaaca ttaccaccta gtgtcaagga gattgctatt 600
agtaagtggg gccattttta tattaatggt tacaatttct ttagcacatt tcctattgat 660
tgtatatctt ttaatttgac tactggtgat agtgacgtct tctggacaat agcttacaca 720
tcgtacactg aagcattagt acaagttgaa aacacagcta ttacaaatgt gacgtattgt 780
aatagttatg ttaataacat taaatgctct caacttactg ctaatttgaa taatggattt 840
tatcctgttt cttcaagtga agttggttct gtcaataaga gtgttgtgtt actacctagc 900
tttctgacac ataccattgt taacataact attggtcttg gtatgaagcg tagtggttat 960
ggtcaaccca tagcctcaac gctaagtaac attacactac caatgcagga taacaacaac 1020
gatgtgtact gtgttcgttc tgaccaattt tcagtttatg ttcattctac ttgcaaaagt 1080
gttttatggg acaatgtttt taagcgaaac tgcacggacg ttttagatgc cacagctgtt 1140
ataaaaactg gtacttgtcc tttctcattt gataaattga acaattactt aacttttaac 1200
aagttctgtt tgtcgttgag tcccgttggt gctaattgta agtttgatgt agctgcccgt 1260
acaagaacca atgatcaggt tgttagaagt ttgtatgtaa tatatgaaga aggagacagc 1320
atagttggtg taccgtctga caatagtggt ttgcacgatt tgtcagtgct acacctagat 1380
tcgtgcacag attacaatat atatggtaga actggtgttg gtattattag acaaactaac 1440
aggacgatac ttagtggctt atattacaca tcactatctg gtgatttgtt aggttttaca 1500
aatgttagtg atggtgttat ctactctgta acgccatgtg atgttagcgc acaagcagct 1560
attattgatg gtaccatagt tggggctatc acttccatta acagtgaatt gttaggtcta 1620
acacattgga caacaacacc taatttttat tactactcta tatataatta cacaaatgat 1680
aagactcgtg gcactccaat tggcagtaat gacgttgatt gtgaacctgt cataacctat 1740

-continued

```
tctaacatag gtgtttgtaa aaatggtgct ttggttttta ttaacgtcac acattctgat   1800
ggagacgtgc aaccaattag cactggtaac gtcacgatac ctactaactt tactatatcc   1860
gtgcaagtcg aatacattca ggtttacact acaccagtgt caatagactg ttcaagatat   1920
gtttgtaatg gcaaccctag gtgtaacaaa ctgttaacac aatacgtttc tgcatgtcaa   1980
actattgagc aagcacttgc aatgggtgcc agacttgaaa acatggaagt tgattccatg   2040
ttatttgttt ctgaaaatgc ccttaaattg gcttctgtcg aagcattcaa tagttcagaa   2100
actttagatc ctatttacaa agaatggcct aatataggtg gcttttggct agaaggtcta   2160
aaatacatac ttccgtccga taatagcaaa cgtaagtatc gttcagctat agaggacttg   2220
ctttttteta aggttgtaac atctggttta ggtacagttg atgaagatta caaacgttgt   2280
acaggtggtt atgacatagc tgacttagta tgtgctcaat actataatgg cattatggtg   2340
ctacctggtg tggctaatgc tgacaaaatg actatgtaca cagcatccct cgcaggtggt   2400
ataacattag gtgcacttgg tggaggcgcc gtggctatac cttttgcagt agcagttcag   2460
gctagactta attatgttgc tctacaaact gatgtattga acaaaaacca gcagatcctg   2520
gctagtgctt ttaatcaagc tattggtaac attacacagt catttggtaa ggttaatgat   2580
gctatacatc aaacatcacg aggtcttaca actgttgcta aagcattggc aaaagtgcaa   2640
gatgttgtca acacacaagg tcaagcttta agacacctaa cagtacaatt gcaaaataat   2700
ttccaagcca ttagtagttc tattagtgac atttataata ggcttgatga attgagtgct   2760
gatgcacaag tcgacaggct gatcacagga agacttacag cacttaatgc atttgtgtct   2820
cagactctaa ccagacaagc cgaggttagg gctagtagac aacttgctaa agacaaggtt   2880
aatgaatgcg ttaggtctca gtctcagaga ttcggcttct gtggtaatgg tacacatttg   2940
ttttcactcg caaatgcagc accaaatggc atgatcttct ttcacacagt gctattacca   3000
acggcgtatg aaactgtgac tgcttggtca ggtatttgtg ctttagatgt tgatcgcact   3060
tttggacttg tcgttaaaga tgtccagttg actttatttc gtaatctaga tgacaagttc   3120
tatttgacac ccagaactat gtatcagcct agagtggcaa ctagttctga ttttgttcaa   3180
attgaagggt gcgatgtgct gtttgttaat acaactgtaa gtgatttgcc tagtattata   3240
cctgattata ttgatattaa tcagactgtt caagacatat tagaaaattt tagaccaaat   3300
tggactgtac ctgagctgac attggacgtt tttaacgcaa cctatttaaa cctgactggt   3360
gaaattgatg acttagagtt taggtcagaa aagctacata acactactgt agaacttgcc   3420
attctcattg acaacattaa caatacagta gtcaatcttg aatggcttaa tagaattgaa   3480
acttatgtaa aatggccttg gtatgtgtgg ctactaatag gcttagtagt aatattttgc   3540
ataccattac tgctattttg ctgttgtagt acaggttgct gtggatgcat aggttgttta   3600
ggaagttgtt gtcactctat attcagtaga agacaatttg aaaattatga acctattgaa   3660
aaagtgcacg tccattaa                                                 3678
```

<210> SEQ ID NO 5
<211> LENGTH: 3522
<212> TYPE: DNA
<213> ORGANISM: Human coronavirus OC43

<400> SEQUENCE: 5

```
atgtttgttt tgcttgttgc atatgccttg ttgcatattg ctggttgtca aactacaaat     60
gggctgaaca ctagttactc tgtttgcaac ggctgtgttg gttattcaga aaatgtattt    120
```

-continued

```
gctgttgaga gtggtggtta tataccctcc gactttgcat tcaataattg gttccttcta    180
actaatacct catctgttgt agatggtgtt gtgaggagtt ttcagccttt gttgcttaat    240
tgcttatggt ctgtttctgg cttgcggttt actactggtt ttgtctattt taatggtact    300
gggagaggtg attgtaaagg tttttcctca gatgttttgt ctgatgtcat acgttacaac    360
ctcaattttg aagaaaacct tagacgtgga accattttgt ttaaaacatc ttatggtgtt    420
gttgtgtttt attgtaccaa caacacttta gtttcaggtg atgctcacat accatttggt    480
acagttttgg gcaattttta ttgctttgta aatactacta ttggcaatga aactacgtct    540
gcttttgtgg gtgcactacc taagacagtt cgtgagtttg ttatttcacg cacaggacat    600
ttttatatta atggctatcg ctatttcact ttaggtaatg tagaagccgt taatttcaat    660
gtcactactg cagaaaccac tgatttttgt actgttgcgt tagcttctta tgctgacgtt    720
ttggttaatg tgtcacaaac ctctattgct aatataattt attgcaactc tgttattaac    780
agactgagat gtgaccagtt gtcctttgat gtaccagatg gtttttattc tacaagccct    840
attcaatccg ttgagctacc tgtgtctatt gtgtcgctac ctgtttatca taaacatacg    900
tttattgtgt tgtacgttga cttcaaacct cagagtggcg gtggcaagtg ctttaactgt    960
tatcctgctg gtgttaatat tacactggcc aattttaatg aaactaaagg gcctttgtgt   1020
gttgacacat cacacttcac taccaaatac gttgctgttt atgccaatgt tggtaggtgg   1080
agtgctagta ttaacacggg aaattgccct ttttcttttg gcaaagttaa taactttgtt   1140
aaatttggca gtgtatgttt ttcgctaaag gatatacccg gtggttgcgc aatgcctata   1200
gtggctaatt gggcttatag taagtactat actataggct cattgtatgt ttcttggagt   1260
gatggtgatg gaattactgg cgtcccacaa cctgttgagg gtgttagttc ctttatgaat   1320
gttacattgg acaaatgtac taaatataat atttatgatg tatctggtgt gggtgttatt   1380
cgcgttagca atgacacctt tcttaatgga attacgtaca catcaacttc aggtaacctt   1440
ctgggtttta aagatgttac taagggcacc atctactcta tcactccttg taacccacca   1500
gatcagcttg ttgtttatca gcaagctgtt gttggtgcta tgttgtctga aaattttact   1560
agttacggct tttctaatgt tgtagaactg ccgaaatttt tctatgcgtc caatggcact   1620
tataattgca cagacgctgt tttaacttat tctagttttg gcgtttgtgc agatggttct   1680
ataattgctg ttcaaccacg taatgtttca tatgatagtg tttcagctat cgtcacagct   1740
aatttgtcta taccttccaa ttggaccact tcggtccagg ttgagtattt acaaattaca   1800
agtacaccta tcgtagttga ttgctccact tatgtttgca atggtaatgt gcgctgtgtt   1860
gaattgctta agcagtatac ttctgcttgt aaaactattg aagacgcctt aagaaatagc   1920
gccaggctgg agtctgcaga tgttagtgag atgctcactt ttgacaagaa agcgtttaca   1980
cttgctaatg ttagtagttt tggtgactac aaccttagca gcgtcatacc tagcttgccc   2040
acaagtggta gtagagtggc tggtcgcagt gccatagaag acatactttt tagcaaactt   2100
gttacttctg gacttggcac tgtggacgca gactacaaaa agtgcactaa gggtctttcc   2160
attgctgact tggcttgtgc tcaatattat aatggcatta tggttttgcc tggcgtcgct   2220
gatgctgaac gaatggccat gtatacaggt tctttaattg gtggaattgc tttaggaggt   2280
ctaacatcag ccgtttcaat accattttca ttagcaattc aggcacgttt aaattatgtt   2340
gcattgcaga ctgatgtttt acaagaaaat cagaaaattc ttgctgcatc ttttaacaaa   2400
gcaatgacca acatagtaga tgcctttact ggtgttaatg atgctattac acaaacttca   2460
caagccctac aaacagttgc tactgcactt aacaagatcc aggatgttgt taatcaacaa   2520
```

-continued ggcaactcat tgaaccattt aacttctcag ttgaggcaga attttcaagc tatctctagc 2580
tctattcagg ctatctatga cagacttgac actattcagg ctgatcaaca agtagatagg 2640
ctgattactg gtagattggc tgctttgaat gtattcgttt ctcatacatt gactaagtac 2700
actgaagttc gtgcttccag acagcttgca caacaaaaag tgaatgagtg tgtcaaatcc 2760
cagtctaagc gttatggctt ctgtggaaat ggcactcaca ttttctcaat tgttaatgct 2820
gctcctgagg ggcttgtttt tctccacact gtcttgttgc cgacacaata taaggatgtt 2880
gaagcgtggt ctgggttgtg cgttgatggt acaaacggtt atgtgttgcg acaacctaat 2940
cttgctcttt acaaagaagg caattattat agaatcacat ctcgcataat gtttgaacca 3000
cgtattccta ccatggcaga ttttgttcaa attgaaaatt gcaatgtcac atttgttaac 3060
atttctcgct ctgagttgca aaccattgtg ccagagtata ttgatgttaa taagacgctg 3120
caagaattaa gttacaaatt gccaaattac actgttccag acctagttgt cgaacagtac 3180
aaccagacta ttttgaattt gaccagtgaa attagcaccc ttgaaaataa atctgcggag 3240
cttaattaca ctgttcaaaa attgcaaact ctgattgaca acataaatag cacattagtc 3300
gacttaaagt ggctcaaccg ggttgagact tacatcaagt ggccgtggtg ggtgtggttg 3360
tgcatttcag tcgtgctcat ctttgtggtg agtatgttgc tattatgttg ttgttctact 3420
ggttgctgtg gcttctttag ttgttttgca tcttctatta gaggttgttg tgaatcaact 3480
aaacttcctt attacgacgt tgaaaagatc cacatacagt aa 3522

<210> SEQ ID NO 6
<211> LENGTH: 4152
<212> TYPE: DNA
<213> ORGANISM: Porcine epidemic diarrhea virus

<400> SEQUENCE: 6
atgaggtctt taatttactt ctggttgctc ttaccagtac ttccaacact cagcctacca 60
caagatgtca ctaggtgcca gtctactact aactttaggc ggttcttttc aaaatttaat 120
gttcaggcac ctgccgtcgt cgttttgggt ggttacctac ctagtatgaa ctcttctagc 180
tggtactgtg gcacaggcat tgaaactgct agtggcgttc atggtatttt tctcagctac 240
atcgattctg gtcagggctt tgagattggc atttcgcaag agccgtttga tcctagtggt 300
taccagcttt atttacataa ggccactaat ggtaacacta atgctattgc acgactgcgc 360
atttgccagt ttcccgataa taaaacattg ggccctactg ttaatgatgt tacaacaggt 420
cgtaactgcc tattcaacaa agccattcca gcttatatgc gtgatggaaa agatattgtt 480
gtcggcataa catgggataa tgatcgtgtc actgtttttg ctgacaagat ctatcatttt 540
tatcttaaaa atgattggtc ccgcgttgcg acaagatgtt acaatcgcag aagttgtgct 600
atgcaatatg tttatacacc tacctactac atgcttaatg ttactagtgc aggtgaggat 660
ggcatttatt atgaaccctg tacagctaat tgcactggtt acgctgccaa tgtatttgcc 720
actgattcca atggccatat accagaaggt tttagtttta ataattggtt tcttttatcc 780
aatgactcca ctttgttgca tggtaaagtg gtttccaacc aacccttgtt ggtcaattgt 840
cttttggcca ttcctaagat ttatggacta ggccaatttt tctcattcaa tcacacgatg 900
gatggcgttt gtaatggagc tgctgtggat cgtgccccag aggctctgag gtttaatatt 960
aatgacacct ccgtcattct tgctgaaggc tcaattgtac ttcatactgc tttaggaaca 1020
aatctttctt ttgtttgcag taattcctca gatcctcatt tagccatctt tgccatacct 1080

-continued

```
ctgggtgcta ctgaagtacc ctactattgc tttcttaaag tggatactta caactccact   1140
gtttataaat tcttggctgt tttacctcct actgtcaggg aaattgtcat caccaagtat   1200
ggtgatgttt atgtcaatgg gtttggctat ttgcatctcg gtttgttgga tgctgtcaca   1260
attaatttca ctggtcatgg cactgacgat gacgtttcag gtttctggac catagcatcg   1320
actaattttg ttgatgcact catcgaggtt caaggaactt ccattcagcg tattctttat   1380
tgtgatgatc ctgttagcca actcaagtgt tctcaggttg cttttgacct tgacgatggt   1440
ttttacccca tctcttctag aaaccttctg agtcacgaac agccaatttc ttttgttact   1500
ttgccatcat ttaatgatca ttcttttgtt aatattactg tctctgcggc ttttggtggt   1560
cttagtagtg ccaatctcgt tgcatctgac actactatca atgggtttag ttctttctgt   1620
gttgacacta gacaatttac cattacactg ttttataatg ttacaaacag ttatggttat   1680
gtgtctaaat cacaggatag taattgtcct ttcaccttgc aatctgttaa tgattacctg   1740
tcttttagca aattttgtgt ttcaaccagc cttttggctg gtgcttgtac catagatctt   1800
tttggttacc ctgcgttcgg tagtggtgtt aagttgacgt ccctttattt tcaattcaca   1860
aaaggtgagt tgattactgg cacgcctaaa ccacttgaag gtatcacaga cgtttctttt   1920
atgactctgg atgtgtgtac caagtatact atctatggct ttaaaggtga gggtattatt   1980
acccttacaa attctagcat tttggcaggt gtttattata catctgattc tggacagttg   2040
ttagccttta agaatgtcac tagtggtgct gtttattctg tcacgccatg ttctttttca   2100
gagcaggctg catatgttaa tgatgatata gtgggtgtta tttctagttt gtctaactcc   2160
acttttaaca atactaggga gttgcctggt ttcttctacc attctaatga cggctccaat   2220
tgtacagagc ctgtgttggt gtatagtaac ataggtgttt gtaaatctgg cagtattggc   2280
tatgttccat ctcagtatgg ccaagtcaag attgcaccca cggttactgg gaatattagt   2340
attcccacca actttagtat gagtattaga acagaatatt tacagcttta caacacgcct   2400
gttagtgttg attgtgctac atatgtttgt aatggtaact ctcgttgtaa acaattactc   2460
acccagtaca ctgcagcatg taagaccata gagtcagcat tacaactcag cgctaggctt   2520
gagtctgttg aagttaactc tatgcttacc atttctgaag aggctttaca gttagctacc   2580
atcagttcgt ttaatggtga tggatataac tttactaatg tgctgggtgc ttccgtgtac   2640
gatcctgcaa gtggcagggt ggtacaaaaa aggtctgtta ttgaagactt gctttttaat   2700
aaagtggtta ctaatggcct tggtactgtt gatgaagact ataagcgctg ttctaatggt   2760
cgctctgtgg ctgatctagt ctgtgcgcag tattactctg gtgtcatggt actacctggc   2820
gttgttgacg ctgagaagct tcacatgtac agtgcgtctc tcataggtgg tatggcgcta   2880
ggaggtataa ctgctgcagc ggcattgcct tttagctatg ctgttcaagc gagactcaat   2940
tatcttgctt tacagacgga tgttctacag cggaaccagc aattgcttgc tgagtctttt   3000
aactctgcta ttggtaatat aacttcagcc tttgagagtg ttaaagaggc tattagtcaa   3060
acttccaagg gtttgaacac tgtggctcat gcgcttacta aggttcaaga ggttgttaat   3120
tcgcagggtt cagctttgaa ccaacttacc gtacagctgc aacacaactt ccaagccatt   3180
tctagttcta ttgatgacat ttattcccga ctggacattc tttcagccga tgttcaggtt   3240
gatcgtctca tcaccggcag attatcagca cttaatgctt ttgttgccca aaccctcact   3300
aagtatactg aggttcaggc tagcaggaag ctagcacagc aaaaggttaa tgagtgcgtc   3360
aaatcgcaat ctcagcgtta cggtttttgt ggtggtgatg gcgagcacat tttctctctg   3420
gtacaggccg cacctcaggg cctgctgttc ttacatacag tacttgtacc gggtgatttt   3480
```

-continued

```
gtaaatgttc ttgccatcgc tggcttatgc gttaatggtg aaattgcctt gactctacgt   3540

gagcctggct tagtcttgtt tacgcatgaa cttcaaactt atactgcgac ggaatatttt   3600

gtttcatcgc gacgtatgtt tgaacctaga aaacctaccg ttagtgattt tgttcaaatt   3660

gagagttgtg tggtcaccta tgtcaatctg actagcgacc agctaccaga tgtaatccca   3720

gattacatcg atgttaacaa aacacttgat gagattttag cttctctgcc caatagaact   3780

ggtccaagtc ttcccctaga tgtttttaat gccacttatc ttaatcttac tggtgaaatt   3840

gcagatctag agcagcgttc agagtctctc cgtaatacta cagaagagct ccgaagtctc   3900

attaacaaca tcaacaacac acttgttgac cttgagtggc tcaaccgagt tgagacatac   3960

atcaagtggc cgtggtgggt ttggttgatc attgttattg ttctcatctt tgttgtgtca   4020

ttactagtgt tctgctgcat ttccacgggt tgttgtggat gctgcggttg ctgcggtgct   4080

tgtttttcag gttgttgtag ggtcctaga cttcaacctt acgaagcttt tgaaaaggtc   4140

cacgtgcagt ga                                                         4152
```

<210> SEQ ID NO 7
<211> LENGTH: 3768
<212> TYPE: DNA
<213> ORGANISM: SARS coronavirus urbani

<400> SEQUENCE: 7

```
atgtttattt tcttattatt tcttactctc actagtggta gtgaccttga ccggtgcacc     60

acttttgatg atgttcaagc tcctaattac actcaacata cttcatctat gaggggggtt    120

tactatcctg atgaaatttt tagatcagac actctttatt taactcagga tttatttctt    180

ccattttatt ctaatgttac agggtttcat actattaatc atacgtttgg caaccctgtc    240

ataccttta aggatggtat ttattttgct gccacagaga aatcaaatgt tgtccgtggt     300

tgggtttttg gttctaccat gaacaacaag tcacagtcgg tgattattat taacaattct    360

actaatgttg ttatacgagc atgtaacttt gaattgtgtg acaacccttt ctttgctgtt    420

tctaaaccca tgggtacaca gacacatact atgatattcg ataatgcatt taattgcact    480

ttcgagtaca tatctgatgc cttttcgctt gatgtttcag aaaagtcagg taattttaaa    540

cacttacgag agtttgtgtt taaaaataaa gatgggtttc tctatgttta taagggctat    600

caacctatag atgtagttcg tgatctacct tctggtttta acactttgaa acctattttt    660

aagttgcctc ttggtattaa cattacaaat tttagagcca ttcttacagc cttttcacct    720

gctcaagaca tttggggcac gtcagctgca gcctattttg ttggctattt aaagccaact    780

acatttatgc tcaagtatga tgaaaatggt acaatcacag atgctgttga ttgttctcaa    840

aatccacttg ctgaactcaa atgctctgtt aagagctttg agattgacaa aggaatttac    900

cagacctcta atttcagggt tgttccctca ggagatgttg tgagattccc taatattaca    960

aacttgtgtc cttttggaga ggtttttaat gctactaaat tcccttctgt ctatgcatgg   1020

gagagaaaaa aaatttctaa ttgtgttgct gattactctg tgctctacaa ctcaacattt   1080

ttttcaacct ttaagtgcta tggcgtttct gccactaagt tgaatgatct ttgcttctcc   1140

aatgtctatg cagattcttt tgtagtcaag ggagatgatg taagacaaat agcgccagga   1200

caaactggtg ttattgctga ttataattat aaattgccag atgatttcat gggttgtgtc   1260

cttgcttgga atactaggaa cattgatgct acttcaactg gtaattataa ttataaatat   1320

aggtatctta gacatggcaa gcttaggccc tttgagagag acatatctaa tgtgcctttc   1380
```

-continued

```
tcccctgatg gcaaaccttg caccccacct gctcttaatt gttattggcc attaaatgat   1440
tatggttttt acaccactac tggcattggc taccaacctt acagagttgt agtactttct   1500
tttgaacttt taaatgcacc ggccacggtt tgtggaccaa aattatccac tgaccttatt   1560
aagaaccagt gtgtcaattt taattttaat ggactcactg gtactggtgt gttaactcct   1620
tcttcaaaga gatttcaacc atttcaacaa tttggccgtg atgtttctga tttcactgat   1680
tccgttcgag atcctaaaac atctgaaata ttagacattt caccttgctc ttttgggggt   1740
gtaagtgtaa ttacacctgg aacaaatgct tcatctgaag ttgctgttct atatcaagat   1800
gttaactgca ctgatgtttc tacagcaatt catgcagatc aactcacacc agcttggcgc   1860
atatattcta ctggaaacaa tgtattccag actcaagcag gctgtcttat aggagctgag   1920
catgtcgaca cttcttatga gtgcgacatt cctattggag ctggcatttg tgctagttac   1980
catacagttt ctttattacg tagtactagc caaaaatcta ttgtggctta tactatgtct   2040
ttaggtgctg atagttcaat tgcttactct aataacacca ttgctatacc tactaacttt   2100
tcaattagca ttactacaga agtaatgcct gtttctatgg ctaaaacctc cgtagattgt   2160
aatatgtaca tctgcggaga ttctactgaa tgtgctaatt tgcttctcca atatggtagc   2220
ttttgcacac aactaaatcg tgcactctca ggtattgctg ctgaacagga tcgcaacaca   2280
cgtgaagtgt tcgctcaagt caaacaaatg tacaaaaccc caactttgaa atattttggt   2340
ggttttaatt tttcacaaat attacctgac cctctaaagc caactaagag gtcttttatt   2400
gaggacttgc tctttaataa ggtgacactc gctgatgctg gcttcatgaa gcaatatggc   2460
gaatgcctag gtgatattaa tgctagagat ctcatttgtg cgcagaagtt caatggactt   2520
acagtgttgc cacctctgct cactgatgat atgattgctg cctacactgc tgctctagtt   2580
agtggtactg ccactgctgg atggacattt ggtgctggcg ctgctcttca aatacctttt   2640
gctatgcaaa tggcatatag gttcaatggc attggagtta cccaaaatgt tctctatgag   2700
aaccaaaaac aaatcgccaa ccaatttaac aaggcgatta gtcaaattca agaatcactt   2760
acaacaacat caactgcatt gggcaagctg caagacgttg ttaaccagaa tgctcaagca   2820
ttaaacacac ttgttaaaca acttagctct aattttggtg caatttcaag tgtgctaaat   2880
gatatccttt cgcgacttga taaagtcgag gcggaggtac aaattgacag gttaattaca   2940
ggcagacttc aaagccttca aacctatgta acacaacaac taatcagggc tgctgaaatc   3000
agggcttctg ctaatcttgc tgctactaaa atgtctgagt gtgttcttgg acaatcaaaa   3060
agagttgact tttgtggaaa gggctaccac cttatgtcct tcccacaagc agccccgcat   3120
ggtgttgtct tcctacatgt cacgtatgtg ccatcccagg agaggaactt caccacagcg   3180
ccagcaattt gtcatgaagg caaagcatac ttccctcgtg aaggtgtttt tgtgtttaat   3240
ggcacttctt ggtttattac acagaggaac ttcttttctc cacaaataat tactacagac   3300
aatacatttg tctcaggaaa ttgtgatgtc gttattggca tcattaacaa cacagtttat   3360
gatcctctgc aacctgagct cgactcattc aaagaagagc tggacaagta cttcaaaaat   3420
catacatcac cagatgttga tcttggcgac atttcaggca ttaacgcttc tgtcgtcaac   3480
attcaaaaag aaattgaccg cctcaatgag gtcgctaaaa atttaaatga atcactcatt   3540
gaccttcaag aattgggaaa atatgagcaa tatattaaat ggccttggta tgtttggctc   3600
ggcttcattg ctggactaat tgccatcgtc atggttacaa tcttgctttg ttgcatgact   3660
agttgttgca gttgcctcaa gggtgcatgc tcttgtggtt cttgctgcaa gtttgatgag   3720
gatgactctg agccagttct caagggtgtc aaattacatt acacataa                3768
```

<210> SEQ ID NO 8
<211> LENGTH: 3768
<212> TYPE: DNA
<213> ORGANISM: SARS coronavirus Tor2

<400> SEQUENCE: 8
atgtttattt tcttattatt tcttactctc actagtggta gtgaccttga ccggtgcacc 60
acttttgatg atgttcaagc tcctaattac actcaacata cttcatctat gaggggggtt 120
tactatcctg atgaaatttt tagatcagac actctttatt taactcagga tttatttctt 180
ccattttatt ctaatgttac agggtttcat actattaatc atacgtttgg caaccctgtc 240
atacctttta aggatggtat ttattttgct gccacagaga aatcaaatgt tgtccgtggt 300
tgggtttttg gttctaccat gaacaacaag tcacagtcgg tgattattat taacaattct 360
actaatgttg ttatacgagc atgtaacttt gaattgtgtg acaacccttt ctttgctgtt 420
tctaaaccca tgggtacaca gacacatact atgatattcg ataatgcatt taattgcact 480
ttcgagtaca tatctgatgc cttttcgctt gatgtttcag aaaagtcagg taattttaaa 540
cacttacgag agtttgtgtt taaaaataaa gatgggtttc tctatgttta taagggctat 600
caacctatag atgtagttcg tgatctacct tctggtttta acactttgaa acctattttt 660
aagttgcctc ttggtattaa cattacaaat tttagagcca ttcttacagc cttttcacct 720
gctcaagaca tttggggcac gtcagctgca gcctattttg ttggctattt aaagccaact 780
acatttatgc tcaagtatga tgaaaatggt acaatcacag atgctgttga ttgttctcaa 840
aatccacttg ctgaactcaa atgctctgtt aagagctttg agattgacaa aggaatttac 900
cagacctcta atttcagggt tgttccctca ggagatgttg tgagattccc taatattaca 960
aacttgtgtc cttttggaga ggtttttaat gctactaaat tcccttctgt ctatgcatgg 1020
gagagaaaaa aaatttctaa ttgtgttgct gattactctg tgctctacaa ctcaacattt 1080
ttttcaacct ttaagtgcta tggcgtttct gccactaagt tgaatgatct ttgcttctcc 1140
aatgtctatg cagattcttt tgtagtcaag ggagatgatg taagacaaat agcgccagga 1200
caaactggtg ttattgctga ttataattat aaattgccag atgatttcat gggttgtgtc 1260
cttgcttgga atactaggaa cattgatgct acttcaactg gtaattataa ttataaatat 1320
aggtatctta gacatggcaa gcttaggccc tttgagagag acatatctaa tgtgcctttc 1380
tcccctgatg gcaaaccttg caccccacct gctcttaatt gttattggcc attaaatgat 1440
tatggttttt acaccactac tggcattggc taccaacctt acagagttgt agtactttct 1500
tttgaacttt taaatgcacc ggccacggtt tgtggaccaa aattatccac tgaccttatt 1560
aagaaccagt gtgtcaattt taattttaat ggactcactg gtactggtgt gttaactcct 1620
tcttcaaaga gatttcaacc atttcaacaa tttggccgtg atgtttctga tttcactgat 1680
tccgttcgag atcctaaaac atctgaaata ttagacattt caccttgcgc ttttgggggt 1740
gtaagtgtaa ttacacctgg aacaaatgct tcatctgaag ttgctgttct atatcaagat 1800
gttaactgca ctgatgtttc tacagcaatt catgcagatc aactcacacc agcttggcgc 1860
atatattcta ctggaaacaa tgtattccag actcaagcag gctgtcttat aggagctgag 1920
catgtcgaca cttcttatga gtgcgacatt cctattggag ctggcatttg tgctagttac 1980
catacagttt ctttattacg tagtactagc caaaaatcta ttgtggctta tactatgtct 2040
ttaggtgctg atagttcaat tgcttactct aataacacca ttgctatacc tactaacttt 2100

-continued tcaattagca ttactacaga agtaatgcct gtttctatgg ctaaaacctc cgtagattgt 2160
aatatgtaca tctgcggaga ttctactgaa tgtgctaatt tgcttctcca atatggtagc 2220
ttttgcacac aactaaatcg tgcactctca ggtattgctg ctgaacagga tcgcaacaca 2280
cgtgaagtgt tcgctcaagt caaacaaatg tacaaaaccc caactttgaa atattttggt 2340
ggttttaatt tttcacaaat attacctgac cctctaaagc caactaagag gtcttttatt 2400
gaggacttgc tctttaataa ggtgacactc gctgatgctg gcttcatgaa gcaatatggc 2460
gaatgcctag gtgatattaa tgctagagat ctcatttgtg cgcagaagtt caatggactt 2520
acagtgttgc cacctctgct cactgatgat atgattgctg cctacactgc tgctctagtt 2580
agtggtactg ccactgctgg atggacattt ggtgctggcg ctgctcttca aatacctttt 2640
gctatgcaaa tggcatatag gttcaatggc attggagtta cccaaaatgt tctctatgag 2700
aaccaaaaac aaatcgccaa ccaatttaac aaggcgatta gtcaaattca agaatcactt 2760
acaacaacat caactgcatt gggcaagctg caagacgttg ttaaccagaa tgctcaagca 2820
ttaaacacac ttgttaaaca acttagctct aattttggtg caatttcaag tgtgctaaat 2880
gatatccttt cgcgacttga taaagtcgag gcggaggtac aaattgacag gttaattaca 2940
ggcagacttc aaagccttca aacctatgta acacaacaac taatcagggc tgctgaaatc 3000
agggcttctg ctaatcttgc tgctactaaa atgtctgagt gtgttcttgg acaatcaaaa 3060
agagttgact tttgtggaaa gggctaccac cttatgtcct tcccacaagc agccccgcat 3120
ggtgttgtct tcctacatgt cacgtatgtg ccatcccagg agaggaactt caccacagcg 3180
ccagcaattt gtcatgaagg caaagcatac ttccctcgtg aaggtgtttt tgtgtttaat 3240
ggcacttctt ggtttattac acagaggaac ttcttttctc cacaaataat tactacagac 3300
aatacatttg tctcaggaaa ttgtgatgtc gttattggca tcattaacaa cacagtttat 3360
gatcctctgc aacctgagct tgactcattc aaagaagagc tggacaagta cttcaaaaat 3420
catacatcac cagatgttga tcttggcgac atttcaggca ttaacgcttc tgtcgtcaac 3480
attcaaaaag aaattgaccg cctcaatgag gtcgctaaaa atttaaatga atcactcatt 3540
gaccttcaag aattgggaaa atatgagcaa tatattaaat ggccttggta tgtttggctc 3600
ggcttcattg ctggactaat tgccatcgtc atggttacaa tcttgctttg ttgcatgact 3660
agttgttgca gttgcctcaa gggtgcatgc tcttgtggtt cttgctgcaa gtttgatgag 3720
gatgactctg agccagttct caagggtgtc aaattacatt acacataa 3768

<210> SEQ ID NO 9
<211> LENGTH: 4092
<212> TYPE: DNA
<213> ORGANISM: Bovine coronavirus

<400> SEQUENCE: 9
atgtttttga tacttttaat ttccttacca atggcttttg ctgttatagg agatttaaag 60
tgtactacgg tttccattaa tgatgttgac accggtgctc cctctattag cactgatatt 120
gtcgatgtta ctaatggttt aggtacttat tatgttttag atcgtgtgta tttaaatact 180
acgttgttgc ttaatggtta ctaccctact tcaggttcta catatcgtaa tatggcactg 240
aagggaactt tactattgag cagactatgg tttaaaccac cttttctttc tgattttatt 300
aatggtattt ttgctaaggt caaaaatacc aaggttatta aaaagggtgt aatgtatagt 360
gagtttcctg ctataactat aggtagtact tttgtaaata catcctatag tgtggtagta 420
caaccacata ctaccaattt ggataataaa ttacaaggtc tcttagagat ctctgtttgc 480

-continued

```
cagtatacta tgtgcgagta cccacatacg atttgtcatc ctaagctggg taataaacgc    540
gtagaactat ggcattggga tacaggtgtt gtttcctgtt tatataagcg taatttcaca    600
tatgatgtga atgctgatta cttgtatttc catttttatc aagaaggtgg tactttttat    660
gcatatttta cagacactgg tgttgttact aagtttctgt ttaatgttta tttaggcacg    720
gtgctttcac attattatgt cctgcctttg acttgttcta gtgctatgac tttagaatat    780
tgggttacac ctctcacttc taaacaatat ttactagctt tcaatcaaga tggtgttatt    840
tttaatgctg ttgattgtaa gagtgatttt atgagtgaga ttaagtgtaa aacactatct    900
atagcaccat ctactggtgt ttatgaatta aacggttaca ctgttcagcc aattgcagat    960
gtttaccgac gtatacctaa tcttcccgat tgtaatatag aggcttggct taatgataag   1020
tcggtgccct ctccattaaa ttgggaacgt aagacctttt caaattgtaa ttttaatatg   1080
agcagcctga tgtcttttat tcaggcagac tcatttactt gtaataatat tgatgctgct   1140
aagatatatg gtatgtgttt ttccagcata actatagata agtttgctat acccaatggt   1200
aggaaggttg acctacaatt gggcaatttg ggctatttgc agtcttttaa ctatagaatt   1260
gatactactg ctacaagttg tcagttgtat tataatttac ctgctgctaa tgtttctgtt   1320
agcaggttta atccttctac ttggaatagg agatttggtt ttacagaaca atttgttttt   1380
aagcctcaac ctgtaggtgt ttttactcat catgatgttg tttatgcaca acattgtttt   1440
aaagctccca aaaatttctg tccgtgtaaa ttggatgggt ctttgtgtgt aggtaatggt   1500
cctggtatag atgctggtta taaaaatagt ggtataggca cttgtcctgc aggtactaat   1560
tatttaactt gccataatgc tgcccaatgt gattgtttgt gcactcccga ccccattaca   1620
tctaaatcta cagggcctta caagtgcccc caaactaaat acttagttgg cataggtgag   1680
cactgttcgg gtcttgctat taaaagtgat tattgtggag gtaatccttg tacttgccaa   1740
ccacaagcat tttgggttg gtctgttgac tcttgtttac aaggggatag gtgtaatatt   1800
tttgctaatt ttatttttca tgatgttaat agtggtacta cttgttctac tgatttacaa   1860
aaatcaaaca cagacataat tcttggtgtt tgtgttaatt atgatcttta tggtattaca   1920
ggccaaggta tttttgttga ggttaatgcg acttattata atagttggca gaacctttta   1980
tatgattcta atggtaatct ctatggtttt agagactact taacaaacag aacttttatg   2040
attcgtagtt gctatagcgg tcgtgtttca gcggcctttc atgctaactc ttccgaacca   2100
gcattgctat ttcggaatat taaatgcaat tacgttttta ataatactct ttcacgacag   2160
ctgcaaccta ttaactattt tgatagttat cttggttgtg ttgtcaatgc tgataatagt   2220
acttctagtg ttgttcaaac atgtgatctc acagtaggta gtggttactg tgtggattac   2280
tctacaaaaa gacgaagtcg tagagcgatt accactggtt atcggtttac taattttgag   2340
ccatttactg ttaattcagt aaatgatagt ttagaacctg taggtggttt gtatgaaatt   2400
caaatacctt cagagtttac tataggtaat atggaggagt ttattcaaac aagctctcct   2460
aaagttacta ttgattgttc tgcttttgtc tgtggtgatt atgcagcatg taaatcacag   2520
ttggttgaat atggtagctt ctgtgacaat attaatgcta tactcacaga agtaaatgaa   2580
ctacttgaca ctacacagtt gcaagtagct aatagtttaa tgaatggtgt cactcttagc   2640
actaagctta aagatggcgt taatttcaat gtagacgaca tcaatttttc ccctgtatta   2700
ggttgtttag gaagcgcttg taataaagtt tccagcagat ctgctataga ggatttactt   2760
ttttctaaag taaagttatc tgatgtcggt ttcgttgagg cttataataa ttgtactgga   2820
```

-continued

```
ggtgccgaaa ttagggacct catttgtgtg caaagttata atggtatcaa agtgttgcct   2880

ccactgctct cagtaaatca gatcagtgga tacactttgg ctgccacctc tgctagtctg   2940

tttcctcctt tgtcagcagc agtaggtgta ccattttatt taaatgttca gtatcgtatt   3000

aatgggattg gtgttaccat ggatgtgtta agtcaaaatc aaaagcttat tgctaatgca   3060

tttaacaatg ctcttgatgc tattcaggaa gggtttgatg ctaccaattc tgctttagtt   3120

aaaattcaag ctgttgttaa tgcaaatgct gaagctctta ataacttatt gcaacaactc   3180

tctaatagat ttggtgctat aagttcttct ttacaagaaa ttctatctag actggatgct   3240

cttgaagcgc aagctcagat agacagactt attaatgggc gtcttaccgc tcttaatgtt   3300

tatgtttctc aacagcttag tgattctaca ctagtaaaat ttagtgcagc acaagctatg   3360

gagaaggtta atgaatgtgt caaaagccaa tcatctagga taaatttttg tggtaatggt   3420

aatcatatta tatcattagt gcagaatgct ccatatggtt tgtattttat ccactttagc   3480

tatgtcccta ctaagtatgt cactgcgaag gttagtcccg gtctgtgcat tgctggtgat   3540

agaggtatag cccctaagag tggttatttt gttaatgtaa ataatacttg gatgttcact   3600

ggtagtggtt attactaccc tgaacccata actggaaata atgttgttgt tatgagtacc   3660

tgtgctgtta actatactaa agcgccggat gtaatgctga acatttcaac acccaacctc   3720

catgatttta aggaagagtt ggatcaatgg tttaaaaacc aaacatcagt ggcaccagat   3780

ttgtcacttg attatataaa tgttacattc ttggacctac aagatgaaat gaataggtta   3840

caggaggcaa taaaagtttt aaatcagagc tacatcaatc tcaaggacat tggtacatat   3900

gagtattatg taaaatggcc ttggtatgta tggcttttaa ttggctttgc tggtgtagct   3960

atgcttgttt tactattctt catatgctgt tgtacaggat gtgggactag ttgttttaag   4020

atatgtggtg gttgttgtga tgattatact ggacaccagg agttagtaat taaaacatca   4080

catgacgact aa                                                       4092
```

<210> SEQ ID NO 10
<211> LENGTH: 4050
<212> TYPE: DNA
<213> ORGANISM: Porcine hemagglutinating encephalomyelitis coronavirus

<400> SEQUENCE: 10

```
atgtttttta tacttttaat ctccctgcct tctgcttttg cagttatagg ggatttaaag     60

tgtactactt cattaattaa tgacgttgac actggtgtgc catctattag ctctgaagtt    120

gttgatgtca ctaatggttt ggggactttc tatgttttag atcgtgtcta tttaaatacc    180

acattgttgc tcaatggtta ttacccaatt tcaggtgcta catttcgtaa tatggctctg    240

aaaggaactc gattattgag caccttgtgg tttaagccgc ctttttttatc accttttaat    300

gatggtattt ttgccaaggt taaaaacagc agattttcta aagatggtgt tatttatagt    360

gagtttcctg ctattactat aggtagtact tttgtaaata cttcctatag catagtagta    420

gagcctcata cctcacttat taatggtaat ttacaaggtt tgttgcaaat ttctgtttgt    480

caatacacta tgtgtgaata cccacatact atttgtcatc ctaatttggg taatcaacgc    540

atagaattat ggcattatga cacagatgtt gtttcttgtt tatacaggcg taatttcaca    600

tatgatgtga atgctgatta tttatatttt cacttttatc aggaaggtgg cactttttat    660

gcatacttta cagatactgg ttttgtgacc aagtttctgt ttaagttgta tttaggcact    720

gtgctgtcac attattatgt tatgccattg acttgtaata gcgctttatc tttagaatac    780

tgggttacac ctctcactac tagacaattt cttctagcct ttgaccagga tggtgtttta    840
```

-continued

```
taccatgctg ttgattgtgc tagtgatttt atgagtgaga ttatgtgtaa aacttcttca    900
attacaccac ctactggtgt ttatgaacta aacggttaca cagttcaacc tgttgccact    960
gtatatcgta gaatacctga tttacccaat tgcgatatcg aagcttggct taattctaag   1020
accgtttctt cgcctcttaa ttgggaacgt aaaatttttt ctaattgtaa ttttaacatg   1080
ggcaggctga tgtcttttat tcaggctgac tcttttggtt gtaacaatat tgatgcttct   1140
cgcttatatg gtatgtgttt tggtagcatt actattgata agtttgctat acccaatagt   1200
agaaaggttg atctgcaagt gggtaaatct ggttatttac aatcttttaa ttataagatt   1260
gacactgctg ttagcagttg tcaactctat tatagtttgc ctgcagcaaa cgtatctgtc   1320
actcattata atccttcatc ttggaataga aggtatgggt ttaataatca gagttttggt   1380
tccagaggcc ttcatgatgc tgtttattca cagcaatgtt ttaatacacc taacacatat   1440
tgtccttgta gaacaagtca atgcataggt ggtgcaggca caggaacttg tcctgtaggc   1500
accactgtgc gcaagtgttt tgctgcagtt acaaaagcta ctaagtgtac ttgctggtgt   1560
caaccagatc cttccacata taaaggtgta aacgcctgga cttgtccgca atctaaagtt   1620
tctatacaac caggtcagca ttgccctggt ttgggtcttg tggaggatga ttgctctggc   1680
aacccttgca cttgtaaacc acaggctttc ataggctgga gttcagaaac ttgtttgcaa   1740
aatggtaggt gtaatatttt tgctaatttt attctgaatg atgttaatag cggtacaacc   1800
tgttctactg atttacaaca gggtaatact attattacta ctgatgtttg tgttaattat   1860
gacctatatg gcattacagg ccagggcata cttatagaag ttaatgccac ttattataat   1920
agttggcaga atcttcttta tgattctagt ggtaatctct atggctttag agattattta   1980
tcaaatagaa cttttcttat tcgtagctgc tatagtggaa gagtttcagc agtttttcat   2040
gctaactcat ctgaaccagc tttgatgttt cgtaatctta aatgcagcca cgtttttaat   2100
aataccattt taagacaaat acagcttgtt aactattttg atagttacct tggttgtgtt   2160
gttaatgctt ataataatac agctagtgct gtaagtactt gtgatttaac cgttggtagc   2220
ggctattgtg ttgattatgt tacagcactt agatcacgta gatcttttac tacaggttat   2280
cgctttacta attttgaacc atttgccgct aatttggtaa atgatagtat agaacctgtt   2340
ggtggtttgt atgaaataca gataccttca gagtttacca ttggtaattt agaagagttc   2400
attcaaacga gatcccctaa ggttactata gactgtgcta catttgtttg tggtgactat   2460
gcagcatgta gacaacagtt agctgagtat ggtagttttt gtgagaacat taatgctata   2520
ctcacagaag taaatgaact acttgacact acacagttgc aagtagctaa tagtttaatg   2580
aatggagtca cccttagtac caagattaag gatggcatta atttcaatgt tgacgatatc   2640
aacttctccc ctgtattagg ttgtttagga agcgaatgta atagagcttc cactagatct   2700
gctatagagg atttactttt tgataaagta aaattgtctg atgtcggctt tgtacaggcc   2760
tataataact gcactggagg tgccgaaatt agggatctca tttgtgtgca aagttataat   2820
ggtatcaaag tgttgcctcc attgttatct gaaaatcaga tcagtggcta cactttggca   2880
gccaccgctg ctagcttatt ccctccttgg acagctgcag caggtgtacc attttattta   2940
aatgttcagt atcgtataaa tgggcttggc gtcactatgg atgtgctaag tcaaaaccaa   3000
aagcttattg ctagtgcatt taacaatgct cttgatgcta tccaggaagg gttcgacgca   3060
accaattctg ctttagttaa aattcaggct gttgttaatg caaatgctga agcacttaat   3120
aacttattgc agcaactctc taacagattt ggtgccataa gtgcctcttt acaagaaatt   3180
```

-continued

```
ttatccaggc tcgatgctct tgaagctaaa gctcagatag acagacttat caatgggcgt   3240

ctcaccgctc ttaatgctta tgtttctcag cagcttagtg attctacact agtaaaattt   3300

agtgcagcac aagctattga gaaagttaat gaatgtgtta aaagccaatc atctaggata   3360

aatttctgtg gtaatggtaa tcatattata tcattagtac agaatgctcc atatggtttg   3420

tattttatcc attttagcta tgtccccacc aagtatgtta cagcaaaggt tagtcctggt   3480

ttgtgcattg ctggcgatat aggaatatcg cctaagagtg gttattttat taatgtaaat   3540

aattcttgga tgttcactgg tagtagctat tactaccctg aacctataac ccaaaataat   3600

gttgttgtga tgagtacctg tgctgttaat tatactaaag caccggatct aatgctgaac   3660

acatcgacac ccaaccttcc tgacttcaag gaagaattgt atcaatggtt taaaaaccaa   3720

tcttcagtgg caccagattt gtcacttgat tatattaatg ttacgttctt ggacctacaa   3780

gatgaaatga ataggttaca agaggctata aaagttttaa atcagagcta catcaatctc   3840

aaggacattg gtacatatga gtattatgtg aaatggcctt ggtatgtatg gcttttaatt   3900

ggccttgctg gtgtagctat gcttgtttta ctattcttca tatgctgctg tacaggatgt   3960

gggactagtt gttttaagaa atgtggcggt tgttgtgatg attatactgg acaccaggag   4020

tttgtaatca aaacttcaca tgacgattaa                                    4050
```

<210> SEQ ID NO 11
<211> LENGTH: 4086
<212> TYPE: DNA
<213> ORGANISM: Murine hepatitis virus

<400> SEQUENCE: 11

```
atgctattcg tgtttttaac cttgttgccc tcttctctag ggtatattgg tgattttaga     60

tgtatccaac ttgtaaatac cgacacctct aatgccagcg ctccaagcgt tagtacagag    120

gtagttgatg tttccaaagg gattggtact tattatgttt tagatcgagt ctatttaaat    180

gccacactat tgcttactgg ttattaccct gtagatgggt ccatgtatag aaacatggct    240

ctaacgggaa ttaataccat aagccttaat tggtacaaac cacccttttt atcagagttt    300

aatgatggca tatttgctaa ggtaaagaac cttaaagcat ctttgcccaa agattctatt    360

tcatatttcc ctactataat tataggtagt aattttgtca ccacttccta tactgtagta    420

ttggaaccgt ataatggtat aattatggca tccatttgcc agtataccat ttgtcaacta    480

ccgtacacgg attgcaaacc gaatacgggc ggtaataagt taattggctt ttggcacaca    540

gagctaaaat cccctgtgtg cattttaaag cgtaatttta cgtttaatgt taatgccgaa    600

tggctttatt ttcattttta ccagcagggt ggtacttttt atgcgtatta tgcggatgtt    660

tcttctgcta ctacgttttt gtttagtatg tatattggtg atgtgttaac acaatatttt    720

gtgttgcctt atatgtgtac tctcactaca acaggtgtct tttcaccgca gtattgggtt    780

acacctcttg tcaagcgcca atatttattt aattttaatc aaaagggtat tattactagt    840

gctgttgatt gtgctagtag ttataccagc gaaataaagt gtaagaccca aagtatgaat    900

cccaatacgg gagtttatga tttatccggt tacaccgtcc aacctgtagg attagtgtac    960

cggcgtgtta gaaatttgcc tgattgtaaa attgaggaat ggctaactgc taagtctgta   1020

ccttctcctc tcaattggga gcgcaaaaca tttcaaaatt gtaacttcga cctgagcagt   1080

ctattaagat ttgttcaggc tgagtcactc tcatgtagta atatagatgc ttccaaggtt   1140

tatggtatgt gctttggtag tatatctata gacaagtttg cgatacccaa tagacgccga   1200

gttgatttgc agctaggcaa ctctgggttt ttgcaatcct ttaattacaa aatagataca   1260
```

-continued

```
agagctactt cgtgtcagct ctattatagt cttgcaaaaa ataatgtcac tgtcaataac   1320
cataacccgt cctcttggaa caggcgttat gggttcaatg atgtggctac atttggaact   1380
ggtaaacatg acgttgctta tgctgaggct tgttttaccg tgggagcatc atattgccct   1440
tgcgcgaacc ccagcatagt gtcgccatgt accactggaa aacctaactt tgccaattgc   1500
cctacaggca cctcgaatcg tgagtgcact gttatgccat tggctaataa tcaatttaag   1560
tgtgattgca cttgtaaccc tagtcctcta accacctatg atcttagatg tctccaagca   1620
agaagcatgc ttggcgtagg tgatcattgt gaaggtctag gagttttaga agataaatgt   1680
ggtggcagca acacctgcaa ttgttctgct catgcctttg ttggctgggc taaggatagt   1740
tgcttggcta atggccgctg tcacattttt agtaatttga tgttaaatgg cattaatagt   1800
ggtactacat gttccatgga tttgcaattg cctaatactg aagtggtcac tggcgtctgc   1860
gtcaaatatg acctctacgg tataacaggc caaggtattt ttaaggaggt taaggctgac   1920
tattatcata gttggcaaaa cctcttatat gatgttaatg gcaacttaat cggatttcgc   1980
gattttgttg ctaataagag ttatactatt cgaagttgct atagtgggcg ggtctcggct   2040
gcatatcatc aagatgcacc agaaccagcg ctactatatc gcaatttaaa atgtgactat   2100
gtctttaaca acaacatatc ccgtgaggag acaccactta actatttcga tagttatctt   2160
ggttgtgttg ttaatgctga caactcaact gaagaagctg ttgacgcgtg tgatttgcgt   2220
atgggtagtg ggctttgtgt caactattca acgtctcacc gcgctcgcag ctctgtcagc   2280
acgggttata aattaactac ttttgaacca tttacagtcc gcattgtcaa tgatagtgtt   2340
gagtctgttg atgggttata tgagctgcaa ataccaacca actttactat agctagccat   2400
caggagttcg ttcaaacgag gtctccaaag gttactatag actgtgctgc atttgtctgt   2460
ggtggccaca cagcatgccg tcagcagttg gttgagtacg gctcattctg tgataatatt   2520
aatgccattc ttggcgaggt aaataacctc atagatacta tgcaacttca agttgcaagt   2580
gctttaatcc aaggtgtcac gttaagctca cgcttatcgg atggcattgg tggtcaaata   2640
gatgatatta attttagtcc tctgcttggt tgtttaggtt ctgactgtgg cgaagttacc   2700
atggcagctc aaaccggacg atctgctata gaggatgtat tatttgacaa agtcaaactc   2760
tctgatgttg gctttgtcga agcatataac aattgcactg gaggccaaga agttagagac   2820
ctactttgtg tgcaatcttt taatggcatc aaagtgctac cgcctgtgtt gtctgagaat   2880
caaatttctg gttatacagc gggagctact gtatctgcta tgttcccatg gtctgcagct   2940
gcaggtgtgc cattttcttt aagtgttcaa tatagaatta atggtcttgg tgtcactatg   3000
aatgttctta gtgaaaatca gaaaatgata gcaagtgcat ttaacaacgc gataggtgct   3060
atacaggaag ggtttgctgc aaccaattct gccttagcaa aaatgcagtt cgttgtcaat   3120
gcaaatgcgg aagcactcaa taatttatta aaccagcttt ccaataggtt tggtgcaatt   3180
agtgcttctt tacaagaaat tctatctcgc ctagatgctc ttgaagcgca ggctcagata   3240
gaccgtctta ttaatggcag attaactgca cttaatgcat atgtctctaa gcagctgagt   3300
gacatgaccc ttgttaaggt gagtgcagcc caggctatag agaaagttaa tgagtgtgtt   3360
aaaagccaat catctaggat aaatttctgt ggcaatggca atcatatatt gtcattagtc   3420
cagaatgcgc cttatggttt atattttatt catttcagct atgtgcctac ttcctttaca   3480
acggcaaatg tgagtcctgg gctatgcatt tctggtgata gaggattagc acctaaagct   3540
ggatattttg ttcaagatga tggagagtgg aagttcacag gtagtaatta ttattaccct   3600
```

-continued

```
gaacccatta cagataaaaa tagtgtcgtg atgagtagtt gcgcagcaaa ctacacaaag   3660

gcacctgaag ttttcttgaa cacttcaata cctaatctac ccgactttaa ggaggagtta   3720

gataaatggt ttaaaaatca gacgtctatt gcgcctgatt tatctctcga tttcgagaaa   3780

ttaaacgtta ccctcctgga cctgactgat gagatgaaca ggattcagga tgcaattaag   3840

aagttaaatg agagttacat caacctcaag gacgttggca catatgaaat gtatgtgaaa   3900

tggccttggt atgtgtggtt gctaattgga ttagctggtg tagctgtttg tgtgttgtta   3960

tttttcatat gttgctgcac gggttgtggc tcatgttgtt tcaagaagtg tggaaattgt   4020

tgtgatgagt gtggaggaca ccaggacagt attgtgatac ataatatttc ctctcatgag   4080

gattga                                                              4086
```

<210> SEQ ID NO 12
<211> LENGTH: 4083
<212> TYPE: DNA
<213> ORGANISM: Rat coronavirus

<400> SEQUENCE: 12

```
atgctattcg tgtttttaac cctattgccc tcttgtctag ggtatattgg tgattttaga     60

tgtatcaacc ttgtaaacac ccgcatttct aatgcgcgcg cacccagtgt tagcacagag    120

gtagttgatg tttctaaagg tcttggtaca tattacgttt tagatcgtgt ttatttaaat    180

gccacgttat tgcttactgg ttactaccct gtagatgggt ccatgtatcg taacatggct    240

ctaatgggta ctaatacctt aagccttaat tggtttgaac cgcccttttt atcagagttt    300

aacgatggca tatatgctaa ggtaaagaac ctcaaagcat ctttgcccat aggctcggct    360

tcatactttc ctactataat tataggtagt aattttgtta atacttccta tactgtagta    420

ttggaaccat acaatggtat tattatggca tctatttgcc agtataccat ttgtcaatta    480

ccgcacacgg attgcaaacc taacacgggc ggtaacacgc taattggttt ttggcacaca    540

gatttaaggc ctccggtgtg cattttaaag cgtaatttta cgtttaatgt taatgccgaa    600

tggctttatt ttcattttta ccagcagggt ggtacttttt atgcgtatta tgcagatgtt    660

tcttctgcca ctacgttttt gtttagttcg tatattggtg ctgtgttaac acagtatttt    720

gtgttgcctt atatgtgtag tcccactacc tcaggtgttt cctcaccgca gtattgggtt    780

acaccacttg ttaagcgcca atatttattt aattttaacc aaaagggtat tattactagc    840

gctgttgatt gtgctagtag ttataccagt gaaataaagt gtaagactca aagtatgaat    900

cccaatacgg gagtctatga tttatccggt tacaccgtcc aacctgtagg actagtgtac    960

cggcgtgtta gaaatttgcc tgattgtaaa attgaggaat ggttggctgc taacacagta   1020

ccctctcctc tcaattggga gcgcaaaaca tttcaaaatt gtaacttcaa cctgagcagt   1080

ctattaagat ttgttcaggc tgagtcactc tcatgtagta atatagatgc ttccaaggtt   1140

tatggaatgt gctttggtag catatctata gataaatttg caatacccaa cagtcgccgt   1200

gttgatcttc agctaggtaa atcgggtctt ttgcaatctt ttaattataa aattgataca   1260

agagcgacct cgtgtcagct ctattacagt cttgcacaag ataatgtcac tgtcattaac   1320

cacaacccat cctcctggaa taggcgttat ggatttaatg acgtggctac atttcatagt   1380

ggtgaacatg acgttgctta tgcagaggca tgtttcactg ttggagcttc atattgccct   1440

tgtgcgaagc ccagcacagt ctattcatgt gtcacaggta aacctaagtc tgctaattgc   1500

ccaacaggta cctcgaatcg tgagtgtaat gttcaggctt caggttttaa gtctaagtgc   1560

gattgcacat gtaaccctag tcctctaacc acctatgatc ctagatgtct tcaagcgcgg   1620
```

-continued

```
agcatgcttg gcgtaggtga tcattgtgaa ggtctaggta ttttagaaga taaatgtggt   1680
ggcagcaaca tatgcaattg ttcggctgat gcctttgttg gctgggctat ggacagctgt   1740
ctatctaatg cccgctgcca tatttttagt aatttgatgt taaatggcat taatagtggt   1800
actacatgtt ccacggattt tcaattgcct aatacggaag tggtcactgg cgtttgtgtc   1860
aagtatgacc tctacggtag tacaggccaa ggtgttttta aggaggttaa ggctgattat   1920
tacaatagtt ggcagaacct cttatatgat gttaatggta acttaaatgg tttccgtgac   1980
attgttacca ataagactta tttattaaga agttgctata gtgggcgcgt ttcggctgca   2040
tatcatcaag atgcacctga accagcgcta ctatatcgca atttaaaatg tgattatgtg   2100
tttaataaca acatatcccg tgaggagaca ccacttaact attttgatag ttatttgggt   2160
tgtgttatta atgctgataa ctcaactgag cagtctgttg acgcgtgtga tttgcgtatg   2220
ggtagtgggc tttgtgtcaa ctattcaatc gctcaccgtg cgcgcaggtc tgtcagtacg   2280
ggttataaat taactacttt tgaaccattt acagtcagca ttgtcaatga tagtgttgag   2340
tctgttggtg gattatatga gatgcaaata cctactaatt ttactatagc tagccatcag   2400
gagttcattc aaacgaggtc tccgaaggtt actatagatt gtgctgcatt tgtctgtggt   2460
gattatacag cgtgtagaca acagttggtt gattatggct ctttttgtga taatattaat   2520
gccattcttg gcgaggtgaa taacctcata gatactatgc aattacaagt tgctagtgct   2580
ctgatccaag gtgtcacgct aagttcacgc ttggcagatg gcatctcagg tcagattgat   2640
gatattaatt ttagtcctct tctaggttgc cttggctcag attgtagcga aggcaccaag   2700
gcagcgcaag ggcgatctgc tatagaggat gtattatttg ataaggtcaa actctctgat   2760
gttggctttg tcgaatcata taataattgc actggaggtc aagaagttag agacctactt   2820
tgtgtgcaat cttttaatgg cattaaagtg ctaccgcctg tattatccga gagtcaaatc   2880
tctggttata cagcgggagc tactgcatct gctatgttcc ctccatggtc tgcagctgca   2940
ggtgtgccat ttgctttaag tgttcaatat agaattaatg gtcttggtgt cactatgaat   3000
gttcttagtg aaaaccagaa aatgatagct agttcattta acaacgcgat aggtgctata   3060
caggaagggt tcgatgcaac caattctgct ttagcgaaaa ttcagtccgt tgtcaacgca   3120
aatgcagaag cactcaataa ccttttgaat cagctttcca ataggtttgg tgcaattagt   3180
gcttctttac aggaaattct atctcgcctc gatgctcttg aagctcaggc tcagatagac   3240
cgtcttatta atggcagatt aactgcactt aatgcatatg tctctaagca gctgagcgac   3300
atgaccctta ttaaggtgag tgctgcccag gctatagaga aagttaatga gtgtgttaaa   3360
agccaatcac ctaggataaa tttctgtggc aatggcaatc atatattgtc attagtccag   3420
aatgcgcctt acggtttata ttttattcat ttcagctatg tgcctacatc ctttacaacg   3480
gtaaatgtga gtcctggact atgcatttct ggtgatagag gattagcacc taaagctgga   3540
tattttgttc aagatcatgg agaatggaag ttcacaggta gcaattatta ctaccctgaa   3600
tccattacag ataaaaacag tgtcgtgatg agtagttgcg cagtaaacta cacaaaggca   3660
cctgaagttt tcttgaacac ttcaataact aatctacccg actttaagga ggagttagat   3720
aaatggttta agaatcagac gtctattgtg cctgatttat ctttcgatat cgggaaatta   3780
aatgttacat tccttgacct gtcctatgag atgaacagga ttcaggatgc aattaagaat   3840
ttaaatgaga gttacatcaa cctcaaggaa attggcacat atgagatgta tgtgaaatgg   3900
ccttggtatg tttggctgct aattggatta gctggtgtag ctgtttgtgt tttgttattt   3960
```

-continued

```
tttatatgtt gctgcacagg ttgtggctct tgttgtttta agaaatgtgg aaattgttgt   4020

gatgagtatg gaggacgtca ggcaggtatt gtgatacata atatttcctc tcatgaggat   4080

tga                                                                 4083
```

<210> SEQ ID NO 13
<211> LENGTH: 3489
<212> TYPE: DNA
<213> ORGANISM: Infectious bronchitis virus

<400> SEQUENCE: 13

```
atgttggtaa cacctctttt actagtgact cttttgtgtg cactatgtag tgctgttttg     60

tatgacagta gttcttacgt ttactactac caaagtgcct tcagaccacc tagtggttgg    120

catttacaag gggtgctta tgcggtagtt aacatttcta gcgaatttaa taatgcaggc    180

tcttcatcag ggtgtactgt tggtattatt catggtggtc gtgttgttaa tgcttcttct    240

atagctatga cggcaccgtc atcaggtatg gcttggtcta gcagtcagtt ttgtactgca    300

cactgtaatt tttcagatac tacagtgttt gttacacatt gttataaaca tggtgggtgt    360

cctttaactg gcatgcttca acagaatctt atacgtgttt ctgctatgaa aaatggccag    420

cttttctata atttaacagt tagtgtagct aagtacccta cttttagatc atttcagtgt    480

gttaataatt taacatccgt atatttaaat ggtgatcttg tttacacctc taatgagacc    540

atagatgtta catctgcagg tgtttatttt aaagctggtg gacctataac ttataaagtt    600

atgagagaag ttaaagccct ggcttatttt gttaatggta ctgcacaaga tgttattttg    660

tgtgatggat cacctagagg cttgttagca tgccagtata atactggcaa tttttcagat    720

ggcttttatc cttttactaa tagtagttta gttaagcaga agtttattgt ctatcgtgaa    780

aatagtgtta atactacttg tacgttacac aatttcattt ttcataatga gactggcgcc    840

aaccctaatc ctagtggtgt tcagaatatt caaacttacc aaacaaaaac agctcagagt    900

ggttattata attttaattt ttcctttctg agtagttttg tttataagga gtctaatttt    960

atgtatggat cttatcaccc aagttgtaaa tttagactag aaactattaa taatggcttg   1020

tggtttaatt cactttcagt ttcaattgct tacggtcctc ttcaaggtgg ttgcaagcaa   1080

tctgtcttta aaggtagagc aacttgttgt tatgcttatt catatggagg tccttcgctg   1140

tgtaaaggtg tttattcagg tgagttagat cataattttg aatgtggact gttagtttat   1200

gttactaaga gcggtggctc tcgtatacaa acagccactg aaccgccagt tataactcaa   1260

aacaattata ataatattac tttaaatact tgtgttgatt ataatatata tggcagaact   1320

ggccaaggtt ttattactaa tgtgaccgac tcagctgtta gttataatta tctagcagac   1380

gcaggtttgg ctattttaga tacatctggt tccatagaca tctttgttgt acaaggtgaa   1440

tatggtctta attattataa ggttaaccct tgcgaagatg tcaaccagca gtttgtagtt   1500

tctggtggta aattagtagg tattcttact tcacgtaatg agactggttc tcagcttctt   1560

gagaaccagt tttacatcaa aatcactaat ggaacacgtc gttttagacg ttctattact   1620

gaaaatgttg caaattgccc ttatgttagt tatggtaagt tttgtataaa acctgatggc   1680

tcaattgcca caatagtacc aaaacaattg gaacagtttg tggcaccttt atttaatgtt   1740

actgaaaatg tgctcatacc taacagtttc aacttaactg ttacagatga gtacatacaa   1800

acgcgtatgg ataaggtcca aattaattgc ctgcagtatg tttgtggcag ttctctggat   1860

tgtagaaagt tgtttcaaca atatgggcct gtttgcgaca acatattgtc tgtagtaaat   1920

agtgttggtc aaaaagaaga tatggaactt ttgaatttct attcttctac taaaccggct   1980
```

-continued ggttttaata caccagttct tagtaatgtt agcactggtg agtttaatat ttctcttctg 2040
ttaacaaatc ctagtagtcg tagaaagcgt tctcttattg aagaccttct atttacaagc 2100
gttgaatctg ttggactacc aacaaatgac gcatataaaa attgcactgc aggaccttta 2160
ggctttttta aggaccttgc gtgtgctcgt gaatataatg gtttgcttgt gttgcctcct 2220
atcataacag cagaaatgca agctttgtat actagttctc tagtagcttc tatggctttt 2280
ggtggtatta ctgcagctgg tgctatacct tttgccacac aactgcaggc tagaattaat 2340
cacttgggta ttacccagtc acttttgttg aagaatcaag aaaaaattgc tgcttccttt 2400
aataaggcca ttggtcatat gcaggaaggt tttagaagta catctctagc attacaacaa 2460
attcaagatg ttgttagtaa acagagtgct attcttactg agactatggc atcacttaat 2520
aaaaattttg gtgctatttc ttctgtgatt caagaaatct accagcaatt tgacgccata 2580
caagcaaatg ctcaagtgga tcgtcttata actggtagat tgtcatcact ttctgtttta 2640
gcatctgcta agcaggcgga gtatattaga gtgtcacaac agcgtgagtt agctactcag 2700
aaaattaatg agtgtgttaa gtcacagtct attaggtact ccttttgtgg taatggacga 2760
catgttctaa ccataccgca aaatgcacct aatggtatag tgtttataca cttttcttat 2820
actccagata gttttgttaa tgttactgca atagtgggtt tttgtgtaaa gccagctaat 2880
gctagtcagt atgcaatagt gcccgctaat ggtaggggta tttttataca agttaatggt 2940
agttactaca tcactgcacg agatatgtat atgccaagag ctattactgc aggagatgta 3000
gttacgctta cttcttgtca agcaaattat gtaagtgtaa ataagaccgt cattactaca 3060
ttcgtagaca atgatgattt tgattttaat gacgaattgt caaaatggtg gaatgatact 3120
aagcatgagc taccagactt tgacaaattc aattacacag tacctatact tgacattgat 3180
agtgaaattg atcgtattca aggcgttata cagggtctta atgactctct aatagacctt 3240
gaaaaacttt caatactcaa aacttatatt aagtggcctt ggtatgtgtg gttagccata 3300
gcttttgcca ctattatctt catcttaata ctaggatggg ttttcttcat gactggttgt 3360
tgtggttgtt gttgtggatg ctttggcatt atgcctctaa tgagtaagtg tggtaagaaa 3420
tcttcttatt acacgacttt tgataacgat gtggtaactg aacaatacag acctaaaaag 3480
tctgtttga 3489

<210> SEQ ID NO 14
<211> LENGTH: 36
<212> TYPE: DNA
<213> ORGANISM: SARS coronavirus GD69

<400> SEQUENCE: 14
cccacgccag aaggtagatc acgaactaca cgtggg 36

<210> SEQ ID NO 15
<211> LENGTH: 95
<212> TYPE: DNA
<213> ORGANISM: SARS coronavirus GD69

<400> SEQUENCE: 15
ctctatgttt ataagggcta tcaacctata gatgtagttc gtgatctacc ttctggtttt 60
aacactttga aacctatttt taagttgcct cttgg 95

<210> SEQ ID NO 16
<211> LENGTH: 26
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 16

ctctatgttt ataagggcta tcaacc                                          26


<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17

ccaagaggca acttaaaaat aggtttc                                         27


<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18

aggctgtaag aa                                                         12


<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

gcccacgcca gaaggtagat cacgaactac acgtgggc                             38


<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

taatacgact cactataggc tctatgttta taagggctat caacc                     45


<210> SEQ ID NO 21
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

aggctgtaag aaccaagagg caacttaaaa ataggtttc                            39


<210> SEQ ID NO 22
<211> LENGTH: 231
<212> TYPE: DNA
<213> ORGANISM: SARS coronavirus urbani
```

-continued

<400> SEQUENCE: 22
atgtactcat tcgtttcgga agaaacaggt acgttaatag ttaatagcgt acttcttttt 60
cttgctttcg tggtattctt gctagtcaca ctagccatcc ttactgcgct tcgattgtgt 120
gcgtactgct gcaatattgt taacgtgagt ttagtaaaac caacggttta cgtctactcg 180
cgtgttaaaa atctgaactc ttctgaagga gttcctgatc ttctggtcta a 231

<210> SEQ ID NO 23
<211> LENGTH: 231
<212> TYPE: DNA
<213> ORGANISM: SARS coronavirus Tor2

<400> SEQUENCE: 23
atgtactcat tcgtttcgga agaaacaggt acgttaatag ttaatagcgt acttcttttt 60
cttgctttcg tggtattctt gctagtcaca ctagccatcc ttactgcgct tcgattgtgt 120
gcgtactgct gcaatattgt taacgtgagt ttagtaaaac caacggttta cgtctactcg 180
cgtgttaaaa atctgaactc ttctgaagga gttcctgatc ttctggtcta a 231

<210> SEQ ID NO 24
<211> LENGTH: 234
<212> TYPE: DNA
<213> ORGANISM: Human coronavirus OC43

<400> SEQUENCE: 24
atgttcctta agctagtgga tgatcatgct ttggttgtta atgtactact ctggtgtgtg 60
gtgcttatag tgatactact agtgtgtatt acaataatta aactaattaa gctttgtttc 120
acttgccata tgttttgtaa tagaacagtt tatggcccca ttaaaaatgt gtaccacatt 180
taccaatcat atatgcacat agaccctttc cctaaacgag ttattgattt ctaa 234

<210> SEQ ID NO 25
<211> LENGTH: 231
<212> TYPE: DNA
<213> ORGANISM: Porcine epidemic diarrhea virus

<400> SEQUENCE: 25
atgctacaat tagtgaatga taatggtcta gtagttaatg ttatactttg gcttttcgta 60
ctctttttcc tgcttattat aagcattacc ttcgtccaat tggttaatct gtgcttcact 120
tgtcaccggt tgtgtaatag cgcagtttat acacctatag ggcgcctgta tagagtttat 180
aagtcttaca tgcgaattga ccccctcccc agtactgtta ttgacgtata a 231

<210> SEQ ID NO 26
<211> LENGTH: 249
<212> TYPE: DNA
<213> ORGANISM: Transmissible gastroenteritis virus

<400> SEQUENCE: 26
atgacgtttc ctagggcatt gactgtcata gatgacaatg gaatggtcat taacatcatt 60
ttctggttcc tgttgataat tatattgata ttactttcaa tagcattgct aaatataatt 120
aagctatgca tggtgtgttg caatttagga aggacagtta ttattgttcc agcgcaacat 180
gcttacgatg cctataagaa ttttatgcga attaaagcat acaaccccga tggagcactc 240
cttgcttga 249

<210> SEQ ID NO 27

-continued

<211> LENGTH: 249
<212> TYPE: DNA
<213> ORGANISM: Porcine respiratory coronavirus

<400> SEQUENCE: 27
atgacgtttc ctagggcatt gactgtcata gatgacaacg gaatggtcat tagcatcatt 60
ttttggttcc tgttgataat tatattgata ttactttcaa tagcattgct aaatataatt 120
aagctatgca tggtgtgttg caatttagga aggacagtta ttattgttcc agtgcaacat 180
gcttacgatg cctataagaa ttttatgcga attaaagcat acaaccctga tggagcactc 240
cttgtttga 249

<210> SEQ ID NO 28
<211> LENGTH: 249
<212> TYPE: DNA
<213> ORGANISM: Canine coronavirus

<400> SEQUENCE: 28
atgacgttcc ctcgggcatt gactgtcata gatgacaatg gaatggtcat tagtatcatt 60
ttctggttcc tgttgataat tatattgata ttattttcaa tagcattgct aaatataatt 120
aagctatgca tggtatgttg caatttagga agaacagtta ttattgttcc agctcgacat 180
gcctatgatg cctataagaa ttttatgcaa attagagcat acaaccctga tgaagcactc 240
cttgtttga 249

<210> SEQ ID NO 29
<211> LENGTH: 249
<212> TYPE: DNA
<213> ORGANISM: Feline coronavirus

<400> SEQUENCE: 29
atgacgttcc ctagggcatt tactatcata gatgaccatg gcatggttgt tagcgtcttc 60
ttctggctcc tgttgataat tatattgata ttgttttcaa tagcattgct aaatgttatt 120
aaattgtgca tggtatgttg caatttgggt aagactatta tagtactacc tgcacgccat 180
gcatatgatg cctataagac ctttatgcaa accaaggcat ataatcccga cgaagcattt 240
ttggtttga 249

<210> SEQ ID NO 30
<211> LENGTH: 267
<212> TYPE: DNA
<213> ORGANISM: Murine hepatitis virus

<400> SEQUENCE: 30
atgtttaatt tattccttac agatacagta tggtatgtgg ggcagattat ttttatagtc 60
gcagtgtgtt tgatggtcac cataatagtg gttgccttcc ttgcgtctat caaactttgt 120
attcaacttt gcggtttgtg taatactttg ttgctgtctc cttctatttg tgtgtataat 180
aggagtaagc agctttataa gtattataat gaagaagtga gaccgccccc gttagaggtg 240
gatgatataa taatccaaac attatga 267

<210> SEQ ID NO 31
<211> LENGTH: 267
<212> TYPE: DNA
<213> ORGANISM: Rat coronavirus

<400> SEQUENCE: 31
atgtttaatt tattccttat agacacagta tggtacgtgg ggcagattat ttttatagtc 60

-continued gcagtgtgtt tgatggtcac cataattgtg gttgccttcc ttgcgtctat taaactttgt 120
attcaacttt gcggtttgtg taatactttg ttgctgtctc cttctattta tgtgtataat 180
aggagtaagc agctttataa gtattataat gaagaagtga gaccgccccc gttagaggtg 240
gatgatataa taatccaaac attatga 267

<210> SEQ ID NO 32
<211> LENGTH: 255
<212> TYPE: DNA
<213> ORGANISM: Bovine coronavirus

<400> SEQUENCE: 32
atgtttatgg ctgatgctta ttttgcagac actgtgtggt atgtggggca aataattttt 60
atagttgcca tttgtttatt ggttataata gttgtagtgg catttttggc aacttttaaa 120
ttgtgtattc aactttgcgg tatgtgtaat accttagtac tgtccccttc tatttatgtg 180
tttaatagag gtaggcagtt ttatgagttt tacaacgatg taaaaccacc agttcttgat 240
gtggatgacg tttag 255

<210> SEQ ID NO 33
<211> LENGTH: 327
<212> TYPE: DNA
<213> ORGANISM: Infectious bronchitis virus

<400> SEQUENCE: 33
atgaatttat tgaataagtc gctagaggag aatggaagtt ttctaacagc gctttacata 60
attgtaggat ttttagcact ttatcttcta ggtagagcac ttcaagcatt tgtacaggct 120
gctgatgctt gttgtttatt ttggtataca tgggtagtaa ttccaggagc taagggtaca 180
gcctttgtat acaagtatac atatggtaga aaacttaaca atccggaatt agaagcagtt 240
attgttaacg agtttcctaa gaacggttgg aataataaaa atccagcaaa ttttcaagat 300
gcccaacgag acaaattgta ctcttga 327

<210> SEQ ID NO 34
<211> LENGTH: 38
<212> TYPE: DNA
<213> ORGANISM: SARS coronavirus GD69

<400> SEQUENCE: 34
cctccgcacg aaagcaagaa aaagaagtac gccggagg 38

<210> SEQ ID NO 35
<211> LENGTH: 95
<212> TYPE: DNA
<213> ORGANISM: SARS coronavirus GD69

<400> SEQUENCE: 35
cggaagaaac aggtacgtta atagttaata gcgtacttct ttttcttgct ttcgtggtat 60
tcttgctagt cacactagcc atccttactg cgctt 95

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36

-continued

```
cggaagaaac aggtacgtta atag                                          24


<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

aagcgcagta aggatggcta                                               20


<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

tattgcagca gtac                                                     14


<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

gcctccgcac gaaagcaaga aaaagaagta cgccggaggc                         40


<210> SEQ ID NO 40
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

taatacgact cactataggc ggaagaaaca ggtacgttaa tag                     43


<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

tattgcagca gtacaagcgc agtaaggatg gcta                               34


<210> SEQ ID NO 42
<211> LENGTH: 789
<212> TYPE: DNA
<213> ORGANISM: Transmissible gastroenteritis virus

<400> SEQUENCE: 42

atgaagattt tgttaatatt agcgtgtgtg attgcatgcg catgtggaga acgctattgt    60

gctatgaaat ccgatacaga tttgtcatgt cgcaatagta cagcgtctga ttgtgagtca   120
```

-continued

```
tgcttcaacg gaggcgatct tatttggcat cttgcaaact ggaacttcag ctggtctata    180

atattgatcg tttttataac tgtgctacaa tatggaagac ctcaattcag ctggttcgtg    240

tatggcatta aaatgcttat aatgtggcta ttatggcccg ttgttttggc tcttacgatt    300

tttaatgcat actcggaata ccaagtgtcc agatatgtaa tgttcggctt tagtattgca    360

ggtgcaattg ttacatttgt actctggatt atgtattttg taagatccat tcagttgtac    420

agaaggacta agtcttggtg gtctttcaac cctgaaacta aagcaattct ttgcgttagt    480

gcattaggaa gaagctatgt gcttcctctc gaaggtgtgc caactggtgt cactctaact    540

ttgctttcag ggaatttgta cgctgaaggg ttcaaaattg caggtggtat gaacatcgac    600

aatttaccaa aatacgtaat ggttgcatta cctagcagga ctattgtcta cacacttgtt    660

ggcaagaagt tgaaagcaag tagtgcgact ggatgggctt actatgtaaa atctaaagct    720

ggtgattact caacagaggc aagaactgat aatttgagtg agcaagaaaa attattacat    780

atggtataa                                                            789
```

<210> SEQ ID NO 43
<211> LENGTH: 789
<212> TYPE: DNA
<213> ORGANISM: Porcine respiratory coronavirus

<400> SEQUENCE: 43

```
atgaagattt tgttgatatt agcgtgtgcg attgcatgca catgtggaga acgctattgt     60

gctatgaaag acgatacagg tttgtcatgt cgcaatggca cggcgtctga ttgtgagtca    120

tgcttcaaca gaggcgatct tatttggctt cttgcaaact ggaacttcag ctggtctata    180

atattgatca tttttattac tgtgctacaa tatggaagac ctcaattcag ctggttcgtg    240

tatggcatta aaatgcttat aatgtggcta ttatggccga ttgttttggc tcttacgatt    300

tttaatgcat actcggaata ccaagtgtcc aggtatgtaa tgttcggctt tagtattgca    360

ggtgcaattg ttacatttgt actctggatt atgtattttg taagatccat tcagttgtac    420

agaaggacta agtcttggtg gtccttcaac cctgaaacta acgcaattct ttgcgttagt    480

gcattaggaa gaagctatgt gcttcctctc gaaggtgtgc caactggtgt cactctaact    540

ttgctttcag ggaatttgta cgctgaaggg ttcaaaattg caggtggtat gaccatcgac    600

aatttgccaa aatacgtaat ggttgcatta cccagcagga ctattgttta cacacttgtt    660

ggcaagaagt tgaaagcaag tagtgcgact ggatgggctt actatgtaaa atctaaagct    720

ggtgattact caacagaggc aagaactgat aatttgagtg agcaagaaaa attattacat    780

atggtataa                                                            789
```

<210> SEQ ID NO 44
<211> LENGTH: 789
<212> TYPE: DNA
<213> ORGANISM: Canine coronavirus

<400> SEQUENCE: 44

```
atgaagaaaa ttttgttttt actagcgtgt gcaattgcat gcgtctatgg agaacgctat     60

tgtgccatga ctgaaagttc tacgtcatgt cgtaatagca cggctggcaa ctgtgcttca    120

tgcttcgaaa caggtgatct tatttggcat cttgcaaact ggaacttcag ctggtctgta    180

atattgatca tttttataac agtgttacaa tatggaagac ctcaatttag ctggttcgtg    240

tgtggcatta aaatgcttat tatgtggctg ttatggccca ttgttttagc tcttacgatt    300
```

-continued

```
tttaatgcat acctggaata ccgagtttcc agatatgtaa tgttcggctt tagtgttgca    360

ggtgcaactg ttacatttat actttggatt atgtattttg ttagatccat tcagttatac    420

agaaggacta agtcttggtg gtctttcaac cctgaaacta gcgcaattct ttgcgttagt    480

gcgttaggaa gaagctatgt gcttcctctt gaaggtgtgc caactggtgt cactctaaca    540

ttgctttcag ggaatttgtg tgctgaaggg ttcaaaattg caggtggtat gaacatcgac    600

aatttaccaa aatatgtaat ggttgcatta cctgtcagaa ccatagtcta cacacttgtt    660

ggcaagaaat tgaaagcaag tagtgcaaca ggatgggctt actatgtaaa gtctaaagct    720

ggtgattact caacagatgc acgaactgat aatttgagtg agcatgaaaa attattacat    780

atggtataa                                                            789
```

<210> SEQ ID NO 45
<211> LENGTH: 870
<212> TYPE: DNA
<213> ORGANISM: Feline coronavirus

<400> SEQUENCE: 45

```
atgcatatga tgcctataag acctttatgc aaaccaaggc atataatccc gacgaagcat     60

ttttggtttg aactaaacaa aatgaagtac attttgctaa tactcgcgtg cataattgca    120

tgcgtttatg gtgaacgcta ctgtgccatg caagacagtg gcttgcagtg tattaatggc    180

acaaattcaa gatgtcaaac ctgctttgaa cgtggtgatc ttatttggca tcttgctaac    240

tggaacttca gctggtctgt aatattgatt gtttttataa cagtgttaca atatggcaga    300

ccacaattta gctggctcgt ttatggcatt aaaatgctga tcatgtggct attatggcct    360

attgttctag cgcttacgat ttttaatgca tactctgagt accaagtttc cagatatgta    420

atgttcggct ttagtgttgc aggtgcagtt gtaacgtttg cactttggat gatgtatttt    480

gtgagatctg ttcagctata tagaagaacc aaatcatggt ggtcttttaa tcctgagact    540

aatgcaattc tttgtgttaa tgcattgggt agaagttatg tgcttccctt agatggtact    600

cctacaggtg ttacccttac tctactttca ggaaatctat atgctgaagg tttcaaaatg    660

gctggtggtt taaccatcga gcatttgcct aaatacgtca tgattgctac acctagtaga    720

accatcgttt atacattagt tggaaaacaa ttaaaagcaa ctactgccac aggatgggct    780

tactacgtaa aatctaaagc tggtgattac tcaacagaag cacgtactga caatttgagt    840

gaacatgaaa aattattaca tatggtgtaa                                     870
```

<210> SEQ ID NO 46
<211> LENGTH: 678
<212> TYPE: DNA
<213> ORGANISM: Human coronavirus OC43

<400> SEQUENCE: 46

```
atgtcaaatg acaattgtac gggtgacatt gtcacccatt tgaagaattg gaattttggt     60

tggaatgtta ttctaaccat attcattgtt attcttcagt ttggacacta taaatactcc    120

agattgtttt atggtttgaa gatgcttgta ctgtggcttc tttggccact cgtacttgct    180

ttgtcaatct ttgacacctg ggctaattgg gattctaatt gggcctttgt tgcatttagc    240

ttttttatgg ccgtatcaac actcgttatg tgggtgatgt acttcgcaaa cagtttcaga    300

cttttccgac gtgctcgaac tttttgggca tggaatcctg aggttaatgc aatcactgtc    360

acaaccgtgt tgggacagac atactatcaa cccattcaac aagctccaac aggcattact    420

gtgaccttgc tgagcggcgt gctttacgtt gacggacata gattggcttc aggtgttcag    480
```

-continued gttcataacc tacctgaata catgacagtt gccgtgccga gcactactat aatttatagt 540
agagtcggaa ggtccgtaaa ttcacaaaat agcacaggct gggttttcta cgtacgagta 600
aaacacggtg atttttctgc agtgagctct cccatgagca acatgacaga aaacgaaaga 660
ttgcttcatt ttttctaa 678

<210> SEQ ID NO 47
<211> LENGTH: 681
<212> TYPE: DNA
<213> ORGANISM: Porcine epidemic diarrhea virus

<400> SEQUENCE: 47
atgtctaacg gttctattcc cgttgatgag gtgattgaac accttagaaa ctggaatttc 60
acatggaata tcatactgac gatactactt gtagtgcttc agtatggcca ttacaagtac 120
tctgtgttct tgtatggtgt caagatggct attctatgga tactttggcc tcttgtgttg 180
gcactgtcac tttttgacgc atgggctagc ttccaggtca actgggtctt tttcgctttc 240
agcatcctta tggcttgcat cactcttatg ctgtggataa tgtattttgt caatagcatt 300
cggttgtggc gcaggacaca ttcttggtgg tctttcaatc ctgaaactga cgcgcttctc 360
actacttctg tgatgggccg acaggtctgc attccagtgc ttggagcacc aactggtgta 420
acgctaacac tccttagtgg tacattgctt gtagagggct ataaggttgc tactggcgta 480
caggtaagtc aattacctaa tttcgtcaca gtcgccaagg ccactacaac aattgtctac 540
ggacgtgttg gtcgttcagt caatgcttca tctggcactg gttgggcttt ctatgtccgg 600
tcaaaacacg gcgactattc agctgtgagt aatccgagtg cggttctcac agatagtgag 660
aaagtgcttc atttagtcta a 681

<210> SEQ ID NO 48
<211> LENGTH: 693
<212> TYPE: DNA
<213> ORGANISM: Bovine coronavirus

<400> SEQUENCE: 48
atgagtagtg taactacacc agcaccagtt tacacctgga ctgctgatga agctattaaa 60
ttcctaaagg aatggaactt ttctttgggt attatactac tttttattac aatcatattg 120
caatttggat atacaagtcg cagtatgttt gtttatgtta ttaagatgat cattttgtgg 180
cttatgtggc cccttactat catcttaact attttcaatt gcgtgtatgc gttgaataat 240
gtgtatcttg gcttttctat agttttcact atagtggcca ttatcatgtg gattgtgtat 300
tttgtgaata gtatcaggtt gtttattaga actggaagtt ggtggagttt caacccagaa 360
acaaacaact tgatgtgtat agatatgaag ggaaggatgt atgttaggcc gataattgag 420
gactaccata cccttacggt cacaataata cgtggtcatc tttacatgca aggtataaaa 480
ctaggtactg gctattcttt gtcagatttg ccagcttatg tgactgttgc taaggtctca 540
cacctgctca cgtataagcg tggttttctt gacaagatag gcgatactag tggttttgct 600
gtttatgtta agtccaaagt cggtaattac cgactgccat caacccaaaa gggttctggc 660
atggacaccg cattgttgag aaataatatc taa 693

<210> SEQ ID NO 49
<211> LENGTH: 693
<212> TYPE: DNA
<213> ORGANISM: Porcine hemagglutinating encephalomyelitis coronavirus -continued

<400> SEQUENCE: 49
atgagtagtc caactacacc agtaccagtt attagctgga ctgctgatga agctattaaa 60
ttcctaaagg aatggaattt ttctttgggt ataatagtac tctttatcac aatcatactt 120
caatttggat atacaagtcg cagtatgttt gtttatgtta ttaagatggt tattctgtgg 180
ctcatgtggc ctcttactat aattttaact atcttcaact gcgtatacgc gttgaataat 240
gtgtaccttg gcttctctat agtttttact atagtggcca ttattatgtg ggttgtttat 300
tttgtgaata gtatcaggtt gtttattaga actggaagtt ggtggagttt caacccagaa 360
acaaacaact tgatgtgtat agatatgaag ggaagaatgt atgttaggcc gattattgag 420
gactaccaca cccttactgc cacaataata cgtggccacc tctacatcca aggtataaaa 480
ctaggtactg gctattcttt gtcagatttg cctgcttatg tgaccgttgc taaggttaca 540
cacctgtgca catataagcg tggttttctt gataggatag gcgatactag tggttttgct 600
gtttatgtta agtccaaagt cggtaattat cgattgcctt caacccataa gggctcaggc 660
atggacaccg cattgttgag aaataatatc taa 693

<210> SEQ ID NO 50
<211> LENGTH: 687
<212> TYPE: DNA
<213> ORGANISM: Murine hepatitis virus

<400> SEQUENCE: 50
atgactagta ccactcaggc tccacagcct gtttatcagt ggacggctga tgaggcaatt 60
cgattcctta aggaatggaa tttctctctc ggcattatac tactttttgt tactatcata 120
ctacagttcg gttacacgag ccgtagcatg tttgtttatg ttgtgaaaat gatacttttg 180
tggcttatgt ggccactaac tattgttttg tgtattttta actgcgtcta tgcgctaaat 240
aatgtgtatc ttggattttc tatagtgttt actatagtgt ccattataat gtggattatg 300
tattttgtta atagcatcag gttgtttatc aggactggca gctggtggag cttcaacccc 360
gaaacaaaca acctaatgtg tatagatatg aaaggtactg tgtatgttag acccattata 420
gaggattacc atacactaac agccactatc attcgtggtc acctctatat gcaaggtgtt 480
aagctaggca ctggcttctc tttgtctgat ttgcctgctt atgttacagt tgctaaggtg 540
tctcaccttt gcacttataa gcgcgcattc ttagacaagg tagacggtgt tagcggtttt 600
gctgtttatg tgaagtccaa ggtcggaaat taccgactgc cctcaaataa accgagtggc 660
atggacaccg cattgttgag aatctaa 687

<210> SEQ ID NO 51
<211> LENGTH: 687
<212> TYPE: DNA
<213> ORGANISM: Rat coronavirus

<400> SEQUENCE: 51
atgagtagta ccactccagc cccccagact gtctatcaat ggacggccga tgtggcagtt 60
cgattcctta aggaatggaa cttcttgttg ggcattatac tactctttat tactatcata 120
ctacagttcg gttacacgag ccgtagcatg tttatatatg ttgtgaaaat gataatcttg 180
tggttaatgt ggccactgac tattgttttg tgtattttta attgcgtgta tgcgctaaat 240
aatgtgtatc ttggattttc tatagtgttt actatagtgt ccattgtaat gtggattatg 300
tattttgtta atagcataag gttgtttatc aggactggta gctggtggag cttcaaccct 360
gaaacaaaca acctaatgtg tatagatgtg aaaggtactg tgtatgttag acccattatt 420

-continued gaagattacc atacactaac agccacaaat gtacgtggcc acctttatat gcaaggtgtt 480
aagctaggca ctggcttctc tttgtctgat ttgcccgctt atgttacagt tgctaaggtg 540
tcgcaccttt gcacttataa gcgcgcattt ttagacaagg ttgacggtgt tagcggtttt 600
gctgtttatg tgaagtccaa ggtcggtaat taccgactgc cctcaaataa accgagtggc 660
gcggacaccg cattgttgag aatctaa 687

<210> SEQ ID NO 52
<211> LENGTH: 675
<212> TYPE: DNA
<213> ORGANISM: SARS coronavirus urbani

<400> SEQUENCE: 52
ttgcttatca tggcagacaa cggtactatt accgttgagg agcttaaaca actcctggaa 60
caatggaacc tagtaatagg tttcctattc ctagcctgga ttatgttact acaatttgcc 120
tattctaatc ggaacaggtt tttgtacata ataaagcttg ttttcctctg gctcttgtgg 180
ccagtaacac ttgcttgttt tgtgcttgct gctgtctaca gaattaattg ggtgactggc 240
gggattgcga ttgcaatggc ttgtattgta ggcttgatgt ggcttagcta cttcgttgct 300
tccttcaggc tgtttgctcg tacccgctca atgtggtcat tcaacccaga aacaaacatt 360
cttctcaatg tgcctctccg ggggacaatt gtgaccagac cgctcatgga aagtgaactt 420
gtcattggtg ctgtgatcat tcgtggtcac ttgcgaatgg ccggacaccc cctagggcgc 480
tgtgacatta aggacctgcc aaaagagatc actgtggcta catcacgaac gctttcttat 540
tacaaattag gagcgtcgca gcgtgtaggc actgattcag gttttgctgc atacaaccgc 600
taccgtattg gaaactataa attaaataca gaccacgccg gtagcaacga caatattgct 660
ttgctagtac agtaa 675

<210> SEQ ID NO 53
<211> LENGTH: 675
<212> TYPE: DNA
<213> ORGANISM: SARS coronavirus Tor2

<400> SEQUENCE: 53
ttgcttatca tggcagacaa cggtactatt accgttgagg agcttaaaca actcctggaa 60
caatggaacc tagtaatagg tttcctattc ctagcctgga ttatgttact acaatttgcc 120
tattctaatc ggaacaggtt tttgtacata ataaagcttg ttttcctctg gctcttgtgg 180
ccagtaacac ttgcttgttt tgtgcttgct gctgtctaca gaattaattg ggtgactggc 240
gggattgcga ttgcaatggc ttgtattgta ggcttgatgt ggcttagcta cttcgttgct 300
tccttcaggc tgtttgctcg tacccgctca atgtggtcat tcaacccaga aacaaacatt 360
cttctcaatg tgcctctccg ggggacaatt gtgaccagac cgctcatgga aagtgaactt 420
gtcattggtg ctgtgatcat tcgtggtcac ttgcgaatgg ccggacactc cctagggcgc 480
tgtgacatta aggacctgcc aaaagagatc actgtggcta catcacgaac gctttcttat 540
tacaaattag gagcgtcgca gcgtgtaggc actgattcag gttttgctgc atacaaccgc 600
taccgtattg gaaactataa attaaataca gaccacgccg gtagcaacga caatattgct 660
ttgctagtac agtaa 675

<210> SEQ ID NO 54
<211> LENGTH: 678
<212> TYPE: DNA

-continued

<213> ORGANISM: Infectious bronchitis virus

<400> SEQUENCE: 54

```
atgcccaacg agacaaattg tactcttgac tttgaacagt cagttcagct ttttaaagag     60

tataatttat ttataactgc attcttgttg ttcttaacca taatacttca gtatggctat    120

gcaacaagaa gtaaggttat ttatacactg aaaatgatag tgttatggtg cttttggccc    180

cttaacattg cagtaggtgt aatttcatgt acatacccac caaacacagg aggtcttgtc    240

gcagcgataa tacttacagt gtttgcgtgt ctgtcttttg taggttattg gatccagagt    300

attagactct ttaagcggtg taggtcatgg tggtcattta atccagaatc taatgccgta    360

ggttcaatac tcctaactaa tggtcaacaa tgtaattttg ctatagagag tgtgccaatg    420

gtgctttctc caattataaa gaatggtgtt ctttattgtg agggtcagtg gcttgctaag    480

tgtgaaccag accacttgcc taaagatata tttgtttgta caccggatag acgtaatatc    540

taccgtatgg tgcagaaata tactggtgac caaagcggaa ataagaaaag gtttgctacg    600

tttgtctatg caaagcagtc agtagatact ggcgagctag aaagtgtagc aacaggagga    660

agtagtcttt acacataa                                                   678
```

<210> SEQ ID NO 55
<211> LENGTH: 38
<212> TYPE: DNA
<213> ORGANISM: SARS coronavirus GD69

<400> SEQUENCE: 55

```
cctccgaccc aattaattct gtagacagca gccggagg                             38
```

<210> SEQ ID NO 56
<211> LENGTH: 107
<212> TYPE: DNA
<213> ORGANISM: SARS coronavirus GD69

<400> SEQUENCE: 56

```
cttgttttcc tctggctctt gtggccagta acacttgctt gttttgtgct tgctgctgtc     60

tacagaatta attgggtgac tggcgggatt gcgattgcaa tggcttg                  107
```

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57

```
cttgttttcc tctggctctt g                                               21
```

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58

```
caagccattg caatcgcaat c                                               21
```

<210> SEQ ID NO 59
<211> LENGTH: 14

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59

aagcaacgaa gtag                                                    14


<210> SEQ ID NO 60
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60

gcctccgacc caattaattc tgtagacagc agccggaggc                        40


<210> SEQ ID NO 61
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61

taatacgact cactataggc ttgttttcct ctggctcttg                        40


<210> SEQ ID NO 62
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62

aagcaacgaa gtagcaagcc attgcaatcg caatc                             35


<210> SEQ ID NO 63
<211> LENGTH: 1149
<212> TYPE: DNA
<213> ORGANISM: Transmissible gastroenteritis virus

<400> SEQUENCE: 63

atggccaacc agggacaacg tgtcagttgg ggagatgaat ctaccaaaac acgtggtcgt     60

tccaattccc gtggtcggaa gaataataac atacctcttt cattcttcaa ccccataacc    120

ctccaacaag gttcaaaatt ttggaactta tgtccgagag actttgtacc caaaggaata    180

ggtaacaggg atcaacagat tggttattgg aatagacaaa ctcgctatcg catggtgaag    240

ggccaacgta aagagcttcc tgaaaggtgg ttcttctact acttaggtac tggacctcat    300

gcagatgcca aatttaaaga taaattagat ggagttgtct gggttgccaa ggatggtgcc    360

atgaacaaac caaccacgct tggtagtcgt ggtgctaata atgaatccaa agctttgaaa    420

ttcgatggta aagtgccagg cgaatttcaa cttgaagtta atcaatcaag agacaattca    480

aggtcacgct ctcaatctag atctcggtct agaaatagat ctcaatctag aggcaggcaa    540

caattcaata acaagaagga tgacagtgta gaacaagctg ttcttgccgc acttaaaaag    600

ttaggtgttg acacagaaaa acaacagcaa cgctctcgtt ctaaatctaa agaacgtagt    660
```

-continued

```
aactctaaga caagagatac tacacctaag aatgaaaaca aacacacctg gaagagaact    720

gcaggtaaag gtgatgtgac aagattttat ggagctagaa gcagttcagc caattttggt    780

gacactgacc tcgttgccaa tgggagcagt gccaagcatt acccacaact ggctgaatgt    840

gttccatctg tgtctagcat tctgtttgga agctattgga cttcaaagga agatggcgac    900

cagatagaag tcacgttcac acacaaatac cacttgccaa aggatgatcc taagactgga    960

caattccttc agcagattaa tgcctatgct cgtccatcag aagtggcaaa agaacagaga   1020

aaaagaaaat ctcgttctaa atctgcagaa aggtcagagc aagatgtggt acctgatgca   1080

ttaatagaaa attatacaga tgtgtttgat gacacacagg ttgagataat tgatgaggta   1140

acgaactaa                                                           1149
```

<210> SEQ ID NO 64
<211> LENGTH: 1149
<212> TYPE: DNA
<213> ORGANISM: Porcine respiratory coronavirus

<400> SEQUENCE: 64

```
atggccaacc agggacaacg tgtcagttgg ggggatgaat ccaccaaaat acgtggtcgc     60

tccaattccc gtggtcggaa gattaataac atacctcttt cattcttcaa ccccataacc    120

ctccagcaag gtgcaaaatt ttggaactca tgtccgagag attttgtacc caaaggaata    180

ggtaataggg atcaacagat tggttattgg aatagacaaa ctcgctatcg catggtgaag    240

ggccaacgta aagagcttcc tgaaaggtgg ttcttttact acttaggcac tggacctcat    300

gcagatgcca aatttaaaga taaattagat ggagttgtct gggttgccaa ggatggtgcc    360

atgaacaaac caaccacgct tggtagtcgt ggtgctaata atgaatccaa agctttgaaa    420

ttcgatggta aagtgccagg cgaatttcaa cttgaagtta accagtctag ggacaactca    480

aggtcacgct ctcaatctag atcgcggtct agaaacagat ctcaatctag aggtaggcaa    540

caatccaata acaagaagga tgacagtgta gaacaagctg ttcttgccgc acttaaaaag    600

ttaggtgttt acacagaaaa acaacagcaa cgctctcgtt ctaaatctaa agaacgtagt    660

aactctaaaa caagagatac tacgcctaag aatgaaaaca aacacacctg gaagagaact    720

gcaggtaaag gtgatgtgac aagattttat ggagctagaa gcagctcagc caattttggt    780

gacagtgacc tcgttgccaa tgggagcagt gccaagcatt acccacaatt ggctgaatgt    840

gttccatctg tgtctagcat tttgtttgga agctattgga cttcaaagga agatggcgac    900

cagatagaag tcacgttcac acacaaatac cacttgccaa aggatcatcc taaaactgaa    960

caattccttc agcagattaa tgcctatgct agcccatcag aattggcaaa agaacagaga   1020

aaaagaaagt ctcgttctaa atctgcagaa aggtcagagc aagaggtggt acctgattca   1080

ttaatagaaa actatacaga tgtgtttgat gacacacagg ttgagatgat tgacgaggta   1140

acgaactaa                                                           1149
```

<210> SEQ ID NO 65
<211> LENGTH: 1146
<212> TYPE: DNA
<213> ORGANISM: Canine coronavirus

<400> SEQUENCE: 65

```
atggcctctc agggacaacg tgtcagttgg ggagatgaat ccaccaagag acgcggtcgt     60

tctaattctc gtggccggaa gaataatgat atacctcttt cattcttcaa ccccattacc    120

ctcgagcaag gatcaaagtt ttgggactta tgtccgagag actttgtacc caaaggaata    180
```

-continued

```
ggtaataagg atcaacaaat tggttattgg aacaggcaaa cccgttatcg catggtgaag    240

ggtcgacgta aaaatcttcc tgaaaagtgg ttcttctact atttaggaac tggacctcat    300

gctgatgcca aatttaagca aaaattagat ggagttgtct gggttgctag gggagattcc    360

atgactaagc caacaactct tggtactcgt ggcactaata atgaatcaaa ggctttgaaa    420

ttcgatgtca aagtaccatc agaatttcac cttgaagtga accaattaag ggacaattca    480

aggtctaggt ctcaatctag atctcagtcc agaaataggt ctcaatctag aggaaggcaa    540

ctatccaata ataagaagga tgacaatgtt gaacaagctg ttcttgctgc actcaaaaag    600

ttaggtgttg acacagaaaa acaacaaaga tctcgttcca aatctaagga acgtagcagc    660

tctaagacaa gagatactac acctaagaat gaaaacaaac acacctggaa gagaactgca    720

ggtaaaggtg atgtgacaaa attttatgga gctagaagta gttcagccaa ttttggtgac    780

agcgatcttg ttgccaatgg gaacggtgcc aagcattacc cacaactggc tgaatgtgtt    840

ccatctgtat ctagcattct gtttggaagc cattggactg ctaaggaaga tggtgaccag    900

attgaagtca cattcacaca caaataccac ttgccaaagg atgatcctaa gactggacaa    960

ttccttcagc agattaatgc atacgcccgt ccatcagagg tggctaaaga acagagacaa   1020

cgcaaagctc gttctaaatc tgtagaaagg gtagagcaag aggttgtacc tgatgcatta   1080

acagaaaatt acacagatgt gtttgatgac acacaggttg agattattga tgaggtaacg   1140

aactaa                                                              1146
```

<210> SEQ ID NO 66
<211> LENGTH: 1134
<212> TYPE: DNA
<213> ORGANISM: Feline coronavirus

<400> SEQUENCE: 66

```
atggccacac agggacaacg cgtcaactgg ggagatgaac cttccaaaag acgtggtcgt     60

tctaactctc gtggtcggaa gaataatgat ataccctttgt cattctacaa ccccattacc   120

ctcgaacaag gatctaaatt ttggaattta tgtccgagag accttgttcc caaaggaata    180

ggtaataagg atcaacaaat tggttattgg aatagacaga ttcgttatcg tattgtaaaa    240

ggccagcgta aggaactcgc tgagaggtgg ttctttttact tcttaggtac aggacctcat   300

gctgatgcta aattcaaaga caagattgat ggagtcttct gggttgcaag ggatggtgcc    360

atgaacaagc ccacaacgct tggcactcgt ggaaccaata acgaatccaa accactgaga    420

tttgatggta agataccgcc acagtttcag cttgaagtga accgttctag gaacaattca    480

aggtctggtt ctcagtctag atctgtttca agaaacagat ctcaatctag aggaagacac    540

cattccaata accagaataa taatgttgag gatacaattg tagccgtgct tgaaaaatta    600

ggtgttactg acaaacaaag gtcacgttct aaacctagag aacgtagtga ttccaaacct    660

agggacacaa cacctaagaa tgccaacaaa cacacctgga agaaaactgc aggcaaggga    720

gatgtgacaa ctttctatgg tgctagaagt agttcagcta actttggtga tagtgatctc    780

gttgccaatg gtaacgctgc caaatgctac cctcagatag ctgaatgtgt tccatcagtg    840

tctagcataa tctttggcag tcaatggtct gctgaagaag ctggtgatca agtgaaagtc    900

acgctcactc acacctacta cctgccaaag gatgatgcca aaactagtca attcctagaa    960

cagattgacg cttacaagcg accttctgaa gtggctaagg atcagaggca aagaagatcc   1020

cgttctaagt ctgctgataa gaagcctgag gagttgtctg taactcttgt ggaggcatac   1080
```

-continued acagatgtgt ttgatgacac acaggttgag atgattgatg aggttacgaa ctaa 1134

<210> SEQ ID NO 67
<211> LENGTH: 1269
<212> TYPE: DNA
<213> ORGANISM: SARS coronavirus urbani

<400> SEQUENCE: 67
atgtctgata atggacccca atcaaaccaa cgtagtgccc cccgcattac atttggtgga 60
cccacagatt caactgacaa taaccagaat ggaggacgca atggggcaag gccaaaacag 120
cgccgacccc aaggtttacc caataatact gcgtcttggt tcacagctct cactcagcat 180
ggcaaggagg aacttagatt ccctcgaggc cagggcgttc caatcaacac caatagtggt 240
ccagatgacc aaattggcta ctaccgaaga gctacccgac gagttcgtgg tggtgacggc 300
aaaatgaaag agctcagccc cagatggtac ttctattacc taggaactgg cccagaagct 360
tcacttccct acggcgctaa caaagaaggc atcgtatggg ttgcaactga gggagccttg 420
aatacaccca aagaccacat tggcacccgc aatcctaata acaatgctgc caccgtgcta 480
caacttcctc aaggaacaac attgccaaaa ggcttctacg cagagggaag cagaggcggc 540
agtcaagcct cttctcgctc ctcatcacgt agtcgcggta attcaagaaa ttcaactcct 600
ggcagcagta ggggaaattc tcctgctcga atggctagcg gaggtggtga aactgccctc 660
gcgctattgc tgctagacag attgaaccag cttgagagca aagtttctgg taaaggccaa 720
caacaacaag gccaaactgt cactaagaaa tctgctgctg aggcatctaa aaagcctcgc 780
caaaaacgta ctgccacaaa acagtacaac gtcactcaag catttgggag acgtggtcca 840
gaacaaaccc aaggaaattt cggggaccaa gacctaatca gacaaggaac tgattacaaa 900
cattggccgc aaattgcaca atttgctcca agtgcctctg cattctttgg aatgtcacgc 960
attggcatgg aagtcacacc ttcgggaaca tggctgactt atcatggagc cattaaattg 1020
gatgacaaag atccacaatt caaagacaac gtcatactgc tgaacaagca cattgacgca 1080
tacaaaacat tcccaccaac agagcctaaa aaggacaaaa agaaaaagac tgatgaagct 1140
cagcctttgc cgcagagaca aaagaagcag cccactgtga ctcttcttcc tgcggctgac 1200
atggatgatt tctccagaca acttcaaaat tccatgagtg gagcttctgc tgattcaact 1260
caggcataa 1269

<210> SEQ ID NO 68
<211> LENGTH: 1269
<212> TYPE: DNA
<213> ORGANISM: SARS coronavirus Tor2

<400> SEQUENCE: 68
atgtctgata atggacccca atcaaaccaa cgtagtgccc cccgcattac atttggtgga 60
cccacagatt caactgacaa taaccagaat ggaggacgca atggggcaag gccaaaacag 120
cgccgacccc aaggtttacc caataatact gcgtcttggt tcacagctct cactcagcat 180
ggcaaggagg aacttagatt ccctcgaggc cagggcgttc caatcaacac caatagtggt 240
ccagatgacc aaattggcta ctaccgaaga gctacccgac gagttcgtgg tggtgacggc 300
aaaatgaaag agctcagccc cagatggtac ttctattacc taggaactgg cccagaagct 360
tcacttccct acggcgctaa caaagaaggc atcgtatggg ttgcaactga gggagccttg 420
aatacaccca aagaccacat tggcacccgc aatcctaata acaatgctgc caccgtgcta 480
caacttcctc aaggaacaac attgccaaaa ggcttctacg cagagggaag cagaggcggc 540

-continued

```
agtcaagcct cttctcgctc ctcatcacgt agtcgcggta attcaagaaa ttcaactcct    600
ggcagcagta ggggaaattc tcctgctcga atggctagcg gaggtggtga aactgccctc    660
gcgctattgc tgctagacag attgaaccag cttgagagca aagtttctgg taaaggccaa    720
caacaacaag gccaaactgt cactaagaaa tctgctgctg aggcatctaa aaagcctcgc    780
caaaaacgta ctgccacaaa acagtacaac gtcactcaag catttgggag acgtggtcca    840
gaacaaaccc aaggaaattt cggggaccaa gacctaatca gacaaggaac tgattacaaa    900
cattggccgc aaattgcaca atttgctcca agtgcctctg cattctttgg aatgtcacgc    960
attggcatgg aagtcacacc ttcgggaaca tggctgactt atcatggagc cattaaattg   1020
gatgacaaag atccacaatt caaagacaac gtcatactgc tgaacaagca cattgacgca   1080
tacaaaacat tcccaccaac agagcctaaa aaggacaaaa agaaaaagac tgatgaagct   1140
cagcctttgc cgcagagaca aaagaagcag cccactgtga ctcttcttcc tgcggctgac   1200
atggatgatt tctccagaca acttcaaaat tccatgagtg gagcttctgc tgattcaact   1260
caggcataa                                                            1269
```

<210> SEQ ID NO 69
<211> LENGTH: 1347
<212> TYPE: DNA
<213> ORGANISM: Bovine coronavirus

<400> SEQUENCE: 69

```
atgtctttta ctcctggtaa gcaatccagt agtagagcgt cctttggaaa tcgttctggt     60
aatggcatcc ttaagtgggc cgatcagtcc gaccaatcta gaaatgttca aaccaggggt    120
agaagagctc aacccaagca aactgctact tctcagctac catcaggagg gaatgttgta    180
ccctactatt cttggttctc tggaattact cagtttcaaa aaggaaagga gtttgaattt    240
gcagagggac aaggtgtgcc tattgcacca ggagtcccag ctactgaagc taaggggtac    300
tggtacagac acaacagacg ttcttttaaa acagccgatg gcaaccagcg tcaactgctg    360
ccacgatggt atttttacta tcttggaaca ggaccgcatg ccaaagacca gtatggcacc    420
gatattgacg gagtcttctg ggtcgctagt aaccaggctg atgtcaatac cccggctgac    480
attctcgatc gggacccaag tagcgatgag gctattccga ctaggtttcc gcctggcacg    540
gtactccctc agggttacta tattgaaggc tcaggaaggt ctgctcctaa ttccagatct    600
acttcacgcg catccagtag agcctctagt gcaggatcgc gtagtagagc caattctggc    660
aacagaaccc ctacctctgg tgtaacacct gatatggctg atcaaattgc tagtcttgtt    720
ctggcaaaac ttggcaagga tgccactaag ccacagcaag taactaagca gactgccaaa    780
gaaatcagac agaaaatttt gaataagccc cgccagaaga ggagccccaa taaacaatgc    840
actgttcagc agtgttttgg gaagagaggc cccaatcaga attttggtgg tggagaaatg    900
ttaaaacttg gaactagtga cccacagttc cccattcttg cagaactcgc acccacagct    960
ggtgcgtttt tctttggatc aagattagag ttggccaaag tgcagaattt gtctgggaat   1020
cttgacgagc cccagaagga tgtttatgaa ttgcgctata atggtgcaat tagatttgac   1080
agtacacttt caggttttga gaccataatg aaggtgttga atgagaattt gaatgcatat   1140
caacaacaag atggtatgat gaatatgagt ccaaaaccac agcgtcagcg tggtcagaag   1200
aatggacaag gagaaaatga taatataagt gttgcagcgc ctaaaagccg tgtgcagcaa   1260
aataagagta gagagttgac tgcagaggac atcagccttc ttaagaagat ggatgagccc   1320
```

-continued tatactgaag acacctcaga aatataa 1347

<210> SEQ ID NO 70
<211> LENGTH: 1350
<212> TYPE: DNA
<213> ORGANISM: Porcine hemagglutinating encephalomyelitis coronavirus

<400> SEQUENCE: 70
atgtctttca ctcctggcaa gcagtccagc agtagagcgt cctctggaaa tcgttctggt 60
aatggcatcc ttaagtgggc cgatcagtcc gaccagtcta gaaatgttca aaccaggggt 120
agaagagttc aatccaagca aactgctact tctcagcaac catcaggagg gactgttgta 180
ccctactatt cttggttctc tggaattact cagtttcaaa agggaaagga gtttgaattt 240
gcagagggac aaggtgtgcc tattgcacca ggagtcccat ctactgaagc taaggggtac 300
tggtacagac acaacagacg ttcttttaaa acagccgacg gcaatcagcg tcaactgctg 360
ccacgatggt acttttacta cctgggaaca ggaccgcatg ccaaagacca gtacggcacc 420
gacattgacg gagtcttctg ggtcgctagt aaccaggctg atattaatac cccggctgac 480
attgtcgatc gggatccaag tagcgatgag gctattccga ctaggtttcc gcctggcacg 540
gtactccctc aaggttacta tattgaaggc tcaggaaggt ctgctcctaa ttccagatct 600
acttcgcgtg cacccaatag agcccctagt gcaggatcgc gtagtagagc caattctggc 660
aatagaacct ctacccctgg tgtaacacct gacatggctg atcaaattgc tagtcttgtt 720
ctggcaaaac ttggcaagga tgccactaag cctcagcaag taactaagca gactgccaaa 780
gaggtcagac agaaaatctt gaataagccc cgccagaaga ggagccccaa caaacaatgc 840
actgttcagc agtgttttgg gaagagaggc cccaatcaga attttggtgg tggagaaatg 900
ttaaaacttg gaactagtga cccacagttc cccattcttg cagaactcgc acccacagct 960
ggtgcgtttt tctttggatc aagattagag ttggccaaag tgcagaattt gtctgggaat 1020
cctgacgagc cccagaagga tgtttatgaa ttgcgctata atggcgcgat tagatttgac 1080
agcacactct caggttttga aaccattatg aaggtgctta accagaattt gaatgcctat 1140
caacatcagg aagatgggat gatgaatatt agtcctaaac cacagcggca gcgtggtcag 1200
aagaatggac aagtagaaaa tgataatgta agtgttgcag cgcctaaaag ccgtgtgcag 1260
caaaataaga gtagagagtt gacagcagag gacatcagcc ttcttaagaa gatggatgag 1320
ccctatactg aagatacctc agaaatataa 1350

<210> SEQ ID NO 71
<211> LENGTH: 1356
<212> TYPE: DNA
<213> ORGANISM: Murine hepatitis virus

<400> SEQUENCE: 71
atgtcttttg ttcctgggca agaaaatgcc ggtagcagaa gctcctctgg aaaccgcgct 60
ggtaatggca tcctcaagaa gaccacttgg gctgaccaaa ccgagcgtgg aaatagaggc 120
agaaggaacc atcccaagca gactgcaact actcagccca atgccgggag tgtggttccc 180
cattactctt ggttttcggg catcacccag tttcaaaagg gaaaggagtt ccagtttgca 240
caaggacagg gagtgcctat tgccagtgga atccccgctt cagagcaaaa gggatattgg 300
tatagacaca accgacgttc ttttaaaaca cctgatggcc agcacaagca gctactgccc 360
agatggtatt tttactatct tggaacaggg ccccatgctg gcgcagagta tggcgacgat 420
atcgaaggag ttgtctgggt cgcaagccaa caggccgaca ctaagaccac tgccgatgtt 480

-continued gttgaaaggg acccaagcag tcatgaggct attcctacta ggtttgcgcc cggcacggta 540
ttgcctcagg gcttttatgt agaaggctcg ggaaggtctg cacctgctag tcgatctggt 600
tcgcggtcac aatcccgtgg gccaaataat cgcgctagaa gcagttccaa ccagcgccag 660
cctgcctctg ctgtaaaacc tgacatggcc gaagaaattg ctgctcttgt tttggctaag 720
cttggtaaag atgccggcca gcccaagcag gtaactaagc aaagcgccaa agaagtcagg 780
cagaaaattt taactaagcc tcgtcaaaag aggactccaa acaagcagtg cccagtgcag 840
cagtgttttg ggaagagagg ccctaatcag aactttggag gctctgaaat gttaaaactt 900
ggaactagtg atccgcagtt ccccattctt gcagagttgg ctccaacacc tagtgccttc 960
ttctttggat ctaaattaga attggtcaaa aagaactctg gtggtgctga tgaacccacc 1020
aaagatgttt atgaattgca gtattcaggt gcaattagat ttgatagtac tctacccggt 1080
tttgagacta tcatgaaagt gttgactgag aatttgaatg cctaccagga ccaagctggt 1140
agtgtagatc tagtgagccc aaagcctcca agaagaggtc gtagacaggc tcaagaaaag 1200
aaagatgaag tagataatgt aagcgttgca aagcccaaaa gcttggtgca gcgaaatgta 1260
agtagagaat taacccccga ggatcgtagc ctgctggctc agatcctaga cgatggcgtt 1320
gtgccagatg ggttggaaga tgactctaat gtgtaa 1356

<210> SEQ ID NO 72
<211> LENGTH: 1365
<212> TYPE: DNA
<213> ORGANISM: Rat coronavirus

<400> SEQUENCE: 72
atgtcttttg ttcccggaca agaaaacgcc ggtagcagaa gctcctctgg aaaccgcgct 60
ggtaatggaa tcctcaagaa gaccacttgg gctgaccaaa ccgagcgcgg acaaaataat 120
ggaaatagag gcagaaggaa tcagcccaag cagactgcaa ctactcagcc caataccggg 180
agtgtggttc cccattactc ttggttttcg ggcattaccc aattccagaa gggaaaagag 240
ttccagtttg caggtggaca aggagtgcct attgccaatg gaatcccacc ttctgagcaa 300
aagggatatt ggtatagaca caaccgtcgt tcttttaaaa cacctgatgg gcagcagaag 360
caactactcc ccagatggta tttttactat cttgggacgg gcccccatgc tggagccagt 420
ttcggagaca gcattgaggg agtcttctgg gttgcaaata gtcaggcgga taccaacacc 480
tctgctgaca ttgttgaaag ggacccaagt agccatgagg ctattcctac taggtttgcg 540
cccggtacgg tattgcctca gggtttctat gttgaaggct cgggaaggtc tgcacctgct 600
agtcgatctg gttcgcggtc acaatcccgt gggccaaata atcgcgctag aagcagttcc 660
aaccagcgcc agcctgcctc tactgtaaaa cctgatatgg ccgaagaaat tgctgctctt 720
gttttggcta atctaggcaa agatgccgga cagcctaagc aagtaactaa gcaaagtgcc 780
aaagaagtca ggcagaaaat tttaaataag cctcgccaaa agaggactcc aaacaagcag 840
tgcccagtgc agcagtgttt tggaaagaga ggccccaatc agaattttgg aggccctgaa 900
atgttaaaac ttggaactag tgatccacag ttccccattc ttgcagagtt ggccccaaca 960
cctggtgcct tcttctttgg atctaaatta gaattggtca aaaagaattc tggtggcgtt 1020
gatgaaccca ccaaagatgt gtatgagctg caatattcag gtgcagtcag atttgatagt 1080
actctacctg gttttgagac tatcatgaaa gtgttgaatg agaatttgaa tgcctaccag 1140
aatcaagctg gtggtgcaga tgtagtgagc ccaaagcccc aaagaaagag agggacgaaa 1200

-continued

```
caaacggctc agaaagaaga attagatagt ataagcgttg caaagcccaa aagtgccgtg   1260

cagcgaaatg taagcagaga attaacccca gaggatagaa gcctgttggc gcagatccta   1320

gatgatggcg ttgtgcctga tgggttagat gactctaatg tgtaa                    1365
```

<210> SEQ ID NO 73
<211> LENGTH: 1111
<212> TYPE: DNA
<213> ORGANISM: Human coronavirus OC43

<400> SEQUENCE: 73

```
atggctacag tcaaatgggc tgatgcatct gaaccacaac gtggtcgtca gggtagaata     60

ccttattctc tttatagccc tttgcttgtt gatagtgaac aaccttggaa ggtgatacct    120

cgtaatttgg tacccatcaa caagaaagac aaaaataagc ttataggcta ttggaatgtt    180

caaaaacgtt tcagaactag aaagggcaaa cgggtggatt tgtcacccaa gctgcatttt    240

tattatcttg gcacaggacc ccataaagat gcaaaattta gagagcgtgt tgaaggtgtc    300

gtctgggttg ctgttgatgg tgctaaaact gaacctacag gttacggtgt taggcgcaag    360

aattcagaac cagagatacc acacttcaat caaaagctcc caaatggtgt tactgttgtt    420

gaagaacctg actcccgtgc tccttcccgg tctcagtcga ggtcgcagag tcgcggtcgt    480

ggtgaatcca aacctcaatc tcggaatcct tcaagtgaca gaaaccataa cagtcaggat    540

gacatcatga aggcagttgc tgcggctctt aaatctttag gttttgacaa gcctcaggaa    600

aaagataaaa agtcagcgaa aacgggtact cctaagcctt ctcgtaatca gagtcctgct    660

tcttctcaaa cttctgccaa gagtcttgct cgttctcaga gttctgaaac aaaagaacaa    720

aagcatgaaa tgcaaaagcc acggtggaaa agacagccta atgatgatgt gacatctaat    780

gtcacacaat gttttggccc cagagacctt gaccacaact ttggaagtgc aggtgttgtg    840

gccaatggtg ttaaagctaa aggctatcca caatttgctg agcttgtgcc gtcaacagct    900

gctatgctgt ttgatagtca cattgtttcc aaagagtcag gcaacactgt ggtcttgact    960

ttcactacta gagtgactgt gcccaaagac catccacact tgggtaagtt tcttgaggag   1020

ttaaatgcat tcactagaga aatgcaacaa cactgaacca gtgcgtgatg aagtttctat   1080

tgaaactgac ataattgatg aagtaaacta a                                  1111
```

<210> SEQ ID NO 74
<211> LENGTH: 1326
<212> TYPE: DNA
<213> ORGANISM: Porcine epidemic diarrhea virus

<400> SEQUENCE: 74

```
atggcttctg tcagctttca ggatcgtggc cgcaaacggg tgccattatc tctctatgcc     60

cctcttaggg ttactaatga caagcccctt tctaaggtac ttgcaaacaa cgctgtaccc    120

actaacaagg ggaataagga ccagcaaatt gggtactgga atgagcaaat tcgctggcgc    180

atgcgccgtg gtgagcgaat tgaacaacct tccaattggc atttctacta cctcggaaca    240

ggacctcacg gcgacctccg ttataggact cgtactgagg gtgttttctg ggttgctaaa    300

gaaggcgcaa agactgaacc cactaatttg ggtgtcagaa aggcgtctga aaagccaatc    360

attccaaaat tctctcaaca gctccccagt gtagttgaga ttgttgaacc taacacacct    420

cctgcttcac gtgcaaattc gcgtagcagg agtcgtggca atggcaacaa taggtctaga    480

tctccaagta acaacagagg caataaccag tcccgtggta attcacagaa tcgtggaaat    540

aaccagggtc gtggagcttc tcagaacaga ggaggcaata ataataacaa taacaagtct    600
```

-continued

```
cgtaaccagt ccaataacag gaaccagtca aatgaccgtg gtggtgtaac atcacgcgat    660

gatctggtgg ctgctgtcaa ggatgcactt aaatctttgg gtattggaga aaatcctgac    720

aggcataagc aacagcagaa gcctaagcag gaaaagtctg acaacagcgg caaaaataca    780

cctaagaaga acaaatccag ggccacttcg aaggaacgtg acctcaaaga catcccagag    840

tggaggagaa ttcccaaggg cgaaaatagc gtagcagctt gcttcggacc cagagggggc    900

ttcaaaaact ttggagatgc ggaatttgtc gaaaaaggtg ttgatgcgtc aggctatgct    960

cagatcgcca gtttagcacc aaatgttgca gcattgctct ttggtggtaa tgtggctgtt   1020

cgtgagctag cggactctta cgagattaca tacaactata aaatgactgt gccaaagtca   1080

gatccaaatg ttgagcttct tgtttcacag gtggatgcat ttaaaactgg gaatgcaaaa   1140

ctccagagaa agaaggaaaa gaagaacaag cgtgaaacca cgctgcagca gcatgaagag   1200

gccatctacg atgatgtggg tgcgccatct gatgtgaccc atgccaatct ggaatgggac   1260

acagctgttg atggtggtga tacggccgtt gaaattatca acgagatctt cgatacagga   1320

aattaa                                                              1326
```

<210> SEQ ID NO 75
<211> LENGTH: 1230
<212> TYPE: DNA
<213> ORGANISM: Infectious bronchitis virus

<400> SEQUENCE: 75

```
atggcaagcg gtaaagcagc tggaaaaaca gacgccccag cgccagtcat taaactagga     60

ggaccaaaac cacctaaagt cggttcttct ggaaatgcat cttggtttca agcaataaaa    120

gccaagaagt taaatacacc tccgcccaag tttgaaggta gcggtgttcc tgataacgaa    180

aacattaagc caagccagca acatggatac tggagacgcc aagccaggtt taagccaggc    240

aaaggtggaa gaaaaccagt cccagatgct tggtactttt actatactgg aacaggacct    300

gccgctgacc tgaactgggg tgatactcaa gatggtatag tgtgggttgc tgctaagggt    360

gctgatacta aatctagatc caatcagggt acaagagatc ctgataagtt tgaccaatac    420

ccactacgat tctcggatgg cggacctgat ggtaatttcc gttgggactt cattcccctg    480

aaccgtggta ggagtggaag atcaacagca gcttcatcag cagcagctag tagagcacca    540

tcacgtgaag gttcgcgtgg tcgtagaagt gattctggag atgaccttat tgctcgtgca    600

gcaaagataa tccaggatca gcagaaaaag ggctctcgca ttaccaaggc aaaggcagat    660

gaaatggctc atcgccggta ttgcaagcgc actatcccac ctaattatag ggttgatcaa    720

gtgtttggtc cccgtactaa aggtaaggag gggaattttg gtgatgacaa gatgaatgag    780

gaaggtatta aggatgggcg tgttacagca atgctcaacc tagtccctag cagccatgct    840

tgtctttttg gaagtagagt gacacccaaa cttcaactag atgggcttca cttgagattt    900

gaatttacta ctgtggtccc atgtgatgac ccgcagtttg ataattatgt gaaaatttgt    960

gatcagtgtg tcgatggtgt aggaacgcgt ccaaaagatg acgaaccaaa accaaagtca   1020

cgctcaagtt caagacctgc tacaagagga aattctccag cgccaagaca acagcgccca   1080

aagaaggaga aaaagctaaa gaagcaggat gatgaagcag ataaagcatt gacctcagat   1140

gaggagagga acaatgcaca gctggaattt tatgatgagc ccaaggtaat taactggggg   1200

gatgcagctc taggagagaa tgaactttga                                    1230
```

<210> SEQ ID NO 76

-continued

```
<211> LENGTH: 38
<212> TYPE: DNA
<213> ORGANISM: SARS coronavirus GD69

<400> SEQUENCE: 76

cctccgtacc atctggggct gagctctttc atcggagg                              38


<210> SEQ ID NO 77
<211> LENGTH: 95
<212> TYPE: DNA
<213> ORGANISM: SARS coronavirus GD69

<400> SEQUENCE: 77

acgagttcgt ggtggtgacg gcaaaatgaa agagctcagc cccagatggt acttctatta     60

cctaggaact ggcccagaag cttcacttcc ctacg                                 95


<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78

acgagttcgt ggtggtgac                                                   19


<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

cgtagggaag tgaagcttc                                                   19


<210> SEQ ID NO 80
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

gccttctttg ttag                                                        14


<210> SEQ ID NO 81
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

gcctccgtac catctggggc tgagctcttt catcggaggc                            40


<210> SEQ ID NO 82
<211> LENGTH: 38
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 82
taatacgact cactatagga cgagttcgtg gtggtgac 38

<210> SEQ ID NO 83
<211> LENGTH: 33
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
gccttctttg ttagcgtagg gaagtgaagc ttc 33

<210> SEQ ID NO 84
<211> LENGTH: 40
<212> TYPE: DNA
<213> ORGANISM: SARS coronavirus GD69

<400> SEQUENCE: 84
gcccacgtac catctggggc tgtagacagc agccgtgggc 40

<210> SEQ ID NO 85
<211> LENGTH: 98
<212> TYPE: DNA
<213> ORGANISM: SARS coronavirus GD69

<400> SEQUENCE: 85
ctctatgttt ataagggcta tcaacctata gatgctgctg tctacagccc cagatggtag 60
tattcttgct agtcacacta gccatcctta ctgcgctt 98

<210> SEQ ID NO 86
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
tacacacctc agcgttg 17

<210> SEQ ID NO 87
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
cacgaacgtg acgaat 16

<210> SEQ ID NO 88
<211> LENGTH: 26
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (21)..(26)
<223> OTHER INFORMATION: a, c, g, t, unknown, or other -continued

<400> SEQUENCE: 88
gccggagctc tgcagaattc nnnnnn 26

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 89
gccggagctc tgcagaattc 20

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 90
gggttgggac tatcctaagt gtga 24

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic primer
<220> FEATURE:
<221> NAME/KEY: modified_base
<222> LOCATION: (11)
<223> OTHER INFORMATION: i

<400> SEQUENCE: 91
taacacacaa ncccatcatc a 21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 92
ctaacatgct taggataatg g 21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 93
gcctctcttg ttcttgctcg c 21

<210> SEQ ID NO 94
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      primer

<400> SEQUENCE: 94

caggtaagcg taaaactcat c                                                21
```